US011185548B2

(12) United States Patent
Yildirim et al.

(10) Patent No.: US 11,185,548 B2
(45) Date of Patent: Nov. 30, 2021

(54) INHIBITORS OF CYTOCHROME P450 FAMILY 7 SUBFAMILY B MEMBER 1 (CYP7B1) FOR USE IN TREATING DISEASES

(71) Applicant: HELMHOLTZ ZENTRUM MÜNCHEN—DEUTSCHES FORSCHUNGSZENTRUM FÜR GESUNDHEIT UND UMWELT (GMBH), Neuherberg (DE)

(72) Inventors: Ali Oender Yildirim, Neuherberg (DE); Oliver Eickelberg, Munich (DE)

(73) Assignee: HELMHOLTZ ZENTRUM MUNCHEN—DEUTSCHES FORSCHUNGSZENTRUM FÜR GESUNDHEIT UND UMWELT (GMBH), Neuherberg (DE)

( * ) Notice: Subject to any disclaimer, the term of this patent is extended or adjusted under 35 U.S.C. 154(b) by 0 days.

(21) Appl. No.: 16/470,702

(22) PCT Filed: Dec. 21, 2017

(86) PCT No.: PCT/EP2017/084157
§ 371 (c)(1),
(2) Date: Jun. 18, 2019

(87) PCT Pub. No.: WO2018/115319
PCT Pub. Date: Jun. 28, 2018

(65) Prior Publication Data
US 2020/0085833 A1 Mar. 19, 2020

(30) Foreign Application Priority Data
Dec. 23, 2016 (LU) .......................... 93397

(51) Int. Cl.
| A61K 31/5377 | (2006.01) |
| A61P 11/00 | (2006.01) |
| A61K 31/4164 | (2006.01) |
| A61K 31/4196 | (2006.01) |
| A61K 31/427 | (2006.01) |
| A61K 31/444 | (2006.01) |
| A61K 31/454 | (2006.01) |
| A61K 31/496 | (2006.01) |
| C12N 5/0781 | (2010.01) |
| G01N 33/50 | (2006.01) |

(52) U.S. Cl.
CPC ...... *A61K 31/5377* (2013.01); *A61K 31/4164* (2013.01); *A61K 31/4196* (2013.01); *A61K 31/427* (2013.01); *A61K 31/444* (2013.01); *A61K 31/454* (2013.01); *A61K 31/496* (2013.01); *A61P 11/00* (2018.01); *C12N 5/0635* (2013.01); *G01N 33/5052* (2013.01); *C12N 2501/052* (2013.01); *C12N 2501/999* (2013.01)

(58) Field of Classification Search
CPC .......................... A61K 31/5377; A61P 35/00
See application file for complete search history.

(56) References Cited

U.S. PATENT DOCUMENTS

2002/0193384 A1* 12/2002 Fladung ............. A61K 31/4164
514/254.07

FOREIGN PATENT DOCUMENTS

| WO | 2009/015028 A1 | 1/2009 |
| WO | WO2018/096405 | * 5/2018 |

OTHER PUBLICATIONS

Hilberg et al., "Remarkably efficient inhaled antifungal monotherapy for invasive pulmonary aspergillosis," European Respiratory Journal, 2012, 40:271-273.
Liu et al., "Oxysterols direct B-cell migration through EB12," Nature, 2011, 475(7357):519-523.
Slama, "Treatment of Disseminated and Progressive Cavitary Histoplasmosis with Ketoconazole," American Journal of Medicine, Excerpta Medica, Inc., US, 74(1):70-733, 1983.
Yantsevich et al., "Human steriod and oxysterol 7a-hydroxylase CYP7B1: substrate specificity, azole binding and misfolding of clinically relevant mutants," FEBS Journal, 281(6):1700-1713, 2014.

* cited by examiner

*Primary Examiner* — Rei Tsang Shiao
(74) *Attorney, Agent, or Firm* — Riverside Law LLP

(57) ABSTRACT

The present invention relates to compounds for use in treating a disease that is associated with (related to) CYP7B1 wherein the compound inhibits CYP7B1. The present invention further relates to a method of treating or preventing such a disease by administering an inhibitor of CYP7B1. The present invention also relates to a method of determining whether a compound is effective in treating or preventing a disease associated with the formation of inducible bronchus-associated lymphoid tissue (iBALT).

5 Claims, 37 Drawing Sheets

C e

INHIBITORS OF CYTOCHROME P450 FAMILY 7 SUBFAMILY B MEMBER 1 (CYP7B1) FOR USE IN TREATING DISEASES

CROSS-REFERENCE TO RELATED APPLICATIONS

This application is the U.S. national phase application filed under 35 U.S.C. § 371 and claims priority to International Patent Application No. PCT/EP2017/084157, filed on Dec. 21, 2017, and Luxembourg Application Serial No. 93397, filed Dec. 23, 2016, the disclosure of which is incorporated herein by reference in its entirety.

FIELD OF THE INVENTION

The present invention relates to the use of inhibitors of cytochrome P450 family 7 subfamily B member 1 (CYP7B1) for treating diseases that (are related to CYP7B1) and can be treated by inhibiting the activity of CYP7B1. Such diseases include pulmonary diseases, transplant rejection or autoimmune diseases, for example. The invention also relates to methods of identifying CYP7B1-inhibitors that are suitable for treating such diseases.

BACKGROUND

Chronic obstructive pulmonary disease (COPD) is a type of obstructive lung disease characterized by long term poor airflow and affects more than 200 million people worldwide and is estimated to become the third leading cause of deaths in 2030. The main symptoms include shortness of breath and cough with sputum production. Tobacco smoking is the most common cause of COPD with a number of other factors such as air pollution and genetics playing a smaller role. COPD typically worsens over time.

Emerging evidence supports a crucial role for inducible bronchus-associated lymphoid tissue (iBALT) in the development of chronic obstructive pulmonary disease (COPD) (Hogg et al., The New England journal of medicine 350, 2645-2653 (2004); Faner et al., American journal of respiratory and critical care medicine 193, 1242-1253 (2016); Hwang et al., Frontiers in immunology 7, 258 (2016)) as well as other pulmonary diseases such as pulmonary hypertension, lung cancer, transplant rejection, pulmonary fibrosis, cystic fibrosis and autoimmunity (Pitzalis et al., Nature reviews. Immunology 14, 447-462 (2014)). iBALT is composed of B and T cells and is positioned within the lung predominantly alongside the bronchial epithelium (Gregson et al., British journal of experimental pathology 60, 471-482 (1979)). But the functional presence of iBALT for pulmonary diseases remains poorly understood.

It has been shown that an absence of iBALT prevented cigarette smoke induced emphysema (John-Schuster et al., American journal of physiology. Lung cellular and molecular physiology 307, L692-706 (2014); Bracke et al., American journal of respiratory and critical care medicine 188, 343-355 (2013)). B-cells which have been shown to be organized in iBALTs contribute to cigarette-smoke induced emphysema, hence aggravating the COPD symptoms. Consequently, when depleting B cells in mice, the formation of iBALTs is prevented. However, the mechanism underlying iBALT generation, particularly during chronic cigarette smoke exposure, is still unknown.

There is no curative therapy available for COPD. Currently available treatments are only able to alleviate symptoms. The standard therapy for the treatment of COPD is based on bronchodilators, including long-acting β2-agonists (LABAs) and long-acting muscarinic antagonists (LAMAs), while inhaled corticosteroids are recommended only for patients with severe disease or frequent exacerbations. Furthermore, a number of LABA-LAMA combinations are applicable for COPD patients. Another COPD symptomatic management is the reduction of risk factors, particularly smoking cessation and prevention of infection. However, an attempt to treat COPD by depleting B cells in patients using rituximab recently failed because of an increased risk of infectious complications (Brusselle et al., The European respiratory journal 34, 219-230 (2009)).

Therefore, there is an urgent need for curative treatments for COPD.

SUMMARY OF THE INVENTION

In the present invention it has been surprisingly discovered that the oxysterol synthesis pathway (cf. FIG. 9) regulates cigarette-smoke induced B cell migration and is thus critically involved in the immune pathogenesis of COPD. The present inventors have demonstrated that compounds according to formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, which are described in more detail herein, inhibit this pathway by inhibiting the 25-hydroxycholesterol 7-alpha-hydroxylase CYP7B1 and thus prevent or reverse iBALT formation and protect against cigarette-smoke induced emphysema in vivo. Consequently, the present inventors provide for the first time a preventive and curative treatment for disease that can be treated by inhibiting the activity of CYP7B1 (CYP7B1-inhibitors) such as COPD and other chronic diseases driven by the generation of ectopic lymphoid tissue. However, the invention is not limited to the treatment of COPD but the treatment of any disease associated with CYP7B1 by administration of a CYP7B1-inhibitor is within the scope of the present invention.

Consequently, the present invention relates to a compound for use in treating a disease that can be treated by (or is amenable to) inhibition of cytochrome P450 family 7 subfamily B member 1(CYP7B1), wherein the compound inhibits the activity of CYP7B1 (CYP7B1 inhibitor).

In one illustrative embodiment of the invention the compound (the CYP7B1-inhibitor) has the following formula (V):

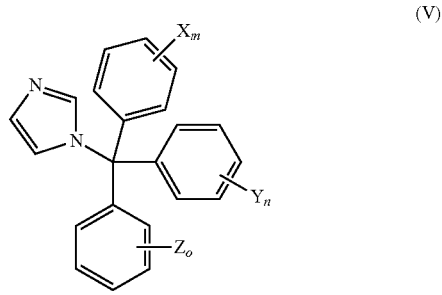

wherein
X, Y and Z are each, independently, selected from the group consisting of $(C_1$-$C_4)$alkyl and an electronegative substituent, wherein preferably the electronegative substituent is selected from the group consisting of F, Cl, Br, I, $NO_2$, $CF_3$, CN, $SCH_3$ and $OCH_3$; and m, n and o are each independently 0, 1 or 2;
or a pharmaceutically acceptable salt, solvate or hydrate thereof.

In another Illustrative embodiment of the invention the compound has the following formula (I):

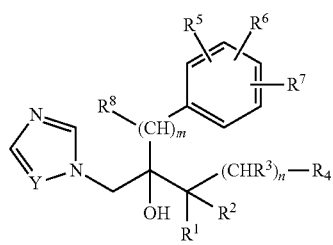

(I)

wherein
$R^1$ is selected from the group consisting of (i) $(C_1$-$C_5)$alkyl, said $(C_1$-$C_5)$alkyl being optionally substituted with a member selected from the group consisting of halogen, $(C_1$-$C_5)$alkoxy, phenyl-$(C_1$-$C_3)$alkoxy, phenoxy, $(C_1$-$C_5)$alkylthio, phenyl-$(C_1$-$C_3)$alkylthio and phenylthio, wherein each phenyl group is optionally substituted with a member selected from the group consisting of $(C_1$-$C_5)$alkyl, halogen, $(C_1$-$C_5)$haloalkyl, $(C_1$-$C_5)$alkoxy and $(C_1$-$C_5)$haloalkoxy, (ii) $(C_2$-$C_5)$alkenyl, said $(C_2$-$C_5)$alkenyl being optionally substituted with halogen, (iii) $(C_2$-$C_5)$alkynyl, said $(C_2$-$C_5)$alkynyl being optionally substituted with halogen, (iv) $(C_3$-$C_7)$cycloalkyl, said $(C_3$-$C_7)$cycloalkyl being optionally substituted with $(C_1$-$C_5)$alkyl, (iv) phenyl, said phenyl being optionally substituted with a member selected from the group consisting of halogen and $(C_1$-$C_5)$alkyl;
$R^2$ and $R^3$, independently, are hydrogen or have an $R^1$ significance, wherein $R^1$ and $R^2$ are optionally linked together to form a $(C_3$-$C_7)$cycloalkyl group;
m is 0 or 1;
n is 0, 1 or 2; and
$R^4$ is $(C_3$-$C_7)$cycloalkyl, said $(C_3$-$C_7)$cycloalkyl being optionally substituted with $(C_1$-$C_5)$alkyl;
$R^5$ and $R^6$ are the same or different and are selected from the group consisting of (i) hydrogen, (ii) halogen, (iii) optionally halogenated $(C_1$-$C_5)$alkyl, (iv) optionally halogenated $(C_2$-$C_5)$alkenyl, (v) optionally halogenated $(C_2$-$C_5)$alkinyl, (vi) optionally halogenated $(C_1$-$C_5)$alkoxy, (vii) phenyl, said phenyl being optionally substituted with a member selected from the group consisting of $CH_3$, F, Cl, Br, I, $CH_3O$, $C_6H_5$, $CF_3O$ and $C_2H_5$, (vii) phenoxy, said phenoxy being optionally substituted with a member selected from the group consisting of $CH_3$, F, Cl, Br, I, $CH_3O$, $C_6H_5$, $CF_3O$ and $C_2H_5$, (viii) and $NO_2$;
$R^7$ is selected from the group consisting of hydrogen, $(C_1$-$C_5)$alkyl and halogen;
$R^8$ is hydrogen or $(C_1$-$C_5)$alkyl;
Y is CH or N;
or a pharmaceutically acceptable salt, ether, ester solvate or hydrate thereof.

In another illustrative embodiment of the invention the compound has the following formula (II):

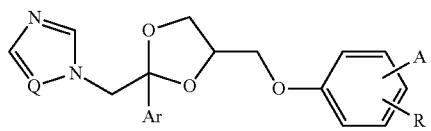

(II)

wherein
Q is a member selected from the group consisting of CH and N;
Ar is a member selected from the group consisting of phenyl and substituted phenyl, said substituted phenyl being phenyl having from 1 to 3 substituents independently selected from the group consisting of halogen, $(C_1$-$C_6)$alkyl and $(C_1$-$C_6)$alkyloxy;
the substituent A is of the formula

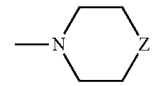

wherein
Z is a member selected from the group consisting of a direct bond, $CH_2$, oxygen and N—$R^4$, wherein $R^4$ is selected from the group consisting of hydrogen, $(C_1$-$C_6)$alkyl, hydroxy-$(C_1$-$C_6)$alkyl), $((C_1$-$C_6)$alkyloxy)-$(C_1$-$C_6)$alkyl, $(C_1$-$C_6)$alkanoyl, $(C_1$-$C_6)$alkylsulfonyl, phenylmethylsulfonyl, $(C_1$-$C_6)$alkyloxycarbonyl, $(C_1$-$C_6)$alkyloxycarbonylmethyl, phenoxycarbonyl, aminocarbonyl, mono- and di$((C_1$-$C_6)$alkyl)aminocarbonyl, aminocarbonylmethyl, $((C_1$-$C_6)$alkyl)aminocarbonylmethyl, $((C_1$-$C_6)$alkyl)aminothiocarbonyl, $((C_1$-$C_6)$alkylthio)thiocarbonyl, phenyl, phenylmethyl, benzoyl and substituted benzoyl, said substituted benzoyl being benzoyl having from 1 to 2 substituents independently selected from the group consisting of halogen, $(C_1$-$C_6)$alkyl and $(C_1$-$C_6)$alkyloxy;
R is a member selected from the group consisting of hydrogen and $NO_2$;
or a pharmaceutically acceptable salt, ether, ester solvate or hydrate thereof.

In another illustrative embodiment of the invention the compound has the following formula (III):

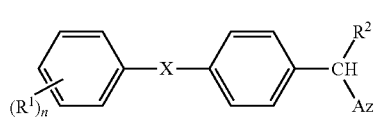

(III)

wherein
$R^1$ is selected from the group consisting of halogen, $(C_1$-$C_6)$haloalkyl, $(C_1$-$C_6)$alkyl, $(C_1$-$C_6)$alkoxy, $NO_2$ and cyano;
$R^2$ is $(C_1$-$C_6)$alkyl, or optionally substituted $(C_6$-$C_{10})$aryl;
X is selected from the group consisting of a single carbon-carbon bond, oxygen, sulphur, thionyl and sulphonyl;
Az is selected from the group consisting of imidazol-1-yl, pyrazol-1-yl, 1,2,4-triazol-1-yl and 1,2,4-triazol-4-yl;
n is an integer of from 0 to 4;
or a pharmaceutically acceptable salt, solvate or hydrate thereof.

In another embodiment of the invention the compound has the following formula (IV):

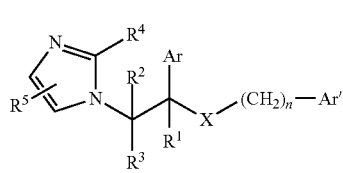

(IV)

$R^1$, $R^2$, and $R^3$ are each, independently, a member selected from the group consisting of hydrogen and $(C_1-C_6)$alkyl;
X is a member selected from the group consisting of oxygen and NH;
n is an integer of 0, 1 or 2;
Ar is a member selected from the group consisting of phenyl, substituted phenyl, thienyl and halothienyl, said substituted phenyl containing at least one substituent selected from the group consisting of halogen, $(C_1-C_6)$alkyl and $(C_1-C_6)$alkoxy;
Ar' is a member selected from the group consisting of phenyl, substituted phenyl and α-tetralyl, said substituted phenyl containing at least one substituent selected from the group consisting of halogen, $(C_1-C_6)$alkyl, $(C_1-C_6)$alkoxy, cyano, $NO_2$ and amino;
$R^4$ is a member selected from the group consisting of hydrogen, methyl and ethyl;
$R^5$ is a member selected from the group consisting of hydrogen and methyl;
provided that:
  (i) when said X is NH, then said R is hydrogen;
  (ii) when said Ar' is a substituted phenyl containing at least one substituent selected from the group consisting of $NO_2$ and amino, then said X is oxygen and said n is 0;
  (iii) when said Ar' is a α-tetralyl, then said X is NH and said n is 0; and
  (iv) when said X is oxygen and said Ar' is a member selected from the group consisting of phenyl and substituted phenyl containing at least one substituent selected from the group consisting of halogen, $(C_1-C_6)$alkyl, $(C_1-C_6)$alkoxy and cyano, then said n is other than 0;
or a pharmaceutically acceptable salt, solvate or hydrate thereof.

In another embodiment of the invention the compound has the following formula (VI):

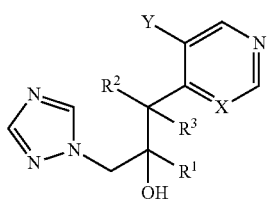

(VI)

wherein
$R^1$ is phenyl substituted with 1 to 3 substituents each independently selected from halogen, —$CF_3$ and —$OCF_3$;
$R^2$ is $(C_1-C_4)$alkyl;
$R^3$ is hydrogen or $(C_1-C_4)$alkyl;
X is CH or N;
Y is F or Cl;
or a pharmaceutically acceptable salt, solvate or hydrate thereof.

In another illustrative embodiment of the invention the compound has the following formula (VII):

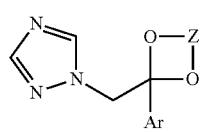

(VII)

wherein
Z is an alkylene selected from the group consisting of
—$CH_2$—$CH_2$—, —$CH_2$—$CH_2$—$CH_2$—,

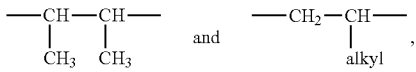

wherein said alkyl has from 1 to 10 carbon atoms;
Ar is a member selected from the group consisting of phenyl, substituted phenyl, thienyl, 5-chloro-2-thienyl, naphthyl and fluorenyl, wherein "substituted phenyl" has the meaning of a phenyl radical having thereon from 1 to 3 substituents each selected independently from the group consisting of halogen, $(C_1-C_6)$alkyl, $(C_1-C_6)$alkyloxy, cyano and $NO_2$;
or a pharmaceutically acceptable salt, solvate or hydrate thereof.

In another illustrative embodiment of the invention the compound has the following formula (IX):

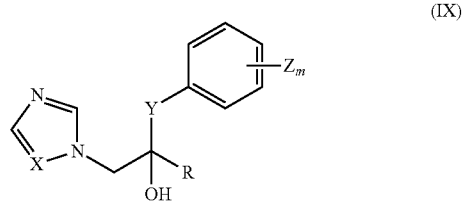

(IX)

wherein
R is selected from the group consisting of (i) $(C_1-C_6)$alkyl, (ii) $(C_3-C_7)$cycloalkyl, said $(C_3-C_7)$cycloalkyl being optionally substituted with $(C_1-C_2)$alkyl, and (iii) phenyl, said phenyl being optionally substituted with a group selected from halogen, $(C_1-C_4)$alkyl and $(C_1-C_2)$haloalkyl;
X is nitrogen or CH;
Y is selected from the group consisting of —$OCH_2$, —$CH_2CH_2$—, and —CH=CH—;
Z is selected from the group consisting of (i) halogen, (ii) $(C_1-C_4)$alkyl, (iii) $(C_5-C_7)$cycloalkyl, (iv) $(C_1-C_4)$alkoxy, (v) $(C_1-C_4)$alkylthio, (vi) $(C_1-C_2)$haloalkyl, (vii) $(C_1-C_2)$haloalkoxy, (viii) $(C_1-C_2)$haloalkylthio, (ix) phenyl, said phenyl being optionally substituted with halogen and/or $(C_1-C_4)$alkyl, (x) phenoxy, said phenoxy being optionally substituted with halogen and/or $(C_1-C_4)$alkyl, (xi) phenyl$(C_1-C_2)$alkyl, said phenyl$(C_1-C_2)$alkyl being optionally substituted with halogen and/or $(C_1-C_4)$alkyl, and (xii) phenyl$(C_1-C_2)$alkoxy, said phenyl$(C_1-C_2)$alkoxy being optionally substituted with halogen and/or $(C_1-C_4)$alkyl;
m is an integer of 0, 1, 2 or 3;
or a pharmaceutically acceptable salt, solvate or hydrate thereof.

In another illustrative embodiment of the invention the compound has the following formula (X):

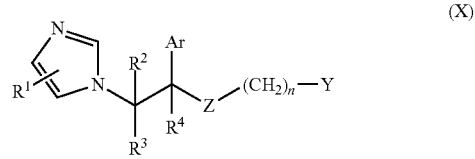

(X)

wherein
R$^1$, R$^2$, R$^3$ and R$^4$ are each, independently, hydrogen or (C$_1$-C$_6$)alkyl;
Ar is selected from the group consisting of (i) unsubstituted phenyl, (ii) phenyl substituted with a member selected from the group consisting of halogen, (C$_1$-C$_6$)alkyl and (C$_1$-C$_6$)alkoxy, (iii) thienyl and (iv) halothienyl;
Z is oxygen or sulfur;
n is 1 or 2;
Y is (C$_3$-C$_{10}$)heteroaryl, said (C$_3$-C$_{10}$)heteroaryl being optionally substituted with a member selected from the group consisting of halogen, (C$_1$-C$_6$)alkyl and (C$_1$-C$_6$)alkoxy;
or a pharmaceutically acceptable salt, solvate or hydrate thereof.

In another illustrative embodiment of the invention the compound has the following formula (XI):

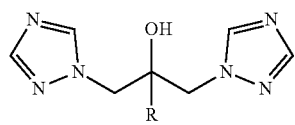
(XI)

wherein
R is selected from the group consisting of (i) naphthyl, (ii) biphenylyl and (iii) phenyl, said phenyl being optionally substituted with 1 to 3 substituents each independently selected from F, Cl, Br, I, CF$_3$, (C$_1$-C$_4$)alkyl and (C$_1$-C$_4$)alkoxy; or R is a 5-chloro-pyrid-2-yl group;
or a pharmaceutically acceptable salt, solvate or hydrate thereof.

In another illustrative embodiment of the invention the compound has the following formula (XII):

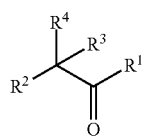
(XII)

wherein
R$^1$ and R$^2$ are each independently selected from the group consisting of 3-pyridyl and 4-pyridyl;
R$^3$ and R$^4$ are each independently (C$_1$-C$_6$)alkyl;
or a pharmaceutically acceptable salt, solvate or hydrate thereof.

In another embodiment of the invention the compound has the following formula (XIV):

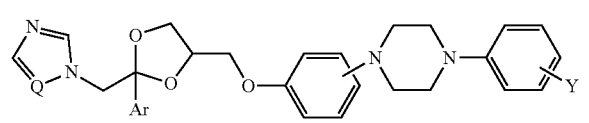
(XIV)

wherein
Q is selected from the group consisting of CH and N;
Ar is selected from the group consisting of (i) phenyl, (ii) thienyl, (iii) halothienyl and (iv) substituted phenyl, said substituted phenyl having from 1 to 3 substituents each independently selected from the group consisting of halogen, (C$_1$-C$_6$)alkyl, (C$_1$-C$_6$)alkyloxy and trifluoromethyl;
Y is a 2,3-dihydro-4H-1,2,4-triazol-4-yl of the formula

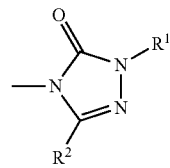

wherein
R$^1$ is selected from the group consisting of (C$_1$-C$_6$)alkyl and (C$_6$-C$_{10}$)aryl-(C$_1$-C$_6$)alkyl;
R$^2$ is selected from the group consisting of hydrogen, (C$_1$-C$_6$)alkyl, and (C$_6$-C$_{10}$)aryl-(C$_1$-C$_6$)alkyl;
or a pharmaceutically acceptable salt, solvate or hydrate thereof.

In another illustrative embodiment of the invention the compound has the following formula (XV):

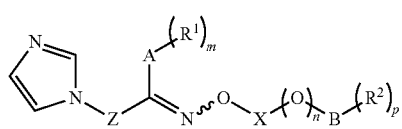
(XV)

wherein
Z is selected from the group consisting of straight and branched chain (C$_1$-C$_4$)alkylene group;
A is selected from the group consisting of phenyl and naphthyl;
R$^1$ is selected from the group consisting of halogen, NO$_2$, (C$_1$-C$_6$)alkyl and (C$_1$-C$_6$)alkoxy;
X is a (C$_1$-C$_8$)alkylene group;
B is selected from the group consisting of hydrogen, phenyl and naphthyl;
R$^2$ is selected from the group consisting of halogen, NO$_2$, (C$_1$-C$_6$)alkyl and (C$_1$-C$_6$)alkoxy;
m is 0 or an integer of from 1 to 3;
n is 0 or 1;
p is 0 or an integer of from 1 to 3 with the proviso that when B is hydrogen both n and p are 0;
or a pharmaceutically acceptable salt, solvate or hydrate thereof. (Oxiconazole)

In another illustrative embodiment of the invention the compound has the following formula (XVI):

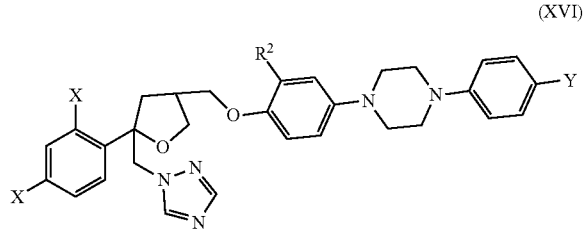
(XVI)

wherein
X is independently both F or both Cl; or one X is independently F and the other is independently Cl;

$R^1$ is a straight or branched chain $(C_3-C_8)$alkyl group substituted with one or two hydroxy moieties;
$R^2$ is H or a $(C_1-C_8)$alkyl group; preferably H or a methyl group;
Y is

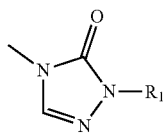

or —CONHArZ;
Ar is phenyl;
Z is F.

In another illustrative embodiment of the invention the compound has the following formula (XVII):

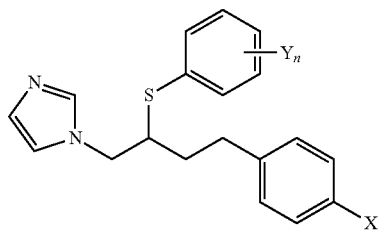

(XVII)

wherein
X is Cl or F;
Y is Br or Cl or F, at least one Y being in the 2'-position;
n is an integer of from 1 to 5 when Y is Cl; or n is 1 or 2 when Y is other than Cl;
or a pharmaceutically acceptable salt, solvate or hydrate thereof.

In another illustrative embodiment of the invention the compound has the following formula (XVIII):

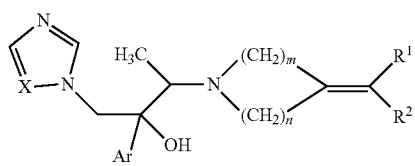

(XVIII)

wherein
Ar is a non-substituted phenyl group or a phenyl group substituted with 1 to 3 substituents each independently selected from halogen and $CF_3$;
$R^1$ and $R^2$ are the same or different and are selected from the group consisting of (i) hydrogen, (ii) $(C_1-C_6)$alkyl, (iii) non-substituted $(C_6-C_{10})$aryl, (iv) a $(C_6-C_{10})$aryl group substituted with 1 to 3 substituents each independently selected from halogen and $(C_1-C_6)$alkyl, (v) $(C_2-C_6)$alkenyl, (vi) $(C_2-C_6)$alkynyl and (vii) $(C_6-C_{10})$aryl$(C_1-C_6)$alkyl;
m is 2 or 3;
n is 1 or 2;
X is N or CH;
or a pharmaceutically acceptable salt, solvate or hydrate thereof.

In another illustrative embodiment of the invention the compound has the following formula (XIX):

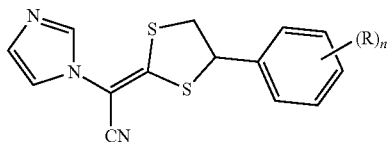

(XIX)

wherein
R is each, independently, halogen selected from the group consisting of F, Cl and Br;
n is an integer of 0, 1, 2 or 3;
or a pharmaceutically acceptable salt, solvate or hydrate thereof.

In another illustrative embodiment of the invention the compound has the following formula (XX):

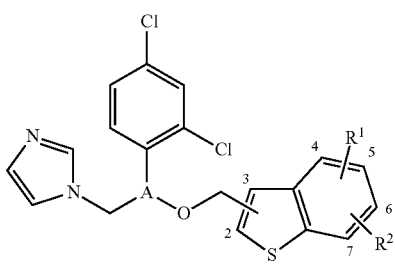

(XX)

wherein
A is an imino-

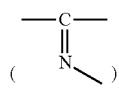

or methine

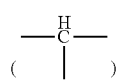

group;
$R^1$ and $R^2$, which may be the same or different, are hydrogen or halogen, said halogen being attached to the benzo[b]-thiophene group in the 2, 4, 5, 6 or 7 position and the methylene group being bonded to the benzo[b]-thiophene group in 2 or 3 position;
or a pharmaceutically acceptable salt, solvate or hydrate thereof.

In another illustrative embodiment of the invention the compound has the following formula (XXI):

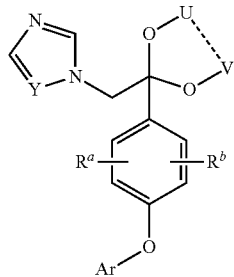

(XXI)

wherein
Y is CH or N;
$R^a$ and $R^b$ are each independently selected from the group consisting of hydrogen, halogen, $(C_1-C_3)$alkyl, $(C_1-C_3)$alkoxy and $NO_2$;
Ar is phenyl or naphthyl, each of which is independently unsubstituted or mono- or polysubstituted with halogen, $(C_1-C_7)$alkyl, $(C_1-C_7)$alkoxy, $NO_2$ and/or $CF_3$;
U and V are each, independently, $(C_1-C_{12})$alkyl which is unsubstituted or substituted with halogen or $(C_1-C_6)$alkoxy; or together form the following alkylene bridge

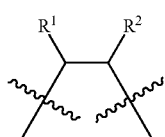

wherein
$R^1$ and $R^2$ are each, independently, selected from the group consisting of (i) hydrogen, (ii) $C_{12}$alkyl, (iii) $(C_1-C_{12})_{alkyl}$ which is mono- or polysubstituted with halogen, (iv) phenyl, (v) phenyl which is mono- or polysubstituted with halogen and/or $(C_1-C_3)$alkyl, and (vi) a —$CH_2$—Z—$R^7$ group;
wherein
Z is oxygen or sulfur;
$R^7$ is selected from the group consisting of (i) hydrogen, (ii) $(C_1-C_8)$alkyl, (iii) $(C_1-C_8)$alkyl which is substituted with $(C_1-C_2)$alkoxy, (iv) $(C_3-C_4)$alkenyl, (v) prop-2-ynyl, (vi) 3-haloprop-2-ynyl, (vii) phenyl, (viii) phenyl which is mono- or polysubstituted with $(C_1-C_3)$haloalkyl, $(C_1-C_3)$alkoxy, $NO_2$ and/or $CF_3$, (ix) benzyl and (x) benzyl which is mono- or polysubstituted with halogen, $(C_1-C_3)$alkyl and/or $(C_1-C_3)$alkoxy;
or a pharmaceutically acceptable salt, solvate or hydrate thereof.

In another illustrative embodiment of the invention the compound has the following formula (XXII):

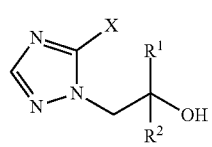

(XXII)

wherein
$R^1$ and $R^2$ are the same or different and are selected from the group consisting of optionally substituted $(C_1-C_6)$alkyl, optionally substituted $(C_2-C_6)$alkenyl, optionally substituted $(C_3-C_7)$cycloalkyl, optionally substituted $(C_6-C_{10})$aryl$(C_1-C_4)$alkyl, optionally substituted $(C_6-C_{10})$aryl$(C_2-C_4)$alkenyl, optionally substituted $(C_6-C_{10})$aryloxy$(C_1-C_4)$alkyl, optionally substituted $(C_6-C_{10})$aryl and optionally substituted $(C_3-C_{10})$heteroaryl;
X is selected from the group consisting of —SH; —$SR^3$, —$SO_2R^3$ and $SO_3H$;
$R^3$ is selected from the group consisting of (i) $(C_1-C_6)$alkyl optionally substituted with fluorine and/or chlorine, (ii) $(C_2-C_6)$alkenyl optionally substituted with fluorine and/or chlorine, (iii) optionally substituted $(C_6-C_{10})$aryl$(C_1-C_4)$alkyl and (iv) optionally substituted $(C_6-C_{10})$aryl;
or a pharmaceutically acceptable salt, solvate or hydrate thereof.

In another embodiment of the invention the compound has the following formula (XXIII):

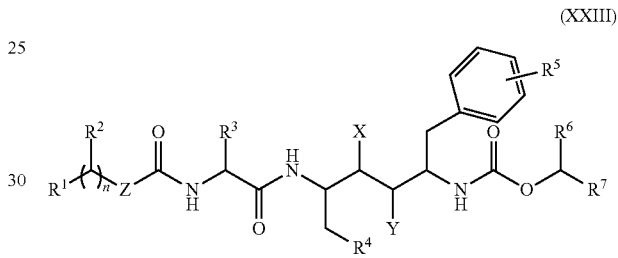

(XXIII)

wherein
$R^1$ is monosubstituted thiazolyl, monosubstituted oxazolyl, monosubstituted isoxazolyl or monosubstituted isothiazolyl, wherein the substituent is each independently selected from (i) $(C_1-C_6)$alkyl, (ii) $(C_2-C_6)$alkenyl, (iii) $(C_3-C_7)$cycloalkyl, (iv) $(C_3-C_7)$cycloalkyl$(C_1-C_6)$alkyl, (v) $(C_5-C_7)$cycloalkenyl, (vi) $(C_5-C_7)$cycloalkenyl$(C_1-C_6)$alkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halogen, $(C_1-C_6)$alkyl, hydroxy, alkoxy and thioalkoxy, (viii) (heterocyclic)$(C_1-C_6)$alkyl wherein heterocyclic is defined as above, (ix) $(C_1-C_6)$alkoxy$(C_1-C_6)$alkyl, (x) thio$(C_1-C_6)$alkoxy$(C_1-C_6)$alkyl, (xi) $(C_1-C_6)$alkylamino, (xii) di$(C_1-C_6)$alkylamino, (xiii) phenyl wherein the phenyl ring is unsubstituted or substituted with a substituent selected from halo, $(C_1-C_6)$alkyl, hydroxy, $(C_1-C_6)$alkoxy and $(C_1-C_6)$thioalkoxy, (xiv) phenyl$(C_1-C_6)$alkyl wherein the phenyl ring is unsubstituted or substituted as defined above, (xv) di$(C_1-C_6)$alkylamino$(C_1-C_6)$alkyl, (xvi) $(C_1-C_6)$alkoxy and (xvii) $(C_1-C_6)$thioalkoxy;
n is 1, 2 or 3;
$R^2$ is hydrogen or $(C_1-C_6)$alkyl;
$R^3$ is $(C_1-C_6)$alkyl;
$R^4$ is phenyl, thiazolyl or oxazolyl, wherein the phenyl, thiazolyl or oxazolyl ring is unsubstituted or substituted with a substituent selected from (i) halogen, (ii) $(C_1-C_6)$alkyl, (iii) hydroxy, (iv) $(C_1-C_6)$alkoxy and (v) $(C_1-C_6)$thioalkoxy;
$R^5$ is hydrogen, halogen, $(C_1-C_6)$alkyl, hydroxy, $(C_1-C_6)$alkoxy or $(C_1-C_6)$thioalkoxy;

$R^6$ is hydrogen or $(C_1-C_6)$alkyl;
$R^7$ is thiazolyl, oxazolyl, isoxazolyl or isothiazolyl, wherein the thiazolyl, oxazolyl, isoxazolyl or isothiazolyl ring is unsubstituted or substituted with $(C_1-C_6)$alkyl;
X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted;
Z is absent, —O—, —S—, —CH$_2$— or —N($R^8$)— wherein $R^8$ is $(C_1-C_6)$alkyl, $(C_3-C_7)$cycloalkyl, —OH or —NHR$^{8a}$ wherein $R^{8a}$ is hydrogen, $(C_1-C_6)$alkyl or an N-protecting group;
or a pharmaceutically acceptable salt, solvate or hydrate thereof.

In another illustrative embodiment of the invention the compound has the following formula (XXIV):

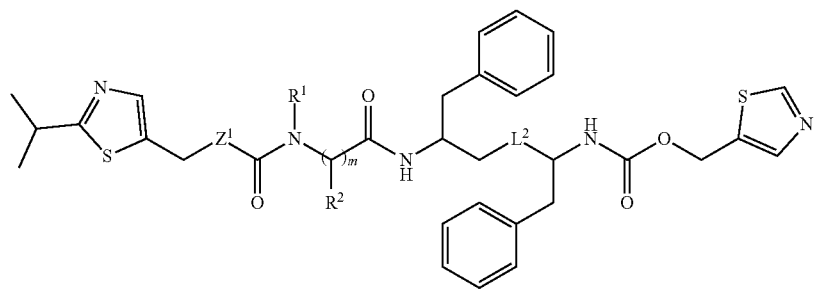

(XXIV)

$Z^1$ is —O— or —N($R^7$)—;
$L^2$ is a covalent bond, —C($R^6$)$_2$— or —C(O)—;
$R^1$ is independently selected from the group consisting of hydrogen, $(C_1-C_6)$alkyl, substituted $(C_1-C_6)$alkyl, $(C_6-C_{10})$aryl$(C_1-C_6)$alkyl, and substituted $(C_6-C_{10})$aryl$(C_1-C_6)$alkyl;
$R^2$ is each independently selected from the group consisting of H, $(C_1-C_6)$alkyl, substituted $(C_1-C_6)$alkyl, $(C_1-C_6)$alkoxy $(C_1-C_6)$alkyl, hydroxy$(C_1-C_6)$alkyl, $(C_6-C_{10})$aryl$(C_1-C_6)$ heteroalkyl, substituted $(C_6-C_{10})$aryl$(C_1-C_6)$heteroalkyl, $(C_6-C_{10})$aryl$(C_1-C_6)$alkyl, substituted $(C_6-C_{10})$aryl$(C_1-C_6)$alkyl, $(C_3-C_7)$heterocyclyl$(C_1-C_6)$alkyl, substituted $(C_1-C_6)$ heterocyclyl$(C_1-C_6)$alkyl, $(C_1-C_6)$aminoalkyl, substituted $(C_1-C_6)$aminoalkyl, —$(C_1-C_6)$alkylene-C(O)—OH, —$(C_1-C_6)$alkylene-C(O)—O—$(C_1-C_6)$alkyl, —$(C_1-C_6)$alkylene-C(O)amino, and —$(C_1-C_6)$alkylene-C(O)—$(C_1-C_6)$alkyl;
$R^6$ is selected from the group consisting of hydrogen, $(C_1-C_6)$alkyl, substituted $(C_1-C_6)$alkyl, and $(C_1-C_6)$heteroalkyl;
$R^7$ is selected from the group consisting of hydrogen, $(C_1-C_6)$alkyl, substituted $(C_1-C_6)$alkyl, $(C_1-C_6)$heteroalkyl, $(C_3-C_7)$carbocyclyl, substituted $(C_3-C_7)$carbocyclyl, $(C_3-C_7)$heterocyclyl, and substituted $(C_3-C_7)$heterocyclyl;
m is 1 or 2;
or a pharmaceutically acceptable salt, solvate or hydrate thereof.

In another embodiment of the invention the compound is selected from the group consisting of cyproconazole, ketoconazole, bifonazole, miconazole, clotrimazole, voriconazole, propiconazole, econazole, tebuconazole, tioconazole, fluconazole, metyrapone, isoconazole, itraconazole, oxiconazole, posaconazole, butoconazole, efinaconazole, luliconazole, sertaconazole, difenoconazole, prothioconazole, ritonavir, cobicistat and PC945.

In another embodiment of the invention the compound is a small organic molecule comprising at least two carbon atoms having a molecular weight in the range between 100 and 2000 Dalton.

In another illustrative embodiment of the invention the compound reduces or prevents the formation of inducible bronchus-associated lymphoid tissue (iBALT).

In another embodiment of the invention the disease that can be treated by inhibition of CYP7B1 disease is a pulmonary disease, transplant rejection or an autoimmune disease. In illustrative embodiment the pulmonary disease is selected from the group consisting of lung cancer, cystic fibrosis, pulmonary hypertension, emphysema, chronic obstructive pulmonary disease, pulmonary fibrosis.

In a further embodiment the present invention relates to a method of treating or preventing a disease by inhibition of CYP7B1, the method comprising administering a CYP7B1 inhibitor to a subject suffering from a disease or being at risk of developing a disease that is associated with CYP7B1.

In a further embodiment the present invention relates to a method of determining whether a compound is effective in treating or preventing a disease associated with the formation of inducible bronchus-associated lymphoid tissue (iBALT), the method comprising:
(a) providing activated B cells and culture supernatant from primary airway lung tissue cultured with cigarette smoke extract, optionally in combination with lipopolysaccharide (LPS) and said compound, wherein the B cells and the culture supernatant are spatially separated from each other; and
(b) determining migration of the activated B cells towards the culture supernatant,
wherein a decreased migration of the activated B cells compared to a control sample indicates that the compound is effective in treating or preventing a disease associated with the formation of iBALT.

In one embodiment of the method of the invention for determining whether a compound is effective in treating or preventing a disease associated with the formation of iBALT, the control sample is culture supernatant obtained from primary airway lung tissue cultured with cigarette smoke extract and optionally in combination with lipopolysaccharide (LPS).

In another embodiment of the method of the invention for determining whether a compound is effective in treating or preventing a disease associated with the formation of iBALT, the activated B cells and the culture supernatant are comprised by a cell culture vessel and separated by a cell permeable membrane. In one embodiment the cell permeable membrane is a 5.0 μm pore sized transwell insert. In another embodiment the activated B-cells are placed on the membrane and the culture supernatant is placed below the membrane in the cell culture vessel.

In another embodiment of the method of the invention for determining whether a compound is effective in treating or preventing a disease associated with the formation of iBALT, migration of the activated B cells is determined towards primary airway lung tissue cultured with cigarette smoke extract and optionally in combination with lipopolysaccharide (LPS) or with cigarette smoke extract, optionally in combination with lipopolysaccharide (LPS) and said compound. In one embodiment, migration is determined by counting of the migrated B cells.

In another embodiment of the method of the invention for determining whether a compound is effective in treating or preventing a disease associated with the formation of iBALT, migration is determined after at least 30 minutes, after at least 1 hour, at least 2 hours or at least 3 hours of incubation of the activated B cells with the culture supernatant or the primary airway lung tissue.

In another embodiment of the method of the invention for determining whether a compound is effective in treating or preventing a disease associated with the formation of iBALT, activated B cells are obtainable by bringing an antibody specific for the heavy chain of IgM into contact with isolated B cells.

In another embodiment of the method of the invention for determining whether a compound is effective in treating or preventing a disease associated with the formation of iBALT, the primary airway lung tissue is cultured with cigarette smoke extract and optionally in combination with lipopolysaccharide (LPS) for at least 6 h, for at least 12 h, for at least 18 h or for at least 24 h prior to incubation of the culture supernatant with the activated B cells.

In another embodiment of the method of the invention for determining whether a compound is effective in treating or preventing a disease associated with the formation of iBALT, the primary airway lung tissue is cultured with said compound for at least 1 h, for at least 2 h or for at least 3 h prior to incubation of the culture supernatant with the activated B cells.

In another embodiment of the method of the invention for determining whether a compound is effective in treating or preventing a disease associated with the formation of iBALT, the primary airway lung tissue is cultured with cigarette smoke extract at a concentration of at least 1%, at least 2%, at least 5% or at least 10%. Optionally the primary airway lung tissue is cultured, besides the cigarette smoke extract, additionally with at least 1 µg/ml, preferably with at least 4 µg/ml, more preferably with at least 7 µg/ml, most preferably with at least 10 µg/ml lipopolysaccharide (LPS).

In another embodiment of the method of the invention for determining whether a compound is effective in treating or preventing a disease associated with the formation of iBALT, the compound is effective in inhibiting the formation of 7α,25-dihydroxycholesterol (25HC) and preferably in inhibiting cholesterol-25-hydroxylase (Ch25h) or CYP7B1.

In another embodiment of the method of the invention for determining whether a compound is effective in treating or preventing a disease associated with the formation of iBALT, the primary airway lung tissue and the B cells are obtained from a mammal, such as rat, rabbit, guinea pig, pig, horse, monkey, human and preferably from mouse.

The invention will be better understood with reference to the detailed description when considered in conjunction with the non-limiting examples and the accompanying drawings. The figures illustrate embodiments of methods of the invention.

BRIEF DESCRIPTION OF THE FIGURES

FIG. 6(a) Ch25h, Cyp7b1 and Cxcl13 mRNA abundance from CSE treated airways dissected from wild-type (WT) or Ch25h-deficient (Ch25h$^{-/-}$) mice. Experiment repeated twice. n=3 per group. Data are mean±s.d. *P<0.05 and **P<0.0001 one-way ANOVA and Bonferroni's post hoc test. (b) Schematic representation of ex vivo B cell migration assay. (c) Ebi2 and Cxcr5 mRNA abundance from IgM cross-linked B cells isolated from the spleen of C57BL/6 mice. Experiment repeated twice. n=3 per group. Data are mean±s.d. (d) Frequency of IgM cross-linked splenic B cells migrating towards medium from CSE treated airways dissected from WT or Ch25h$^{-/-}$ mice. Experiment repeated twice. n=3 per group. Data are mean±s.d. P<0.01 one-way ANOVA and Bonferroni's post hoc test. (e) Schematic representation of the metabolism of 7α,25-OHC from cholesterol. (f) Ch25h and Cyp7b1 mRNA abundance from CSE treated airways, in the absence or presence of 1 μM clotrimazole, dissected from C57BL/6 mice. Experiment repeated twice. n=3 per group. Data are mean±s.d. *P<0.05, P<0.01 and *P<0.001 one-way ANOVA and Bonferroni's post hoc test. (g) Frequency of IgM cross-linked splenic B cells migrating towards medium from CSE treated airways, in the absence or presence of 1 μM clotrimazole, dissected from C57BL/6 mice. Experiment repeated twice. n=3 per group. Data are mean±s.d. ****P<0.0001 one-way ANOVA and Bonferroni's post hoc test.

The combination of 10% cigarette smoke extract and lipopolysaccharide efficiently induced Ch25h and Cyp7b1 expression, and the pro-inflammatory effect of this treatment was confirmed by the increase in Tnf expression. The induction of all three genes was inhibited after addition of clotrimazole.

Figure 11:
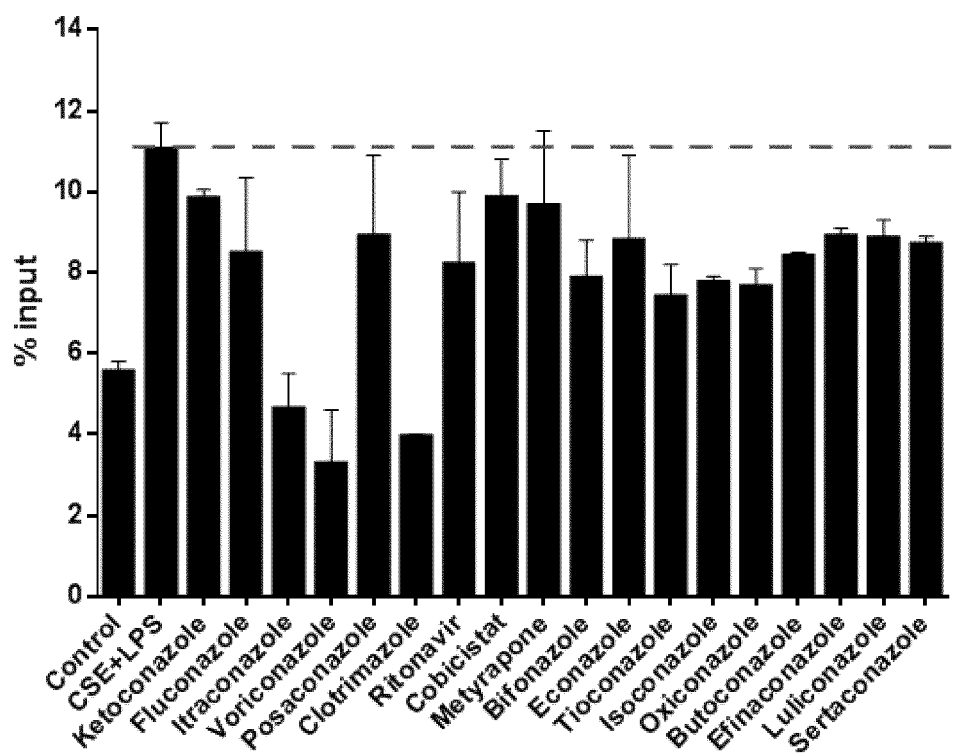

FIG. 11: Effect of 18 CYP7B1 inhibitory compounds on B cell migration.

The cultures were supplemented with the 18 indicated compounds (1 μM). Conditioned medium was transferred to the bottom of transwell plates. Primary mouse B cells, pre-stimulated with anti-IgM were seeded in the upper inserts and allowed to migrate for 6h at 37° C., 5% $CO_2$. Migration was quantified by fluorescence-activated cell sorting (FACS). The dotted line indicates the level of the positive control, n=2 mice.

DETAILED DESCRIPTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments described throughout the specification should not be construed to limit the present invention to only the explicitly described embodiments. This description should be understood to support and encompass embodiments which combine the explicitly described embodiments with any number of the disclosed and/or preferred elements. Furthermore, any permutations and combinations of all elements described herein should be considered disclosed by the description of the present application unless the context indicates otherwise. For example, if in one embodiment $R^1$ of the compounds of the invention is heteroaryl (such as pyrazolyl) and in another embodiment of the compounds of the invention B is a substituted or unsubstituted phenyl ring, then in a preferred embodiment, $R^1$ of the compounds of the invention is heteroaryl (such as pyrazolyl) and B is a substituted or unsubstituted phenyl ring.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Compounds

In order that the present invention may be more readily understood, certain terms are first defined. Additional definitions are set forth throughout the description.

As used herein and throughout the entire description, the term "alkyl" refers to a monoradical of a saturated straight or branched hydrocarbon. Preferably, the alkyl group comprises from 1 to 6 carbon atoms, i.e., 1, 2, 3, 4, 5 or 6 carbon atoms, preferably 1 to 4 carbon atoms. In some embodiments, the alkyl group employed contains 1-5 carbon atoms (($C_1$-$C_5$)alkyl). In some embodiments, the alkyl group employed contains 1-4 carbon atoms (($C_1$-$C_4$)alkyl). In some embodiments, the alkyl group employed contains 1-3 carbon atoms (($C_1$-$C_3$)alkyl). In some embodiments, the alkyl group employed contains 1-2 carbon atoms (($C_1$-$C_2$)alkyl). In some embodiments, the alkyl group employed is methyl. Examples of alkyl radicals include, but are not limited to, methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl and the like, which may bear one or more substituents. Alkyl group substituents include, but are not limited to, any of the substituents described herein, that result in the formation of a stable moiety. A substituted alkyl group can be substituted in any positions, provided that the resulting compound is sufficiently stable and is suitable as a pharmaceutical active compound. The prerequisite that a specific group and a compound of any one of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV disclosed herein is sufficiently stable and suitable as a pharmaceutical active compound, applies in general with respect to all groups in the compounds of any one of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV described herein. If an alkyl group can be monosubstituted or polysubstituted by fluorine, it can be unsubstituted, i.e. not carry fluorine atoms, or substituted, for example by 1, 2, 3, 4, 5, 6, 7, 8, 9, 10 or 11 fluorine atoms, preferably by 1, 2, 3, 4 or 5 fluorine atoms, which can be present in any positions. For example, in a fluoro-substituted alkyl group one or more methyl groups can carry three fluorine atoms each and be present as trifluoromethyl groups, and/or one or more methylene groups ($CH_2$) can carry two fluorine atoms each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S(O)$_m$— groups are trifluoromethanesulfanyl- ($CF_3$—S—, trifluoromethylsulfanyl-), trifluoromethanesulfinyl- ($CF_3$—S(O)—) and trifluoromethanesulfonyl- ($CF_3$—S(O)$_2$—). In some embodiments the alkyl group may be substituted by one or more identical or different substituents chosen from halogen, hydroxyl, cyano, $(C_1-C_6)$alkyl-O— and $(C_1-C_6)$alkyl-S(O)$_m$—. Examples of $(C_1-C_6)$alkyl-O— are methoxy, ethoxy, n-propoxy, isopropoxy, n-butoxy, isobutoxy, tert-butoxy and n-pentoxy. Examples of alkyl-S (O)$_m$— are methanesulfanyl- ($CH_3$—S—, methylsulfanyl), methanesulfinyl- ($CH_3$—S(O)—), methanesulfonyl- ($CH_3$—S(O)$_2$—), ethanesulfanyl-($CH_3$—$CH_2$—S—, ethylsulfanyl-), ethanesulfinyl- ($CH_3$—$CH_2$—S(O)—), ethanesulfonyl- ($CH_3$—$CH_2$—S(O)$_2$—), 1-methylethanesulfanyl- (($CH_3$)$_2$CH—S—, 1-methylethylsulfanyl-), 1-methylethanesulfinyl-(($CH_3$)$_2$CH—S(O)—) and 1-methylethanesulfonyl- (($CH_3$)$_2$CH—S(O)$_2$—). In one embodiment of the invention the number m is chosen from 0 and 2, wherein all numbers m are independent of each other and can be identical or different. For example, if the alkyl group is substituted by a $CF_3$—S— group, the $CF_3$—S— group is bonded to this alkyl group via the sulfur as it is symbolized by the terminal line (hyphen) next to the sulfur atom representing a free bond. In some embodiments the alkyl chain is a linear. In some embodiments the alkyl chain is branched. In some embodiments the alkyl chain is substituted. In some embodiment the alkyl chain is unsubstituted. In some embodiments the alkyl chain is linear and substituted or unsubstituted. In some embodiments the alkyl chain is branched and substituted or unsubstituted.

The term "alkoxy", as used herein, unless otherwise indicated, includes O-alkyl groups wherein alkyl is as defined above, and includes optionally substituted alkyl groups as also defined above.

The term "alkanoyl", as used herein, unless otherwise indicated, includes straight and branched chained alkanoyl radicals. Preferably, the alkanoyl group comprises from 1 to 6 carbon atoms, i.e., 1, 2, 3, 4, 5 or 6 carbon atoms, preferably 1 to 4 carbon atoms. Examples of alkanoyl radicals include, but are not limited to, formyl, acetyl, propanoyl, 2-methylpropanoyl, butanoyl, pentanoyl, hexanoyl and the like.

As used herein and throughout the entire description, the term "alkylene" refers to a diradical of a saturated straight or branched hydrocarbon. Preferably, the alkylene comprises from 1 to 6 carbon atoms, i.e., 1, 2, 3, 4, 5 or 6 carbon atoms, more preferably 1 to 4 carbon atoms. Exemplary alkylene groups include methylene, ethylene (i.e., 1,1-ethylene, 1,2-ethylene), propylene (i.e., 1,1-propylene, 1,2-propylene (—CH($CH_3$)$CH_2$—), 2,2-propylene (—C($CH_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylenisomers (e.g., 1,1-hexylene, 1,2-hexylene, 1,3-hexylene, 1,4-hexylene, 1,5-hexylene, 1,6-hexylene, and 1,1-isohexylene), and the like. Alkylene groups may be cyclic or acyclic, branched or unbranched, substituted or unsubstituted. Alkylene group substituents include, but are not limited to, any of the substituents described herein, that result in the formation of a stable moiety.

As used herein and throughout the entire description, the term "haloalkyl" refers to an alkyl group substituted by one halogen substituent up to per halo-substitution. The halogen substituent is preferably fluorine. The haloalkyl is preferably a perfluoroalkyl. In some embodiments, the haloalkyl group employed in the invention contains 1-6 carbon atoms (($C_1$-$C_6$)haloalkyl). In some embodiments, the haloalkyl group employed contains 1-5 carbon atoms (($C_1$-$C_5$)haloalkyl). In some embodiments, the haloalkyl group employed contains 1-4 carbon atoms (($C_1$-$C_4$)haloalkyl). In some embodiments, the haloalkyl group employed contains 1-3 carbon atoms (($C_1$-$C_3$)haloalkyl). In some embodiments, the haloalkyl group employed contains 1-2 carbon atoms (($C_1$-$C_2$)haloalkyl). In some embodiments, the haloalkyl group employed contains 1-carbon atom (($C_1$)haloalkyl). In some embodiments, the haloalkyl group employed is trifluoromethyl. Exemplary fluoro-substituted ($C_1$-$C_2$)alkyl includes —$CFH_2$, —$CF_2H$, —$CF_3$, $CH_2CH_2F$, —$CH_2CHF_2$, —$CHFCH_3$, —$CHFCH_3$, —$CF_2CHF_2$. Perfluoro-substituted ($C_1$-$C_2$)haloalkyl, for example include —$CF_3$, and —$CF_2CF_3$.

As used herein and throughout the entire description, the term "heteroalkyl", as used herein, refers to an alkyl moiety, as defined herein, which contains one or more heteroatoms (e.g., oxygen, sulfur, nitrogen, phosphorus, or silicon atoms) in between carbon atoms. The heteroalkyl may be substituted or unsubstituted. In some embodiments, the heteroalkyl group contains 1-6 carbon atoms and 1-3 heteroatoms (($C_1$-$C_6$)heteroalkyl). In some embodiments, the heteroalkyl group contains 1-5 carbon atoms and 1-3 heteroatoms (($C_1$-$C_5$)heteroalkyl). In some embodiments, the heteroalkyl group contains 1-4 carbon atoms and 1-2 heteroatoms (($C_1$-$C_4$)heteroalkyl). In some embodiments, the heteroalkyl group contains 1-3 carbon atoms and 1 heteroatom (($C_1$-$C_3$) heteroalkyl). In some embodiments, the heteroalkyl group contains 1-2 carbon atoms and 1 heteroatom (($C_1$-$C_2$)heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. In certain embodiments the heteroalkyl group is a substituted heteroalkyl group containing 1-6 carbon atoms and 1-3 heteroatoms (($C_1$-$C_6$)heteroalkyl). In certain embodiments the heteroalkyl group is an unsubstituted heteroalkyl group containing 1-6 carbon atoms and 1-3 heteroatoms (($C_1$-$C_6$)heteroalkyl). In some embodiments the heteroalkyl is an alkyl moiety wherein on methylene group is replaced by S. In some embodiments the heteroalkyl is an alkyl moiety wherein on methylene group is replaced by 0. In some embodiments the heteroalkyl is an alkyl moiety wherein on methylene group is replaced by NR$^A$, wherein R$^A$ is selected from the group consisting of hydrogen, substituted or unsubstituted ($C_1$-$C_6$)alkyl, substituted or unsubstituted ($C_3$-$C_8$)cycloalkyl, substituted or unsubstituted ($C_6$-$C_{14}$)aryl and substituted or unsubstituted ($C_3$-$C_{14}$)heteroaryl. In some embodiments heteroalkyl is —$CH_2SCH_3$. In some embodiments heteroalkyl is —$CH_2OCH_3$.

As used herein and throughout the entire description, the term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. In some embodiments, the alkenyl group employed in the invention contains 2-20 carbon atoms (($C_2$-$C_{20}$)alkenyl). In some embodiments, the alkenyl group employed in the invention contains 2-15 carbon atoms (($C_2$-$C_{15}$)alkenyl). In some embodiments, the alkenyl group employed contains 2-10 carbon atoms (($C_2$-$C_{10}$)alkenyl). In some embodiments, the alkenyl group contains 2-8 carbon atoms (($C_2$-$C_8$)alkenyl). In some embodiments, the alkenyl group contains 2-6 carbons (($C_2$-$C_6$)alkenyl). In some embodiments, the alkenyl group contains 2-5 carbons (($C_2$-$C_5$)alkenyl). In some embodiments, the alkenyl group contains 2-4 carbons (($C_2$-$C_4$)alkenyl). In some embodiments, the alkenyl group contains 2-3 carbons (($C_2$-$C_3$)alkenyl). In some embodiments, the alkenyl group contains 2 carbons (($C_2$)alkenyl). The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. Alkenyl group substituents include, but are not limited to, any of the substituents described herein, that result in the formation of a stable moiety.

A substituted alkenyl group can be substituted in any positions, provided that the resulting compound is sufficiently stable and is suitable as a pharmaceutical active compound. The prerequisite that a specific group and a compound of any one of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV disclosed herein is sufficiently stable and suitable as a pharmaceutical active compound, applies in general with respect to all groups in the compounds of any one of the formulas I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV disclosed herein. In some embodiments the alkenyl group may be substituted by one or more identical or different substituents chosen from halogen, hydroxyl, cyano, ($C_1$-$C_6$)alkyl-O— and ($C_1$-$C_6$)alkyl-S(O)$_m$—. In some embodiments of the invention the number m is chosen from 0 and 2, wherein all numbers m are independent of each other and can be identical or different. In some embodiments the alkenyl chain is a linear. In some embodiments the alkenyl chain is branched. In some embodiments the alkenyl chain is substituted. In some embodiment the alkenyl chain is unsubstituted. In some embodiments the alkenyl chain is linear and substituted or unsubstituted. In some embodiments the alkenyl chain is branched and substituted or unsubstituted. Alkenyl group substituents include, but are not limited to, any of the substituents described herein, that result in the formation of a stable moiety.

The term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom.

As used herein and throughout the entire description, the term "cycloalkyl" or "cycloaliphatic" or "carbocyclic" or "carbocycle" or "carbocyclyl" represents cyclic non-aromatic versions of "alkyl" and "alkenyl" with preferably 3 to 8 carbon atoms i.e., 3, 4, 5, 6, 7 or 8 carbon atoms, more preferably 3 to 7 carbon atoms. In some embodiments, the cycloalkyl group employed in the invention contains 3-7 carbon atoms (($C_3$-$C_7$)cycloalkyl). In some embodiments, the cycloalkyl group employed in the invention contains 3-6 carbon atoms (($C_3$-$C_6$)cycloalkyl). In some embodiments, the cycloalkyl group employed in the invention contains 3-5 carbon atoms (($C_3$-$C_5$)cycloalkyl). In some embodiments, the cycloalkyl group employed in the invention contains 3-4 carbon atoms (($C_3$-$C_4$)cycloalkyl). In some embodiments, the cycloalkyl group employed in the invention contains 3 carbon atoms (($C_3$)cycloalkyl). Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl and cyclooctenyl. The double bond in a cycloalkenyl group can be present in any position with respect to the carbon atom in position 1 via which the group is bonded to the remainder of the molecule, i.e. for example to the nitrogen atom in the compounds having a structure according to formula I, and cycloalkenyl can thus be cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, for example. In preferred embodiments of the present invention, a cycloalkyl group, such as ($C_3$-$C_7$)cycloalkyl, in the definition of any group is chosen from a subgroup of any two or more of the said specific cycloalkyl groups, for example from cyclopropyl and cyclobutyl, or from cyclopropyl, cyclobutyl and cyclopentyl, or from cyclopropyl, cyclopentyl and cyclohexyl, or from cyclopentyl and cyclohexyl, or from cyclopentyl, cyclohexyl and cycloheptyl. Similarly, in preferred embodiments a cycloalkenyl group is chosen from a subgroup of any two or more of the said specific cycloalkenyl groups, for example from cyclopentenyl and cyclohexenyl, or from cyclohexenyl and cycloheptenyl, or from cyclopent-1-enyl, cyclopent-2-enyl, cyclohex-1-enyl, cyclohex-2-enyl, cyclohept-1-enyl and cyclohept-2-enyl, or from cyclopent-2-enyl, cyclopent-3-enyl, cyclohex-2-enyl, cyclohex-3-enyl, cyclohept-2-enyl, cyclohept-3-enyl and cyclohept-4-enyl, or from cyclopent-2-enyl and cyclohex-2-enyl, or from cyclopent-2-enyl, cyclohex-2-enyl and cyclohept-2-enyl. Cycloalkyl groups and cycloalkenyl groups generally are optionally substituted by one or more ($C_1$-$C_4$)alkyl substituents. I.e., they are unsubstituted, i.e. do not carry alkyl substituents, or substituted, for example by 1, 2, 3 or 4 identical or different ($C_1$-$C_4$)alkyl substituents, for example by methyl groups and/or ethyl groups and/or isopropyl groups and/or tert-butyl groups, in particular by methyl groups, which substituents can be present in any positions. Examples of alkyl-substituted cycloalkyl groups are 1-methyl- cyclopropyl, 2,2-dimethyl-cyclopropyl, 1-methyl-cyclopentyl, 2,3-dimethyl-cyclopentyl, 1-methyl-cyclohexyl, 4-methyl-cyclohexyl, 4-isopropyl-cyclohexyl, 4-tert-butyl- cyclohexyl and 3,3,5,5-tetramethyl-cyclohexyl. Examples of alkyl-substituted cycloalkenyl groups are 1-methyl-cyclopent-2-enyl, 2-methyl-cyclopent-2-enyl, 3-methyl-cyclopent-2-enyl, 3,4-dimethyl-cyclopent-3-enyl, 1-methyl-cyclohex-2-enyl, 2-methyl-cyclohex-2-enyl, 3-methyl-cyclohex-2-enyl, 4-methyl-cyclohex-2-enyl, 2-methyl-cyclohex-3-enyl, 3-methyl-cyclohex-3-enyl, 4-methyl-cyclohex-3-enyl, 2,3-dimethyl-cyclohex-2-enyl, 4,4-dimethyl-cyclohex-2-enyl, 3,4-dimethyl-cyclohex-3-enyl. Cycloalkyl groups and cycloalkenyl groups generally also are optionally substituted by one or more fluorine atoms. I.e., they are unsubstituted, i.e. do not carry fluorine atoms, or substituted, for example by 1, 2, 3, 4, 5, 6, 7, 8, 9, 10 or 11 fluorine atoms, preferably by 1, 2, 3, 4, 5 or 6 fluorine atoms. Cycloalkyl groups and cycloalkenyl groups can also be substituted simultaneously by fluorine and alkyl. The fluorine atoms can be present in any positions and can also be present in an alkyl substituent. Examples of fluoro-substituted cycloalkyl groups are 1-fluoro-cyclopropyl, 2,2-difluoro-cyclopropyl, 3,3-difluoro-cyclobutyl, 1-fluoro-cyclohexyl, 4,4-difluoro- cyclohexyl and 3,3,4,4,5,5-hexafluoro-cyclohexyl. Examples of fluoro-substituted cycloalkenyl groups are 1-fluoro-cyclopent-2-enyl, 1-fluoro-cyclohex-2-enyl, 4-fluoro- cyclohex-2-enyl, 4,4-difluoro-cyclohex-2-enyl. In some embodiments of the invention, cycloalkyl groups are not optionally substituted by substituents chosen from fluorine and ($C_1$-$C_4$) alkyl. If a cycloalkyl group or cycloalkenyl group can be substituted by further substituents like hydroxy, it can be substituted by one or more such further substituents like hydroxy only and not by substituents chosen from fluorine and ($C_1$-$C_4$)alkyl, or by one or more such further substituents and simultaneously by one or more substituents chosen from fluorine and ($C_1$-$C_4$)alkyl. The number of such further substituents like hydroxy which can be present on a cycloalkyl or cycloalkenyl group, preferably is 1, 2 or 3, more preferably 1 or 2, for example 1. The total number of all substituents in a cycloalkyl group or cycloalkenyl group preferably is 1, 2, 3, 4, 5, 6, 7 or 8, more preferably 1, 2, 3, 4 or 5, for example 1, 2 or 3. Such further substituents like hydroxy can be present in any positions, provided that the resulting compound is sufficiently stable and is suitable as a subgroup in a pharmaceutical active compound. Preferably, a hydroxy substituent is not present in position 1 of a cycloalkenyl group or cycloalkyl group and in a cycloalkenyl group a hydroxy substituent is not present on a carbon atom which is part of the double bond. Examples of hydroxy-substituted cycloalkyl groups are 3-hydroxy-cyclobutyl, 2-hydroxy-cyclopentyl, 3-hydroxy-cyclopentyl, 3,4-dihydroxy-cyclopentyl, 2-hydroxy-cyclohexyl, 3-hydroxy-cyclohexyl, 4-hydroxy-cyclohexyl, 2,3-dihydroxy-cyclohexyl, 2,4-dihydroxy-cyclohexyl, 3,4-dihydroxy-cyclohexyl, 3,5-dihydroxy-cyclohexyl, 3,4,5-trihydroxy-cyclohexyl, 2-hydroxy-cycloheptyl, 3-hydroxy-cycloheptyl, 4-hydroxy-cycloheptyl. Examples of hydroxy-substituted cycloalkenyl groups are 5-hydroxy-cyclopent-2-enyl, 4-hydroxy-cyclohex-2-enyl, 5-hydroxy-cyclohex-2-enyl, 6-hydroxy-cyclohex-2-enyl, 6-hydroxy-cyclohex-3-enyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include ($C_3$-$C_8$) cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl. Cycloalkyl group substituents include, but are not limited to, any of the substituents described herein, that result in the formation of a stable moiety.

As used herein and throughout the entire description, the term "cyclopropylene" means a cyclopropyl group as defined above in which one hydrogen atom has been removed resulting in a diradical. The cyclopropylene may link two atoms or moieties via the same carbon atom (1,1-cyclopropylene, i.e., a geminal diradical) or via two carbon atoms (1,2-cyclopropylene).

As used herein and throughout the entire description, the term "aryl" or "aromatic ring" refers to an aromatic mono- or polycyclic ring system having 6-10 ring atoms, of which all the ring atoms are carbon, and which may be substituted or unsubstituted. In certain embodiments of the present invention, "aryl" refers to a mono or bicyclic $C_6$-$C_{10}$ aromatic ring system having one or two aromatic rings which include, but are not limited to, phenyl, biphenyl, naphthyl, and the like, which may bear one or more substituents. Preferably, the aryl group contains 6 to 10 carbon atoms, which can be arranged in one ring (e.g., phenyl) or two or more condensed rings (e.g., naphthyl). Exemplary aryl groups include cyclopropenylium, cyclopentadienyl, phenyl, indenyl, naphthyl and azulenyl. Preferably, "aryl" refers to a monocyclic ring containing 6 carbon atoms or an aromatic bicyclic ring system containing 10 carbon atoms. Preferred examples are substituted or unsubstituted phenyl and naphthyl. Even more preferred is substituted or unsubstituted phenyl. In some embodiments, the aryl group employed in the invention contains 7-10 carbon atoms (($C_7$-$C_{10}$)aryl). In some embodiment, the aryl group employed in the invention contains 6-8 carbon atoms (($C_6$-$C_8$) aryl). In some embodiments, the aryl group employed in the invention contains 6 carbon atoms (($C_6$)aryl). In some embodiments, the aryl group employed in the invention contains 10 carbon atoms (($C_{10}$)aryl).

In substituted aryl groups, the substituents can be present in any positions. In monosubstituted phenyl groups, the substituent can be present in the 2-position, the 3-position or the 4-position. In disubstituted phenyl groups, the substituents can be present in 2,3-position, 2,4-position, 2,5-position, 2,6-position, 3,4-position or 3,5-position. In trisubstituted phenyl groups, the substituents can be present in 2,3,4-position, 2,3,5-position, 2,3,6-position, 2,4,5-position, 2,4,6-position or 3,4,5-position. If a phenyl group carries four substituents, of which one, two, three or four substituents can be fluorine atoms, for example, the unsubstituted ring carbon atom can be present in the 2-position, the 3-position or the 4-position. If a polysubstituted phenyl group or heteroaryl group carries different substituents, each substituent can be present in any suitable position, and the present invention comprises all positional isomers. The number of substituents in a substituted phenyl group can be 1, 2, 3, 4 or 5. Preferably, a substituted phenyl group, and likewise a substituted heteroaryl group, carries 1, 2 or 3, in particular 1 or 2, identical or different substituents. In a preferred embodiment the substituted phenyl group carries 1 substituent in 2, 3 or 4-position. In preferred embodiments of the invention, the substituents in substituted phenyl and heteroaryl groups are chosen from any subgroup of the substituents listed in the respective definition, for example by substituents chosen from halogen, substituted or unsubstituted ($C_1$-$C_6$)alkyl, ($C_1$-$C_4$)haloalkyl, —$NO_2$, cyano, halogen, substituted or unsubstituted ($C_1$-$C_6$)alkyl-O—, substituted or unsubstituted ($C_6$-$C_{14}$)aryl($C_1$-$C_6$)alkyl-O—, —C(O)$NH_2$, —C(O)NH(($C_1$-$C_6$)-alkyl), —C(O)N(($C_1$-$C_6$)-alkyl)$_2$, —NH(($C_1$-$C_6$)alkyl-O($C_1$-$C_6$)alkyl)), —NH(($C_1$-$C_6$)alkyl-OH), azido, —NH(C(=O)($C_1$-$C_6$)alkyl) and —N(($C_1$-$C_6$)alkyl)(C(=O)($C_1$-$C_6$)alkyl).

As used herein and throughout the entire description, the term "arylene" refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety.

The term "aryloxy", as used herein, unless otherwise indicated, refers to the group aryl-O— wherein the aryl group is as defined above, and includes optionally substituted aryl groups as also defined above.

As used herein and throughout the entire description, the term "heteroaryl" or "heteroaromatic ring" means an aryl group as defined above in which one or more carbon atoms in the aryl group are replaced by heteroatoms of O, S, or N. Preferably, the heteroaryl group contains 3 to 10 carbon atoms. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. In some embodiments, the heteroaryl group employed in the invention is a five membered aromatic monocyclic ring wherein 1, 2, or 3 carbon atoms are replaced by the same or different heteroatoms of O, N, or S. In some embodiments, the heteroaryl group employed in the invention is a five membered aromatic monocyclic ring wherein 1, 2, or 3 carbon atoms are replaced by the same or different heteroatoms of O. In some embodiments, the heteroaryl group employed in the invention is a five membered aromatic monocyclic ring wherein 1, 2, or 3 carbon atoms are replaced by the same or different heteroatoms of O and N. In some embodiments, the heteroaryl group employed in the invention is a five membered aromatic monocyclic ring wherein 1, 2, or 3 carbon atoms are replaced by the same or different heteroatoms of O and S. In some embodiments, the heteroaryl group employed in the invention is a five membered aromatic monocyclic ring wherein 1, 2, or 3 carbon atoms are replaced by the same or different heteroatoms of N and S. In some embodiments, the heteroaryl group employed in the invention is a six membered aromatic monocyclic ring wherein 1, 2, or 3 carbon atoms are replaced by the same or different heteroatoms of O, S or N. In some embodiments, the heteroaryl group employed in the invention is a six membered aromatic monocyclic ring wherein 1, 2, or 3 carbon atoms are replaced by N. In some embodiments, the heteroaryl group employed in the invention is an aromatic bicyclic system wherein 1, 2, 3, 4, or 5 carbon atoms are replaced with the same or different heteroatoms of O, N, or S. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, azaindolyl (4-, 5-6- and 7-), diazaindolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, pyrrolopyrrolyl, and the like, which may bear one or more substituents. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl. Exemplary bicyclic heteroaryl groups 7-azaindolyl, 6-azaindolyl, 5-azaindolyl, 4-azaindolyl, benzofuranyl and indolyl. Heteroaryl substituents include, but are not limited to, any of the substituents described herein, that result in the formation of a stable moiety.

In substituted heteroaryl groups, the substituents can be present in any positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position, in a 1H-pyrazol-4-yl group in the 3-position and/or in the 5-position and/or in the 1-position, in a 1H-pyrazol-1-yl group in the 3-position and/or in the 5-position and/or in the 4-position, in a 1H-indol-1-yl group in the 2-position and/or in the 3-position and/or in the 4-position and/or in the 5-position and/or in the 6-position and/or in the 7-position, in a 1H-indol-3-yl group in the 1-position and/or in the 2-position and/or in the 4-position and/or in the 5-position and/or in the 6-position and/or in the 7-position. The substituted heteroaryl groups can be monosubstituted or polysubstituted, i.e. they carry more than one substituent. In preferred embodiments a 1H-indol-1-yl group is substituted in 2-position and 3-position and/or in 6-position and 7-position. In other preferred embodiments a 1H-indol-3-yl group is substituted in 1-position and 7-position and/or in 6-position and 7-position. Preferably, a substituted heteroaryl group is substituted by one, two or three, in particular one or two, for example one, identical or different substituents. If a ring nitrogen atom is present which can carry a hydrogen atom or a substituent, the substituent on this nitrogen atom can be a methyl group, an ethyl group, a propyl group or a tert-butyl group, for example, which groups can also be monosubstituted or polysubstituted by fluorine. Generally, suitable ring nitrogen atoms in an aromatic ring of a heteroaryl group, for example the nitrogen atom in a pyridinyl group can also carry an oxido substituent —O⁻ and thus be present in the form of an N-oxide.

As used herein and throughout the entire description, the term "heteroarylene" refers to a biradical derived from a heteroaryl group, as defined herein, by removal of two hydrogen atoms. Heteroarylene groups may be substituted or unsubstituted.

As used herein and throughout the entire description, the terms "arylalkyl" and "heteroarylalkyl" are meant to include those radicals in which an aryl group and heteroaryl group, respectively, is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Preferably the arylalkyl is a substituted or unsubstituted ($C_6$-$C_{10}$)aryl($C_1$-$C_6$)alkyl. Preferably the Heteroarylalkyl is a substituted or unsubstituted ($C_3$-$C_{10}$)heteroaryl($C_1$-$C_6$)alkyl. In some embodiments the alkyl chain is linear. In some embodiments the alkyl chain is branched. In some embodiments the alkyl chain is substituted. In some embodiments the alkyl chain is unsubstituted. In some embodiments the alkyl chain is linear and substituted or unsubstituted. In some embodiments the alkyl chain is branched and substituted or unsubstituted.

As used herein and throughout the entire description, the terms "arylheteroalkyl" and "heteroarylheteroalkyl" are meant to include those radicals in which an aryl group and heteroaryl group, respectively, is attached to an heteroalkyl group. In some embodiments the heteroalkyl chain is a linear. In some embodiments the heteroalkyl chain is branched. In some embodiments the heteroalkyl chain is substituted. In some embodiments the heteroalkyl chain is unsubstituted. In some embodiments the heteroalkyl chain is linear and substituted or unsubstituted. In some embodiments the heteroalkyl chain is branched and substituted or unsubstituted.

As used herein and throughout the entire description, the term "heterocyclyl" or "heterocyclic ring" or "heterocycle" or "heterocyclic" refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. The heterocyclic group may be substituted or unsubstituted. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Preferably, in each ring of the heterocyclyl group the maximum number of O atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydrobenzofuranyl (1- and 2-), di- and tetrahydroindolyl, di- and tetrahydroisoindolyl, di- and tetrahydrobenzothienyl (1- and 2), di- and tetrahydro-1H-indazolyl, di- and tetrahydrobenzimidazolyl, di- and tetrahydrobenzoxazolyl, di- and tetrahydroindoxazinyl, di- and tetrahydrobenzisoxazolyl, di- and tetrahydrobenzothiazolyl, di- and tetrahydrobenzisothiazolyl, di- and tetrahydrobenzotriazolyl, di- and tetrahydroquinolinyl, di- and tetrahydroisoquinolinyl, di- and tetrahydrobenzodiazinyl, di- and tetrahydroquinoxalinyl, di- and tetrahydroquinazolinyl, di- and tetrahydrobenzotriazinyl (1,2,3- and 1,2,4-), di- and tetrahydropyridazinyl, di- and tetrahydrophenoxazinyl, di- and tetrahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro[1,3]thiazolo[5,4-c]pyridin-2-yl or 4,5,6-7-tetrahydro[1,3]thiazolo[4,5-c]pyridin-2-yl), di- and tetrahydropyrrolothiazolyl (such as 5,6-dihydro-4H-pyrrolo[3,4-d][1,3]thiazolyl), di- and tetrahydrophenothiazinyl, di- and tetrahydroisobenzofuranyl, di- and tetrahydrochromenyl, di- and tetrahydroxanthenyl, di- and tetrahydrophenoxathiinyl, di- and tetrahydropyrrolizinyl, di- and tetrahydroindolizinyl, di- and tetrahydroindazolyl, di- and tetrahydropurinyl, di- and tetrahydroquinolizinyl, di- and tetrahydrophthalazinyl, di- and tetrahydronaphthyridinyl (1,5-, 1,6-, 1,7-, 1,8-, and 2,6-), di- and tetrahydrocinnolinyl, di- and tetrahydropteridinyl, di- and tetrahydrocarbazolyl, di- and tetrahydrophenanthridinyl, di- and tetrahydroacridinyl, di- and tetrahydroperimidinyl, di- and tetrahydrophenanthrolinyl (1,7-, 1,8-, 1,10-, 3,8-, and 4,7-), di- and tetrahydrophenazinyl, di- and tetrahydrooxazolopyridinyl, di- and tetrahydroisoxazolopyridinyl, di- and tetrahydropyrrolooxazolyl, and di- and tetrahydropyrrolopyrrolyl. Exemplary 5- or 6-membered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydropyridazinyl and the like, which may bear one or more substituents. In preferred embodiments the heterocyclyl group is morpholino, wherein the morpholino moiety is bound to the remainder of the molecule via the N-atom. In some embodiments, the heterocyclyl group is a substituted or unsubstituted $(C_3-C_{14})$heterocyclyl group, wherein 1, 2, 3, 4, or 5 carbon atoms are replaced with the same or different heteroatoms of O, N, or S. Heterocyclyl group substituents include, but are not limited to, any of the substituents described herein, that result in the formation of a stable moiety. A substituted heterocyclyl group can be substituted in any positions, provided that the resulting compound is sufficiently stable and is suitable as a pharmaceutical active compound. The prerequisite that a specific group and a compound of any one of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV described hereon is sufficiently stable and suitable as a pharmaceutical active compound, applies in general with respect to all groups in the compounds of any one of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV described herein. In some embodiments the heterocyclyl group may be substituted by one or more identical or different substituents chosen from halogen, hydroxyl, $-NO_2$, cyano, $(C_1-C_6)$alkyl-O— and $(C_1-C_6)$alkyl-$S(O)_m$—. In some embodiments of the invention the number m is chosen from 0 and 2, wherein all numbers m are independent of each other and can be identical or different.

As used herein and throughout the entire description, the term "halogen" or "halo" or "halogen substituent" means fluoro, chloro, bromo, or iodo.

As used herein and throughout the entire description, the term "cyano" means —CN.

As used herein and throughout the entire description, the term "azido" means $N_3$.

As used herein and throughout the entire description, the term "optionally substituted" or "substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group different from hydrogen such as $(C_1-C_6)$alkyl, $(C_1-C_6)$heteroalkyl, $(C_1-C_6)$haloalkyl; $(C_2-C_6)$alkenyl, $(C_3-C_8)$cycloalkyl, $(C_6-C_{10})$aryl, $(C_6-C_{10})$aryl$(C_1-C_6)$alkyl, $(C_3-C_{10})$heteroaryl, $(C_3-C_{10})$heteroaryl$(C_1-C_6)$alkyl, halogen, —CN, —$NO_2$, —$OR^{161}$, —$N(R^{162})(R^{163})$, —$N(R^{161})(OR^{161})$, —$S(O)_{0-2}R^{161}$, —$S(O)_{1-2}OR^{161}$, —$OS(O)_{1-2}R^{161}$, —$OS(O)_{1-2}OR^{161}$, —$S(O)_{1-2}N(R^{162})(R^{163})$, —$OS(O)_{1-2}N(R^{162})(R^{163})$, —$N(R^{161})S(O)_{1-2}R^{161}$, —$NR^{161}S(O)_{1-2}OR^{161}$, —$NR^{161}S(O)_{1-2}N(R^{162})(R^{163})$, —$C(=W)R^{161}$, —$C(=W)WR^{161}$, —$WC(=W)R^{161}$, and —$WC(=W)WR^{161}$; wherein $R^{161}$, $R^{162}$, and $R^{163}$ are independently selected from the group consisting of —H, alkyl, alkenyl, alkynyl, cycloalkyl, aryl and heteroaryl, preferably wherein $R^{161}$, $R^{162}$, and $R^{163}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl; $R^{164}$ is independently selected from the group consisting of —H, alkyl, alkenyl, alkynyl, cycloalkyl, aryl, heteroaryl, and —$OR^{161}$; W is independently selected from O, S, and $N(R^{164})$.

As used herein and throughout the entire description, the term "optional" or "optionally" as used herein means that the subsequently described event, circumstance or condition may or may not occur, and that the description includes instances where said event, circumstance, or condition occurs and instances in which it does not occur.

As used herein and throughout the entire description, the term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

As used herein and throughout the entire description, the term "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Physiologically acceptable salts of the compounds of the present invention are in particular salts with a nontoxic salt component and preferably are pharmaceutically utilizable salts. They can contain inorganic or organic salt components. Such salts can be formed, for example, from compounds of the present invention which contain an acidic group, for example a carboxylic acid group (HO—CO—) or a sulfonic acid group (HO—$S(O)_2$—) and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the present invention with bases for the preparation of the salts are in general carried out according to customary procedures in a solvent or diluent. On account of the physiological and chemical stability, advantageous salts of acidic groups are in many cases sodium, potassium, magnesium or calcium salts or ammonium salts which can also carry one or more organic groups on the nitrogen atom. Compounds of the present invention which contain a basic, i.e. protonatable, group, for example an amino group or another basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the present invention by reaction with an acid in a solvent or diluent according to customary procedures. As usual, in particular in the case of acid addition salts of a compound containing two or more basic groups, in an obtained salt the ratio of the salt components can deviate upward or downward from the stoichiometric ratio, such as the molar ratio 1:1 or 1:2 in the case of the acid addition salt of a compound of the present invention containing one or two basic groups with a monovalent acid, and vary depending on the applied conditions. The present invention comprises also salts containing the components in a non-stoichiometric ratio, and an indication that an acid addition salt of a compound of the present invention contains an acid in equimolar amount, for example, also allows for a lower or higher amount of acid in the obtained salt, for example about 0.8 or about 1.1 mol of acid per mol of compound of the present invention. If the compounds of the present invention simultaneously contain an acidic and a basic group in the molecule, the invention also includes internal salts (betaines, zwitterions) in addition to the salt forms mentioned. The present invention also comprises all salts of the compounds of the present invention which, because of low physiological tolerability, are not directly suitable for use as a pharmaceutical, but are suitable as intermediates for chemical reactions or for the preparation of physiologically acceptable salts, for example by means of anion exchange or cation exchange. A subject of the present invention also are solvates of the compounds of the present invention and their salts, such as hydrates and adducts with alcohols like ($C_1$-$C_4$)alkanols, in particular physiologically acceptable solvates, as well as active metabolites of compounds of the present invention.

As used herein and throughout the entire description, the term "pharmaceutically acceptable" may in particular mean approved by a regulatory agency or other generally recognized pharmacopoeia for use in animals, and more particularly in humans.

The present invention comprises all stereoisomeric forms of the compounds of the formula I, for example, all possible enantiomers and diastereomers including cis/trans isomers. The invention likewise comprises mixtures of two or more stereoisomeric forms, for example mixtures of enantiomers and/or diastereomers including cis/trans isomers, in all ratios.

Asymmetric centers contained in the compounds of the formula I for example in unsubstituted or substituted alkyl groups or in the stereogenic carbon CH—B, in case that p and q are not equal, depicted in formula I, can all independently of one another have the S configuration or the R configuration. The invention relates to enantiomers, both the levorotatory and the dextrorotatory antipode, in enantiomerically pure form and substantially enantiomerically pure form and in the form of racemates and in the form of mixtures of the two enantiomers in all ratios. The invention likewise relates to diastereomers in the form of pure and substantially pure diastereomers and in the form of mixtures of two or more diastereomers in all ratios. The invention also comprises all cis/trans isomers of the compounds of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV disclosed herein, for example, in pure form and substantially pure form and in the form of mixtures of the cis isomer and the trans isomer in all ratios. Cis/trans isomerism can occur in substituted cycloalkane rings for example. The preparation of individual stereoisomers, if desired, can be carried out by resolution of a mixture according to customary methods, for example by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV disclosed herein or at the stage of an intermediate in the course of the synthesis. The invention also comprises all tautomeric forms of the compounds of the present invention.

In some aspects, the present invention provides compounds for use in treating a disease that is associated with CYP7B1, said compounds having a structure according to formula I, in any of their stereoisomeric forms or a mixture of stereoisomeric forms in any ratio, and the pharmaceutically acceptable salts thereof, and the pharmaceutically acceptable ethers, esters, solvates or hydrates of any of them,

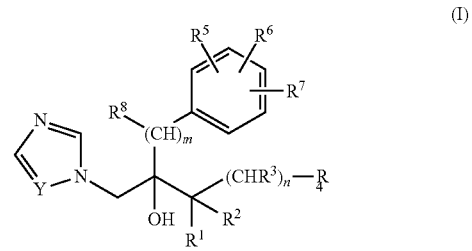

(I)

wherein
$R^1$ is selected from the group consisting of (i) ($C_1$-$C_5$)alkyl, said ($C_1$-$C_5$)alkyl being optionally substituted with a member selected from the group consisting of halogen, ($C_1$-$C_5$) alkoxy, phenyl-($C_1$-$C_3$)alkoxy, phenoxy, ($C_1$-$C_5$)alkylthio, phenyl-($C_1$-$C_3$)alkylthio and phenylthio, wherein each phenyl group is optionally substituted with a member selected from the group consisting of ($C_1$-$C_5$)alkyl, halogen, ($C_1$-$C_5$) haloalkyl, ($C_1$-$C_5$)alkoxy and ($C_1$-$C_5$)haloalkoxy, (ii) ($C_2$-$C_5$)alkenyl, said ($C_2$-$C_5$)alkenyl being optionally substituted with halogen, (iii) ($C_2$-$C_5$)alkynyl, said ($C_2$-$C_5$)alkynyl being optionally substituted with halogen, (iv) ($C_3$-$C_7$)cycloalkyl, said ($C_3$-$C_7$)cycloalkyl being optionally substituted with ($C_1$-$C_5$)alkyl, (iv) phenyl, said phenyl being optionally substituted with a member selected from the group consisting of halogen and ($C_1$-$C_5$)alkyl;
$R^2$ and $R^3$, independently, are hydrogen or have an $R^1$ significance, wherein $R^1$ and $R^2$ are optionally linked together to form a ($C_3$-$C_7$)cycloalkyl group;
m is 0 or 1;
n is 0, 1 or 2; and
$R^4$ is ($C_3$-$C_7$)cycloalkyl, said ($C_3$-$C_7$)cycloalkyl being optionally substituted with ($C_1$-$C_5$)alkyl;
$R^5$ and $R^6$ are the same or different and are selected from the group consisting of (i) hydrogen, (ii) halogen, (iii) optionally halogenated ($C_1$-$C_5$)alkyl, (iv) optionally halogenated ($C_2$-$C_5$)alkenyl, (v) optionally halogenated ($C_2$-$C_5$)alkynyl, (vi) optionally halogenated ($C_1$-$C_5$)alkoxy, (vii) phenyl, said phenyl being optionally substituted with a member selected from the group consisting of $CH_3$, F, Cl, Br, I, $CH_3O$, $C_6H_5$, $CF_3O$ and $C_2H_5$, (vii) phenoxy, said phenoxy being optionally substituted with a member selected from the group consisting of $CH_3$, F, Cl, Br, I, $CH_3O$, $C_6H_5$, $CF_3O$ and $C_2H_5$, (viii) and $NO_2$;
$R^7$ is selected from the group consisting of hydrogen, ($C_1$-$C_5$)alkyl and halogen;
$R^8$ is hydrogen or ($C_1$-$C_5$)alkyl; and
Y is CH or N.

The compounds of formula (I) and syntheses thereof are, for example, described in published German patent application (Offenlegungsschrift) DE 34 06 993 A1.

In some embodiments in the formula (I) $R^1$ is selected from the group consisting of ($C_1$-$C_5$)alkyl, said ($C_1$-$C_5$)alkyl being optionally substituted with a member selected from the group consisting of halogen and ($C_1$-$C_5$)alkoxy; $R^2$ and $R^3$, independently, are hydrogen or have an $R^1$ significance, m is 0 or 1; n is 0 or 1; and $R^4$ is ($C_3$-$C_7$)cycloalkyl, said ($C_3$-$C_7$)cycloalkyl being optionally substituted with ($C_1$-$C_5$) alkyl; $R^5$ and $R^6$ are the same or different and are selected from the group consisting of (i) hydrogen, (ii) halogen and (iii) optionally halogenated ($C_1$-$C_5$)alkyl; $R^7$ is selected from the group consisting of hydrogen, ($C_1$-$C_5$)alkyl and halogen; $R^8$ is hydrogen; and Y is CH or N. In some of these embodiments, "halogen" or "halogenated" at each occurrence is independently F or Cl. In some of these embodiments "halogen" or "halogenated" at each occurrence is Cl. In some of these embodiments $R^5$ is hydrogen; $R^6$ is 4-F or 4-Cl; and $R^7$ is hydrogen. In some of these embodiments $R^5$ is hydrogen; $R^6$ is 4-F; and $R^7$ is hydrogen. In some of these embodiments $R^5$ is hydrogen; $R^6$ is 4-Cl; and $R^7$ is hydrogen. In some of these embodiments $R^5$ is 2-F or 2-Cl; $R^6$ is 4-F or 4-Cl; and $R^7$ is hydrogen. In some of these embodiments $R^5$ is 2-F; $R^6$ is 4-F; and $R^7$ is hydrogen. In some of these embodiments $R^5$ is 2-Cl; $R^6$ is 4-Cl; and $R^7$ is hydrogen.

In some embodiments in the formula (I) $R^1$ is selected from the group consisting of ($C_1$-$C_3$)alkyl, said ($C_1$-$C_3$)alkyl being optionally substituted with a member selected from the group consisting of halogen and ($C_1$-$C_3$)alkoxy; $R^2$ and $R^3$, independently, are hydrogen or have an $R^1$ significance, m is 0 or 1; n is 0 or 1; and $R^4$ is ($C_3$-$C_5$)cycloalkyl, said ($C_3$-$C_5$)cycloalkyl being optionally substituted with ($C_1$-$C_3$) alkyl; $R^5$ and $R^6$ are the same or different and are selected from the group consisting of (i) hydrogen, (ii) halogen and (iii) optionally halogenated ($C_1$-$C_3$)alkyl; $R^7$ is selected from the group consisting of hydrogen, ($C_1$-$C_3$)alkyl and halogen; $R^8$ is hydrogen; and Y is CH or N. In some of these embodiments, "halogen" or "halogenated" at each occurrence is independently F or Cl. In some of these embodiments "halogen" or "halogenated" at each occurrenceis Cl. In some of these embodiments $R^5$ is hydrogen; $R^6$ is 4-F or 4-Cl; and $R^7$ is hydrogen. In some of these embodiments $R^5$ is hydrogen; $R^6$ is 4-F; and $R^7$ is hydrogen. In some of these embodiments $R^5$ is hydrogen; $R^6$ is 4-Cl; and $R^7$ is hydrogen. In some of these embodiments $R^5$ is 2-F or 2-Cl; $R^6$ is 4-F or 4-Cl; and $R^7$ is hydrogen. In some of these embodiments $R^5$ is 2-F; $R^6$ is 4-F; and $R^7$ is hydrogen. In some of these embodiments $R^5$ is 2-Cl; $R^6$ is 4-Cl; and $R^7$ is hydrogen.

In some embodiments in the formula (I) $R^1$ is selected from the group consisting of ($C_1$-$C_2$)alkyl, said ($C_1$-$C_2$)alkyl being optionally substituted with a member selected from the group consisting of halogen and ($C_1$-$C_2$)alkoxy; $R^2$ and $R^3$, independently, are hydrogen or have an $R^1$ significance, m is 0 or 1; n is 0 or 1; and $R^4$ is ($C_3$-$C_5$)cycloalkyl, said ($C_3$-$C_5$)cycloalkyl being optionally substituted with ($C_1$-$C_2$) alkyl; $R^5$ and $R^6$ are the same or different and are selected from the group consisting of (i) hydrogen, (ii) halogen and (iii) optionally halogenated ($C_1$-$C_2$)alkyl; $R^7$ is selected from the group consisting of hydrogen, ($C_1$-$C_2$)alkyl and halogen; $R^8$ is hydrogen; and Y is CH or N. In some of these embodiments, "halogen" or "halogenated" at each occurrence is independently F or Cl. In some of these embodiments "halogen" or "halogenated" at each occurrence is Cl. In some of these embodiments $R^5$ is hydrogen; $R^6$ is 4-F or 4-Cl; and $R^7$ is hydrogen. In some of these embodiments $R^5$ is hydrogen; $R^6$ is 4-F; and $R^7$ is hydrogen. In some of these embodiments $R^5$ is hydrogen; $R^6$ is 4-Cl; and $R^7$ is hydrogen. In some of these embodiments $R^5$ is 2-F or 2-Cl; $R^6$ is 4-F or 4-Cl; and $R^7$ is hydrogen. In some of these embodiments $R^5$ is 2-F; $R^6$ is 4-F; and $R^7$ is hydrogen. In some of these embodiments $R^5$ is 2-Cl; $R^6$ is 4-Cl; and $R^7$ is hydrogen.

In some embodiments in formula (I) $R^1$ is methyl, said methyl being optionally substituted with a member selected from the group consisting of halogen and methoxy; $R^2$ and $R^3$, independently, are hydrogen or have an $R^1$ significance, m is 0 or 1; n is 0 or 1; and $R^4$ is cyclopropyl, said cyclopropyl being optionally substituted with methyl; $R^5$, $R^6$ and $R^7$ are the same or different and are selected from the group consisting of hydrogen and halogen; $R^8$ is hydrogen; and Y is CH or N. In some of these embodiments, "halogen" or "halogenated" at each occurrence is independently F or Cl. In some of these embodiments "halogen" or "halogenated" at each occurrence is Cl. In some of these embodiments $R^5$ is hydrogen; $R^6$ is 4-F or 4-Cl; and $R^7$ is hydrogen. In some of these embodiments $R^5$ is hydrogen; $R^6$ is 4-F; and $R^7$ is hydrogen. In some of these embodiments $R^5$ is hydrogen; $R^6$ is 4-Cl; and $R^7$ is hydrogen. In some of these embodiments $R^5$ is 2-F or 2-Cl; $R^6$ is 4-F or 4-Cl; and $R^7$ is hydrogen. In some of these embodiments $R^5$ is 2-F; $R^6$ is 4-F; and $R^7$ is hydrogen. In some of these embodiments $R^5$ is 2-Cl; $R^6$ is 4-Cl; and $R^7$ is hydrogen.

In some embodiments in the formula (I) $R^1$ is ($C_1$-$C_5$) alkyl; $R^2$ and $R^3$, independently, are hydrogen or ($C_1$-$C_5$) alkyl, m is 0 or 1; n is 0 or 1; and $R^4$ is ($C_3$-$C_7$)cycloalkyl; $R^5$ and $R^6$ are the same or different and are selected from the group consisting of (i) hydrogen, (ii) halogen and (iii) optionally halogenated ($C_1$-$C_5$)alkyl; $R^7$ is selected from the group consisting of hydrogen, ($C_1$-$C_5$)alkyl and halogen; $R^8$ is hydrogen; and Y is CH or N. In some of these embodiments, "halogen" or "halogenated" at each occurrence is independently F or Cl. In some of these embodiments "halogen" or "halogenated" at each occurrence is Cl. In some of these embodiments $R^5$ is hydrogen; $R^6$ is 4-F or 4-Cl; and $R^7$ is hydrogen. In some of these embodiments $R^5$ is hydrogen; $R^6$ is 4-F; and $R^7$ is hydrogen. In some of these embodiments $R^5$ is hydrogen; $R^6$ is 4-Cl; and $R^7$ is hydrogen. In some of these embodiments $R^5$ is 2-F or 2-Cl; $R^6$ is 4-F or 4-Cl; and $R^7$ is hydrogen. In some of these embodiments $R^5$ is 2-F; $R^6$ is 4-F; and $R^7$ is hydrogen. In some of these embodiments $R^5$ is 2-Cl; $R^6$ is 4-Cl; and $R^7$ is hydrogen.

In some embodiments in the formula (I) $R^1$ is ($C_1$-$C_3$) alkyl; $R^2$ and $R^3$, independently, are hydrogen or ($C_1$-$C_3$) alkyl, m is 0 or 1; n is 0 or 1; and $R^4$ is ($C_3$-$C_5$)cycloalkyl; $R^5$ and $R^6$ are the same or different and are selected from the group consisting of (i) hydrogen, (ii) halogen and (iii) optionally halogenated ($C_1$-$C_3$)alkyl; $R^7$ is selected from the group consisting of hydrogen, ($C_1$-$C_3$)alkyl and halogen; $R^8$ is hydrogen; and Y is CH or N. In some of these embodiments, "halogen" or "halogenated" at each occurrence is independently F or Cl. In some of these embodiments "halogen" or "halogenated" at each occurrence is Cl. In some of these embodiments $R^5$ is hydrogen; $R^6$ is 4-F or 4-Cl; and $R^7$ is hydrogen. In some of these embodiments $R^5$ is hydrogen; $R^6$ is 4-F; and $R^7$ is hydrogen. In some of these embodiments $R^5$ is hydrogen; $R^6$ is 4-Cl; and $R^7$ is hydrogen. In some of these embodiments $R^5$ is 2-F or 2-Cl; $R^6$ is 4-F or 4-Cl; and $R^7$ is hydrogen. In some of these embodiments $R^5$ is 2-F; $R^6$ is 4-F; and $R^7$ is hydrogen. In some of these embodiments $R^5$ is 2-Cl; $R^6$ is 4-Cl; and $R^7$ is hydrogen. In some of these embodiments $R^4$ is cyclopropyl.

In some embodiments in the formula (I) $R^1$ is ($C_1$-$C_2$) alkyl; $R^2$ and $R^3$, independently, are hydrogen or ($C_1$-$C_2$) alkyl, m is 0 or 1; n is 0 or 1; and $R^4$ is ($C_3$-$C_5$)cycloalkyl; $R^5$ and $R^6$ are the same or different and are selected from the group consisting of (i) hydrogen, (ii) halogen and (iii)

optionally halogenated (C$_1$-C$_2$)alkyl; R$^7$ is selected from the group consisting of hydrogen, (C$_1$-C$_2$)alkyl and halogen; R$^8$ is hydrogen; and Y is CH or N. In some of these embodiments, "halogen" or "halogenated" is independently F or Cl. In some of these embodiments "halogen" or "halogenated" is Cl. In some of these embodiments R$^5$ is hydrogen; R$^6$ is 4-F or 4-Cl; and R$^7$ is hydrogen. In some of these embodiments R$^5$ is 2-F or 2-Cl; R$^6$ is 4-F or 4-Cl; and R$^7$ is hydrogen. In some of these embodiments R$^5$ is 2-F; R$^6$ is 4-F; and R$^7$ is hydrogen. In some of these embodiments R$^5$ is 2-Cl; R$^6$ is 4-Cl; and R$^7$ is hydrogen. In some of these embodiments R$^4$ is cyclopropyl.

In some embodiments in formula (I) R$^1$ is (C$_1$-C$_5$)alkyl; R$^2$ is hydrogen, m is 0; n is 0; and R$^4$ is (C$_3$-C$_7$)cycloalkyl; R$^5$, R$^6$ and R$^7$ are the same or different and are selected from the group consisting of hydrogen and halogen; and Y is N. In some of these embodiments, "halogen" or "halogenated" at each occurrence is independently F or Cl. In some of these embodiments "halogen" or "halogenated" at each occurrence is Cl. In some of these embodiments R$^5$ is hydrogen; R$^6$ is 4-F or 4-Cl; and R$^7$ is hydrogen. In some of these embodiments R$^5$ is hydrogen; R$^6$ is 4-F; and R$^7$ is hydrogen. In some of these embodiments R$^5$ is hydrogen; R$^6$ is 4-Cl; and R$^7$ is hydrogen. In some of these embodiments R$^5$ is 2-F or 2-Cl; R$^6$ is 4-F or 4-Cl; and R$^7$ is hydrogen. In some of these embodiments R$^5$ is 2-F; R$^6$ is 4-F; and R$^7$ is hydrogen. In some of these embodiments R$^5$ is 2-Cl; R$^6$ is 4-Cl; and R$^7$ is hydrogen. In some of these embodiments R$^4$ is cyclopropyl.

In some embodiments in formula (I) R$^1$ is (C$_1$-C$_3$)alkyl; R$^2$ is hydrogen, m is 0; n is 0; and R$^4$ is (C$_3$-C$_5$)cycloalkyl; R$^5$, R$^6$ and R$^7$ are the same or different and are selected from the group consisting of hydrogen and halogen; and Y is N. In some of these embodiments, "halogen" or "halogenated" at each occurrence is independently F or Cl. In some of these embodiments "halogen" or "halogenated" at each occurrence is Cl. In some of these embodiments R$^5$ is hydrogen; R$^6$ is 4-F or 4-Cl; and R$^7$ is hydrogen. In some of these embodiments R$^5$ is hydrogen; R$^6$ is 4-F; and R$^7$ is hydrogen. In some of these embodiments R$^5$ is hydrogen; R$^6$ is 4-Cl; and R$^7$ is hydrogen. In some of these embodiments R$^5$ is 2-F or 2-Cl; R$^6$ is 4-F or 4-Cl; and R$^7$ is hydrogen. In some of these embodiments R$^5$ is 2-F; R$^6$ is 4-F; and R$^7$ is hydrogen. In some of these embodiments R$^5$ is 2-Cl; R$^6$ is 4-Cl; and R$^7$ is hydrogen. In some of these embodiments R$^4$ is cyclopropyl.

In some embodiments in formula (I) R$^1$ is (C$_1$-C$_2$)alkyl; R$^2$ is hydrogen, m is 0; n is 0; and R$^4$ is (C$_3$-C$_5$)cycloalkyl; R$^5$, R$^6$ and R$^7$ are the same or different and are selected from the group consisting of hydrogen and halogen; and Y is N. In some of these embodiments, "halogen" or "halogenated" is independently F or Cl. In some of these embodiments "halogen" or "halogenated" is Cl. In some of these embodiments R$^5$ is hydrogen; R$^6$ is 4-F or 4-Cl; and R$^7$ is hydrogen. In some of these embodiments R$^5$ is 2-F or 2-Cl; R$^6$ is 4-F or 4-Cl; and R$^7$ is hydrogen. In some of these embodiments R$^5$ is 2-F; R$^6$ is 4-F; and R$^7$ is hydrogen. In some of these embodiments R$^5$ is 2-Cl; R$^6$ is 4-Cl; and R$^7$ is hydrogen.

In some embodiments in formula (I) R$^1$ is methyl; R$^2$ is hydrogen, m is 0; n is 0; and R$^4$ is cyclopropyl; R$^5$, R$^6$ and R$^7$ are the same or different and are selected from the group consisting of hydrogen and halogen; and Y is N. In some of these embodiments, "halogen" or "halogenated" at each occurrence is independently F or Cl. In some of these embodiments "halogen" or "halogenated" at each occurrence is Cl. In some of these embodiments R$^5$ is hydrogen; R$^6$ is 4-F or 4-Cl; and R$^7$ is hydrogen. In some of these embodiments R$^5$ is hydrogen; R$^6$ is 4-F; and R$^7$ is hydrogen. In some of these embodiments R$^5$ is hydrogen; R$^6$ is 4-Cl; and R$^7$ is hydrogen. In some of these embodiments R$^5$ is 2-F or 2-Cl; R$^6$ is 4-F or 4-Cl; and R$^7$ is hydrogen. In some of these embodiments R$^5$ is 2-F; R$^6$ is 4-F; and R$^7$ is hydrogen. In some of these embodiments R$^5$ is 2-Cl; R$^6$ is 4-Cl; and R$^7$ is hydrogen. In some of these embodiments R$^4$ is cyclopropyl.

In some embodiments the compound of formula (I) has the structure:

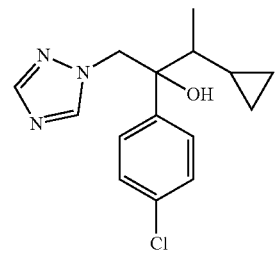

In some embodiments the compound of formula (I) is cyproconazole.

In some aspects, the present invention provides compounds for use in treating a disease that is associated with CYP7B1, said compounds having a structure according to formula II, in any of their stereoisomeric forms or a mixture of stereoisomeric forms in any ratio, and the pharmaceutically acceptable salts thereof, and the pharmaceutically acceptable solvates or hydrates of any of them,

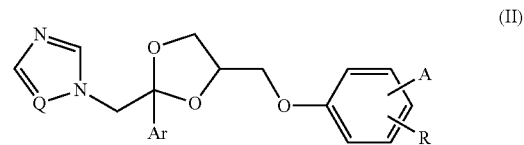

(II)

wherein
Q is a member selected from the group consisting of CH and N;
Ar is a member selected from the group consisting of phenyl and substituted phenyl, said substituted phenyl being phenyl having from 1 to 3 substituents independently selected from the group consisting of halogen, (C$_1$-C$_6$)alkyl and (C$_1$-C$_6$)alkyloxy;
the substituent A is of the formula

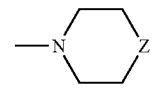

wherein
Z is a member selected from the group consisting of a direct bond, CH$_2$, oxygen and N—R$^4$, wherein R$^4$ is selected from the group consisting of hydrogen, (C$_1$-C$_6$)alkyl, hydroxy-(C$_1$-C$_6$)alkyl), ((C$_1$-C$_6$)alkyloxy)-(C$_1$-C$_6$)alkyl, (C$_1$-C$_6$)alkanoyl, (C$_1$-C$_6$)alkylsulfonyl, phenylmethylsulfonyl, (C$_1$-C$_6$)alkyloxycarbonyl, (C$_1$-C$_6$)alkyloxycarbonylmethyl, phenoxycarbonyl, aminocarbonyl, mono- and di((C$_1$-C$_6$)alkyl)aminocarbonyl, aminocarbonylmethyl, ((C$_1$-C$_6$)alkyl)aminocarbonylmethyl, ((C$_1$-C$_6$)alkyl)aminothiocarbonyl, ((C$_1$-C$_6$)alkylthio)thiocarbonyl, phenyl, phenylmethyl, benzoyl and substituted benzoyl, said substituted benzoyl being benzoyl having from 1 to 2 substituents independently selected from the group consisting of halogen, (C$_1$-C$_6$)alkyl and (C$_1$-C$_6$)alkyloxy; and R is a member selected from the group consisting of hydrogen and NO$_2$.

The compounds of formula (II) and syntheses thereof are, for example, described in U.S. Pat. No. 4,335,125.

In some embodiments in formula (II) Q is a member selected from the group consisting of CH and N; Ar is a member selected from the group consisting of phenyl and substituted phenyl, said substituted phenyl being phenyl having from 1 to 3 substituents independently selected from the group consisting of halogen, (C$_1$-C$_6$)alkyl and (C$_1$-C$_6$) alkyloxy; the substituent A is of the formula

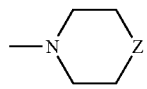

wherein
Z is a member selected from the group consisting of oxygen and N—R$^4$, wherein R$^4$ is selected from the group consisting of hydrogen, (C$_1$-C$_6$)alkyl, hydroxy-(C$_1$-C$_6$)alkyl), ((C$_1$-C$_6$) alkyloxy)-(C$_1$-C$_6$)alkyl, and (C$_1$-C$_6$)alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is a member selected from the group consisting of CH and N; Ar is a member selected from the group consisting of phenyl and substituted phenyl, said substituted phenyl being phenyl having from 1 to 3 substituents independently selected from the group consisting of halogen, (C$_1$-C$_4$)alkyl and (C$_1$-C$_4$) alkyloxy; the substituent A is of the formula

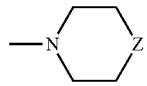

wherein
Z is a member selected from the group consisting of oxygen and N—R$^4$, wherein R$^4$ is selected from the group consisting of hydrogen, (C$_1$-C$_4$)alkyl, hydroxy-(C$_1$-C$_4$)alkyl), ((C$_1$-C$_4$) alkyloxy)-(C$_1$-C$_4$)alkyl, and (C$_1$-C$_4$)alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is a member selected from the group consisting of CH and N; Ar is a member selected from the group consisting of phenyl and substituted phenyl, said substituted phenyl being phenyl having from 1 to 3 substituents independently selected from the group consisting of halogen, (C$_1$-C$_2$)alkyl and (C$_1$-C$_2$) alkyloxy; the substituent A is of the formula

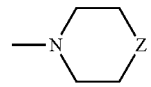

wherein
Z is a member selected from the group consisting of oxygen and N—R$^4$, wherein R$^4$ is selected from the group consisting of hydrogen, (C$_1$-C$_2$)alkyl, hydroxy-(C$_1$-C$_2$)alkyl), ((C$_1$-C$_2$) alkyloxy)-(C$_1$-C$_2$)alkyl, and (C$_1$-C$_2$)alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is CH; Ar is a member selected from the group consisting of phenyl and substituted phenyl, said substituted phenyl being phenyl having from 1 to 3 halogen substituents; the substituent A is of the formula

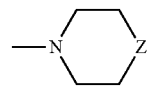

wherein
Z is N—R$^4$, wherein R$^4$ is (C$_1$-C$_6$)alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is CH; Ar is a member selected from the group consisting of phenyl and substituted phenyl, said substituted phenyl being phenyl having from 1 to 3 halogen substituents; the substituent A is of the formula

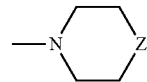

wherein
Z is N—R$^4$, wherein R$^4$ is (C$_1$-C$_4$)alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is CH; Ar is a member selected from the group consisting of phenyl and substituted phenyl, said substituted phenyl being phenyl having from 1 to 3 halogen substituents; the substituent A is of the formula

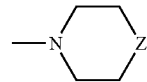

wherein
Z is N—R⁴, wherein R⁴ is $(C_1-C_2)$alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl. In some of these embodiments R⁴ is acetyl.

In some embodiments in formula (II) Q is CH; Ar is substituted phenyl, said substituted phenyl being phenyl having from 1 to 3 halogen substituents; the substituent A is of the formula

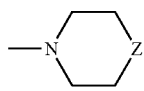

wherein
Z is N—R⁴, wherein R⁴ is $(C_1-C_6)$alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is CH; Ar is substituted phenyl, said substituted phenyl being phenyl having from 1 to 3 halogen substituents; the substituent A is of the formula

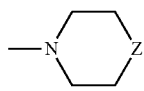

wherein
Z is N—R⁴, wherein R⁴ is $(C_1-C_4)$alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments in formula (II) Q is CH; Ar is substituted phenyl, said substituted phenyl being phenyl having from 1 to 3 halogen substituents; the substituent A is of the formula

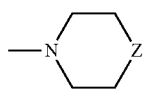

wherein
Z is N—R⁴, wherein R⁴ is $(C_1-C_2)$alkanoyl; and R is hydrogen. In some of these embodiments, "halogen" at each occurrence is independently F or Cl. In some of these embodiments "halogen" at each occurrence is Cl. In some of these embodiments "substituted phenyl" is 2,4-difluorophenyl. In some of these embodiments "substituted phenyl" is 2,4-dichlorophenyl.

In some embodiments the compound of formula (II) has the structure:

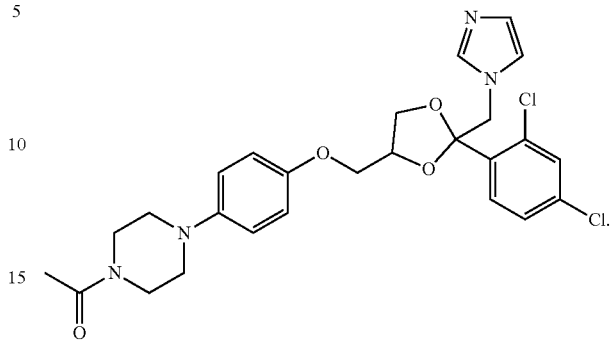

In some embodiments the compound of formula (II) has the structure:

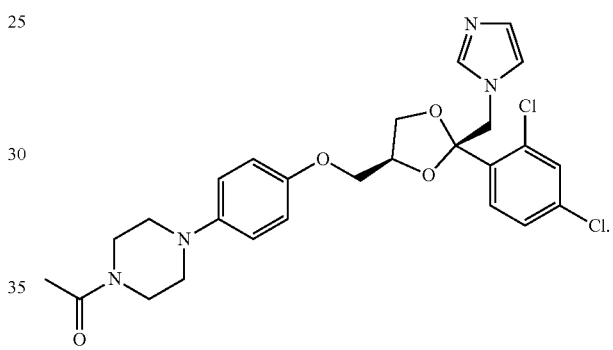

In some embodiments the compound of formula (II) has the structure:

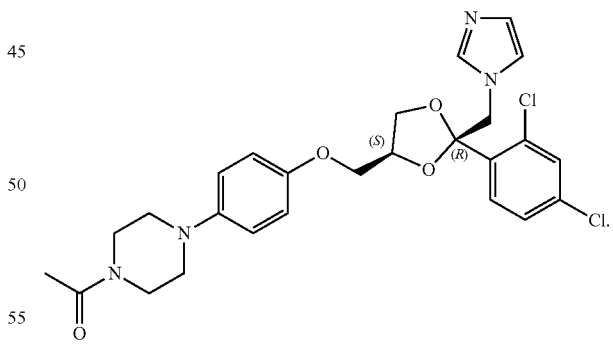

In some embodiments the compound of formula (II) is ketoconazole.

In some aspects, the present invention provides compounds for use in treating a disease that is related to CYP7B1, said compounds having a structure according to formula (III), in any of their stereoisomeric forms or a mixture of stereoisomeric forms in any ratio, and the pharmaceutically acceptable salts thereof, and the pharmaceutically acceptable salts solvates or hydrates of any of them,

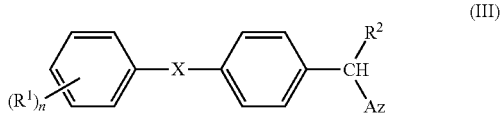

(III)

wherein $R^1$ is selected from the group consisting of halogen, $(C_1-C_6)$haloalkyl, $(C_1-C_6)$alkyl, $(C_1-C_6)$alkoxy, $NO_2$ and cyano;

$R^2$ is $(C_1-C_6)$alkyl, or optionally substituted $(C_6-C_{10})$aryl;

X is selected from the group consisting of a single carbon-carbon bond, oxygen, sulphur, thionyl and sulphonyl;

Az is selected from the group consisting of imidazol-1-yl, pyrazol-1-yl, 1,2,4-triazol-1-yl and 1,2,4-triazol-4-yl; and n is an integer of from 0 to 4.

In some embodiments of the compounds of formula (III) "optionally substituted $(C_6-C_{10})$aryl" refers to $(C_6-C_{10})$aryl optionally substituted with one or two substituents independently selected from the group consisting of fluoro, chloro, bromo, $(C_1-C_6)$alkyl and trifluoromethyl. As a purely illustrative example "optionally substituted $(C_6-C_{10})$aryl" means phenyl optionally substituted with one or two substituents independently selected from the group consisting of fluoro, chloro, bromo, $(C_1-C_6)$alkyl and trifluoromethyl.

The compounds of formula (III) and syntheses thereof are, for example, described in published German patent application (Offenlegungsschrift) DE 24 61 406 and U.S. Pat. No. 4,118,487.

In some embodiments in formula (III) $R^1$ is halogen; $R^2$ is $(C_1-C_6)$alkyl or optionally substituted $(C_6-C_{10})$aryl; X is selected from the group consisting of a single carbon-carbon bond and oxygen; Az is selected from the group consisting of imidazol-1-yl and pyrazol-1-yl; and n is an integer of 0, 1 or 2. In some of these embodiments "halogen" at each occurrence is independently F or Cl. In some of these embodiments "halogen" at each occurrence is Cl. In some of these embodiments n is 0 or 1. In some of these embodiments n is 0. In case n is 0, $R^1$ is absent, the respective phenyl ring in formula (III) thus being unsubstituted.

In some embodiments in formula (III) $R^1$ is halogen; $R^2$ is $(C_1-C_6)$alkyl or optionally substituted phenyl; X is selected from the group consisting of a single carbon-carbon bond and oxygen; Az is selected from the group consisting of imidazol-1-yl and pyrazol-1-yl; and n is an integer of 0, 1 or 2. In some of these embodiments "halogen" at each occurrence is independently F or Cl. In some of these embodiments "halogen" at each occurrence is Cl. In some of these embodiments n is 0 or 1. In some of these embodiments n is 0. In case n is 0, $R^1$ is absent, the respective phenyl ring in formula (III) thus being unsubstituted.

In some embodiments in formula (III) $R^1$ is halogen; $R^2$ is optionally substituted phenyl; X is selected from the group consisting of a single carbon-carbon bond and oxygen; Az is selected from the group consisting of imidazol-1-yl and pyrazol-1-yl; and n is an integer of 0, 1 or 2. In some of these embodiments "halogen" at each occurrence is independently F or Cl. In some of these embodiments "halogen" at each occurrence is Cl. In some of these embodiments n is 0 or 1. In some of these embodiments n is 0. In case n is 0, $R^1$ is absent, the respective phenyl ring in formula (III) thus being unsubstituted.

In some embodiments in formula (III) $R^1$ is halogen; $R^2$ is optionally substituted phenyl; X is a single carbon-carbon bond; Az is selected from the group consisting of imidazol-1-yl and pyrazol-1-yl; and n is an integer of 0, 1 or 2. In some of these embodiments "halogen" at each occurrence is independently F or Cl. In some of these embodiments "halogen" at each occurrence is Cl. In some of these embodiments n is 0 or 1. In some of these embodiments n is 0. In case n is 0, $R^1$ is absent, the respective phenyl ring in formula (III) thus being unsubstituted.

In some embodiments in formula (III) $R^2$ is optionally substituted phenyl; X is a single carbon-carbon bond; Az is imidazol-1-yl; and n is 0. Accordingly, in these embodiments $R^1$ is absent, the respective phenyl ring in formula (III) thus being unsubstituted.

In some embodiments the compound of formula (III) has the structure:

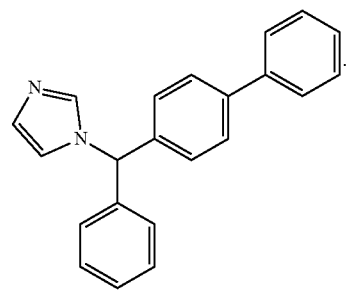 [SMILES: c1ccc(-c2ccc(C(c3ccccc3)n3ccnc3)cc2)cc1]

In some embodiments the compound of formula (III) is bifonazole.

In some aspects, the present invention provides compounds for use in treating a disease that is related to CYP7B1, said compounds having a structure according to formula (IV), in any of their stereoisomeric forms or a mixture of stereoisomeric forms in any ratio, and the pharmaceutically acceptable salts thereof, and the pharmaceutically acceptable solvates or hydrates of any of them,

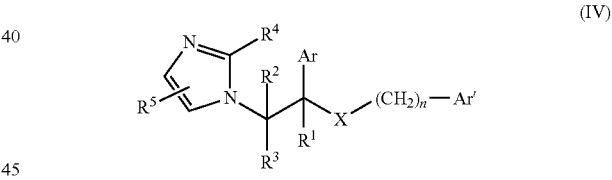

(IV)

$R^1$, $R^2$, and $R^3$ are each, independently, a member selected from the group consisting of hydrogen and $(C_1-C_6)$alkyl;

X is a member selected from the group consisting of oxygen and NH;

n is an integer of 0, 1 or 2;

Ar is a member selected from the group consisting of phenyl, substituted phenyl, thienyl and halothienyl, said substituted phenyl containing at least one substituent selected from the group consisting of halogen, $(C_1-C_6)$alkyl and $(C_1-C_6)$alkoxy;

Ar' is a member selected from the group consisting of phenyl, substituted phenyl and α-tetralyl, said substituted phenyl containing at least one phenyl substituent selected from the group consisting of halogen, $(C_1-C_6)$alkyl, $(C_1-C_6)$alkoxy, cyano, $NO_2$ and amino;

$R^4$ is a member selected from the group consisting of hydrogen, methyl and ethyl;

$R^5$ is a member selected from the group consisting of hydrogen and methyl;

provided that:
(i) when said X is NH, then said R is hydrogen;
(ii) when said Ar' is a substituted phenyl containing at least one phenyl substituent selected from the group consisting of $NO_2$ and amino, then said X is oxygen and said n is 0;
(iii) when said Ar' is a α-tetralyl, then said X is NH and said n is 0; and
(iv) when said X is oxygen and said Ar' is a member selected from the group consisting of phenyl and substituted phenyl containing at least one phenyl substituent selected from the group consisting of halogen, $(C_1-C_6)$alkyl, $(C_1-C_6)$alkoxy and cyano, then said n is other than 0.

The compounds of formula (IV) and syntheses thereof are, for example, described in published German patent application (Offenlegungsschrift) DE 1940 388 and U.S. Pat. No. 3,171,655.

In some embodiments in formula (IV) $R^1$, $R^2$, and $R^3$ are each, independently, a member selected from the group consisting of hydrogen and $(C_1-C_6)$alkyl; X is oxygen; n is an integer of 1 or 2; Ar is a member selected from the group consisting of phenyl and substituted phenyl, said substituted phenyl containing at least one substituent selected from the group consisting of halogen and $(C_1-C_6)$alkyl; Ar' is a member selected from the group consisting of phenyl and substituted phenyl, said substituted phenyl containing at least one substituent selected from the group consisting of halogen and $(C_1-C_6)$alkyl; $R^4$ is a member selected from the group consisting of hydrogen and methyl; and $R^5$ is a member selected from the group consisting of hydrogen and methyl. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments in formula (IV) $R^1$, $R^2$, and $R^3$ are each, independently, a member selected from the group consisting of hydrogen and $(C_1-C_4)$alkyl; X is oxygen; n is an integer of 1 or 2; Ar is a member selected from the group consisting of phenyl and substituted phenyl, said substituted phenyl containing at least one substituent selected from the group consisting of halogen and $(C_1-C_4)$alkyl; Ar' is a member selected from the group consisting of phenyl and substituted phenyl, said substituted phenyl containing at least one substituent selected from the group consisting of halogen and $(C_1-C_4)$alkyl; $R^4$ is a member selected from the group consisting of hydrogen and methyl; and $R^5$ is a member selected from the group consisting of hydrogen and methyl. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments in formula (IV) $R^1$, $R^2$, and $R^3$ are each, independently, a member selected from the group consisting of hydrogen and $(C_1-C_2)$alkyl; X is oxygen; n is an integer of 1 or 2; Ar is a member selected from the group consisting of phenyl and substituted phenyl, said substituted phenyl containing at least one substituent selected from the group consisting of halogen and $(C_1-C_2)$alkyl; Ar' is a member selected from the group consisting of phenyl and substituted phenyl, said substituted phenyl containing at least one substituent selected from the group consisting of halogen and $(C_1-C_2)$alkyl; $R^4$ is a member selected from the group consisting of hydrogen and methyl; and $R^5$ is a member selected from the group consisting of hydrogen and methyl. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments in formula (IV) $R^1$, $R^2$, and $R^3$ are each, independently, a member selected from the group consisting of hydrogen and $(C_1-C_6)$alkyl; X is oxygen; n is an integer of 1 or 2; Ar is a member selected from the group consisting of phenyl and substituted phenyl, said substituted phenyl containing at least one substituent selected from the group consisting of halogen and $(C_1-C_6)$alkyl; Ar' is a member selected from the group consisting of phenyl and substituted phenyl, said substituted phenyl containing at least one substituent selected from the group consisting of halogen and $(C_1-C_6)$alkyl; $R^4$ is hydrogen; and $R^5$ is hydrogen. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments in formula (IV) $R^1$, $R^2$, and $R^3$ are each, independently, a member selected from the group consisting of hydrogen and $(C_1-C_4)$alkyl; X is oxygen; n is an integer of 1 or 2; Ar is a member selected from the group consisting of phenyl and substituted phenyl, said substituted phenyl containing at least one substituent selected from the group consisting of halogen and $(C_1-C_4)$alkyl; Ar' is a member selected from the group consisting of phenyl and substituted phenyl, said substituted phenyl containing at least one substituent selected from the group consisting of halogen and $(C_1-C_4)$alkyl; $R^4$ is hydrogen; and $R^5$ is hydrogen. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments in formula (IV) $R^1$, $R^2$, and $R^3$ are each, independently, a member selected from the group consisting of hydrogen and $(C_1-C_2)$alkyl; X is oxygen; n is an integer of 1 or 2; Ar is a member selected from the group consisting of phenyl and substituted phenyl, said substituted phenyl containing at least one substituent selected from the group consisting of halogen and $(C_1-C_2)$alkyl; Ar' is a member selected from the group consisting of phenyl and substituted phenyl, said substituted phenyl containing at least one substituent selected from the group consisting of halogen and $(C_1-C_2)$alkyl; $R^4$ is hydrogen; and $R^5$ is hydrogen. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments in formula (IV) $R^1$, $R^2$, and $R^3$ are each hydrogen; X is oxygen; n is an integer of 1 or 2; Ar is substituted phenyl, said substituted phenyl containing at least one substituent selected from halogen; Ar' is substituted phenyl, said substituted phenyl containing at least one substituent selected from halogen; $R^4$ is hydrogen; and $R^5$ is hydrogen. In some of these embodiments "halogen" at each occurrence is independently F or Cl. In some of these embodiments "halogen" at each occurrence is Cl. In some of these embodiments Ar is 2,4-dichlorophenyl. In some of these embodiments Ar' is a member selected from the group consisting of 2,4-dichlorophenyl, 2,6-dichlorophenyl and 4-chlorophenyl. In some of these embodiments n is 1.

In some embodiments the compound of formula (IV) has the structure:

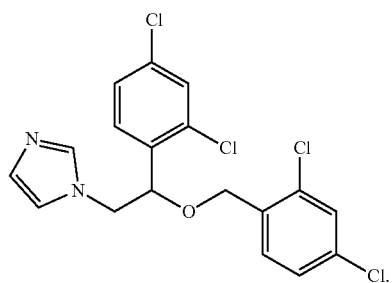 [SMILES: Clc1ccc(COC(Cn2ccnc2)c2ccc(Cl)cc2Cl)c(Cl)c1]

In some embodiments the compound of formula (IV) is miconazole.

In some embodiments the compound of formula (IV) has the structure:

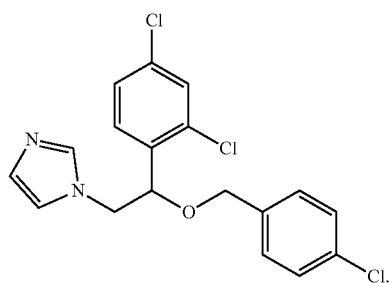 [SMILES: Clc1ccc(COC(Cn2ccnc2)c2ccc(Cl)cc2Cl)cc1]

In some embodiments the compound of formula (IV) is econazole.

In some embodiments the compound of formula (IV) has the structure:

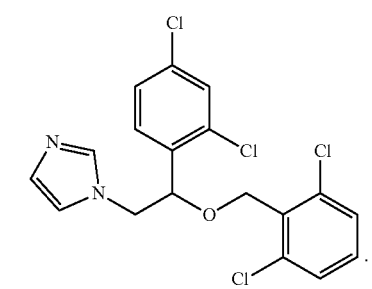 [SMILES: Clc1ccc(C(Cn2ccnc2)OCc2c(Cl)cccc2Cl)c(Cl)c1]

In some embodiments the compound of formula (IV) is isoconazole.

In some aspects, the present invention provides compounds for use in treating a disease that is related to CYP7B1, said compounds having a structure according to formula (V), in any of their stereoisomeric forms or a mixture of stereoisomeric forms in any ratio, and the pharmaceutically acceptable salts thereof, and the pharmaceutically acceptable solvates or hydrates of any of them,

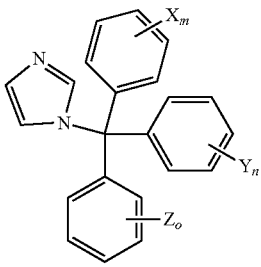

(V)

wherein

X, Y and Z are each, independently, selected from the group consisting of $(C_1-C_4)$alkyl and an electronegative substituent, wherein the electronegative substituent is selected from the group consisting of F, Cl, Br, I, $NO_2$, $CF_3$, CN, $SCH_3$ and $OCH_3$; and m, n and o are each independently 0, 1 or 2.

The compounds of formula (V) and syntheses thereof are, for example, described in U.S. Pat. No. 3,660,577.

In some embodiments in formula (V) X, Y and Z are each, independently, an electronegative substituent, wherein the electronegative substituent is independently selected from the group consisting of F, Cl, Br, I, and $NO_2$; and m, n and o are each, independently, 0, 1 or 2. In some of these embodiments m, n and o are each, independently, 0 or 1.

In some embodiments in formula (V) X, Y and Z are each, independently, an electronegative substituent, wherein the electronegative substituent is independently F or Cl; and m, n and o are each independently 0, 1 or 2. In some of these embodiments m, n and o are each, independently, 0 or 1.

In some embodiments the compound of formula (V) has the formula (Va):

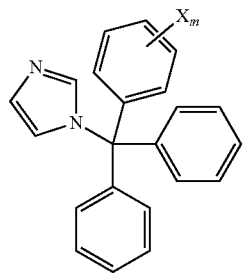

(Va)

wherein

X is independently selected from the group consisting of F, Cl, Br, I, and $NO_2$; and m is 1 or 2. In some of these embodiments X is independently selected from the group consisting of F and Cl. In some of these embodiments X is Cl. In some of these embodiments m is 1.

In some embodiments the compound of formula (V) has the structure:

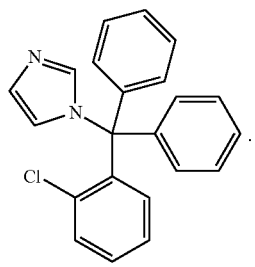 [SMILES: Clc1ccccc1C(c1ccccc1)(c1ccccc1)n1ccnc1]

In some embodiments the compound of formula (V) is clotrimazole.

In some aspects, the present invention provides compounds for use in treating a disease that is associated with CYP7B1, said compounds having a structure according to formula (VI), in any of their stereoisomeric forms or a mixture of stereoisomeric forms in any ratio, and the pharmaceutically acceptable salts thereof, and the pharmaceutically acceptable solvates or hydrates of any of them,

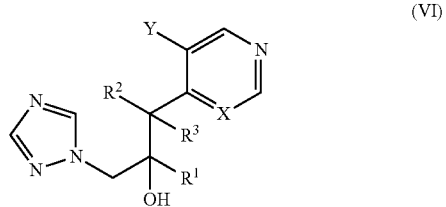

wherein
$R^1$ is phenyl substituted with 1 to 3 substituents each independently selected from halogen, —$CF_3$ and —$OCF_3$;
$R^2$ is ($C_1$-$C_4$)alkyl;
$R^3$ is hydrogen or ($C_1$-$C_4$)alkyl;
X is CH or N; and
Y is F or Cl.

The compounds of formula (VI) and syntheses thereof are, for example, described in published European patent application EP 0 440 372 A1.

In some embodiments in formula (VI) $R^1$ is phenyl substituted with 1 to 3 substituents each independently selected from halogen and —$CF_3$; $R^2$ is ($C_1$-$C_4$)alkyl; $R^3$ is hydrogen or ($C_1$-$C_4$)alkyl; X is CH or N; and Y is F or Cl. In some of these embodiments "halogen" at each occurrence is independently F or Cl. In some of these embodiments "halogen" at each occurrence is F.

In some embodiments in formula (VI) $R^1$ is phenyl substituted with 1 to 3 substituents each independently selected from halogen and —$CF_3$; $R^2$ is ($C_1$-$C_2$)alkyl; $R^3$ is hydrogen or ($C_1$-$C_2$)alkyl; X is CH or N; and Y is F or Cl. In some of these embodiments "halogen" at each occurrence is independently F or Cl. In some of these embodiments "halogen" at each occurrence is F.

In some embodiments in formula (VI) $R^1$ is phenyl substituted with 1 to 3 halogen substituents; $R^2$ is ($C_1$-$C_4$) alkyl; $R^3$ is hydrogen; X is CH or N; and Y is F or Cl. In some of these embodiments "halogen" at each occurrence is independently F or Cl. In some of these embodiments "halogen" at each occurrence is F.

In some embodiments in formula (VI) $R^1$ is phenyl substituted with 1 to 3 halogen substituents; $R^2$ is ($C_1$-$C_2$) alkyl; $R^3$ is hydrogen; X is CH or N; and Y is F or Cl. In some of these embodiments "halogen" at each occurrence is independently F or Cl. In some of these embodiments "halogen" at each occurrence is F.

In some embodiments in formula (VI) $R^1$ is phenyl substituted with 1 to 3 halogen substituents; $R^2$ is ($C_1$-$C_4$) alkyl; $R^3$ is hydrogen; X is N; and Y is F. In some of these embodiments "halogen" at each occurrence is independently F or Cl. In some of these embodiments "halogen" at each occurrence is F.

In some embodiments in formula (VI) $R^1$ is phenyl substituted with 1 to 3 halogen substituents; $R^2$ is ($C_1$-$C_2$) alkyl; $R^3$ is hydrogen; X is N; and Y is F. In some of these embodiments "halogen" at each occurrence is independently F or Cl. In some of these embodiments "halogen" at each occurrence is F.

In some embodiments the compound of formula (VI) has the structure:

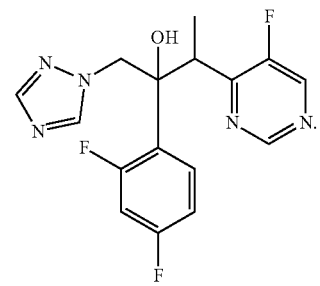 [SMILES: CC(c1ncncc1F)C(O)(Cn1cncn1)c1ccc(F)cc1F]

In some embodiments the compound of formula (VI) has the structure:

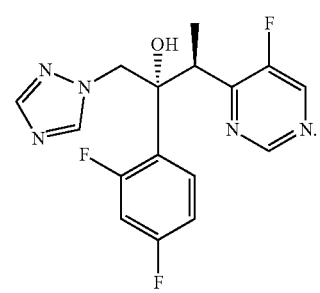 [SMILES: C[C@@H](c1ncncc1F)[C@](O)(Cn1cncn1)c1ccc(F)cc1F]

In some embodiments the compound of formula (VI) has the structure:

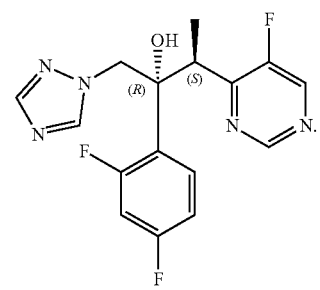

In some embodiments the compound of formula (VI) is voriconazole.

In some aspects, the present invention provides compounds for use in treating a disease that is related to CYP7B1, said compounds having a structure according to formula (VII), in any of their stereoisomeric forms or a mixture of stereoisomeric forms in any ratio, and the pharmaceutically acceptable salts thereof, and the pharmaceutically acceptable solvates or hydrates of any of them,

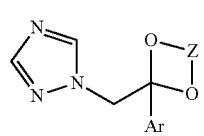

(VII)

wherein
Z is an alkylene selected from the group consisting of
—CH$_2$—CH$_2$—, —CH$_2$—CH$_2$—CH$_2$—,

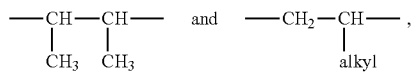

wherein said alkyl has from 1 to 10 carbon atoms; and
Ar is a member selected from the group consisting of phenyl, substituted phenyl, thienyl, 5-chloro-2-thienyl, naphthyl and fluorenyl, wherein "substituted phenyl" has the meaning of a phenyl radical having thereon from 1 to 3 substituents each selected independently from the group consisting of halogen, (C$_1$-C$_6$)alkyl, (C$_1$-C$_6$)alkyloxy, cyano and NO$_2$.

The compounds of formula (VII) and syntheses thereof are, for example, described in U.S. Pat. No. 4,160,838.

In some embodiments in formula (VII) Z is an alkylene selected from the group consisting of

wherein said alkyl has from 1 to 10 carbon atoms; and Ar is a member selected from the group consisting of phenyl, substituted phenyl, and thienyl, wherein "substituted phenyl" has the meaning of a phenyl radical having thereon from 1 to 3 substituents each selected independently from the group consisting of halogen and (C$_1$-C$_6$)alkyl. In some of these embodiments "halogen" at each occurrence is independently F or Cl. In some of these embodiments "halogen" at each occurrence is Cl.

In some embodiments in formula (VII) Z is an alkylene selected from the group consisting of

wherein said alkyl has from 1 to 6 carbon atoms; and Ar is a member selected from the group consisting of phenyl, substituted phenyl, and thienyl, wherein "substituted phenyl" has the meaning of a phenyl radical having thereon from 1 to 3 substituents each selected independently from the group consisting of halogen and (C$_1$-C$_6$)alkyl. In some of these embodiments "halogen" at each occurrence is independently F or Cl. In some of these embodiments "halogen" at each occurrence is Cl.

In some embodiments in formula (VII) Z is an alkylene selected from the group consisting of

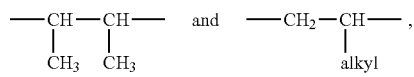

wherein said alkyl has from 1 to 4 carbon atoms; and Ar is a member selected from the group consisting of phenyl, substituted phenyl, and thienyl, wherein "substituted phenyl" has the meaning of a phenyl radical having thereon from 1 to 3 substituents each selected independently from the group consisting of halogen and (C$_1$-C$_4$)alkyl. In some of these embodiments "halogen" at each occurrence is independently F or Cl. In some of these embodiments "halogen" at each occurrence is Cl.

In some embodiments in formula (VII) Z is an alkylene with the structure

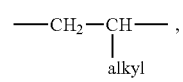

wherein said alkyl has from 1 to 10 carbon atoms; and Ar is a substituted phenyl, wherein "substituted phenyl" has the meaning of a phenyl radical having thereon from 1 to 3 substituents each independently being a halogen. In some of these embodiments "halogen" at each occurrence is independently F or Cl. In some of these embodiments "halogen" at each occurrence is Cl.

In some embodiments in formula (VII) Z is an alkylene with the structure

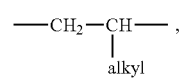

wherein said alkyl has from 1 to 6 carbon atoms; and Ar is a substituted phenyl, wherein "substituted phenyl" has the meaning of a phenyl radical having thereon from 1 to 3 substituents each independently being a halogen. In some of these embodiments "halogen" at each occurrence is independently F or Cl. In some of these embodiments "halogen" at each occurrence is Cl.

In some embodiments in formula (VII) Z is an alkylene with the structure

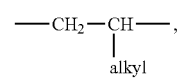

wherein said alkyl has from 1 to 4 carbon atoms; and Ar is a substituted phenyl, wherein "substituted phenyl" has the meaning of a phenyl radical having thereon from 1 to 3 substituents each independently being a halogen. In some of these embodiments the alkyl is n-propyl. In some of these embodiments "halogen" at each occurrence is independently F or Cl. In some of these embodiments "halogen" at each occurrence is Cl.

In some embodiments the compound of formula (VII) has the structure:

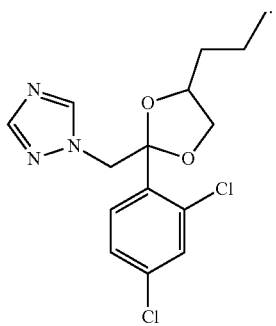 [SMILES: CCCC1COC(Cn2cncn2)(c2ccc(Cl)cc2Cl)O1]

In some embodiments the compound of formula (VII) is propiconazole.

In some aspects, the present invention provides compounds for use in treating a disease that is related to CYP7B1, said compounds having a structure according to formula (IX), in any of their stereoisomeric forms or a mixture of stereoisomeric forms in any ratio, and the pharmaceutically acceptable salts thereof, and the pharmaceutically acceptable solvates or hydrates of any of them,

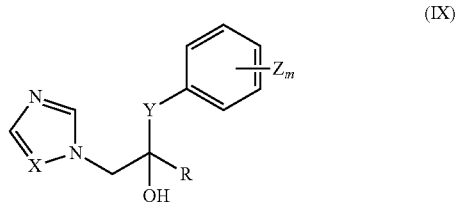

wherein
R is selected from the group consisting of (i) $(C_1-C_6)$alkyl, (ii) $(C_3-C_7)$cycloalkyl, said $(C_3-C_7)$cycloalkyl being optionally substituted with $(C_1-C_2)$alkyl, and (iii) phenyl, said phenyl being optionally substituted with a group selected from halogen, $(C_1-C_4)$alkyl and $(C_1-C_2)$haloalkyl;
X is nitrogen or CH;
Y is selected from the group consisting of —OCH$_2$, —CH$_2$CH$_2$—, and —CH=CH—;
Z is selected from the group consisting of (i) halogen, (ii) $(C_1-C_4)$alkyl, $(C_5-C_7)$cycloalkyl, (iv) $(C_1-C_4)$alkoxy, (v) $(C_1-C_4)$alkylthio, (vi) $(C_1-C_2)$haloalkyl, (vii) $(C_1-C_2)$haloalkoxy, (viii) $(C_1-C_2)$haloalkylthio, (ix) phenyl, said phenyl being optionally substituted with halogen and/or $(C_1-C_4)$alkyl, (x) phenoxy, said phenoxy being optionally substituted with halogen and/or $(C_1-C_4)$alkyl, (xi) phenyl$(C_1-C_2)$alkyl, said phenyl$(C_1-C_2)$alkyl being optionally substituted with halogen and/or $(C_1-C_4)$alkyl, and (xii) phenyl$(C_1-C_2)$alkoxy, said phenyl$(C_1-C_2)$alkoxy being optionally substituted with halogen and/or $(C_1-C_4)$alkyl; and m is an integer of 0, 1, 2 or 3.

The compounds of formula (IX) and syntheses thereof are, for example, described in published German patent application (Offenlegungsschrift) DE 30 18 866 A1.

In some embodiments in formula (IX) R is selected from the group consisting of $(C_1-C_6)$alkyl and $(C_3-C_7)$cycloalkyl, said $(C_3-C_7)$cycloalkyl being optionally substituted with $(C_1-C_2)$alkyl; X is nitrogen or CH; Y is selected from the group consisting of —OCH$_2$ and —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_6)$alkyl; X is nitrogen or CH; Y is selected from the group consisting of —OCH$_2$ and —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_6)$alkyl; X is nitrogen or CH; Y is —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_6)$alkyl; X is nitrogen; Y is selected from the group consisting of —OCH$_2$ and —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_4)$alkyl and $(C_3-C_7)$cycloalkyl, said $(C_3-C_7)$cycloalkyl being optionally substituted with $(C_1-C_2)$alkyl; X is nitrogen or CH; Y is selected from the group consisting of —OCH$_2$ and —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_4)$alkyl; X is nitrogen or CH; Y is selected from the group consisting of —OCH$_2$ and —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_4)$alkyl; X is nitrogen or CH; Y is —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_4)$alkyl; X is nitrogen; Y is selected from the group consisting of —OCH$_2$ and —CH$_2$CH$_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments in formula (IX) R is selected from the group consisting of $(C_1-C_4)$alkyl; X is nitrogen; Y is —$CH_2CH_2$—; Z is halogen; and m is an integer of 0, 1 or 2. In some of these embodiments "halogen" at each occurrence is independently F or Cl. In some of these embodiments "halogen" at each occurrence is Cl. In some of these embodiments m is 1 or 2. In some of these embodiments m is 1.

In some embodiments the compound of formula (IX) has the structure:

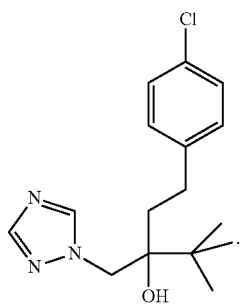 [SMILES: CC(C)(C)C(O)(CCc1ccc(Cl)cc1)Cn1cncn1]

In some embodiment the compound of formula (IX) is tebuconazole.

In some aspects, the present invention provides compounds for use in treating a disease that is related to CYP7B1, said compounds having a structure according to formula (VII), in any of their stereoisomeric forms or a mixture of stereoisomeric forms in any ratio, and the pharmaceutically acceptable salts thereof, and the pharmaceutically acceptable solvates or hydrates of any of them,

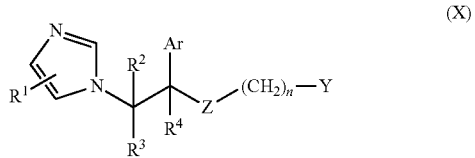

wherein
$R^1$, $R^2$, $R^3$ and $R^4$ are each, independently, hydrogen or $(C_1-C_6)$alkyl;
Ar is selected from the group consisting of (i) unsubstituted phenyl, (ii) phenyl being substituted with a member selected from the group consisting of halogen, $(C_1-C_6)$alkyl and $(C_1-C_6)$alkoxy, (iii) thienyl and (iv) halothienyl;
Z is oxygen or sulfur;
n is 1 or 2; and
Y is $(C_3-C_{10})$heteroaryl, said $(C_3-C_{10})$heteroaryl being optionally substituted with a member selected from the group consisting of halogen, $(C_1-C_6)$alkyl and $(C_1-C_6)$alkoxy.

The compounds of formula (VI) and syntheses thereof are, for example, described in U.S. Pat. No. 4,062,966.

In some embodiments in formula (X) Y is thienyl optionally substituted with halogen. In some of these embodiments Y is 2-chlorothien-3-yl.

In some embodiments in formula (X) $R^1$, $R^2$, $R^3$ and $R^4$ are each, independently, hydrogen or $(C_1-C_6)$alkyl; Ar is selected from the group consisting of (i) unsubstituted phenyl and (ii) phenyl being substituted with a member selected from the group consisting of halogen and $(C_1-C_6)$alkyl; Z is oxygen or sulfur; n is 1 or 2; and Y is $(C_3-C_{10})$heteroaryl, said $(C_3-C_{10})$heteroaryl being optionally substituted with a member selected from the group consisting of halogen and $(C_1-C_6)$alkyl. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each, independently, hydrogen or $(C_1-C_4)$alkyl; Ar is selected from the group consisting of (i) unsubstituted phenyl and (ii) phenyl being substituted with a member selected from the group consisting of halogen and $(C_1-C_4)$alkyl; Z is oxygen or sulfur; n is 1 or 2; and Y is $(C_3-C_5)$heteroaryl, said $(C_3-C_5)$heteroaryl being optionally substituted with a member selected from the group consisting of halogen and $(C_1-C_4)$alkyl. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each, independently, hydrogen or $(C_1-C_2)$alkyl; Ar is selected from the group consisting of (i) unsubstituted phenyl and (ii) phenyl being substituted with a member selected from the group consisting of halogen and $(C_1-C_2)$alkyl; Z is oxygen or sulfur; n is 1 or 2; and Y is $(C_3-C_5)$heteroaryl, said $(C_3-C_5)$heteroaryl being optionally substituted with a member selected from the group consisting of halogen and $(C_1-C_2)$alkyl. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is selected from the group consisting of (i) unsubstituted phenyl and (ii) phenyl being substituted with halogen; Z is oxygen or sulfur; n is 1 or 2; and Y is $(C_3-C_{10})$heteroaryl, said $(C_3-C_{10})$heteroaryl being optionally substituted with a member selected from the group consisting of halogen and $(C_1-C_6)$alkyl. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is selected from the group consisting of (i) unsubstituted phenyl and (ii) phenyl being substituted with halogen; Z is oxygen or sulfur; n is 1 or 2; and Y is $(C_3-C_{10})$heteroaryl, said $(C_3-C_{10})$heteroaryl being optionally substituted with a member selected from the group consisting of halogen and $(C_1-C_6)$alkyl. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is selected from the group consisting of (i) unsubstituted phenyl and (ii) phenyl being substituted with halogen; Z is oxygen or sulfur; n is 1 or 2; and Y is $(C_3-C_5)$heteroaryl, said $(C_3-C_5)$heteroaryl being optionally substituted with a member selected from the group consisting of halogen and $(C_1-C_6)$alkyl. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is selected from the group consisting of (i) unsubstituted phenyl and (ii) phenyl being substituted with halogen; Z is oxygen or sulfur; n is 1 or 2; and Y is $(C_3-C_5)$heteroaryl, said $(C_3-C_5)$heteroaryl being optionally substituted with halogen. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is phenyl being substituted with halogen; Z is oxygen or sulfur; n is 1 or 2; and Y is $(C_3-C_5)$heteroaryl, said $(C_3-C_5)$heteroaryl being optionally substituted with halogen. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is phenyl being substituted with halogen; Z is oxygen or sulfur; n is 1 or 2; and Y is 2-thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl. In some of these embodiments Z is oxygen.

In some embodiments in formula (X) $R^1$, $R^2$, $R^3$ and $R^4$ are each hydrogen; Ar is phenyl being substituted with halogen; Z is oxygen; n is 1; and Y is $(C_3-C_5)$heteroaryl, said $(C_3-C_5)$heteroaryl being optionally substituted with halogen. In some of these embodiments Y is thienyl optionally substituted with halogen. In some of these embodiments Y is 2-chlorothien-3-yl. In some of these embodiments "halogen" at each occurrence is independently F or Cl. In some of these embodiments "halogen" at each occurrence is Cl. In some of these embodiments Ar is 2,4-dichlorophenyl.

In some embodiments the compound of formula (X) has the structure:

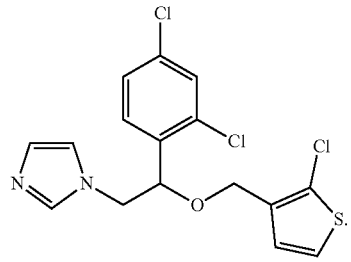 [SMILES: Clc1ccc(C(Cn2ccnc2)OCc2ccsc2Cl)c(Cl)c1]

In some embodiments the compound of formula (X) is tioconazole.

In some aspects, the present invention provides compounds for use in treating a disease that is related to CYP7B1, said compounds having a structure according to formula (XI), in any of their stereoisomeric forms or a mixture of stereoisomeric forms in any ratio, and the pharmaceutically acceptable salts thereof, and the pharmaceutically acceptable solvates or hydrates of any of them,

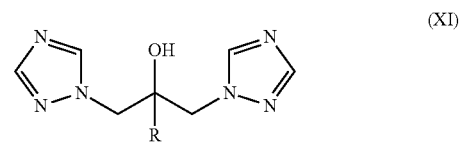

(XI)

wherein

R is selected from the group consisting of (i) naphthyl, (ii) biphenylyl and (iii) phenyl, said phenyl being optionally substituted with 1 to 3 substituents each independently selected from F, Cl, Br, I, $CF_3$, $(C_1-C_4)$alkyl and $(C_1-C_4)$alkoxy; or R is a 5-chloro-pyrid-2-yl group.

The compounds of formula (XI) and syntheses thereof are, for example, described in published European patent application EP 0 096 569 A2.

In some embodiments in formula (XI) R is selected from the group consisting of naphthyl and phenyl, said phenyl being optionally substituted with 1 to 3 substituents each independently selected from F, Cl, Br, I, $CF_3$, $(C_1-C_4)$alkyl and $(C_1-C_4)$alkoxy.

In some embodiments in formula (XI) R is phenyl, said phenyl being optionally substituted with 1 to 3 substituents each independently selected from F, Cl, Br and $CF_3$.

In some embodiments in formula (XI) R is phenyl, said phenyl being optionally substituted with 1 to 3 substituents each independently selected from F, Cl, and $CF_3$.

In some embodiments in formula (XI) R is phenyl, said phenyl being optionally substituted with 1 to 3 substituents each independently selected from F and Cl. In some embodiments R is 2,4-difluorophenyl. In some embodiments R is 2,4-dichlorophenyl.

In some embodiments the compound of formula (XI) has the structure:

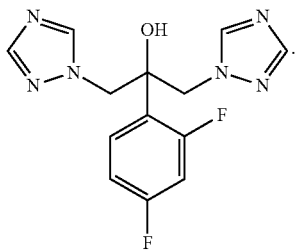 [SMILES: OC(Cn1cncn1)(Cn1cncn1)c1ccc(F)cc1F]

In some of these embodiments the compound of formula (XI) is fluconazole.

In some aspects, the present invention provides compounds for use in treating a disease that is related to CYP7B1, said compounds having a structure according to formula (VII), in any of their stereoisomeric forms or a mixture of stereoisomeric forms in any ratio, and the pharmaceutically acceptable salts thereof, and the pharmaceutically acceptable solvates or hydrates of any of them, (XII)

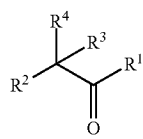

wherein
$R^1$ and $R^2$ are each independently selected from the group consisting of 3-pyridyl and 4-pyridyl; and
$R^3$ and $R^4$ are each independently $(C_1$-$C_6)$alkyl.

The compounds of formula (XII) and syntheses thereof are, for example, described in U.S. Pat. No. 2,966,493.

In some embodiments in formula (XII) $R^1$ and $R^2$ are each independently selected from the group consisting of 3-pyridyl and 4-pyridyl; and $R^3$ and $R^4$ are each independently $(C_1$-$C_4)$alkyl.

In some embodiments in formula (XII) $R^1$ and $R^2$ are each independently selected from the group consisting of 3-pyridyl and 4-pyridyl; and $R^3$ and $R^4$ are each independently $(C_1$-$C_2)$alkyl.

In some embodiments in formula (XII) $R^1$ and $R^2$ are each 3-pyridyl and $R^3$ and $R^4$ are each independently $(C_1$-$C_6)$alkyl.

In some embodiments in formula (XII) $R^1$ and $R^2$ are each 3-pyridyl; and $R^3$ and $R^4$ are each independently $(C_1$-$C_4)$alkyl.

In some embodiments in formula (XII) $R^1$ and $R^2$ are each 3-pyridyl; and $R^3$ and $R^4$ are each independently $(C_1$-$C_2)$alkyl.

In some embodiments the compound of formula (XII) has the structure:

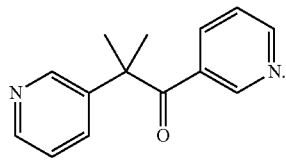 [SMILES: CC(C)(C(=O)c1cccnc1)c1cccnc1]

In some embodiment the compound of formula (XII) is metyrapone.

In some aspects, the present invention provides compounds for use in treating a disease that is related to CYP7B1, said compounds having a structure according to formula (XIV), in any of their stereoisomeric forms or a mixture of stereoisomeric forms in any ratio, and the pharmaceutically acceptable salts thereof, and the pharmaceutically acceptable solvates or hydrates of any of them, (XIV)

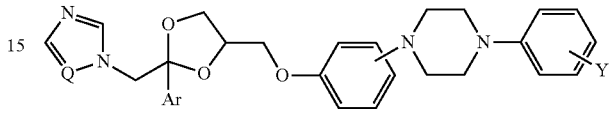

wherein
Q is selected from the group consisting of CH and N;
Ar is selected from the group consisting of (i) phenyl, (ii) thienyl, (iii) halothienyl and (iv) substituted phenyl, said substituted phenyl having from 1 to 3 substituents each independently selected from the group consisting of halogen, $(C_1$-$C_6)$alkyl, $(C_1$-$C_6)$alkyloxy and trifluoromethyl;
Y is a 2,3-dihydro-4H-1,2,4-triazol-4-yl of the formula

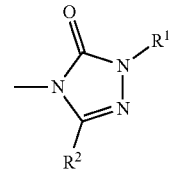

wherein
$R^1$ is selected from the group consisting of $(C_1$-$C_6)$alkyl and $(C_6$-$C_{10})$aryl-$(C_1$-$C_6)$alkyl; and
$R^2$ is selected from the group consisting of hydrogen, $(C_1$-$C_6)$alkyl, and $(C_6$-$C_{10})$aryl-$(C_1$-$C_6)$alkyl.

The compounds of formula (XIV) and syntheses thereof are, for example, described in U.S. Pat. No. 4,267,179.

In some embodiments in formula (XIV) Q is selected from the group consisting of CH and N; Ar is selected from the group consisting of phenyl and substituted phenyl, said substituted phenyl having from 1 to 3 substituents each independently selected from the group consisting of halogen, $(C_1$-$C_6)$alkyl and trifluoromethyl; Y is a 2,3-dihydro-4H-1,2,4-triazol-4-yl of the formula

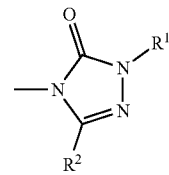

wherein $R^1$ is $(C_1$-$C_6)$alkyl; and $R^2$ is selected from the group consisting of hydrogen and $(C_1$-$C_6)$alkyl. In some of these embodiments "halogen" at each occurrence is independently F or Cl. In some of these embodiments "halogen" at each occurrence is Cl. In some of these embodiments $R^2$ is hydrogen.

In some embodiments in formula (XIV) Q is selected from the group consisting of CH and N; Ar is selected from the group consisting of phenyl and substituted phenyl, said substituted phenyl having from 1 to 3 halogen substituents; Y is a 2,3-dihydro-4H-1,2,4-triazol-4-yl of the formula

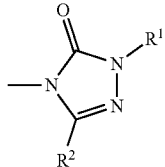

wherein $R^1$ is $(C_1-C_6)$alkyl; and $R^2$ is selected from the group consisting of hydrogen and $(C_1-C_6)$alkyl. In some of these embodiments "halogen" at each occurrence is independently F or Cl. In some of these embodiments "halogen" at each occurrence is Cl. In some of these embodiments $R^2$ is hydrogen.

In some embodiments in formula (XIV) Q is N; Ar is selected from the group consisting of phenyl and substituted phenyl, said substituted phenyl having from 1 to 3 halogen substituents; Y is a 2,3-dihydro-4H-1,2,4-triazol-4-yl of the formula

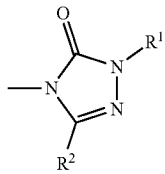

wherein $R^1$ is $(C_1-C_6)$alkyl; and $R^2$ is selected from the group consisting of hydrogen and $(C_1-C_6)$alkyl. In some of these embodiments "halogen" at each occurrence is independently F or Cl. In some of these embodiments "halogen" at each occurrence is Cl. In some of these embodiments $R^2$ is hydrogen.

In some embodiments in formula (XIV) Q is N; Ar is substituted phenyl, said substituted phenyl having from 1 to 3 halogen substituents; Y is a 2,3-dihydro-4H-1,2,4-triazol-4-yl of the formula

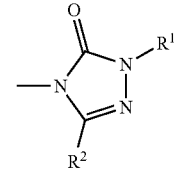

wherein $R^1$ is $(C_1-C_6)$alkyl; and $R^2$ is selected from the group consisting of hydrogen and $(C_1-C_6)$alkyl. In some of these embodiments "halogen" at each occurrence is independently F or Cl. In some of these embodiments "halogen" at each occurrence is Cl. In some of these embodiments $R^2$ is hydrogen.

In some embodiments in formula (XIV) Q is N; Ar is a substituted phenyl, said substituted phenyl having from 1 to 3 halogen substituents; Y is a 2,3-dihydro-4H-1,2,4-triazol-4-yl of the formula

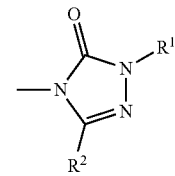

wherein $R^1$ is $(C_1-C_6)$alkyl and $R^2$ is hydrogen. In some of these embodiments $R^1$ is $(C_3-C_5)$alkyl. In some of these embodiments $R^1$ is 2-butyl. In some of these embodiments "halogen" at each occurrence is independently F or Cl. In some of these embodiments "halogen" at each occurrence is Cl.

In some embodiments the compound of formula (XIV) has the structure:

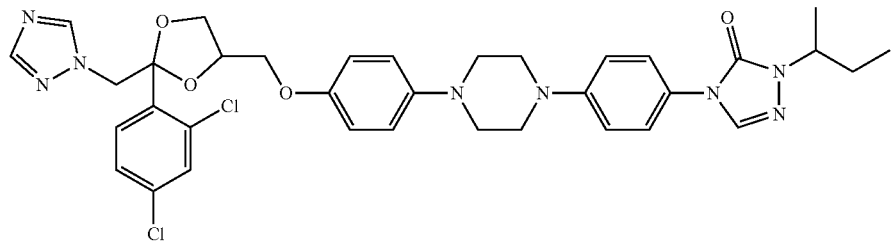

In some embodiments the compound of formula (XIV) has the structure:

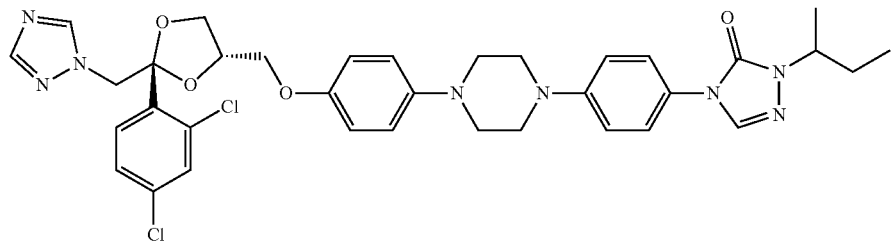

In some embodiments the compound of formula (XIV) has the structure:

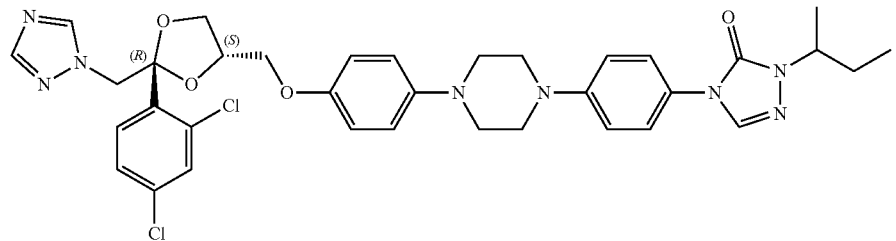

In some embodiments the compound of formula (XIV) is itraconazole.

In some aspects, the present invention provides compounds for use in treating a disease that is related to CYP7B1, said compounds having a structure according to formula (XV), in any of their stereoisomeric forms or a mixture of stereoisomeric forms in any ratio, and the pharmaceutically acceptable salts thereof, and the pharmaceutically acceptable solvates or hydrates of any of them,

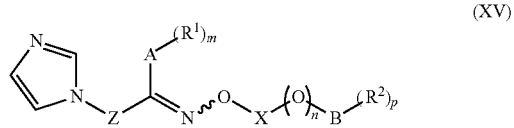
(XV)

wherein
Z is selected from the group consisting of straight and branched chain $(C_1-C_4)$alkylene group;
A is selected from the group consisting of phenyl and naphthyl;
$R^1$ is selected from the group consisting of halogen, $NO_2$, $(C_1-C_6)$alkyl and $(C_1-C_6)$alkoxy;
X is a $(C_1-C_8)$alkylene group;
B is selected from the group consisting of hydrogen, phenyl and naphthyl;
$R^2$ is selected from the group consisting of halogen, $NO_2$, $(C_1-C_6)$alkyl and $(C_1-C_6)$alkoxy;
m is 0 or an integer of from 1 to 3;
n is 0 or 1; and
p is 0 or an integer of from 1 to 3 with the proviso that when B is hydrogen both n and p are 0.

The compounds of formula (XV) and syntheses thereof are, for example, described in U.S. Pat. No. 4,124,767.

As indicated by the wavy bond, the C=N double bond of the oxime ether moiety in formula (XV) may have the E configuration or may have the Z configuration. Accordingly, in some embodiments the double bond in formula (XV) has the Z configuration as shown in the following formula (XVa):

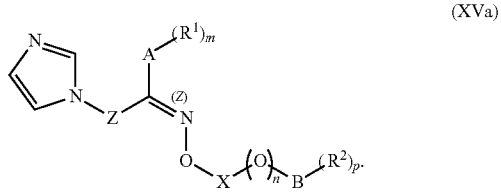
(XVa)

For the purpose of the present description, the term "Z configuration", whenever mentioned herein with regard to the compounds of formula (XV), denotes the configuration of the double bond as shown in formula (XVa). In contrast, in some embodiments the double bond in formula (XV) has the E configuration. In some embodiments the compound of formula (XV) is a mixture of the E isomer and the Z isomer.

In some embodiments in formula (XV) Z is selected from the group consisting of straight and branched chain $(C_1-C_4)$ alkylene group; A is phenyl; $R^1$ is selected from the group consisting of halogen, $NO_2$, $(C_1-C_6)$alkyl and $(C_1-C_6)$ alkoxy; X is a $(C_1-C_6)$alkylene group; B is phenyl; $R^2$ is selected from the group consisting of halogen, $NO_2$, $(C_1-C_6)$alkyl and $(C_1-C_6)$alkoxy; m is 0 or an integer of from 1 to 3; n is 0 or 1; and p is 0 or an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain $(C_1-C_2)$ alkylene group; A is phenyl; $R^1$ is selected from the group consisting of halogen, $NO_2$, $(C_1-C_6)$alkyl and $(C_1-C_6)$ alkoxy; X is a $(C_1-C_4)$alkylene group; B is phenyl; $R^2$ is selected from the group consisting of halogen, $NO_2$, $(C_1-C_6)$alkyl and $(C_1-C_6)$alkoxy; m is 0 or an integer of from 1 to 3; n is 0 or 1; and p is 0 or an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain $(C_1-C_2)$ alkylene group; A is phenyl; $R^1$ is selected from the group consisting of halogen, $NO_2$, $(C_1-C_6)$alkyl and $(C_1-C_6)$ alkoxy; X is a $(C_1-C_2)$alkylene group; B is phenyl; $R^2$ is selected from the group consisting of halogen, $NO_2$, $(C_1-C_6)$alkyl and $(C_1-C_6)$alkoxy; m is 0 or an integer of from 1 to 3; n is 0 or 1; and p is 0 or an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain $(C_1-C_2)$ alkylene group; A is phenyl; $R^1$ is halogen; X is a $(C_1-C_2)$ alkylene group; B is phenyl; $R^2$ is halogen; m is 0 or an integer of from 1 to 3; n is 0 or 1; and p is 0 or an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is a methylene group; A is phenyl; $R^1$ is halogen; X is a methylene group;

B is phenyl; $R^2$ is halogen; m is 0 or an integer of from 1 to 3; n is 0 or 1; and p is 0 or an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain ($C_1$-$C_4$) alkylene group; A is phenyl; $R^1$ is selected from the group consisting of halogen, $NO_2$, ($C_1$-$C_6$)alkyl and ($C_1$-$C_6$)alkoxy; X is a ($C_1$-$C_6$)alkylene group; B is phenyl; $R^2$ is selected from the group consisting of halogen, $NO_2$, ($C_1$-$C_6$)alkyl and ($C_1$-$C_6$)alkoxy; m is an integer of from 1 to 3; n is 0; and p is an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain ($C_1$-$C_2$) alkylene group; A is phenyl; $R^1$ is selected from the group consisting of halogen, $NO_2$, ($C_1$-$C_6$)alkyl and ($C_1$-$C_6$)alkoxy; X is a ($C_1$-$C_4$)alkylene group; B is phenyl; $R^2$ is selected from the group consisting of halogen, $NO_2$, ($C_1$-$C_6$)alkyl and ($C_1$-$C_6$)alkoxy; m is an integer of from 1 to 3; n is 0 or 1; and p is an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain ($C_1$-$C_2$) alkylene group; A is phenyl; $R^1$ is selected from the group consisting of halogen, $NO_2$, ($C_1$-$C_6$)alkyl and ($C_1$-$C_6$)alkoxy; X is a ($C_1$-$C_2$)alkylene group; B is phenyl; $R^2$ is selected from the group consisting of halogen, $NO_2$, ($C_1$-$C_6$)alkyl and ($C_1$-$C_6$)alkoxy; m is an integer of from 1 to 3; n is 0; and p is an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is selected from the group consisting of straight and branched chain ($C_1$-$C_2$) alkylene group; A is phenyl; $R^1$ is halogen; X is a ($C_1$-$C_2$) alkylene group; B is phenyl; $R^2$ is halogen; m is an integer of from 1 to 3; n is 0; and p is an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments in formula (XV) Z is a methylene group; A is phenyl; $R^1$ is halogen; X is a methylene group; B is phenyl; $R^2$ is halogen; m is an integer of from 1 to 3; n is 0; and p is an integer of from 1 to 3. In some of these embodiments "halogen" at each occurrence is independently F or Cl. In some of these embodiments "halogen" at each occurrence is Cl. In some of these embodiments the double bond has the Z configuration.

In some embodiments the compound of formula (XV) has the structure:

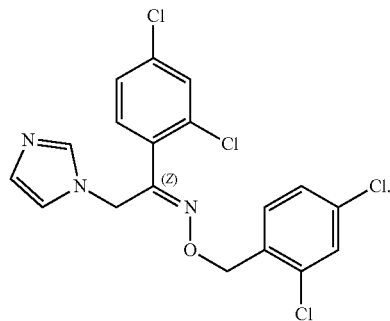 [SMILES: Clc1ccc(CO/N=C(\Cn2ccnc2)c2ccc(Cl)cc2Cl)c(Cl)c1]

In some embodiments the compound of formula (XV) is oxiconazole.

In some aspects, the present invention provides compounds for use in treating a disease that is related to CYP7B1, said compounds having a structure according to formula (XVI), in any of their stereoisomeric forms or a mixture of stereoisomeric forms in any ratio, and the pharmaceutically acceptable salts thereof, and the pharmaceutically acceptable solvates or hydrates of any of them, (XVI)

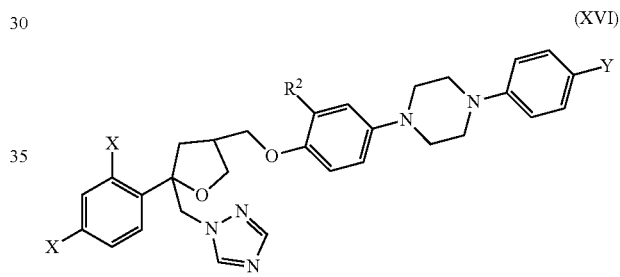

wherein
X is independently both F or both Cl; or one X is independently F and the other is independently Cl;
$R^1$ is a straight or branched chain ($C_3$-$C_8$)alkyl group substituted with one or two hydroxy moieties;
$R^2$ is H or a ($C_1$-$C_8$)alkyl group, preferably H or a methyl group.

More preferably, if Y is —CONHArZ, $R^2$ is a methyl group,
Y is

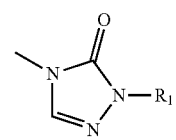

or —CONHArZ;
Ar is phenyl;
Z is F;
Z is a ortho, meta or para substituent of Ar, preferably Z is a para substituent.

The compounds of formula (XVI) and syntheses thereof are, for example, described in published international patent application WO 95/17407 A1 and WO 2016/087880 A1.

In some embodiments in formula (XVI) Y is

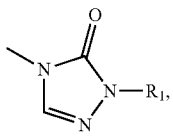

X is independently both F or both Cl, R¹ is a branched chain $(C_3-C_8)$alkyl group substituted with one or two hydroxy moieties, and R² is H.

In some embodiments in formula (XVI) Y is

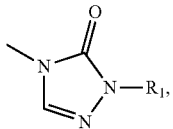

X is both F, R¹ is a branched chain $(C_3-C_8)$alkyl group substituted with one or two hydroxy moieties, and R² is H In some embodiments in formula (XVI) Y is

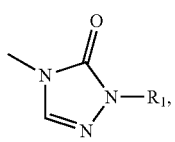

X is both F, R¹ is a branched chain $(C_3-C_8)$alkyl group substituted with one hydroxy moiety, and R² is H.

In some embodiments in formula (XVI) Y is —CONHArZ, X is both F, R² is $(C_1-C_8)$alkyl group, and Z is F.

In some embodiments in formula (XVI) Y is —CONHArZ, X is both F, R² is $(C_1-C_8)$alkyl group, Z is F and F is a para substituent.

In some embodiments in formula (XVI) Y is —CONHArZ, X is both F, R² is a methyl group, and Z is F.

In some embodiments in formula (XVI) Y is —CONHArZ, X is both F, R² is a methyl group, Z is F and Z is a para substituent.

In some embodiments the compound of formula (XVI) has the formula (XVIa):

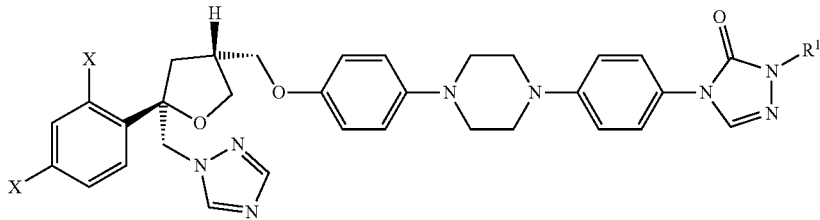

(XVIa)

wherein
X is independently both F or both Cl; or one X is independently F and the other is independently Cl; and
R¹ is a straight or branched chain $(C_3-C_8)$alkyl group substituted with one or two hydroxy moieties.

In some embodiments in formula (XVIa) X is independently both F or both Cl and R¹ is a branched chain $(C_3-C_8)$alkyl group substituted with one or two hydroxy moieties.

In some embodiments in formula (XVIa) X is both F and R¹ is a branched chain $(C_3-C_8)$alkyl group substituted with one or two hydroxy moieties.

In some embodiments in formula (XVIa) X is both F and R¹ is a branched chain $(C_3-C_8)$alkyl group substituted with one hydroxy moiety.

In some embodiments the compound of formula (XVI) has the formula (XVIb):

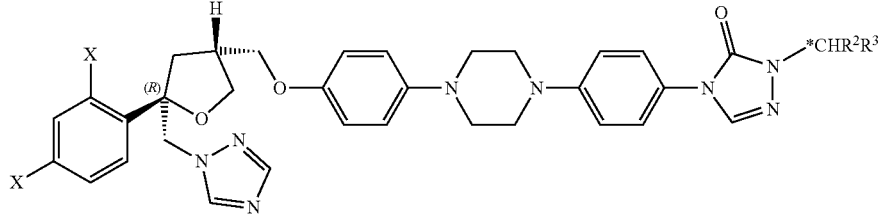

(XVIb)

wherein

X is independently both F or both Cl or one X is independently F and the other is independently Cl; and R² is hydrogen or (C₁-C₃)alkyl and R³ is (C₁-C₃)alkyl substituted by one hydroxy moiety and the carbon with the asterisk (*) has the R or S absolute configuration.

In some embodiments the compound of formula (XVI) has the formula (XVIc):

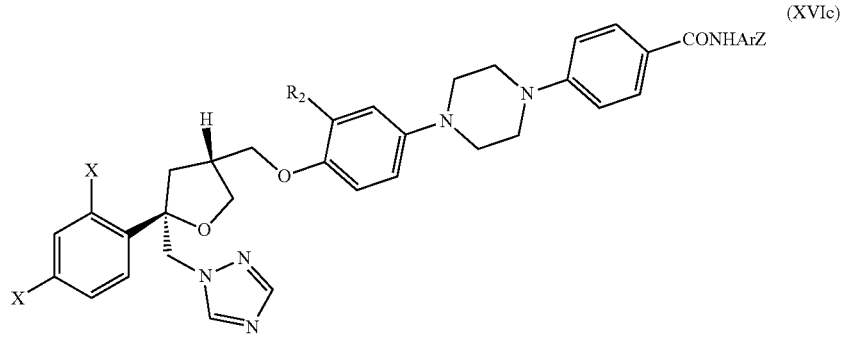

(XVIc)

wherein

X is independently both F or both Cl; or one X is independently F and the other is independently Cl;

R² is H or a (C₁-C₈)alkyl group, preferably H or a methyl group.

More preferably, R² is a methyl group if Y is —CONHArZ,

Ar is phenyl;

Z is F;

Z is a ortho, meta or para substituent of Ar, preferably Z is a para substituent.

In some embodiments the compound of formula (XVI) has the structure:

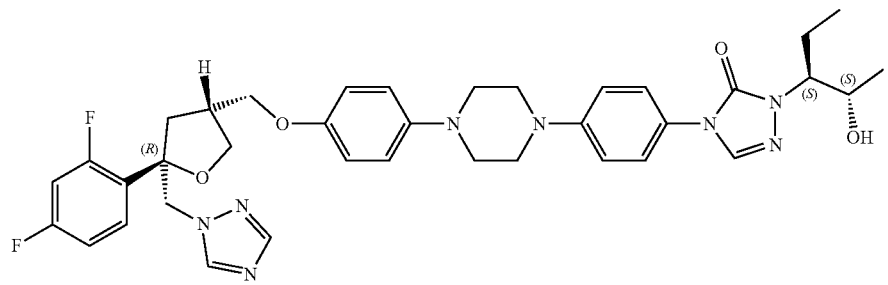

In some embodiments the compound of formula (XVI) is posaconazole.

In some embodiments the compound of formula (XVI) is PC945.

PC945 comprises the racemic form of compound number 25 in table 1, including all stereoisomers. Preferably, PC945 is the stereoisomer according to compound number 25a in table 1.

In some aspects, the present invention provides compounds for use in treating a disease that is related to CYP7B1, said compounds having a structure according to formula (XVII), in any of their stereoisomeric forms or a mixture of stereoisomeric forms in any ratio, and the pharmaceutically acceptable salts thereof, and the pharmaceutically acceptable solvates or hydrates of any of them,

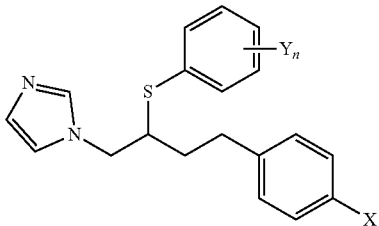

(XVII)

wherein

X is Cl or F;

Y is Br or Cl or F, at least one Y being in the 2'-position; and n is an integer of from 1 to 5 when Y is Cl; or n is 1 or 2 when Y is other than Cl.

The compounds of formula (XVII) and syntheses thereof are, for example, described in published German patent application (Offenlegungsschrift) DE 28 00 755.

In some embodiments in formula (XVII) X is Cl or F; Y is Cl or F, at least one Y being in the 2'-position; and n is an integer of from 1 to 5 when Y is Cl; or n is 1 or 2 when Y is other than Cl.

In some embodiments in formula (XVII) X is Cl or F; Y is Cl or F, at least one Y being in the 2'-position; and n is an integer of from 1 to 3 when Y is Cl; or n is 1 or 2 when Y is other than Cl.

In some embodiments in formula (XVII) X is Cl or F; Y is Cl or F, at least one Y being in the 2'-position; and n is an integer of 1 or 2 when Y is Cl; or n is 1 or 2 when Y is other than Cl.

In some embodiments in formula (XVII) X is Cl; Y is Cl, at least one Y being in the 2'-position; and n is an integer of from 1 to 3. In some of these embodiments n is 2.

In some embodiments the compound of formula (XVII) has the structure:

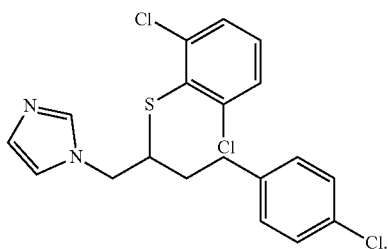 [SMILES: Clc1ccc(CCC(Cn2ccnc2)Sc2c(Cl)cccc2Cl)cc1]

In some embodiments the compound of formula (XVII) is butoconazole.

In some aspects, the present invention provides compounds for use in treating a disease that is related to CYP7B1, said compounds having a structure according to formula (XVIII), in any of their stereoisomeric forms or a mixture of stereoisomeric forms in any ratio, and the pharmaceutically acceptable salts thereof, and the pharmaceutically acceptable solvates or hydrates of any of them,

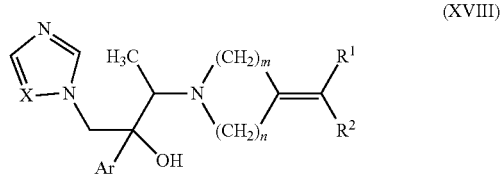

(XVIII)

wherein
Ar is a non-substituted phenyl group or a phenyl group substituted with 1 to 3 substituents each independently selected from halogen and $CF_3$;
$R^1$ and $R^2$ are the same or different and are selected from the group consisting of (i) hydrogen, (ii) $(C_1-C_6)$alkyl, (iii) non-substituted $(C_6-C_{10})$aryl, (iv) a $(C_6-C_{10})$aryl group substituted with 1 to 3 substituents each independently selected from halogen and $(C_1-C_6)$alkyl, (v) $(C_2-C_6)$alkenyl, (vi) $(C_2-C_6)$alkynyl and (vii) $(C_6-C_{10})$aryl$(C_1-C_6)$alkyl;
m is 2 or 3;
n is 1 or 2; and
X is N or CH.

The compounds of formula (XVIII) and syntheses thereof are, for example, described in published European patent application EP 0 698 606 A1.

In some embodiments in formula (XVIII) Ar is a non-substituted phenyl group or a phenyl group substituted with 1 to 3 substituents each independently selected from halogen and $CF_3$; $R^1$ and $R^2$ are the same or different and are selected from the group consisting of hydrogen and $(C_1-C_6)$alkyl; m is 2 or 3; n is 1 or 2; and X is N or CH. In some of these embodiments "halogen" at each occurrence is independently F or Cl. In some of these embodiments "halogen" at each occurrence is F. In some of these embodiments Ar is 2,4-difluorophenyl. In some of these embodiments X is N.

In some embodiments in formula (XVIII) Ar is a phenyl group substituted with 1 to 3 substituents each independently selected from halogen and $CF_3$; $R^1$ and $R^2$ are the same or different and are selected from the group consisting of hydrogen and $(C_1-C_6)$alkyl; m is 2 or 3; n is 1 or 2; and X is N or CH. In some of these embodiments "halogen" at each occurrence is independently F or Cl. In some of these embodiments "halogen" at each occurrence is F. In some of these embodiments Ar is 2,4-difluorophenyl. In some of these embodiments X is N.

In some embodiments in formula (XVIII) Ar is a phenyl group substituted with 1 to 3 halogen substituents; $R^1$ and $R^2$ are the same or different and are selected from the group consisting of hydrogen and $(C_1-C_6)$alkyl; m is 2 or 3; n is 1 or 2; and X is N or CH. In some of these embodiments "halogen" at each occurrence is independently F or Cl. In some of these embodiments "halogen" at each occurrence is F. In some of these embodiments Ar is 2,4-difluorophenyl. In some of these embodiments X is N.

In some embodiments in formula (XVIII) Ar is a phenyl group substituted with 1 to 3 halogen substituents; $R^1$ and $R^2$ are the same or different and are selected from the group consisting of hydrogen and $(C_1-C_4)$alkyl; m is 2 or 3; n is 1 or 2; and X is N or CH. In some of these embodiments "halogen" at each occurrence is independently F or Cl. In some of these embodiments "halogen" at each occurrence is F. In some of these embodiments Ar is 2,4-difluorophenyl. In some of these embodiments X is N.

In some embodiments in formula (XVIII) Ar is a phenyl group substituted with 1 to 3 halogen substituents; $R^1$ and $R^2$ are the same or different and are selected from the group consisting of hydrogen and $(C_1-C_2)$alkyl; m is 2 or 3; n is 1 or 2; and X is N or CH. In some of these embodiments "halogen" at each occurrence is independently F or Cl. In some of these embodiments "halogen" at each occurrence is F. In some of these embodiments Ar is 2,4-difluorophenyl. In some of these embodiments X is N.

In some embodiments in formula (XVIII) Ar is a phenyl group substituted with 1 to 3 halogen substituents; $R^1$ and $R^2$ are both hydrogen; m is 2 or 3; n is 1 or 2; and X is N or CH. In some of these embodiments "halogen" at each occurrence is independently F or Cl. In some of these embodiments "halogen" at each occurrence is F. In some of these embodiments Ar is 2,4-difluorophenyl. In some of these embodiments X is N.

In some embodiments in formula (XVIII) Ar is a phenyl group substituted with 1 to 3 halogen substituents; $R^1$ and $R^2$ are both hydrogen; m is 2 or 3; n is 1 or 2; and X is N. In some of these embodiments "halogen" at each occurrence is independently F or Cl. In some of these embodiments "halogen" at each occurrence is F. In some of these embodiments Ar is 2,4-difluorophenyl.

In some embodiments in formula (XVIII) Ar is a phenyl group substituted with 1 to 3 halogen substituents; $R^1$ and $R^2$ are both hydrogen; m is 2; n is 2; and X is N or CH. In some of these embodiments "halogen" at each occurrence is independently F or Cl. In some of these embodiments "halogen" at each occurrence is F. In some of these embodiments Ar is 2,4-difluorophenyl.

In some embodiments in formula (XVIII) Ar is a phenyl group substituted with 1 to 3 halogen substituents; $R^1$ and $R^2$ are both hydrogen; m is 2; n is 2; and X is N. In some of these embodiments "halogen" at each occurrence is independently F or Cl. In some of these embodiments "halogen" at each occurrence is F. In some of these embodiments Ar is 2,4-difluorophenyl.

In some embodiments the compound of formula (XVIII) has the structure:

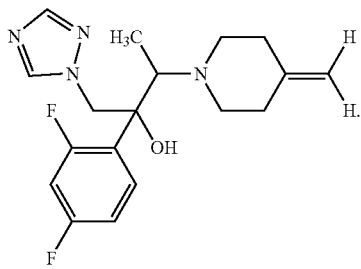

In some embodiments the compound of formula (XVIII) has the structure:

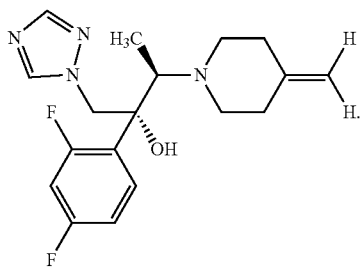

In some embodiments the compound of formula (XVIII) has the structure:

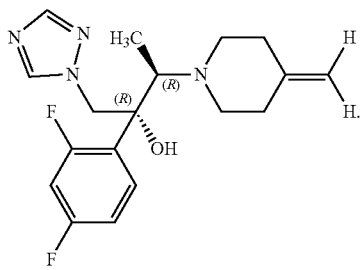

In some embodiments the compound of formula (XVIII) is efinaconazole.

In some aspects, the present invention provides compounds for use in treating a disease that is related to CYP7B1, said compounds having a structure according to formula (XIX), in any of their stereoisomeric forms or a mixture of stereoisomeric forms in any ratio, and the pharmaceutically acceptable salts thereof, and the pharmaceutically acceptable solvates or hydrates of any of them, (XIX)

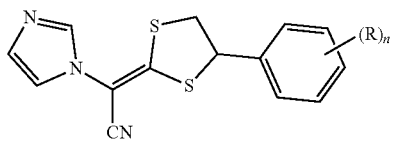

wherein
R is each, independently, halogen selected from the group consisting of F, Cl and Br; and
n is an integer of 0, 1, 2 or 3.

The compounds of formula (XIX) and syntheses thereof are, for example, described in unexamined published Japanese patent application JP-A-60-218387 and international patent application WO 97/02821 A2.

In some embodiments in formula (XIX) R is each, independently, halogen selected from the group consisting of F and Cl; and n is an integer of 0, 1 or 2. In some of these embodiments n is 1 or 2. In some of these embodiments n is 2.

In some embodiments in formula (XIX) R is Cl; and n is an integer of 0, 1 or 2. In some of these embodiments n is 1 or 2. In some of these embodiments n is 2.

In some embodiments the compound of formula (XIX) has the structure:

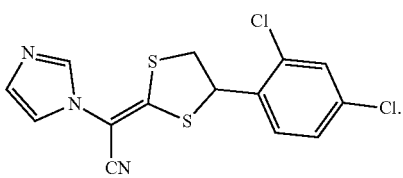 [SMILES: N#C/C(=C1/SCC(c2ccc(Cl)cc2Cl)S1)n1ccnc1]

In some of these embodiments the compound of formula (XIX) has the structure:

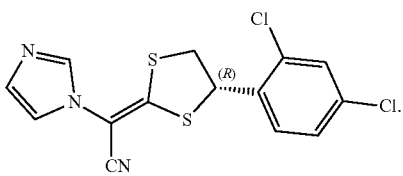

In some embodiments the compound of formula (XIX) is luliconazole.

In some aspects, the present invention provides compounds for use in treating a disease that is related to CYP7B1, said compounds having a structure according to formula (XX), in any of their stereoisomeric forms or a mixture of stereoisomeric forms in any ratio, and the pharmaceutically acceptable salts thereof, and the pharmaceutically acceptable solvates or hydrates of any of them.

(XX)

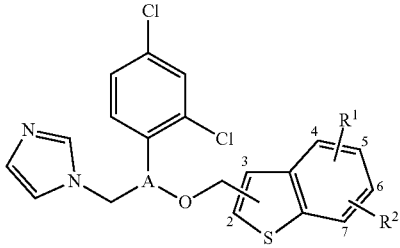

wherein
A is an imino-

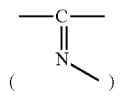

or methine

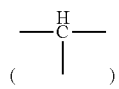

group; and
R¹ and R², which may be the same or different, are hydrogen or halogen, said halogen being attached to the benzo[b]-thiophene group in the 2, 4, 5, 6 or 7 position and the methylene group being bonded to the benzo[b]-thiophene group in 2 or 3 position.

The compounds of formula (XX) and syntheses thereof are, for example, described in published European patent application EP 0 151 477 A2.

In some embodiments in formula (XX) A is an imino-

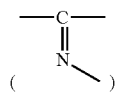

or methine

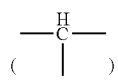

group; and R¹ and R², which may be the same or different, are hydrogen or halogen, said halogen being attached to the benzo[b]-thiophene group in the 5, 6 or 7 position and the methylene group being bonded to the benzo[b]-thiophene group in 2 or 3 position. In some of these embodiments "halogen" at each occurrence is independently F or Cl. In some of these embodiments "halogen" at each occurrence is Cl.

In some embodiments in formula (XX) A is a methine

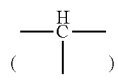

group; and R¹ and R², which may be the same or different, are hydrogen or halogen, said halogen being attached to the benzo[b]-thiophene group in the 5, 6 or 7 position and the methylene group being bonded to the benzo[b]-thiophene group in 2 or 3 position. In some of these embodiments "halogen" at each occurrence is independently F or Cl. In some of these embodiments "halogen" at each occurrence is Cl.

In some embodiments in formula (XX) A is a methine

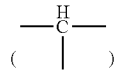

group; and R¹ and R², which may be the same or different, are hydrogen or halogen, said halogen being attached to the benzo[b]-thiophene group in the 5 or 7 position and the methylene group being bonded to the benzo[b]-thiophene group in 2 or 3 position. In some of these embodiments "halogen" at each occurrence is independently F or Cl. In some of these embodiments "halogen" at each occurrence is Cl.

In some embodiments in formula (XX) A is a methine

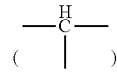

group; and R¹ and R², which may be the same or different, are hydrogen or halogen, said halogen being attached to the benzo[b]-thiophene group in the 6 or 7 position and the methylene group being bonded to the benzo[b]-thiophene group in 3 position. In some of these embodiments "halogen" at each occurrence is independently F or Cl. In some of these embodiments "halogen" at each occurrence is Cl.

In some embodiments the compound of formula (XX) has the structure:

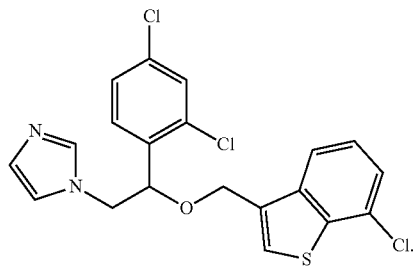 [SMILES: Clc1ccc(C(Cn2ccnc2)OCc2csc3c(Cl)cccc23)c(Cl)c1]

In some embodiments the compound of formula (XX) is sertaconazole.

In some aspects, the present invention provides compounds for use in treating a disease that is related to CYP7B1, said compounds having a structure according to formula (XXI), in any of their stereoisomeric forms or a mixture of stereoisomeric forms in any ratio, and the pharmaceutically acceptable salts thereof, and the pharmaceutically acceptable solvates or hydrates of any of them,

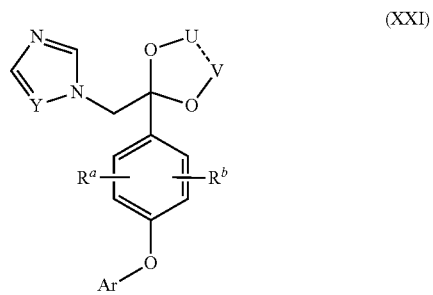

(XXI)

wherein
Y is CH or N;
R$^a$ and R$^b$ are each independently selected from the group consisting of hydrogen, halogen, (C$_1$-C$_3$)alkyl, (C$_1$-C$_3$)alkoxy and NO$_2$;
Ar is phenyl or naphthyl, each of which is independently unsubstituted or mono- or polysubstituted with halogen, (C$_1$-C$_7$)alkyl, (C$_1$-C$_7$)alkoxy, NO$_2$ and/or CF$_3$;
U and V are each, independently, (C$_1$-C$_{12}$)alkyl which is unsubstituted or substituted with halogen or (C$_1$-C$_6$)alkoxy;
or together form the following alkylene bridge

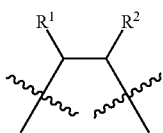

wherein
$R^1$ and $R^2$ are each, independently, selected from the group consisting of (i) hydrogen, (ii) $(C_1-C_{12})$alkyl, (iii) $(C_1-C_{12})$ alkyl which is mono- or polysubstituted with halogen, (iv) phenyl, (v) phenyl which is mono- or polysubstituted with halogen and/or $(C_1-C_3)$alkyl, and (vi) a —$CH_2$—Z—$R^7$ group; wherein
Z is oxygen or sulfur; and
$R^7$ is selected from the group consisting of (i) hydrogen, (ii) $(C_1-C_5)$alkyl, (iii) $(C_1-C_8)$alkyl which is substituted with $(C_1-C_2)$alkoxy, (iv) $(C_3-C_4)$alkenyl, (v) prop-2-ynyl, (vi) 3-haloprop-2-ynyl, (vii) phenyl, (viii) phenyl which is mono- or polysubstituted with $(C_1-C_3)$haloalkyl, $(C_1-C_3)$ alkoxy, $NO_2$ and/or $CF_3$, (ix) benzyl and (x) benzyl which is mono- or polysubstituted with halogen, $(C_1-C_3)$alkyl and/or $(C_1-C_3)$alkoxy.

The compounds of formula (XXI) and syntheses thereof are, for example, described in published European patent application EP 0 065 485 A2.

In some embodiments in formula (XXI) Y is CH or N; $R^a$ and $R^b$ are each independently selected from the group consisting of hydrogen, halogen, and $(C_1-C_3)$alkyl; Ar is phenyl which is independently unsubstituted or mono- or polysubstituted with halogen, $CF_3$ and/or $(C_1-C_7)$alkyl; U and V together are the following alkylene bridge

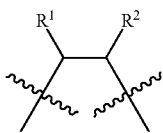

wherein
$R^1$ and $R^2$ are each, independently, selected from the group consisting of (i) hydrogen, (ii) $(C_1-C_{12})$alkyl, and (iii) $(C_1-C_{12})$alkyl which is mono- or polysubstituted with halogen. In some of these embodiments "halogen" at each occurrence is independently F or Cl. In some of these embodiments "halogen" at each occurrence is Cl. In some of these embodiments Ar is 4-chlorophenyl. In some of these embodiments Y is N.

In some embodiments in formula (XXI) Y is CH or N; $R^a$ and $R^b$ are each independently selected from the group consisting of hydrogen and halogen; Ar is phenyl which is independently unsubstituted or mono- or polysubstituted with halogen, $CF_3$ and/or $(C_1-C_7)$alkyl; U and V together are the following alkylene bridge

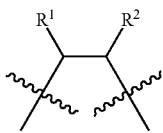

wherein
$R^1$ and $R^2$ are each, independently, selected from the group consisting of (i) hydrogen and (ii) $(C_1-C_{12})$alkyl. In some of these embodiments "halogen" at each occurrence is independently F or Cl. In some of these embodiments "halogen" at each occurrence is Cl. In some of these embodiments Ar is 4-chlorophenyl. In some of these embodiments Y is N.

In some embodiments in formula (XXI) Y is CH or N; $R^a$ and $R^b$ are each independently selected from the group consisting of hydrogen and halogen; Ar is phenyl which is independently unsubstituted or mono- or polysubstituted with halogen, $CF_3$ and/or $(C_1-C_4)$alkyl; U and V together are the following alkylene bridge

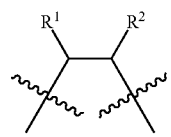

wherein
$R^1$ and $R^2$ are each, independently, selected from the group consisting of (i) hydrogen and (ii) $(C_1-C_6)$alkyl. In some of these embodiments "halogen" at each occurrence is independently F or Cl. In some of these embodiments "halogen" at each occurrence is Cl. In some of these embodiments Ar is 4-chlorophenyl. In some of these embodiments Y is N.

In some embodiments in formula (XXI) Y is CH or N; $R^a$ and $R^b$ are each independently selected from the group consisting of hydrogen and halogen; Ar is phenyl which is independently unsubstituted or mono- or polysubstituted with halogen; U and V together are the following alkylene bridge

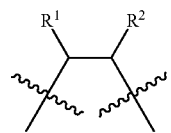

wherein
$R^1$ and $R^2$ are each, independently, selected from the group consisting of (i) hydrogen and (ii) $(C_1-C_6)$alkyl. In some of these embodiments "halogen" at each occurrence is independently F or Cl. In some of these embodiments "halogen" at each occurrence is Cl. In some of these embodiments Ar is 4-chlorophenyl. In some of these embodiments Y is N.

In some embodiments in formula (XXI) Y is CH or N; $R^a$ and $R^b$ are each independently selected from the group consisting of hydrogen and halogen; Ar is phenyl which is independently unsubstituted or mono- or polysubstituted with halogen; U and V together are the following alkylene bridge

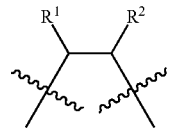

wherein
$R^1$ and $R^2$ are each, independently, selected from the group consisting of (i) hydrogen and (ii) $(C_1-C_3)$alkyl. In some of these embodiments "halogen" at each occurrence is independently F or Cl. In some of these embodiments "halogen"

at each occurrence is Cl. In some of these embodiments Ar is 4-chlorophenyl. In some of these embodiments Y is N.

In some embodiments in formula (XXI) Y is CH or N; $R^a$ and $R^b$ are each independently selected from the group consisting of hydrogen and halogen; Ar is phenyl which is independently unsubstituted or mono- or polysubstituted with halogen; U and V together are the following alkylene bridge

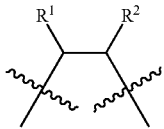

wherein
$R^1$ and $R^2$ are each, independently, selected from the group consisting of (i) hydrogen and (ii) $(C_1-C_2)$alkyl. In some of these embodiments "halogen" at each occurrence is independently F or Cl. In some of these embodiments "halogen" at each occurrence is Cl. In some of these embodiments Ar is 4-chlorophenyl. In some of these embodiments Y is N.

In some embodiments in formula (XXI) Y is N; $R^a$ and $R^b$ are each independently selected from the group consisting of hydrogen and halogen; Ar is phenyl which is independently unsubstituted or mono- or polysubstituted with halogen; U and V together are the following alkylene bridge

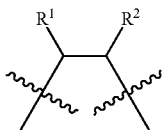

wherein
$R^1$ and $R^2$ are each, independently, selected from the group consisting of (i) hydrogen and (ii) $(C_1-C_3)$alkyl. In some of these embodiments "halogen" at each occurrence is independently F or Cl. In some of these embodiments "halogen" at each occurrence is Cl. In some of these embodiments Ar is 4-chlorophenyl.

In some embodiments in formula (XXI) Y is N; $R^a$ and $R^b$ are each independently selected from the group consisting of hydrogen and halogen; Ar is phenyl which is independently unsubstituted or mono- or polysubstituted with halogen; U and V together are the following alkylene bridge

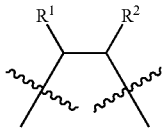

wherein
$R^1$ and $R^2$ are each, independently, selected from the group consisting of (i) hydrogen and (ii) $(C_1-C_2)$alkyl. In some of these embodiments "halogen" at each occurrence is independently F or Cl. In some of these embodiments "halogen" at each occurrence is Cl. In some of these embodiments Ar is 4-chlorophenyl.

In some embodiments the compound of formula (XXI) has the structure:

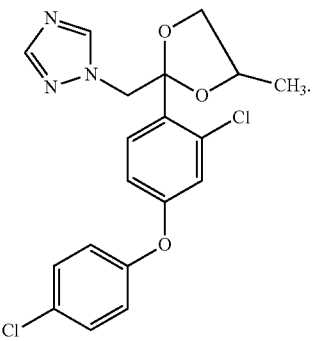 [SMILES: CC1COC(Cn2cncn2)(c2ccc(Oc3ccc(Cl)cc3)cc2Cl)O1]

In some embodiment the compound of formula (XXI) is difenoconazole.

In some aspects, the present invention provides compounds for use in treating a disease that is related CYP7B1, said compounds having a structure according to formula (VII), in any of their stereoisomeric forms or a mixture of stereoisomeric forms in any ratio, and the pharmaceutically acceptable salts thereof, and the pharmaceutically acceptable solvates or hydrates of any of them,

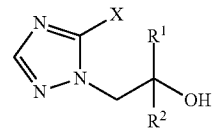

(XXII)

wherein
$R^1$ and $R^2$ are the same or different and are selected from the group consisting of optionally substituted $(C_1-C_6)$alkyl, optionally substituted $(C_2-C_6)$alkenyl, optionally substituted $(C_3-C_7)$cycloalkyl, optionally substituted $(C_6-C_{10})$aryl$(C_1-C_4)$alkyl, optionally substituted $(C_6-C_{10})$aryl$(C_2-C_4)$alkenyl, optionally substituted $(C_6-C_{10})$aryloxy$(C_1-C_4)$alkyl, optionally substituted $(C_6-C_{10})$aryl and optionally substituted $(C_3-C_{10})$heteroaryl;
X is selected from the group consisting of —SH; —SR$^3$, —SO$_2$R$^3$ and SO$_3$H; and
$R^3$ is selected from the group consisting of (i) $(C_1-C_6)$alkyl optionally substituted with fluorine and/or chlorine, (ii) $(C_2-C_6)$alkenyl optionally substituted with fluorine and/or chlorine, (iii) optionally substituted $(C_6-C_{10})$aryl$(C_1-C_4)$alkyl and (iv) optionally substituted $(C_6-C_{10})$aryl.

The compounds of formula (XXII) and syntheses thereof are, for example, described in published German patent application (Offenlegungsschrift) DE 195 28 046 A1.

"Optionally substituted $(C_1-C_6)$alkyl" means with regard to the compounds of formula (XXII) that the $(C_1-C_6)$alkyl is unsubstituted; or that the $(C_1-C_6)$alkyl is substituted with 1 to 4 substituents independently selected from the group consisting of halogen, $(C_1-C_4)$alkoxy, $(C_1-C_4)$alkoxyimino and $(C_3-C_7)$cycloalkyl.

"Optionally substituted $(C_1-C_6)$alkenyl" means with regard to the compounds of formula (XXII) that the $(C_1-C_6)$alkenyl is unsubstituted; or that the $(C_1-C_6)$alkenyl is substituted with 1 to 4 substituents independently selected from the group consisting of halogen, $(C_1-C_4)$alkoxy and $(C_3-C_7)$cycloalkyl.

"Optionally substituted $(C_3-C_7)$cycloalkyl" means with regard to the compounds of formula (XXII) that the $(C_3$-

$C_7$)cycloalkyl is unsubstituted; or that the ($C_3$-$C_7$)cycloalkyl is substituted with 1 to 3 substituents independently selected from the group consisting of halogen, cyano and ($C_1$-$C_4$)alkyl.

"Optionally substituted ($C_6$-$C_{10}$)aryl($C_1$-$C_4$)alkyl" means with regard to the compounds of formula (XXII) that the ($C_6$-$C_{10}$)aryl($C_1$-$C_4$)alkyl is unsubstituted; or that the aryl portion of the ($C_6$-$C_{10}$)aryl($C_1$-$C_4$)alkyl is substituted with 1 to 3 substituents independently selected from the group consisting of halogen, ($C_1$-$C_4$)alkyl, ($C_1$-$C_4$)alkoxy, ($C_1$-$C_4$) alkylthio, ($C_1$-$C_2$)haloalkyl, ($C_1$-$C_5$)haloalkoxy, ($C_1$-$C_2$)haloalkylthio, ($C_3$-$C_7$)cyloalkyl, phenyl, phenoxy, alkoxycarbonyl having 1 to 4 carbon atoms in the alkoxy portion, alkoxyiminoalkyl having 1 to 4 carbon atoms in the alkoxy portion and 1 to 4 carbon atoms in the alkyl portion, nitro and cyano.

"Optionally substituted ($C_6$-$C_{10}$)aryl($C_2$-$C_4$)alkenyl" means with regard to the compounds of formula (XXII) that the ($C_6$-$C_{10}$)aryl($C_2$-$C_4$)alkenyl is unsubstituted; or that the aryl portion of the ($C_6$-$C_{10}$)aryl($C_2$-$C_4$)alkenyl is substituted with 1 to 3 substituents independently selected from the group consisting of halogen, ($C_1$-$C_4$)alkyl, ($C_1$-$C_4$)alkoxy, ($C_1$-$C_4$)alkylthio, ($C_1$-$C_2$)haloalkyl, ($C_1$-$C_5$)haloalkoxy, ($C_1$-$C_2$)haloalkylthio, ($C_3$-$C_7$)cyloalkyl, phenyl, phenoxy, alkoxycarbonyl having 1 to 4 carbon atoms in the alkoxy portion, alkoxyiminoalkyl having 1 to 4 carbon atoms in the alkoxy portion and 1 to 4 carbon atoms in the alkyl portion, nitro and cyano.

"Optionally substituted ($C_6$-$C_{10}$)aryloxy($C_1$-$C_4$)alkyl" means with regard to the compounds of formula (XXII) that the ($C_6$-$C_{10}$)aryloxy($C_1$-$C_4$)alkyl is unsubstituted; or that the aryl portion of the ($C_6$-$C_{10}$)aryl($C_2$-$C_4$)alkenyl is substituted with 1 to 3 substituents independently selected from the group consisting of halogen, ($C_1$-$C_4$)alkyl, ($C_1$-$C_4$)alkoxy, ($C_1$-$C_4$)alkylthio, ($C_1$-$C_2$)haloalkyl, ($C_1$-$C_5$)haloalkoxy, ($C_1$-$C_2$)haloalkylthio, ($C_3$-$C_7$)cyloalkyl, phenyl, phenoxy, alkoxycarbonyl having 1 to 4 carbon atoms in the alkoxy portion, alkoxyiminoalkyl having 1 to 4 carbon atoms in the alkoxy portion and 1 to 4 carbon atoms in the alkyl portion, nitro and cyano.

"Optionally substituted ($C_6$-$C_{10}$)aryl" means with regard to the compounds of formula (XXII) that the ($C_6$-$C_{10}$)aryl is unsubstituted; or that the ($C_6$-$C_{10}$)aryl is substituted with 1 to 3 substituents independently selected from the group consisting of halogen, ($C_1$-$C_4$)alkyl, ($C_1$-$C_4$)alkoxy, ($C_1$-$C_4$)alkylthio, ($C_1$-$C_2$)haloalkyl, ($C_1$-$C_5$)haloalkoxy, ($C_1$-$C_2$)haloalkylthio, ($C_3$-$C_7$)cyloalkyl, phenyl, phenoxy, alkoxycarbonyl having 1 to 4 carbon atoms in the alkoxy portion, alkoxyiminoalkyl having 1 to 4 carbon atoms in the alkoxy portion and 1 to 4 carbon atoms in the alkyl portion, nitro and cyano.

"Optionally substituted ($C_3$-$C_{10}$)heteroaryl" means with regard to the compounds of formula (XXII) that the ($C_3$-$C_{10}$)heteroaryl is unsubstituted; or that the ($C_3$-$C_{10}$)heteroaryl is substituted with 1 to 3 substituents independently selected from the group consisting of halogen, ($C_1$-$C_4$)alkyl, ($C_1$-$C_4$)alkoxy, ($C_1$-$C_4$)alkylthio, ($C_1$-$C_2$)haloalkyl, ($C_1$-$C_5$)haloalkoxy, ($C_1$-$C_2$)haloalkylthio, ($C_3$-$C_7$)cyloalkyl, phenyl, phenoxy, alkoxycarbonyl having 1 to 4 carbon atoms in the alkoxy portion and 1 to 4 carbon atoms in the alkyl portion, nitro and cyano. In formula (XXII) the ($C_3$-$C_{10}$)heteroaryl may comprise 1 to 3 heteroatoms such as nitrogen, sulfur and/or oxygen.

As is readily appreciated by a person skilled in the art the compounds of formula (XXII) in which X represents an SH moiety may exist in the "mercapto" form of formula:

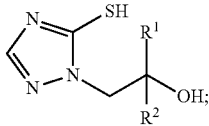

or in the tautomeric "thiono" form of formula:

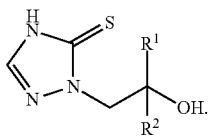

For the sake of simplicity herein only the "mercapto" form is mentioned.

In some embodiments in formula (XXII) $R^1$ and $R^2$ are the same or different and are selected from the group consisting of (i) ($C_1$-$C_6$)alkyl optionally substituted with halogen, (ii) ($C_3$-$C_7$)cycloalkyl optionally substituted with halogen, and (iii) ($C_6$-$C_{10}$)aryl($C_1$-$C_4$)alkyl optionally substituted with halogen in the aryl portion; and X is —SH. In some of these embodiments "halogen" at each occurrence is independently F or Cl. In some of these embodiments "halogen" at each occurrence is Cl.

In some embodiments in formula (XXII) $R^1$ and $R^2$ are the same or different and are selected from the group consisting of (i) ($C_1$-$C_6$)alkyl optionally substituted with halogen, (ii) ($C_3$-$C_7$)cycloalkyl optionally substituted with halogen, and (iii) phenyl($C_1$-$C_4$)alkyl optionally substituted with halogen in the phenyl portion; and X is —SH. In some of these embodiments "halogen" at each occurrence is independently F or Cl. In some of these embodiments "halogen" at each occurrence is Cl.

In some embodiments in formula (XXII) $R^1$ and $R^2$ are the same or different and are selected from the group consisting of (i) ($C_1$-$C_4$)alkyl optionally substituted with halogen, (ii) ($C_3$-$C_5$)cycloalkyl optionally substituted with halogen, and (iii) phenyl($C_1$-$C_4$)alkyl optionally substituted with halogen in the phenyl portion; and X is —SH. In some of these embodiments "halogen" at each occurrence is independently F or Cl. In some of these embodiments "halogen" at each occurrence is Cl.

In some embodiments in formula (XXII) $R^1$ and $R^2$ are the same or different and are selected from the group consisting of (i) ($C_1$-$C_4$)alkyl optionally substituted with halogen, (ii) ($C_3$-$C_5$)cycloalkyl optionally substituted with halogen, and (iii) phenyl($C_1$-$C_2$)alkyl optionally substituted with halogen in the phenyl portion; and X is —SH. In some of these embodiments "halogen" at each occurrence is independently F or Cl. In some of these embodiments "halogen" at each occurrence is Cl.

In some embodiments in formula (XXII) $R^1$ and $R^2$ are the same or different and are selected from the group consisting of (i) ($C_1$-$C_2$)alkyl optionally substituted with halogen, (ii) ($C_3$-$C_5$)cycloalkyl optionally substituted with halogen, and (iii) phenyl($C_1$-$C_2$)alkyl optionally substituted with halogen in the phenyl portion; and X is —SH. In some of these embodiments "halogen" at each occurrence is independently F or Cl. In some of these embodiments "halogen" at each occurrence is Cl.

In some embodiments in formula (XXII) $R^1$ is selected from the group consisting of (i) ($C_1$-$C_6$)alkyl optionally substituted with halogen, and (ii) ($C_3$-$C_7$)cycloalkyl optionally substituted with halogen; R² is (C₆-C₁₀)aryl(C₁-C₄)alkyl optionally substituted with halogen in the aryl portion; and X is —SH. In some of these embodiments R¹ is (C₃-C₇)cycloalkyl optionally substituted with halogen. In some of these embodiments R¹ is cyclopropyl optionally substituted with halogen. In some of these embodiments "halogen" at each occurrence is independently F or Cl. In some of these embodiments "halogen" at each occurrence is Cl. In some of these embodiments R² is 2-chlorobenzyl.

In some embodiments in formula (XXII) R¹ is selected from the group consisting of (i) (C₁-C₆)alkyl optionally substituted with halogen, and (ii) (C₃-C₇)cycloalkyl optionally substituted with halogen; R² is phenyl(C₁-C₄)alkyl optionally substituted with halogen in the phenyl portion; and X is —SH. In some of these embodiments R¹ is (C₃-C₇)cycloalkyl optionally substituted with halogen. In some of these embodiments R¹ is cyclopropyl optionally substituted with halogen. In some of these embodiments "halogen" at each occurrence is independently F or Cl. In some of these embodiments "halogen" at each occurrence is Cl. In some of these embodiments R² is 2-chlorobenzyl.

In some embodiments in formula (XXII) R¹ is selected from the group consisting of (i) (C₁-C₄)alkyl optionally substituted with halogen, and (ii) (C₃-C₅)cycloalkyl optionally substituted with halogen; R² is phenyl(C₁-C₄)alkyl optionally substituted with halogen in the phenyl portion; and X is —SH. In some of these embodiments R¹ is (C₃-C₇)cycloalkyl optionally substituted with halogen. In some of these embodiments R¹ is cyclopropyl optionally substituted with halogen. In some of these embodiments "halogen" at each occurrence is independently F or Cl. In some of these embodiments "halogen" at each occurrence is Cl. In some of these embodiments R² is 2-chlorobenzyl.

In some embodiments in formula (XXII) R¹ is selected from the group consisting of (i) (C₁-C₄)alkyl optionally substituted with halogen, and (ii) (C₃-C₅)cycloalkyl optionally substituted with halogen; R² is phenyl(C₁-C₂)alkyl optionally substituted with halogen in the phenyl portion; and X is —SH. In some of these embodiments R¹ is (C₃-C₅)cycloalkyl optionally substituted with halogen. In some of these embodiments R¹ is cyclopropyl optionally substituted with halogen. In some of these embodiments "halogen" at each occurrence is independently F or Cl. In some of these embodiments "halogen" at each occurrence is Cl. In some of these embodiments R² is 2-chlorobenzyl.

In some embodiments in formula (XXII) R¹ is selected from the group consisting of (i) (C₁-C₂)alkyl optionally substituted with halogen, and (ii) (C₃-C₅)cycloalkyl optionally substituted with halogen; R² is phenyl(C₁-C₂)alkyl optionally substituted with halogen in the phenyl portion; and X is —SH. In some of these embodiments R¹ is (C₃-C₅)cycloalkyl optionally substituted with halogen. In some of these embodiments R¹ is cyclopropyl optionally substituted with halogen. In some of these embodiments "halogen" at each occurrence is independently F or Cl. In some of these embodiments "halogen" at each occurrence is Cl. In some of these embodiments R² is 2-chlorobenzyl.

In some embodiments in formula (XXII) R¹ is (C₃-C₅)cycloalkyl optionally substituted with halogen; R² is phenyl(C₁-C₂)alkyl optionally substituted with halogen in the phenyl portion; and X is —SH. In some of these embodiments R¹ is cyclopropyl optionally substituted with halogen. In some of these embodiments "halogen" at each occurrence is independently F or Cl. In some of these embodiments "halogen" at each occurrence is Cl. In some of these embodiments R² is 2-chlorobenzyl.

In some embodiments in formula (XXII) R¹ is cyclopropyl optionally substituted with halogen; R² is phenyl(C₁-C₂)alkyl optionally substituted with halogen in the phenyl portion; and X is —SH. In some of these embodiments "halogen" at each occurrence is independently F or Cl. In some of these embodiments "halogen" at each occurrence is Cl. In some of these embodiments R² is 2-chlorobenzyl.

In some embodiments the compound of formula (XXII) has the structure:

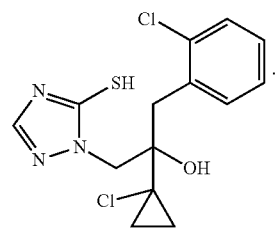 [SMILES: OC(Cc1ccccc1Cl)(Cn1ncnc1S)C1(Cl)CC1]

The corresponding "thiono" form has the structure:

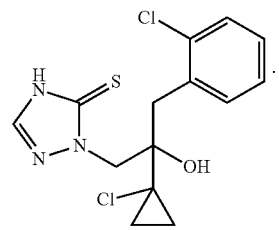 [SMILES: OC(Cc1ccccc1Cl)(Cn1nc[nH]c1=S)C1(Cl)CC1]

In some embodiments the compound of formula (XXII) is prothioconazole.

In some aspects, the present invention provides compounds for use in treating a disease that is related to CYP7B1, said compounds having a structure according to formula (XXIII), in any of their stereoisomeric forms or a mixture of stereoisomeric forms in any ratio, and the pharmaceutically acceptable salts thereof, and the pharmaceutically acceptable solvates or hydrates of any of them,

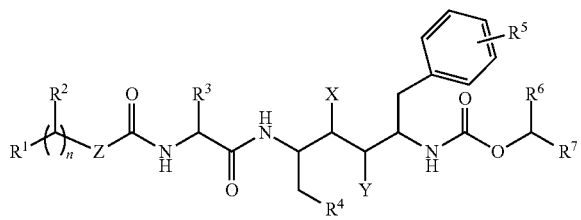

(XXIII)

wherein
R¹ is monosubstituted thiazolyl, monosubstituted oxazolyl, monosubstituted isoxazolyl or monosubstituted isothiazolyl, wherein the substituent is each independently selected from (i) (C₁-C₆)alkyl, (ii) (C₂-C₆)alkenyl, (iii) (C₃-C₇)cycloalkyl, (iv) (C₃-C₇)cycloalkyl(C₁-C₆)alkyl, (v) (C₅-C₇)cycloalkenyl, (vi) (C₅-C₇)cycloalkenyl(C₁-C₆)alkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halogen, $(C_1-C_6)$alkyl, hydroxy, alkoxy and thioalkoxy, (viii) (heterocyclic)$(C_1-C_6)$alkyl wherein heterocyclic is defined as above, (ix) $(C_1-C_6)$alkoxy $(C_1-C_6)$alkyl, (x) thio$(C_1-C_6)$alkoxy$(C_1-C_6)$alkyl, (xi) $(C_1-C_6)$alkylamino, (xii) di$(C_1-C_6)$alkylamino, (xiii) phenyl wherein the phenyl ring is unsubstituted or substituted with a substituent selected from halo, $(C_1-C_6)$alkyl, hydroxy, $(C_1-C_6)$alkoxy and $(C_1-C_6)$thioalkoxy, (xiv) phenyl$(C_1-C_6)$alkyl wherein the phenyl ring is unsubstituted or substituted as defined above, (xv) di$(C_1-C_6)$alkylamino$(C_1-C_6)$alkyl, (xvi) $(C_1-C_6)$alkoxy and (xvii) $(C_1-C_6)$thioalkoxy;
n is 1, 2 or 3;
$R^2$ is hydrogen or $(C_1-C_6)$alkyl;
$R^3$ is $(C_1-C_6)$alkyl;
$R^4$ is phenyl, thiazolyl or oxazolyl, wherein the phenyl, thiazolyl or oxazolyl ring is unsubstituted or substituted with a substituent selected from (i) halogen, (ii) $(C_1-C_6)$alkyl, (iii) hydroxy, (iv) $(C_1-C_6)$alkoxy and (v) $(C_1-C_6)$thioalkoxy;
$R^5$ is hydrogen, halogen, $(C_1-C_6)$alkyl, hydroxy, $(C_1-C_6)$alkoxy or $(C_1-C_6)$thioalkoxy;
$R^6$ is hydrogen or $(C_1-C_6)$alkyl;
$R^7$ is thiazolyl, oxazolyl, isoxazolyl or isothiazolyl, wherein the thiazolyl, oxazolyl, isoxazolyl or isothiazolyl ring is unsubstituted or substituted with $(C_1-C_6)$alkyl;
X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and
Z is absent, —O—, —S—, —$CH_2$— or —N($R^8$)— wherein $R^8$ is $(C_1-C_6)$alkyl, $(C_3-C_7)$cycloalkyl, —OH or —NHR$^{8a}$ wherein $R^{8a}$ is hydrogen, $(C_1-C_6)$alkyl or an N-protecting group.

The compounds of formula (XXIII) and syntheses thereof are, for example, described in published international patent application WO 94/14436 A1.

In some embodiments in formula (XXIII) $R^1$ is monosubstituted thiazolyl, monosubstituted oxazolyl, monosubstituted isoxazolyl or monosubstituted isothiazolyl, wherein the substituent is each independently selected from $(C_1-C_6)$ alkyl and $(C_3-C_7)$cycloalkyl; n is 1 or 2; $R^2$ is hydrogen or $(C_1-C_6)$alkyl; $R^3$ is $(C_1-C_6)$alkyl; $R^4$ is phenyl, wherein the phenyl ring is unsubstituted or substituted with a substituent selected from halogen and $(C_1-C_6)$alkyl; $R^5$ is hydrogen, halogen or $(C_1-C_6)$alkyl; $R^6$ is hydrogen or $(C_1-C_6)$alkyl; $R^7$ is thiazolyl, oxazolyl, isoxazolyl or isothiazolyl, wherein the thiazolyl, oxazolyl, isoxazolyl or isothiazolyl ring is unsubstituted or substituted with $(C_1-C_6)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —$CH_2$— or —N($R^8$)— wherein $R^8$ is $(C_1-C_6)$alkyl or $(C_3-C_7)$cycloalkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is monosubstituted thiazolyl, monosubstituted oxazolyl, monosubstituted isoxazolyl or monosubstituted isothiazolyl, wherein the substituent is each independently selected from $(C_1-C_4)$ alkyl and $(C_3-C_5)$cycloalkyl; n is 1 or 2; $R^2$ is hydrogen or $(C_1-C_4)$alkyl; $R^3$ is $(C_1-C_4)$alkyl; $R^4$ is phenyl, wherein the phenyl ring is unsubstituted or substituted with a substituent selected from halogen and $(C_1-C_4)$alkyl; $R^5$ is hydrogen, halogen or $(C_1-C_4)$alkyl; $R^6$ is hydrogen or $(C_1-C_4)$alkyl; $R^7$ is thiazolyl, oxazolyl, isoxazolyl or isothiazolyl, wherein the thiazolyl, oxazolyl, isoxazolyl or isothiazolyl ring is unsubstituted or substituted with $(C_1-C_4)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —$CH_2$— or —N($R^8$)— wherein $R^8$ is $(C_1-C_4)$alkyl or $(C_3-C_5)$cycloalkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is monosubstituted thiazolyl, monosubstituted oxazolyl, monosubstituted isoxazolyl or monosubstituted isothiazolyl, wherein the substituent is each independently selected from $(C_1-C_3)$ alkyl and $(C_3-C_5)$cycloalkyl; n is 1 or 2; $R^2$ is hydrogen or $(C_1-C_2)$alkyl; $R^3$ is $(C_1-C_3)$alkyl; $R^4$ is phenyl, wherein the phenyl ring is unsubstituted or substituted with a substituent selected from halogen and $(C_1-C_2)$alkyl; $R^5$ is hydrogen, halogen or $(C_1-C_2)$alkyl; $R^6$ is hydrogen or $(C_1-C_2)$alkyl; $R^7$ is thiazolyl, oxazolyl, isoxazolyl or isothiazolyl, wherein the thiazolyl, oxazolyl, isoxazolyl or isothiazolyl ring is unsubstituted or substituted with $(C_1-C_3)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —$CH_2$— or —N($R^8$)— wherein $R^8$ is $(C_1-C_2)$alkyl or $(C_3-C_5)$cycloalkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is monosubstituted thiazolyl, wherein the substituent is selected from $(C_1-C_6)$alkyl and $(C_3-C_7)$cycloalkyl; n is 1 or 2; $R^2$ is hydrogen or $(C_1-C_6)$alkyl; $R^3$ is $(C_1-C_6)$alkyl; $R^4$ is phenyl, wherein the phenyl ring is unsubstituted or substituted with a substituent selected from halogen and $(C_1-C_6)$alkyl; $R^5$ is hydrogen, halogen or $(C_1-C_6)$alkyl; $R^6$ is hydrogen or $(C_1-C_6)$alkyl; $R^7$ is thiazolyl, wherein the thiazolyl ring is unsubstituted or substituted with $(C_1-C_6)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —$CH_2$— or —N($R^8$)— wherein $R^8$ is $(C_1-C_6)$alkyl or $(C_3-C_7)$cycloalkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is monosubstituted thiazolyl, wherein the substituent is $(C_1-C_6)$ alkyl; n is 1 or 2; $R^2$ is hydrogen or $(C_1-C_6)$alkyl; $R^3$ is $(C_1-C_6)$alkyl; $R^4$ is phenyl, wherein the phenyl ring is unsubstituted or substituted with a substituent selected from halogen and $(C_1-C_6)$alkyl; $R^5$ is hydrogen, halogen or $(C_1-C_6)$alkyl; $R^6$ is hydrogen or $(C_1-C_6)$alkyl; $R^7$ is thiazolyl, wherein the thiazolyl ring is unsubstituted or substituted with $(C_1-C_6)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —$CH_2$— or —N($R^8$)— wherein $R^8$ is $(C_1-C_6)$alkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is mono-substituted thiazolyl, wherein the substituent is selected from $(C_1-C_4)$alkyl and $(C_3-C_5)$cycloalkyl; n is 1 or 2; $R^2$ is hydrogen or $(C_1-C_4)$alkyl; $R^3$ is $(C_1-C_4)$alkyl; $R^4$ is phenyl, wherein the phenyl ring is unsubstituted or substituted with a substituent selected from halogen and $(C_1-C_4)$alkyl; $R^5$ is hydrogen, halogen or $(C_1-C_4)$alkyl; $R^6$ is hydrogen or $(C_1-C_4)$alkyl; $R^7$ is thiazolyl, wherein the thiazolyl ring is unsubstituted or substituted with $(C_1-C_4)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —CH$_2$— or —N($R^8$)— wherein $R^8$ is $(C_1-C_4)$alkyl or $(C_3-C_5)$cycloalkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is mono-substituted thiazolyl, wherein the substituent is selected from $(C_1-C_3)$alkyl and $(C_3-C_5)$cycloalkyl; n is 1 or 2; $R^2$ is hydrogen or $(C_1-C_2)$alkyl; $R^3$ is $(C_1-C_3)$alkyl; $R^4$ is phenyl, wherein the phenyl ring is unsubstituted or substituted with a substituent selected from halogen and $(C_1-C_2)$alkyl; $R^5$ is hydrogen, halogen or $(C_1-C_2)$alkyl; $R^6$ is hydrogen or $(C_1-C_2)$alkyl; $R^7$ is thiazolyl, wherein the thiazolyl ring is unsubstituted or substituted with $(C_1-C_3)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —CH$_2$— or —N($R^8$)— wherein $R^8$ is $(C_1-C_2)$alkyl or $(C_3-C_5)$cycloalkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is mono-substituted thiazolyl, wherein the substituent is $(C_1-C_4)$alkyl; n is 1 or 2; $R^2$ is hydrogen or $(C_1-C_4)$alkyl; $R^3$ is $(C_1-C_4)$alkyl; $R^4$ is phenyl, wherein the phenyl ring is unsubstituted or substituted with a substituent selected from halogen and $(C_1-C_4)$alkyl; $R^5$ is hydrogen, halogen or $(C_1-C_4)$alkyl; $R^6$ is hydrogen or $(C_1-C_4)$alkyl; $R^7$ is thiazolyl, wherein the thiazolyl ring is unsubstituted or substituted with $(C_1-C_4)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —CH$_2$— or —N($R^8$)— wherein $R^8$ is $(C_1-C_4)$alkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is mono-substituted thiazolyl, wherein the substituent is $(C_1-C_3)$alkyl; n is 1 or 2; $R^2$ is hydrogen or $(C_1-C_2)$alkyl; $R^3$ is $(C_1-C_3)$alkyl; $R^4$ is phenyl, wherein the phenyl ring is unsubstituted or substituted with a substituent selected from halogen and $(C_1-C_2)$alkyl; $R^5$ is hydrogen, halogen or $(C_1-C_2)$alkyl; $R^6$ is hydrogen or $(C_1-C_2)$alkyl; $R^7$ is thiazolyl, wherein the thiazolyl ring is unsubstituted or substituted with $(C_1-C_3)$alkyl; X is hydrogen and Y is —OH or X is —OH and Y is hydrogen, with the proviso that X is hydrogen and Y is —OH when Z is —N($R^8$)— and $R^7$ is unsubstituted and with the proviso that X is hydrogen and Y is —OH when $R^3$ is methyl and $R^7$ is unsubstituted; and Z is —CH$_2$— or —N($R^8$)— wherein $R^8$ is $(C_1-C_2)$alkyl. In some of these embodiments "halogen" at each occurrence is independently F or Cl. In some of these embodiments "halogen" at each occurrence is Cl. In some of these embodiments n is 1.

In some embodiments in formula (XXIII) $R^1$ is mono-substituted thiazolyl, wherein the substituent is $(C_1-C_6)$alkyl; n is 1 or 2; $R^2$ is hydrogen; $R^3$ is $(C_1-C_6)$alkyl; $R^4$ is phenyl, wherein the phenyl ring is unsubstituted; $R^5$ is hydrogen; $R^6$ is hydrogen; $R^7$ is thiazolyl, wherein the thiazolyl ring is unsubstituted; X is hydrogen and Y is —OH; and Z is —N($R^8$)— wherein $R^8$ is $(C_1-C_6)$alkyl. In some of these embodiments n is 1.

In some embodiments in formula (XXIII) $R^1$ is mono-substituted thiazolyl, wherein the substituent is $(C_1-C_4)$alkyl; n is 1 or 2; $R^2$ is hydrogen; $R^3$ is $(C_1-C_4)$alkyl; $R^4$ is phenyl, wherein the phenyl ring is unsubstituted; $R^5$ is hydrogen; $R^6$ is hydrogen; $R^7$ is thiazolyl, wherein the thiazolyl ring is unsubstituted; X is hydrogen and Y is —OH; and Z is —N($R^8$)— wherein $R^8$ is $(C_1-C_4)$alkyl. In some of these embodiments n is 1.

In some embodiments in formula (XXIII) $R^1$ is mono-substituted thiazolyl, wherein the substituent is $(C_1-C_3)$alkyl; n is 1 or 2; $R^2$ is hydrogen; $R^3$ is $(C_1-C_3)$alkyl; $R^4$ is phenyl, wherein the phenyl ring is unsubstituted; $R^5$ is hydrogen; $R^6$ is hydrogen; $R^7$ is thiazolyl, wherein the thiazolyl ring is unsubstituted; X is hydrogen and Y is —OH; and Z is —N($R^8$)— wherein $R^8$ is $(C_1-C_2)$alkyl. In some of these embodiments n is 1.

In some embodiments the compound of formula (XXIII) has the structure:

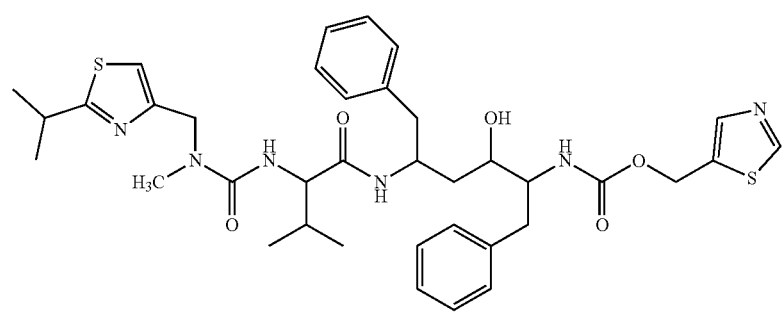

In some embodiments the compound of formula (XXIII) has the structure:

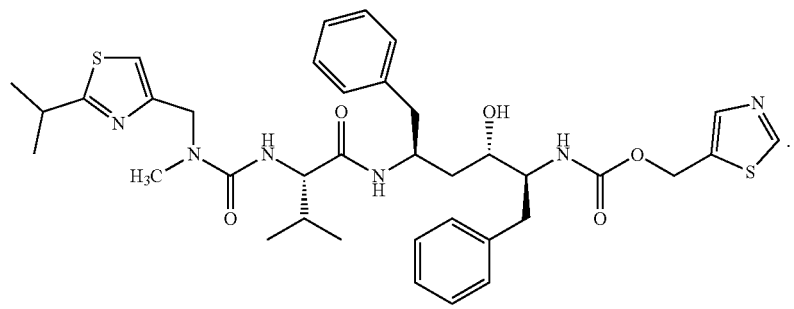 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

In some embodiments the compound of formula (XXIII) has the structure:

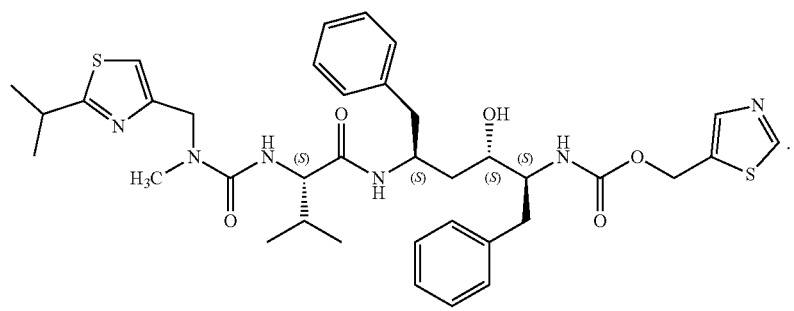

In some embodiments the compound of formula (XXIII) is ritonavir.

In some aspects, the present invention provides compounds for use in treating a disease that is related to CYP7B1, said compounds having a structure according to formula (XXIV), in any of their stereoisomeric forms or a mixture of stereoisomeric forms in any ratio, and the pharmaceutically acceptable salts thereof, and the pharmaceutically acceptable solvates or hydrates of any of them, (XXIV)

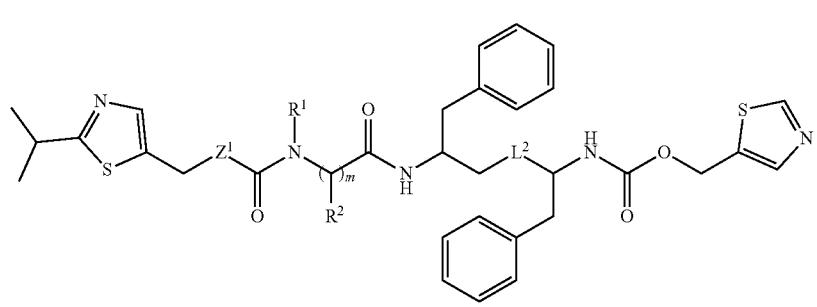

wherein
$Z^1$ is —O— or —N($R^7$)—;
$L^2$ is a covalent bond, —C($R^6$)$_2$— or —C(O)—;
$R^1$ is independently selected from the group consisting of hydrogen, ($C_1$-$C_6$)alkyl, substituted ($C_1$-$C_6$)alkyl, ($C_6$-$C_{10}$)aryl($C_1$-$C_6$)alkyl, and substituted ($C_6$-$C_{10}$)aryl($C_1$-$C_6$)alkyl;
$R^2$ is each independently selected from the group consisting of H, ($C_1$-$C_6$)alkyl, substituted ($C_1$-$C_6$)alkyl, ($C_1$-$C_6$)alkoxy ($C_1$-$C_6$)alkyl, hydroxy($C_1$-$C_6$)alkyl, ($C_6$-$C_{10}$)aryl($C_1$-$C_6$) heteroalkyl, substituted ($C_6$-$C_{10}$)aryl($C_1$-$C_6$)heteroalkyl, ($C_6$-$C_{10}$)aryl($C_1$-$C_6$)alkyl, substituted ($C_6$-$C_{10}$)aryl($C_1$-$C_6$) alkyl, ($C_3$-$C_7$)heterocyclyl($C_1$-$C_6$)alkyl, substituted ($C_1$-$C_6$) heterocyclyl($C_1$-$C_6$)alkyl, ($C_1$-$C_6$)aminoalkyl, substituted ($C_1$-$C_6$)aminoalkyl, —($C_1$-$C_6$)alkylene-C(O)—OH, —($C_1$-$C_6$)alkylene-C(O)—O—($C_1$-$C_6$)alkyl, —($C_1$-$C_6$)alkylene-C (O)amino, and —($C_1$-$C_6$)alkylene-C(O)—($C_1$-$C_6$)alkyl;
$R^6$ is selected from the group consisting of hydrogen, ($C_1$-$C_6$)alkyl, substituted ($C_1$-$C_6$)alkyl, and ($C_1$-$C_6$)heteroalkyl;
$R^7$ is selected from the group consisting of hydrogen, ($C_1$-$C_6$)alkyl, substituted ($C_1$-$C_6$)alkyl, ($C_1$-$C_6$)heteroalkyl, ($C_3$-$C_7$)carbocyclyl, substituted ($C_3$-$C_7$)carbocyclyl, ($C_3$-$C_7$)heterocyclyl, and substituted ($C_3$-$C_7$)heterocyclyl; and
m is 1 or 2.

The compounds of formula (XXIV) and syntheses thereof are, for example, described in published international patent application WO 2008/010921 A2.

With regard to the compounds of formula (XXIV) the term "substituted" in reference to alkyl, alkylene, aryl, arylalkyl, heterocyclyl, heteroaryl, carbocyclyl, etc., for example "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each indecently replaced with a non-hydrogen substituent. Typical substituents include, but are not limited to, —X, —R, —O—, =O, —OR, —SR, —S—, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —NHS(=O)$_2$R, —C(=O)R, —C(=O)NRR, S(=O)$_2$O—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(OR)$_2$, —P(=O)(OH)$_2$, —P(O)(OR)(O$^-$), —C(=O)R, —C(=O) OR, —C(=O)X, —C(S)R, —C(O)OR, —C(O)O$^-$, —C(S) OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or a prodrug moiety. Alkylene, alkenylene, and alkynylene groups may also be similarly substituted. When the number of carbon atoms is designated for a substituted group, the number of carbon atoms refers to the group, not the substituent (unless otherwise indicated). For example, a substituted (C$_1$-C$_4$) alkyl refers to a (C$_1$-C$_4$)alkyl, which can be substituted with groups having more the, e.g., 4 carbon atoms.

In some embodiments in formula (XXIV) Z$^1$ is —O— or —N(R$^7$)—; L$^2$ is a covalent bond or —C(R$^6$)$_2$—; R$^1$ is independently selected from the group consisting of hydrogen and (C$_1$-C$_6$)alkyl; R$^2$ is each independently selected from the group consisting of H, (C$_1$-C$_6$)alkyl, and (C$_3$-C$_7$) heterocyclyl(C$_1$-C$_6$)alkyl; R$^6$ is selected from the group consisting of hydrogen and (C$_1$-C$_6$)alkyl; R$^7$ is selected from the group consisting of hydrogen and (C$_1$-C$_6$)alkyl; and m is 1 or 2. In some of these embodiments m is 1. In some of these embodiments R$^2$ is (C$_3$-C$_7$)heterocyclyl(C$_1$-C$_6$)alkyl, such as, e.g.

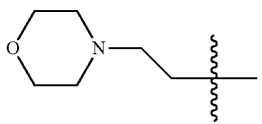

In some embodiments in formula (XXIV) Z$^1$ is —O— or —N(R$^7$)—; L$^2$ is a covalent bond or —C(R$^6$)$_2$—; R$^1$ is independently selected from the group consisting of hydrogen and (C$_1$-C$_4$)alkyl; R$^2$ is each independently selected from the group consisting of H, (C$_1$-C$_4$)alkyl, and (C$_3$-C$_5$) heterocyclyl(C$_1$-C$_4$)alkyl; R$^6$ is selected from the group consisting of hydrogen and (C$_1$-C$_4$)alkyl; R$^7$ is selected from the group consisting of hydrogen and (C$_1$-C$_4$)alkyl; and m is 1 or 2. In some of these embodiments m is 1. In some of these embodiments R$^2$ is (C$_3$-C$_5$)heterocyclyl(C$_1$-C$_4$)alkyl, such as, e.g.

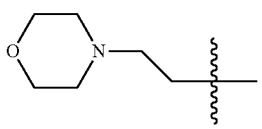

In some embodiments in formula (XXIV) Z$^1$ is —O— or —N(R$^7$)—; L$^2$ is a covalent bond or —C(R$^6$)$_2$—; R$^1$ is independently selected from the group consisting of hydrogen and (C$_1$-C$_2$)alkyl; R$^2$ is each independently selected from the group consisting of H, (C$_1$-C$_2$)alkyl, and (C$_3$-C$_5$) heterocyclyl(C$_1$-C$_2$)alkyl; R$^6$ is selected from the group consisting of hydrogen and (C$_1$-C$_2$)alkyl; R$^7$ is selected from the group consisting of hydrogen and (C$_1$-C$_2$)alkyl; and m is 1 or 2. In some of these embodiments m is 1. In some of these embodiments R$^2$ is (C$_3$-C$_5$)heterocyclyl(C$_1$-C$_4$)alkyl, such as, e.g.

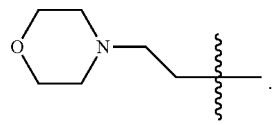 [SMILES: *CCN1CCOCC1]

In some embodiments in formula (XXIV) Z$^1$ is —N(R$^7$)—; L$^2$ is —C(R$^6$)$_2$—; R$^1$ is independently selected from the group consisting of hydrogen and (C$_1$-C$_6$)alkyl; R$^2$ is (C$_3$-C$_7$)heterocyclyl(C$_1$-C$_6$)alkyl; R$^6$ is selected from the group consisting of hydrogen and (C$_1$-C$_6$)alkyl; R$^7$ is selected from the group consisting of hydrogen and (C$_1$-C$_6$) alkyl; and m is 1. In some of these embodiments R$^2$ is

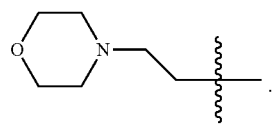 [SMILES: *CCN1CCOCC1]

In some embodiments in formula (XXIV) Z$^1$ is —N(R$^7$)—; L$^2$ is —C(R$^6$)$_2$—; R$^1$ is independently selected from the group consisting of hydrogen and (C$_1$-C$_4$)alkyl; R$^2$ is (C$_3$-C$_5$)heterocyclyl(C$_1$-C$_4$)alkyl; R$^6$ is selected from the group consisting of hydrogen and (C$_1$-C$_4$)alkyl; R$^7$ is selected from the group consisting of hydrogen and (C$_1$-C$_4$) alkyl; and m is 1. In some of these embodiments R$^2$ is

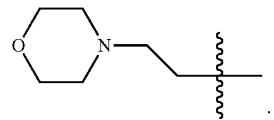 [SMILES: *CCN1CCOCC1]

In some of these embodiments R$^7$ is (C$_1$-C$_4$) alkyl, such as, e.g., methyl.

In some embodiments in formula (XXIV) Z$^1$ is —N(R$^7$)—; L$^2$ is —C(R$^6$)$_2$—; R$^1$ is independently selected from the group consisting of hydrogen and (C$_1$-C$_2$)alkyl; R$^2$ is (C$_3$-C$_5$)heterocyclyl(C$_1$-C$_2$)alkyl; R$^6$ is selected from the group consisting of hydrogen and (C$_1$-C$_2$)alkyl; R$^7$ is selected from the group consisting of hydrogen and (C$_1$-C$_2$) alkyl; and m is 1. In some of these embodiments R$^2$ is

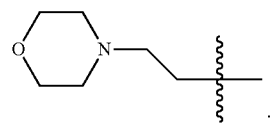 [SMILES: *CCN1CCOCC1]

In some of these embodiments R$^7$ is (C$_1$-C$_2$)alkyl, such as, e.g., methyl.

In some embodiments in formula (XXIV) $Z^1$ is —N($R^7$)—; $L^2$ is —C($R^6$)$_2$—; $R^1$ is hydrogen; $R^2$ is ($C_3$-$C_7$)heterocyclyl($C_1$-$C_6$)alkyl; $R^6$ is hydrogen; $R^7$ is ($C_1$-$C_6$) alkyl; and m is 1. In some of these embodiments $R^2$ is

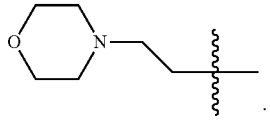

In some embodiments in formula (XXIV) $Z^1$ is —N($R^7$)—; $L^2$ is —C($R^6$)$_2$—; $R^1$ is hydrogen; $R^2$ is ($C_3$-$C_5$)heterocyclyl($C_1$-$C_4$)alkyl; $R^6$ is hydrogen; $R^7$ is ($C_1$-$C_4$) alkyl; and m is 1. In some of these embodiments $R^2$ is

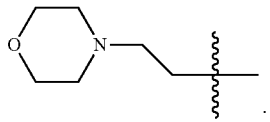 [SMILES: *CCN1CCOCC1]

In some of these embodiments $R^7$ is ($C_1$-$C_2$)alkyl. In some of these embodiments $R^7$ is methyl.

In some embodiments the compound of formula (XXIV) has the structure:

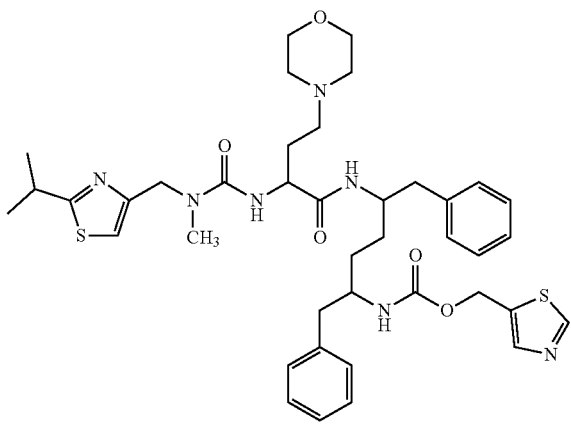 [SMILES: CC(C)c1nc(CN(C)C(=O)NC(CCN2CCOCC2)C(=O)NC(CCC(Cc2ccccc2)NC(=O)OCc2cncs2)Cc2ccccc2)cs1]

In some embodiments the compound of formula (XXIV) has the structure:

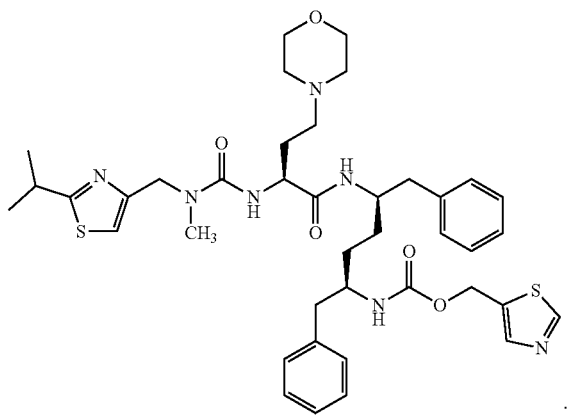 [SMILES: CC(C)c1nc(CN(C)C(=O)N[C@@H](CCN2CCOCC2)C(=O)N[C@H](CC[C@H](Cc2ccccc2)NC(=O)OCc2cncs2)Cc2ccccc2)cs1]

In some of these embodiments the compound of formula (XXIV) has the structure:

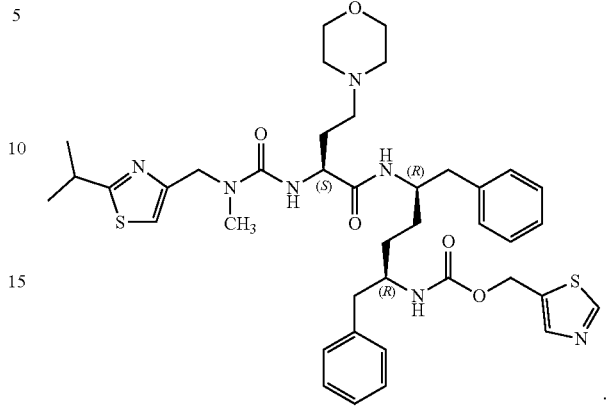

In some embodiments the compound of formula (XXIV) is cobicistat.

In some embodiments the compound is selected from the group consisting of:

2-(4-Chlorophenyl)-3-cyclopropyl-1-(1H-1,2,4-triazol-1-yl)-2-butanol (cyproconazole);

1-[4-(4-{[(2R,4S)-2-(2,4-Dichlorophenyl)-2-(1H-imidazol-1-ylmethyl)-1,3-dioxolan-4-yl]methoxy}phenyl)piperazin-1-yl]ethan-1-one (ketoconazole);

1-[Phenyl(4-phenylphenyl)methyl]-1H-imidazole (bifonazole);

(RS)-1-(2-(2,4-Dichlorobenzyloxy)-2-(2,4-dichlorophenyl)ethyl)-1H-imidazole (miconazole);

1-[(2-Chlorophenyl)(diphenyl)methyl]-1H-imidazole (clotrimazole);

(2R,3S)-2-(2,4-Difluorophenyl)-3-(5-fluoropyrimidin-4-yl)-1-(1H-1,2,4-triazol-1-yl)butan-2-ol (voriconazole);

1-[[2-(2,4-dichlorophenyl)-4-propyl-1,3-dioxolan-2-yl]methyl]-1,2,4-triazole (propiconazole);

(RS)-1-{2-[(4-Chlorophenyl)methoxy]-2-(2,4-dichlorophenyl)ethyl}-1H-imidazole (econazole);

(RS)-1-(4-Chlorophenyl)-4,4-dimethyl-3-(1H,1,2,4-triazol-1-ylmethyl)pentan-3-ol (tebuconazole);

(RS)-1-[2-[(2-Chloro-3-thienyl)methoxy]-2-(2,4-dichlorophenyl)ethyl]-1H-imidazole (tioconazole);

2-(2,4-Difluorophenyl)-1,3-bis(1H-1,2,4-triazol-1-yl)propan-2-ol (fluconazole);

2-methyl-1,2-di(pyridin-3-yl)propan-1-one (metyrapone);

(RS)-1-[2-[(2,6-Dichlorobenzyl)oxy]-2-(2,4-dichlorophenyl)ethyl]-1H-imidazole (isoconazole);

(2R,4S)-rel-1-(Butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-1H-1,2,4-triazol-5-one (itraconazole);

(Z)-[1-(2,4-Dichlorophenyl)-2-(1H-imidazol-1-yl)ethylidene][(2,4-dichlorophenyl)methoxy]amine (oxiconazole);

4-(4-(4-(4-(((3R,5R)-5-(2,4-difluorophenyl)-5-(1,2,4-triazol-1-ylmethyl)oxolan-3-yl)methoxy)phenyl)piperazin-1-yl)phenyl)-2-((2S,3S)-2-hydroxypentan-3-yl)-1,2,4-triazol-3-one (posaconazole);

1-[4-(4-Chlorophenyl)-2-(2,6-dichlorophenyl)sulfanyl-butyl]imidazole (butoconazole);

(2R,3R)-2-(2,4-Difluorophenyl)-3-(4-methylene-1-piperidinyl)-1-(1H-1,2,4-triazol-1-yl)-2-butanol (efinaconazole);

(2E)-[(4R)-4-(2,4-Dichlorophenyl)-1,3-dithiolan-2-ylideneyl](1H-imidazol-1-yl)acetonitrile (luliconazole);

1-{2-[(7-Chloro-1-benzothiophene-3-yl)methoxy]-2-(2,4-dichlorophenyl)ethyl}-1H-imidazole (sertaconazole);

1-[(2-[2-Chlor-4-(4-chlor-phenoxy)-phenyl]-4-methyl[1,3]dioxolan-2-yl)methyl]-1H-1,2,4-triazol (difenoconazole);

2-[2-(1-Chlorocyclopropyl)-3-(2-chlorophenyl)-2-hydroxypropyl]-1,2-dihydro-3H-1,2,4-triazole-3-thione (prothioconazole);

1,3-thiazol-5-ylmethyl N- [(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenyl-hexan-2-yl]carbamate (ritonavir); and 1,3-thiazol-5-ylmethyl[(2R,5R)-5-{[(2S)-2-[(methyl{[2-(propan-2-yl)-1,3-thiazol-4-yl]methyl}carbamoyl)amino]-4-(morpholin-4-yl)butanoyl]amino}-1,6-diphenylhexan-2-yl]carbamate (cobicistat).

A selection of compounds within the scope of, or use within the methods, of the present invention is listed in the following Table 1.

1

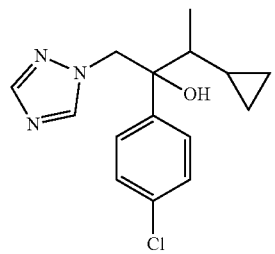

2

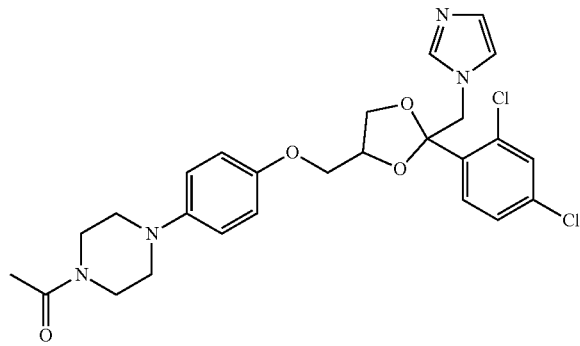

2a

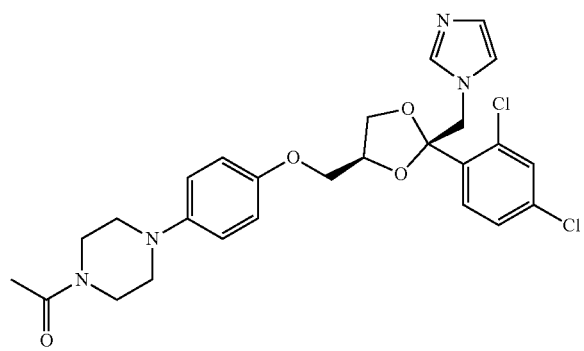

2b

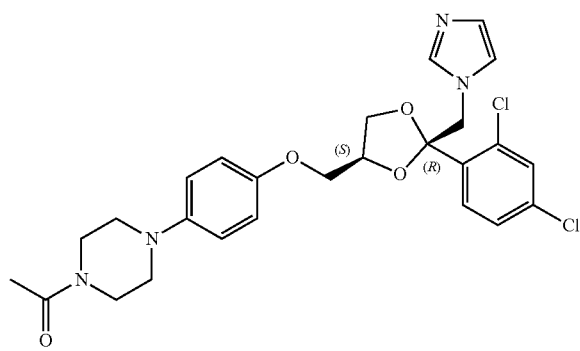

3

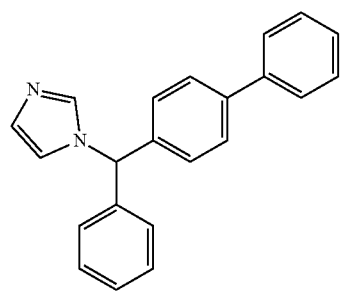

4

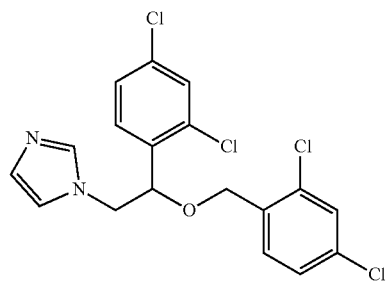

5

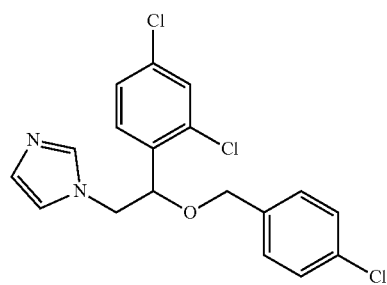

-continued
7
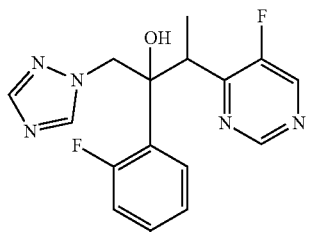
8
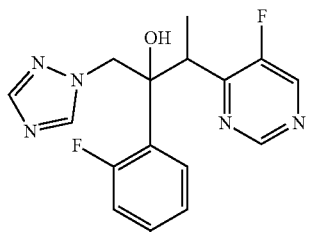
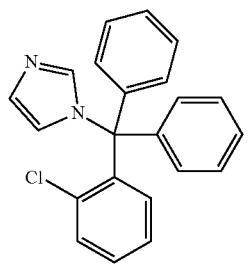
8a
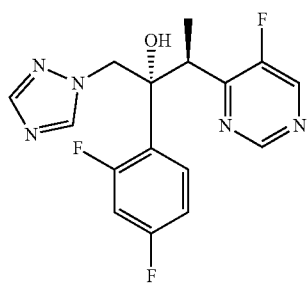
8b
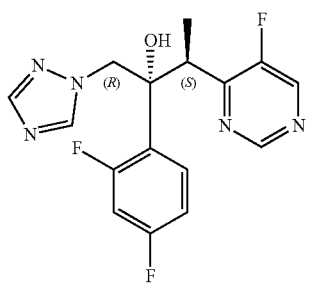
9
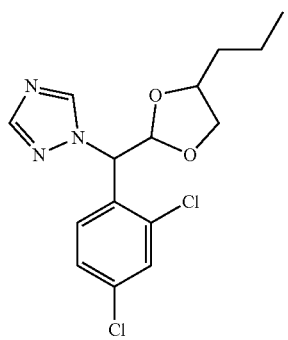
10
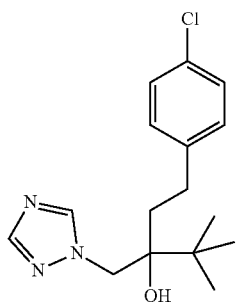
11
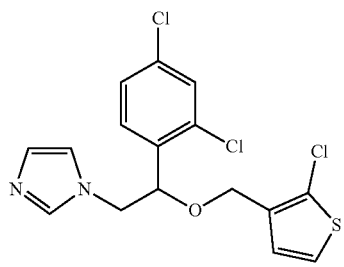
12
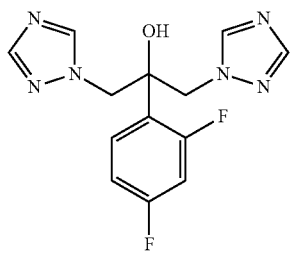
13
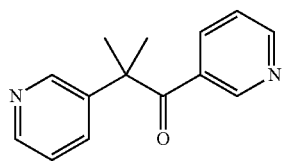
14
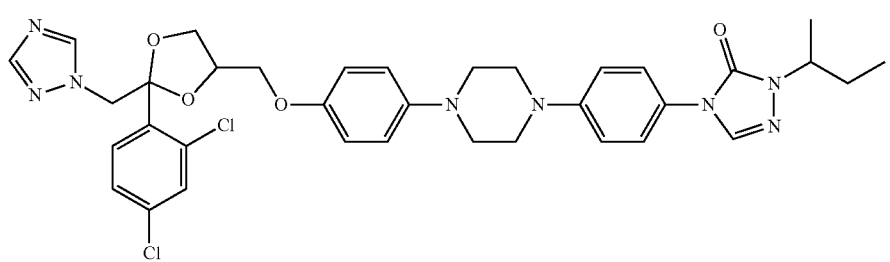

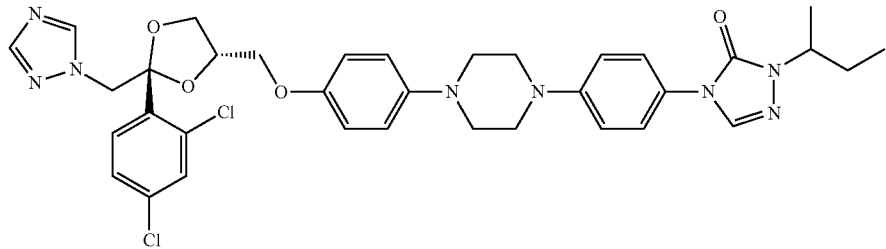
14a
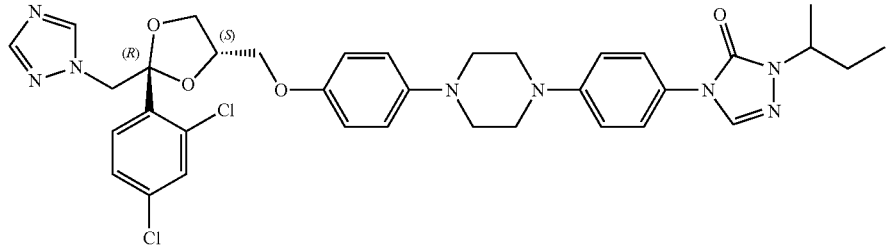
14b
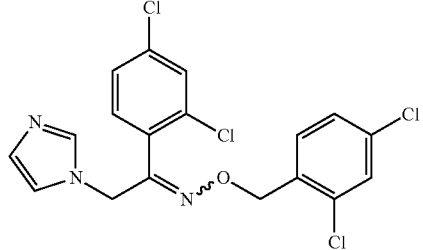
15
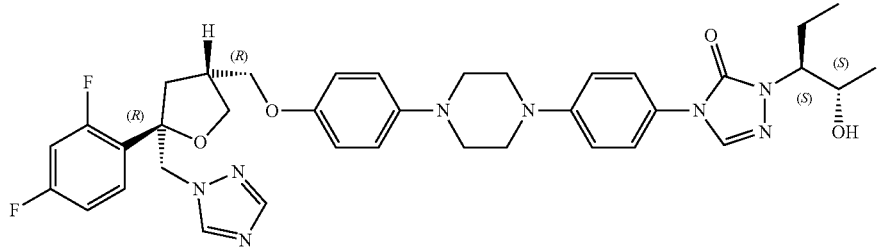
16
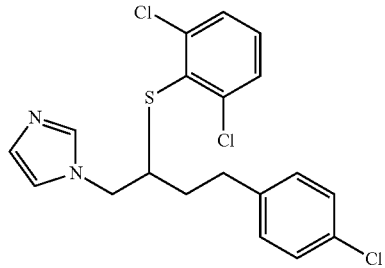
17
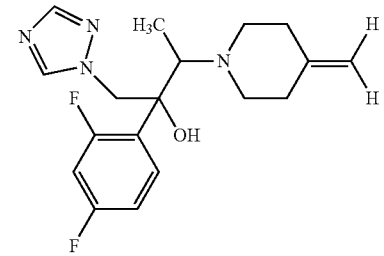
18
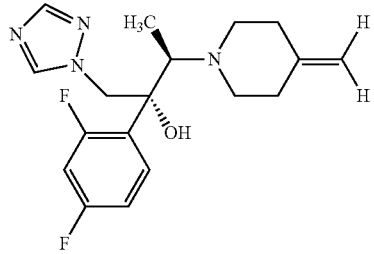
18a
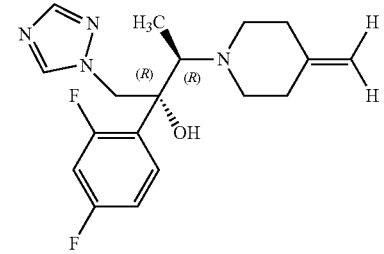
18b

| 19 | 19a |
|---|---|
| 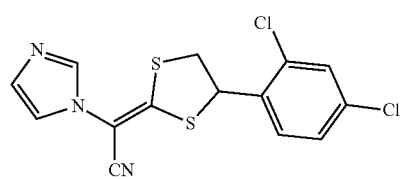 | 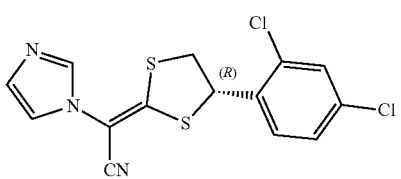 |
| 20 | 21 |
| 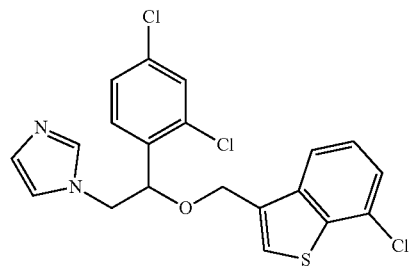 | 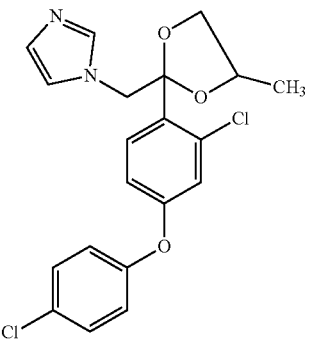 |
| 22 | 22a |
| 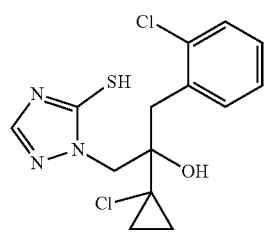 | |
| | 23 |
| 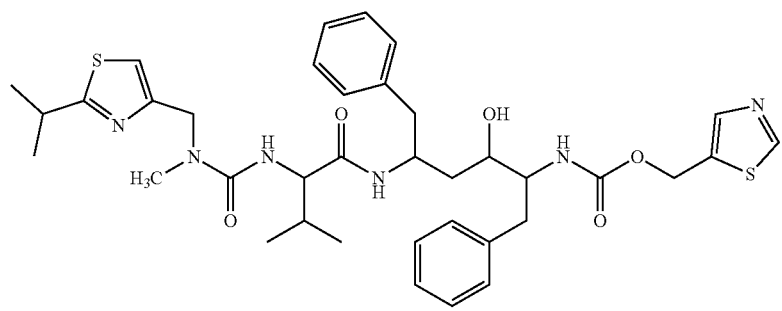 | |
| | 23a |
| 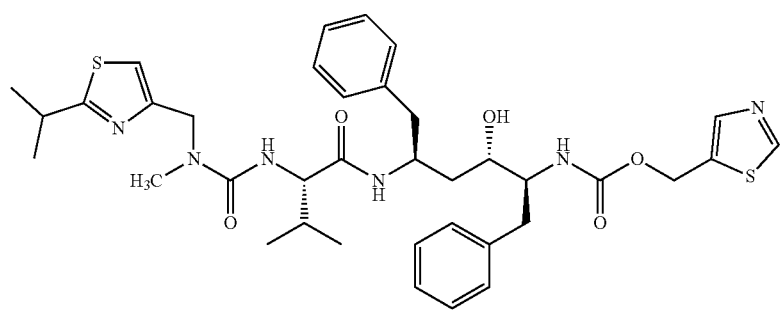 | |

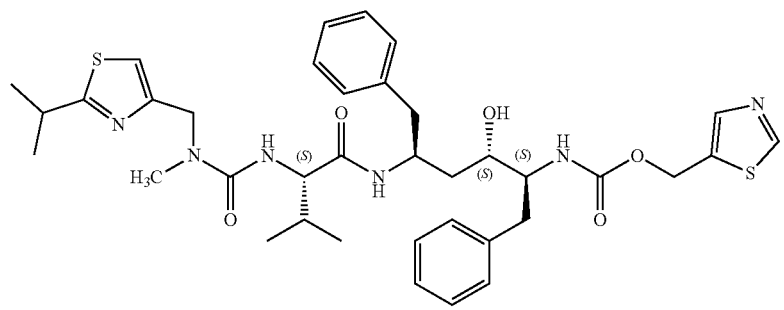
23b
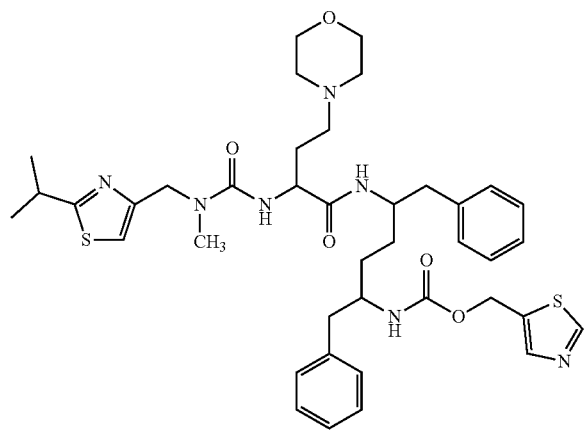
24
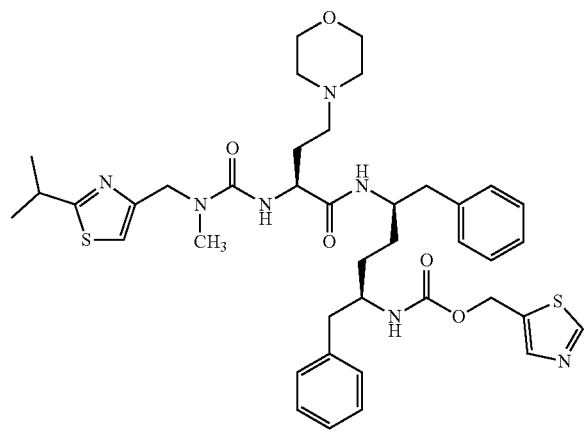
24a
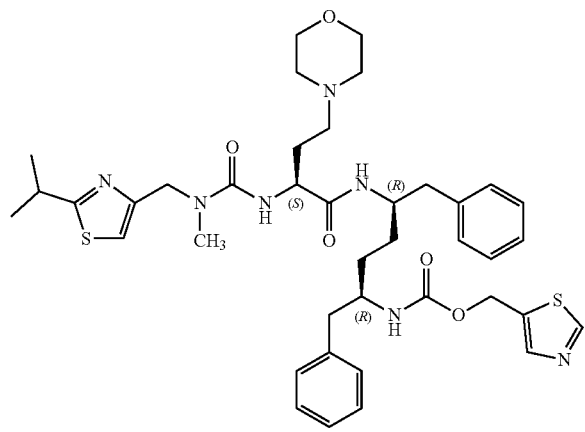
24b
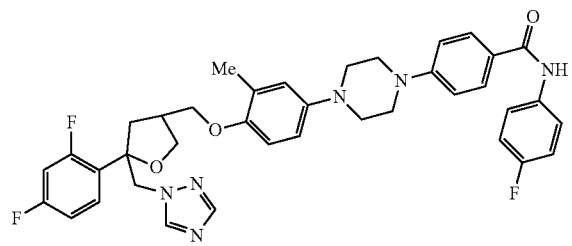
25
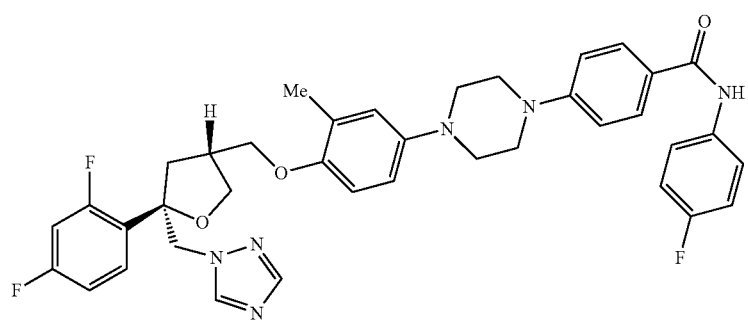
25a In this context, it is noted that the term "disease that is related or associated with cytochrome P450 family 7 subfamily B member 1(CYP7B1)" relates to any disease that can be treated by inhibiting the activity of CYP7B1, or in any other words by a CYP7B1 inhibitor. Such diseases include, but are not limited to pulmonary diseases, transplant rejection or autoimmune diseases. The term "CYP7B1" is used in its regular meaning in the art to mean the respective oxysterol 7α-hydroxylase and member of the cytochrome P450 superfamily of enzymes. The sequence of the human protein that is encoded by the CYPB71 gene is deposited as UniProtKB accession number O75881, for example. It is noted here that while the designation CYP7B1 originally referred to the gene that encodes this oxysterol 7α-hydroxylase, the protein (enzyme) itself is commonly also called CYP7B1. See, for example, Yantsevich et al. "Human steroid and oxysterol 7α-hydroxylase CYP7B1: substrate specificity, azole binding and misfolding of clinically relevant mutants", FEBS Journal 281 (2014) 1700-1713. In the present invention, the functionality and thus suitability of a compound of interest (i.e. its function as CYP7B1 inhibitor) can be tested against the enzyme of any mammalian species, for example, the human enzyme, but also the rat or murine enzyme. The person skilled in the art will readily understand that the term "CYP7B1 inhibitor" is not limited to a particular structure of a small organic molecule but small organic molecules that have no similarity in their chemical structure still share the ability of being CYP7B1 inhibitors—see in this respect, Yantsevich et al. FEBS Journal 281 (2014) 1700-1713 that show in Table 2 azole and numerous other active site ligands binding to CYP7B1 that can act as corresponding CYP7B1 inhibitors. In this context, the suitability of a compound of interest as CYP7B1 inhibitors can be tested in a migration assay using activated B cells as described herein or by Pitzalis et al. (Nature reviews Immunology 14, 447-462 (2014)). In such assays, the formation of lymphoid-like structures such as iBALT in the presence of a compound known or suspected to be a CYP7B1 inhibitor is tested. An assays as used herein is based on the following observations made in the present invention.

Figure 9:
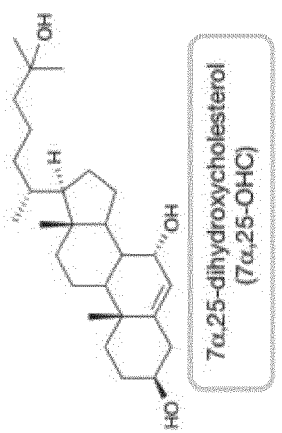
FIG. 9 shows the synthesis pathway of the metabolism of 7α,25-OHC from cholesterol.
Figure 9:
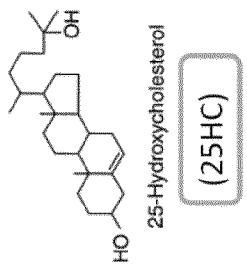
Figure 9:
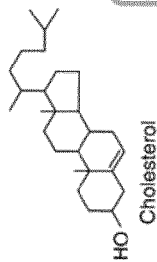

7α,25-dihydroxycholesterol (7α,25-OHC)—a product of the cholesterol metabolism—is involved via its receptor EB12 in the regulation of localization and positioning of B cells in lymphoid follicles. The present inventors surprisingly found that the enzyme Cholesterol 25-hydroxylase (Ch25h, UniProtKB accession number of the human enzyme O95992), which catalyses the first step of the cholesterol→7α,25-OHC pathway (see FIG. 9) is upregulated in cigarette-smoke treated mouse lungs and also in bronchial epithelial cells and small airway epithelium of smokers suffering from COPD. On the contrary, the corresponding mouse knock-out lung (Ch25h$^{-/-}$) showed after chronic smoke exposure an impairment of iBALT formation and a reduction of the emphysema as well as a reduction of inflammatory B cells as compared to wild-type mice after chronic smoke exposure. CYP7B1 (25-HC 7α-hydroxylase) is, as mentioned above, a cytochrome P450 family enzyme and catalyses the second step of the cholesterol→7α,25-OHC pathway (see FIG. 9). 25-Hydroxycholesterol is metabolized by the CYP7B1-mediated hydroxylation at the 7a position for the biosynthesis of 7α,25-OHC. By treating mouse models of COPD (i.e. mice that were exposed to cigarette smoke) with CYP7B1-Inhibitors, the inventors have shown that the symptoms of COPD are released in a preventive/prophylactic and also curative manner. In particular, the present inventors have shown by analysing histologically the occurrence of iBALT structures in lungs of mice that underwent cigarette smoke treatment and were given a CYP7B1-Inhibitor intraperitoneally at different time points that said iBALT structures disappeared or did not show up at all indicating full reversal of COPD phenotypic traits (i.e. healing) or full prevention of COPD traits (i.e. prophylaxis).

The present inventors have demonstrated that 7α,25-OHC surprisingly plays a key role in the formation of iBALT of patients with COPD and is crucial for the formation of tertiary lymphoid organs. Thus, the present inventors surprisingly uncovered that the formation of iBALT can be prevented or reversed by inhibiting the formation of 7α,25-OHC from cholesterol.

As it is evident from the Examples, the inventors uncovered that compounds inhibiting the formation of 7α,25-OHC from cholesterol by inhibiting or reducing the enzymatic activity of CYP7B1 can be used to treat Chronic obstructive pulmonary disease (COPD) and other chronic diseases driven by the generation of ectopic lymphoid tissue. Furthermore, the present inventors demonstrated that a knockout of Ch25h in mice also impairs iBALT formation. Thus, compounds inhibiting Ch25h can be used to treat Chronic obstructive pulmonary disease (COPD) and other chronic diseases driven by the generation of ectopic lymphoid tissue as well. Accordingly, compounds of the present invention can be Ch25h-inhibitors and/or CYP7B1-inhibitors. In some embodiments the compounds of the invention are selective inhibitors of Ch25h. In a preferred embodiment the compounds of the invention are selective inhibitors of CYP7B1. The compounds of the present invention can be used for the curative and prophylactic treatment of any disease such as pulmonary diseases such as COPD that is related to CYP7B1 and which can be treated by inhibiting the activity of CYP7B1.

In preferred compounds of the invention any one or more structural elements such as groups, substituents and numbers are defined as in any of the preferred definitions of the elements or in any specified embodiment and/or can have one or more of the specific meanings which are mentioned as examples of elements, wherein all combinations of one or more preferred definitions and embodiments and/or specific meanings are a subject of the present invention. Also with respect to all preferred compounds of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them, are a subject of the present invention. Similarly, also with respect to all specific compounds disclosed herein, such as the example compounds, which represent embodiments of the invention wherein the various groups and numbers in the general definition of the compounds of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV have the specific meanings present in the respective specific compound, all their stereoisomeric forms and mixtures of stereoisomeric forms in all ratios, and their physiologically acceptable salts, and the physiologically acceptable solvates of any of them, are a subject of the present invention. In particular, a subject of the invention are all specific compounds disclosed herein, independently thereof whether they are disclosed as a free compound and/or as a specific salt, both in the form of the free compound and in the form of all its physiologically acceptable salts, and if a specific salt is disclosed, additionally in the form of this specific salt, and the physiologically acceptable solvates thereof.

Pharmaceutical Compositions

In a further aspect, the present invention provides a pharmaceutical composition comprising a compound as specified above under the heading "Compounds" and one or more pharmaceutically acceptable excipients.

The compounds described in present invention (in particular those specified above such as those of formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, as well as the compounds of table 1 are preferably administered to a patient in need thereof via a pharmaceutical composition. In one embodiment, the pharmaceutical composition comprises a compound as described above (e.g. having the general formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, as well as the compounds of table 1 or a hydrate, solvate, salt, ether, ester, complex, racemic mixture, diastereomer, enantiomer, or tautomer thereof or an isotopically enriched form of any of the foregoing) and one or more pharmaceutically acceptable excipients.

The pharmaceutical composition may be administered to an individual by any route, such as enterally or parenterally and preferably by inhalation.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, or through mucous membranes (such as buccal, sublingual or vaginal)). However, preferred is an administration via inhalation.

The compounds used in the present invention are generally applied in "pharmaceutically acceptable amounts" and in "pharmaceutically acceptable preparations". Such compositions may contain salts, buffers, preserving agents, carriers and optionally other therapeutic agents.

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions described in the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound used in the present invention, either alone or in combination with one or more additional active compounds, may be coated in a material to protect the active compound(s) from the action of acids and other natural conditions that may inactivate the active compound.

Examples of suitable aqueous and non-aqueous carriers which may be employed in the pharmaceutical compositions used according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, injectable organic esters (such as ethyl oleate) and preferably oils, such as vegetable oils or olive oil). In case of inhalation a suitable carrier for the pharmaceutical composition may be e.g. captisol, sugar alcohol or any other aqueous component.

Pharmaceutically acceptable carriers include sterile aqueous solutions or dispersions and sterile powders for the extemporaneous preparation of sterile injectable solutions or dispersions. The use of such media and agents for pharmaceutically active compounds is known in the art. Except insofar as any conventional media or agent is incompatible with the active compound, use thereof in the pharmaceutical compositions used according to the present invention is contemplated.

Additional active compounds can be administered together with, before or after the compound used in the present invention (in particular that specified above such as those of formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, as well as the compounds of table 1 or incorporated into the compositions). In one embodiment, the pharmaceutical composition described herein comprises a compound as described above (e.g. having the general formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, as well as the compounds of table 1 or a hydrate, solvate, salt, complex, racemic mixture, diastereomer, enantiomer, or tautomer thereof or an isotopically enriched form of any of the foregoing) and at least one additional active compound, and one or more pharmaceutically acceptable excipients.

The "additional active compound" (which is not a compound having formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, as well as the compounds of table 1 as specified herein) may be selected from any compound which can be used in the treatment of lung diseases, cancer and/or immune diseases. The additional active compound may induce an additive or synergistic therapeutic effect.

The pharmaceutical composition described herein may comprise, in addition to the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 as described above, at least one, e.g., 1, 2, 3, 4, 5, 6, 7 or 8, additional active compounds. According to the present teaching, the at least additional active compound, for example the anticancer drug, and/or an agent for the treatment of immune diseases, may be formulated together with the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 as described above in a single pharmaceutical composition. Alternatively, the pharmaceutical composition may be structured as kit of parts, wherein the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 is provided in a first formulation and the at least one additional active compound, for example the anticancer drug and/or an agent for the treatment of immune diseases, is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 as described above. Alternatively, the present teaching envisages administering the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 as described above, formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years. In some embodiments the kit of parts comprises a compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 as described above, or a pharmaceutical composition containing a compound having a structure according to formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV, or the compounds of table 1 as described above, and at least one pharmaceutically acceptable carrier.

The compositions may also contain adjuvants such as preservatives, wetting agents, emulsifying agents, pH buffering agents, and dispersing agents. Prevention of the presence of microorganisms may be ensured by sterilization procedures and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Furthermore, pharmaceutical compositions of the compound having a structure according to formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV, or the compounds of table 1 as described above may be prepared as disclosed in WO 2016/087880 A1. In particular, the formulations described on page 16 ff. of WO 2016/087880 A1, comprising formulations for topical administration to the lung and nose, are referenced herein.

Regardless of the route of administration selected, the active compounds, which may be used in a suitable hydrated form, and/or the pharmaceutical compositions used according to the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al., "Pharmaceutical Dosage Forms and Drug Delivery Systems", $7^{th}$ edition, Lippincott Williams & Wilkins Publishers, 1999).

A pharmaceutical composition can be administered by a variety of methods known in the art. As will be appreciated by the skilled artisan, the route and/or mode of administration will vary depending upon the desired results. The pharmaceutical compositions containing one or more active compounds can be prepared with carriers that will protect the one or more active compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such compositions are generally known to those skilled in the art. See, e.g., Sustained and Controlled Release Drug Delivery Systems, J. R. Robinson, ed., Marcel Dekker, Inc., New York, 1978.

To administer a compound used in the present invention by certain routes of administration, it may be necessary to coat the compound with, or co-administer the compound with, a material to prevent its inactivation. For example, the compound may be administered to an individual in an appropriate carrier, for example, liposomes, oil or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7: 27(1984)).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms used according to the present invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions used according to the present invention include those suitable for enteral administration (such as oral or rectal) or parenteral administration (such as nasal, topical (including vaginal, buccal and sublingual), intraperitoneal administration or, in case of treatment of pulmonary diseases, inhalation. The compositions may conveniently be presented in unit dosage form and may be prepared by any methods known in the art of pharmacy. The amount of active ingredient (in particular, the amount of a compound used according to the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound used according to the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound used according to the present invention, in a unit dosage form and/or when administered to an individual or used in therapy, may range from about 0.1 mg to about 10000 mg (for example, from about 1 mg to about 5000 mg, such as from about 10 mg to about 2000 mg) per unit, administration or therapy. In certain embodiments, a suitable amount of such active ingredient may be calculated using the mass or body surface area of the individual, including amounts of between about 1 mg/kg and 500 mg/kg (for example between about 2 mg/kg and 250 mg/kg, such as between about 10 mg/kg and 100 mg/kg), or between about 1 mg/m$^2$ and about 4000 mg/m$^2$ (such as between about 10 mg/m$^2$ and about 3000 mg/m$^2$ or between about 100 mg/m$^2$ and about 2000 mg/m$^2$).

Actual dosage levels of the active ingredients in the pharmaceutical compositions used according to the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds used according to the present invention at levels lower than that required in order to achieve the desired therapeutic effect and gradually increase the dosage until the desired effect is achieved. In general, a suitable daily dose of a composition used according to the present invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound used according to the present invention to be administered alone, it is preferable to administer the compound as a pharmaceutical formulation/composition.

For oral administration, the pharmaceutical composition used according to the present invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

In one embodiment, the compound is orally administered in a concentration of at most 1000 mg/kg body weight (such as at most 500 mg/kg body weight, at most 400 mg/kg body weight, at most 300 mg/kg body weight, at most 200 mg/kg body weight, at most 100 mg/kg body weight, at most 50 mg/kg body weight, at most 40 mg/kg body weight, at most 30 mg/kg body weight, at most 20 mg/kg body weight, at most 10 mg/kg body weight or less).

In one embodiment, the compound is parenterally administered (e.g., intravenously, intramuscularly, subcutaneously of by inhalation), in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight, at most 0.1 mg/kg body weight, at most 0.01 mg/kg body weight).

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The pharmaceutical composition used according to the present invention can be formulated for parenteral administration by injection, for example, by bolus injection, continuous infusion or intraperitoneal injection. In one embodiment, the compounds or compositions used according to the present invention may be administered by slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions used according to the present invention are administered by maintenance therapy, such as, e.g., once a week for a period of 6 months or more.

Formulations for injection can be presented in units dosage form (e.g., in phial, in multi-dose container), and with an added preservative. The pharmaceutical composition used according to the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Dosage forms for the topical, transdermal or inhalation administration of compositions used according to the present invention may include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

In one embodiment, the compounds used according to the present invention may be formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective tumor response.

A "therapeutically effective dosage" for therapy/treatment can also be measured by its ability to stabilize the progression of a condition, disorder or disease. The ability of a compound to inhibit CYP7B1 or Cholesterol 25-hydroxylase (Ch25h) can be evaluated by using the assay described herein measuring B cell migration. Alternatively, the properties of a compound described in the present invention can be evaluated by examining the ability of the compound in appropriate animal model systems known to the skilled practitioner, such as C57BL/6J mice treated with cigarette smoke as described elsewhere herein. A therapeutically effective amount of a compound used according to the present invention can cure, heal, alleviate, relieve, alter, remedy, ameliorate, improve or affect the condition, disorder or disease or the symptoms of the condition, disorder or disease or the predisposition toward the condition, disorder or disease in an individual. Preferably, therapeutically effective amount of a compound used according to the present invention cures the disorder or prevents deterioration. One of ordinary skill in the art would be able to determine such amounts based on such factors as the individual's size, the severity of the individual's symptoms, and the particular composition or route of administration selected.

The pharmaceutical composition used according to the invention can also, if desired, be presented in a pack, or dispenser device which can contain one or more unit dosage forms containing the active compound. The pack can for example comprise metal or plastic foil, such as blister pack. The pack or dispenser device can be accompanied with instruction for administration.

The pharmaceutical composition used according to the invention can be administered as sole active agent or can be administered in combination with other therapeutically and/or cosmetically active agents. In one embodiment, the pharmaceutical composition used according to the invention contains, or is administered with, one or more other therapeutically active agents selected from the group consisting of antiviral agents, antibodies (which are directed against an antigen of an animal pathogenic virus or another microorganism (e.g., a pathogenic bacterium or fungi) or against a cancer antigen or against B cells, such as rituximab), agents stimulating the immune system of the subject (e.g., interferons, such as interferon alpha or interferon beta, imiquimod, and resiquimod), and antimicrobial agents.

Therapeutic and Other Applications

In further aspects, the present application provides a compound as specified above under the heading "Compounds" or a pharmaceutical composition as specified above under the heading "Pharmaceutical compositions" for use in therapy.

Generally, the present invention demonstrates that the compounds described herein, in particular compounds having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compounds of table 1 as described herein under the heading "Compounds" or a pharmaceutical composition as specified above under the heading "Pharmaceutical compositions" inhibit or reduce the enzymatic activity of Ch25h or CYP7B1, in order to treat diseases that are related to an inhibition of either enzyme, in particular diseases that are related to CYP7B1 inhibitions and that can be treated by a CYP7B1 inhibitor as described herein. Examples of such diseases include but are not limited to chronic obstructive pulmonary disease (COPD) and other chronic diseases driven by the generation of ectopic lymphoid tissue.

Thus, in one aspect, the present invention is directed to a compound having a structure according to formula I, II, III, IV, V, Va, VI, VII, IX, X, XI, XII, XIV, XV, XVa, XVI, XVIa, XVIb, XVIcXVII, XVIII, XIX, XX, XXI, XXII, XXIII and XXIV, or a compound of table 1 and hydrates, solvates, salts, ethers, esters, complexes, racemic mixtures, diastereomers, enantiomers, and tautomers thereof and isotopically enriched forms of any of the foregoing, for use in the treatment of a lung disease. In one embodiment the lung disease is chronic obstructive pulmonary disease (COPD). In one embodiment the lung disease is pulmonary hypertension. In one embodiment the lung disease is lung cancer. In one embodiment the lung disease is transplant rejection. In one embodiment the lung disease is pulmonary fibrosis. In one embodiment the lung disease is cystic fibrosis. In one embodiment the lung disease is autoimmunity. Preferred lung diseases are chronic obstructive pulmonary disease (COPD), pulmonary hypertension, emphysema, lung cancer, transplant rejection, pulmonary fibrosis, cystic fibrosis and autoimmunity. More preferred are lung cancer, cystic fibrosis, pulmonary hypertension and chronic obstructive pulmonary disease. Even more preferred is chronic obstructive pulmonary disease. Preferably, a B cell associated lung disease is associated with the formation of lymphoid-like structures such as iBALT as described by Pitzalis et al. (Nature reviews Immunology 14, 447-462 (2014)).

Optionally, the therapeutic application comprises the step of administering at least one additional active compound to the individual. The at least one additional active compound can be administered together with, before or after the compound described herein, in particular the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compound of table 1.

In a preferred embodiment the present invention is directed to a compound having a structure according to formula IV, V, XII and XXIII for use in the treatment of chronic obstructive pulmonary disease (COPD). In an even more preferred embodiment the present invention is directed to the compounds ketoconazole, bifonazole, miconazole, clotrimazole, voriconazole, econazole, tioconazole, fluconazole, metyrapone, isoconazole, itraconazole, oxiconazole, posaconazole, butoconazole, efinaconazole, luliconazole, sertaconazole, ritonavir, cobicistat and/or PC945 and in a particular preferred embodiment to Clotrimazole, Ritonavir, Itracanozole, Voriconazole, Triconazole, Bifoconazole, Isoconazole, Oxiconazole, Butoconazole, Efinaconazole, Luliconazole, Sertaconazole, PC945 and/or Metyrapone, and in the most preferred embodiment to Clomitrazole, Ritonavir, Itracanozole Voriconazole, and/or PC945 for use in the treatment of chronic obstructive pulmonary disease (COPD).

The terms "disease", "disorder" and "condition", when used in the context of treatment or therapy (including prophylactic therapy), are used herein interchangeably and refer to any pathological state, in particular those pathological states described herein.

In a further embodiment, the present invention provides a pharmaceutical composition for use in the treatment of a lung disease, said composition comprising a compound described herein under the heading "Compounds" and in particular a compound having a structure according to formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV, or a compound of table 1, and one or more excipients, and optionally at least one additional active compound. The at least one additional active compound can be administered together with, before or after the compound having a structure according to formula I, II, III, IV, V, Va, VI, VII, IX, X, XI, XII, XIV, XV, XVa, XVI, XVIa, XVIb, XVIcXVII, XVIII, XIX, XX, XXI, XXII, XXIII and XXIV, or the compound of table 1. In one embodiment the lung disease is chronic obstructive pulmonary disease (COPD). In one embodiment the lung disease is pulmonary hypertension. In one embodiment the lung disease is lung cancer. In one embodiment the lung disease is transplant rejection. In one embodiment the lung disease is pulmonary fibrosis. In one embodiment the lung disease is cystic fibrosis. In one embodiment the lung disease is autoimmunity. Preferred lung diseases are chronic obstructive pulmonary disease (COPD), pulmonary hypertension, emphysema, lung cancer, transplant rejection, pulmonary fibrosis, cystic fibrosis and autoimmunity. More preferred are lung cancer, cystic fibrosis, pulmonary hypertension and chronic obstructive pulmonary disease. Even more preferred is chronic obstructive pulmonary disease. Preferably, a lung diseases is associated with the formation of lymphoid-like structures such as iBALT as described by Pitzalis et al. (Nature reviews Immunology 14, 447-462 (2014)).

In a preferred embodiment the present invention is directed to a pharmaceutical composition comprising a compound having a structure according to formula IV, V, XII and XXIII for use in the treatment of chronic obstructive pulmonary disease (COPD). In an even more preferred embodiment the present invention is directed to the compounds Clotrimazole, Ritonavir, Miconazole and Metyrapone for use in the treatment of chronic obstructive pulmonary disease (COPD).

In a further embodiment, the present invention provides a method for treating and/or preventing a lung disease, said method comprising administering a therapeutically effective amount of a compound as described herein (in particular a therapeutically effective amount of a compound having a structure according to formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV, or a compound of table 1 to an individual in need thereof). Optionally, the method comprises the step of administering at least one additional active compound to the individual. The at least one additional active compound can be administered together with, before or after the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compound of table 1. In one embodiment the lung disease is chronic obstructive pulmonary disease (COPD). In one embodiment the lung disease is pulmonary hypertension. In one embodiment the lung disease is lung cancer. In one embodiment the lung disease is transplant rejection. In one embodiment the lung disease is pulmonary fibrosis. In one embodiment the lung disease is cystic fibrosis. In one embodiment the lung disease is autoimmunity. Preferred lung diseases are chronic obstructive pulmonary disease (COPD), pulmonary hypertension, emphysema, lung cancer, transplant rejection, pulmonary fibrosis, cystic fibrosis and autoimmunity. More preferred are lung cancer, cystic fibrosis, pulmonary hypertension and chronic obstructive pulmonary disease. Even more preferred is chronic obstructive pulmonary disease. Preferably, a B cell associated lung diseases is associated with the formation of lymphoid-like structures such as iBALT as described by Pitzalis et al. (Nature reviews Immunology 14, 447-462 (2014)).

In a preferred embodiment the present invention is directed to method for treating and/or preventing chronic obstructive pulmonary disease (COPD), said method comprising administering a therapeutically effective amount of a compound as described in formula IV, V, XII and XXIII. In an even more preferred embodiment the present invention is directed to method for treating and/or preventing chronic obstructive pulmonary disease (COPD), said method comprising administering a therapeutically effective amount of, ketoconazole, bifonazole, miconazole, clotrimazole, voriconazole, econazole, tioconazole, fluconazole, metyrapone, isoconazole, itraconazole, oxiconazole, posaconazole, butoconazole, efinaconazole, luliconazole, sertaconazole, ritonavir, cobicistat and/or PC945 and in a particular preferred embodiment administering a therapeutically effective amount of Clotrimazole, Ritonavir, Itracanozole, Voriconazole, Triconazole, Bifoconazole, Isoconazole, Oxiconazole, Butoconazole, Efinaconazole, Luliconazole, Sertaconazole, PC945 and/or Metyrapone, and in the most preferred embodiment administering a therapeutically effective amount of Clomitrazole, Ritonavir, Itracanozole, Voriconazole and/or PC945.

Furthermore, the invention includes a method of reducing or preventing the formation of inducible bronchus-associated lymphoid tissue (iBALT) in a subject, wherein the method comprises administering to the subject a compound that inhibits the activity of CYP7B1 (CYP7B1 inhibitor). Wherein the compound is preferably the compound according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them.

The invention also includes a method of treating a subject having a pulmonary disease, a transplant rejection or an autoimmune disease, associated with the formation of inducible bronchus-associated lymphoid tissue (iBALT), wherein the method comprises administering to the subject a compound that inhibits the activity of CYP7B1 (CYP7B1 inhibitor). Wherein the compound is preferably the compound according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them. Preferably, the pulmonary disease is selected from the group consisting of lung cancer, cystic fibrosis, pulmonary hypertension, chronic obstructive pulmonary disease, and pulmonary fibrosis.

As published by Rangel-Moreno, et al. (J. Clin. Invest. 116:3183-3194 (2006)), iBALT may be detected in lungs of patients by biopsy.

As used herein and throughout the entire description, the term "Subject" or "individual" are used interchangeably and mean animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. The subject is preferably a mammal, more preferably a human.

As used herein and throughout the entire description, the term "amount effective" in the context of a composition or dosage form for administration to a subject refers to an amount of the composition or dosage form sufficient to provide a benefit in the treatment of lung disease, in particularchronic obstructive pulmonary disease (COPD), pulmonary hypertension, emphysema, lung cancer, transplant rejection, pulmonary fibrosis, cystic fibrosis and autoimmunity. In particular, a therapeutically effective amount means an amount sufficient to provide a therapeutic benefit in viva Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In any of the above therapeutic aspects, the at least one additional active compound may be selected from the additional active compounds described above.

In any of the above therapeutic aspects, wherein the method comprises the steps of administering a compound described herein and in particular a compound having a structure according to formula I, II, III, IV, V, Va, VI, VII, IX, X, XI, XII, XIV, XV, XVa, XVI, XVIa, XVIb, XVIcXVII, XVIII, XIX, XX, XXI, XXII, XXIII and XXIV, or a compound of table 1 as specified above and administering at least one additional active compound, the at least additional active compound, may be formulated together with the compounds of the invention as described above in a single pharmaceutical composition. Alternatively, the pharmaceutical composition may be structured as kit of parts, wherein the compound described herein and in particular a compound having a structure according to formula I, II, III, IV, V, Va, VI, VII, IX, X, XI, XII, XIV, XV, XVa, XVI, XVIa, XVIb, XVIcXVII, XVIII, XIX, XX, XXI, XXII, XXIII and XXIV, or the compound of table 1 is provided in a first formulation and the at least one additional active compound is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the compound described herein and in particular a compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compound of table 1. Alternatively, the present teaching envisages administering the compound described herein and in particular a compound having a structure according to formula I, II, III, IV, V, Va, VI, VII, IX, X, XI, XII, XIV, XV, XVa, XVI, XVIa, XVIb, XVIcXVII, XVIII, XIX, XX, XXI, XXII, XXIII and XXIV, or the compound of table 1 formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease.

Generally, the amount of a compound according to the invention as described herein (in particular the amount of a compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or a compound of table 1) administered daily to an individual may be at most 1000 mg/kg body weight (such as at most 500 mg/kg body weight, at most 400 mg/kg body weight, at most 300 mg/kg body weight, at most 200 mg/kg body weight, at most 100 mg/kg body weight, at most 50 mg/kg body weight, at most 40 mg/kg body weight, at most 30 mg/kg body weight, at most 20 mg/kg body weight, at most 10 mg/kg body weight, at most 1 mg/kg body weight, at most 0.1 mg/kg body weight or less), depending on factors such as the condition of the subject to be treated and the mode of administration. For example, the amount of a compound according to the invention as described herein (in particular the amount of a compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or a compound of table 1) administered daily to an individual may range from about 0.01 mg/kg to 1000 mg/kg (such as from about 0.1 mg/kg to 500 mg/kg, from about 1 mg/kg to 400 mg/kg, from about 2 mg/kg to 300 mg/kg, from about 3 mg/kg to 200 mg/kg, from about 4 mg/kg to 100 mg/kg, from about 5 mg/kg to 90 mg/kg, from about 6 mg/kg to 80 mg/kg, from about 7 mg/kg to 70 mg/kg, from about 8 mg/kg to 60 mg/kg, from about 9 mg/kg to 50 mg/kg, from about 10 mg/kg to 40 mg/kg, or from about 20 mg/kg to 30 mg/kg) depending on factors such as the condition of the subject to be treated and the mode of administration.

In one embodiment, the compound according to the invention as described herein (in particular the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compound of table 1) is orally administered in a concentration of at most 1000 mg/kg body weight (such as at most 500 mg/kg body weight, at most 400 mg/kg body weight, at most 300 mg/kg body weight, at most 200 mg/kg body weight, at most 100 mg/kg body weight, at most 50 mg/kg body weight, at most 40 mg/kg body weight, at most 30 mg/kg body weight, at most 20 mg/kg body weight, at most 10 mg/kg body weight or less).

In one embodiment, the compound according to the invention as described herein (in particular the compound having a structure according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV, or the compound of table 1) is parenterally administered (e.g., intravenously, intramuscularly, or subcutaneously), in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight, at most 0.1 mg/kg body weight, at most 0.01 mg/kg body weight).

The embodiments and definitions of terms described in the context of the means such as compounds according to Formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV and/or Table 1 of the invention are equally applicable to the methods and uses described herein, mutatis mutandis.

The present invention also envisions a method of treating in a subject a lung disease as described elsewhere herein, comprising administering to said subject an efficient amount of a compound according to Formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV and/or Table 1 or a pharmaceutically acceptable salt, ether, ester, solvate or hydrate thereof or a pharmaceutical composition comprising said compound. Said method preferably comprises further administering at least one additional pharmaceutically active compound. The above described aspects, embodiments, definitions, etc. are also applicable to said method of treatment, mutatis mutandis.

Method for Testing Compounds

The present inventors have shown that 7α,25-OHC plays a key role in the formation of iBALT of patients with COPD and is crucial for the formation of tertiary lymphoid organs. Thus, patients with COPD and other diseases described herein can be treated with compounds inhibiting the formation of 7α,25-OHC from cholesterol. The formation of 7α,25-OHC from cholesterol can be inhibited by inhibiting Ch25h and/or CYP7B1. Thus, the present invention relates to Ch25h-inhibitors and CYP7B1 inhibitors for use in the treatment of COPD and other diseases described herein.

Accordingly, the present invention provides a method of determining whether a compound is effective in treating or preventing a disease associated with the formation of inducible bronchus-associated lymphoid tissue (iBALT), such as COPD. The method is based on the surprising finding that airway trees stimulated with cigarette smoke extract (CSE) ex vivo show an increased expression of Ch25h and Cyp7b1 and thus induce the migration of activated B cells.

In line with the above, the present invention provides a method of determining whether a compound is effective in treating or preventing a disease associated with the formation of inducible bronchus-associated lymphoid tissue (iBALT), the method comprising:
(a) providing activated B cells and culture supernatant from primary airway lung tissue cultured with cigarette smoke extract and said compound, wherein the B cells and the culture supernatant are spatially separated from each other; and
(b) determining migration of the activated B cells towards the culture supernatant, wherein a decreased migration of the activated B cells compared to a control sample indicates that the compound is effective in treating or preventing a disease associated with the formation of iBALT.

Without being bound by theory, it is believed that treatment of the primary airway lung tissue with CSE increases the expression of Ch25h and CYP7B1 and consequently the formation of 7α,25-OHC, which is secreted in the culture supernatant and induces B cell migration. Therefore, a compound inhibiting the enzymatic activity of Ch25h or CYP7B1 will reduce the formation of 7α,25-OHC and thus also B cell migration. The present inventors found that this CS-induced B cell migration results in iBALT formation and consequently in iBALT associated disease. Consequently, a suitable control sample is culture supernatant obtained from primary airway lung tissue cultured with cigarette smoke extract. In such a control sample the formation of 7α,25-OHC is not reduced and thus B cell migration occurs.

B cells can be activated by IgM cross-linking. Thus, activated B cells as used in the method described herein are obtainable by bringing an antibody specific for the heavy chain of IgM into contact with isolated B cells. Such B cells are preferably B cells from the spleen. Without being bound by theory, such a cross-linking using anti-IgM mimics the signal provided by the B cell receptor binding to its cognate antigen. The B cells used in the method of the invention can be obtained from a mammal, such as rat, rabbit, guinea pig, pig, horse, monkey, human and preferably from mouse.

The term "culture supernatant", "medium" and "culture medium" are used interchangeably herein and relate to culture medium and preferably airway epithelial cell culture medium that has been used for culturing primary airway lung tissue. Such a culture supernatant may comprise cigarette smoke extract and optionally one or more compounds to be tested in the method of the invention. Consequently, depending on the supplementation of cigarette smoke extract and optionally said compound to be tested to the culture of the primary airway lung tissue, the supernatant will comprise 7α,25-OHC. By way of example, in case only cigarette smoke extract (e.g. 10% in the culture medium) is used for the culture, the supernatant will comprise 7α,25-OHC in an amount sufficient to induce B cell migration. In case a compound inhibiting Ch25h or CYP7B1 is added to the culture medium, the supernatant will comprise less 7α,25-OHC and thus induce less B cell migration or even no B cell migration at all. Accordingly, the culture supernatant used in the method of the invention can be obtained by culturing primary airway lung tissue with cigarette smoke extract and optionally one or more compounds to be tested in the method of the invention.

The term "primary airway lung tissue" as used herein relates to dissected airway trees from the lung. The primary airway lung tissue used in the method of the invention can be obtained from a mammal, such as rat, rabbit, guinea pig, pig, horse, monkey, human and preferably from mouse as described herein in more detail (e.g. under the heading Microdissection of Airways).

The term "cigarette smoke extract" (CSE) as used herein relates to a cigarette smoke mainstream that can be for example generated from 3R4F research cigarettes (Tobacco Research Institute, University of Kentucky) from which the filter has been optionally removed. Such a cigarette smoke extract can have a particle concentration of at least 10 mg/m$^3$, at least 50 mg/m$^3$, at least 100 mg/m$^3$, at least 200 mg/m$^3$, at least 300 mg/m$^3$, at least 400 mg/m$^3$, at least 750 mg/m$^3$, at least 1000 mg/m$^3$ and preferably at least 500 mg/m$^3$. Even more preferred is a particle concentration of 500 mg/m$^3$. However, it is also envisioned herein that other compounds than cigarette smoke extract can be used in the method of the invention for culturing the primary airway lung tissue. Without being bound by theory, such compounds may be any TLR4 ligand, such as lipopolysaccharides. Further compounds that may be used are Ch25H regulators.

The term "compound" and "compound to be tested" are used interchangeably herein. Compounds that can be tested using the method of the invention are in theory any compounds. However, preferred are compounds that are known or suspected to inhibit Ch25h and/or CYP7B1. Even more preferred are compounds according to of the formulas I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them. Compounds to be tested are preferably used in a concentration in the culture medium sufficient to elicit a response on the formation of 7α,25-OHC from cholesterol and more preferably in a concentration sufficient to inhibit Ch25h or CYP7B1. Compounds to be tested can be used for example in a concentration of 0.1 µM, 0.2 µM, 0.3 µM, 0.4 µM, 0.5 µM, 0.6 µM, 0.7 µM, 0.8 µM, 0.9 µM, 1.0 µM, 1.1 µM, 1.2 µM, 1.3 µM, 1.4 µM, 1.5 µM, 1.6 µM, 1.7 µM, 1.8 µM, 1.9 µM, 2 µM, 3 µM, 4 µM, 5 µM, 10 µM, 15 µM, 20 µM, 50 µM, 100 µM or more.

The term "spatially separated" as used herein means that activated B cells and culture supernatant are comprised within one enclosure, wherein activated B cells are placed in a separate compartment within said enclosure. Activated B cells are retained in said separate compartment within the enclosure via a cell permeable membrane. Such a cell permeable membrane used in the method of the invention is preferably permeable for culture supernatant and compounds comprised by the culture supernatant. Therefore, activated B cells will remain within said compartment within the enclosure. However, in case B cell migration is induced (e.g. by culture supernatant comprising 7α,25-OHC in the enclosure), migrating activated B cells are capable of passing the membrane and thus leaving the compartment. Thus, migrating B cells are comprised within the enclosure but outside the compartment. Accordingly, in a preferred embodiment of the invention the activated B cells and the culture supernatant are comprised by a cell culture vessel and separated by a cell permeable membrane. In this preferred embodiment the activated B cells are retained in an insert comprised by the cell culture vessel, wherein the insert comprises a cell permeable membrane. In an even more preferred embodiment of the invention, cell permeable membrane is a 5.0 μm pore sized transwell insert. In another preferred embodiment, activated B-cells are placed on the cell permeable membrane and the culture supernatant is placed below the cell permeable membrane in the cell culture vessel.

The term "determining migration of the activated B cells" as used herein relates to assessing the amount of B cells that have been migrated towards the culture supernatant. In one embodiment the amount of migrated B cells is the ratio of migrated B cells. As described herein, migrating B cells a capable of passing the cell permeable membrane and thus leave the compartment in which the activated B cells have been initially retained. Consequently, migrated B cells can be determined by counting B cells that are inside the enclosure but outside the compartment. In case the compartment is a cell culture vessel, migrated B cells are determined by counting the B cells in the cell culture vessel but outside the insert (i.e. B cells that have passed the cell permeable membrane and thus left the insert). B cell migration can be determined after at least 15 minutes, at least 30 minutes, at least 45 minutes, at least 1 hour, at least 2 hours, at least 3 hours, at least 4 hours, at least 5 hours, at least 6 hours, at least 12 hours, at least 18 hours, or at least 24 hours of incubation of the activated B cells with the culture supernatant or the primary airway lung tissue. However, preferably B cell migration is determined after at least 1 hour, at least 2 hours or at least 3 hours of incubation of the activated B cells with the culture supernatant or the primary airway lung tissue. Even more preferred B cell migration is determined after 3 hours of incubation of the activated B cells with the culture supernatant or the primary airway lung tissue.

In a further preferred embodiment migration of the activated B cells is determined towards primary airway lung tissue cultured with cigarette smoke extract or with cigarette smoke extract and said compound. The above being said with respect to B cell migration towards culture supernatant applies mutatis mutandis to B cell migration towards primary airway lung tissue. However, B cells migrated and the primary airway lung tissue will be comprised within the same compartment of the culture vessel. Thus, in case B cell migration is determined by counting of the B cells, it may be required to isolate B cells prior to counting.

In a further preferred embodiment of the method of the invention the primary airway lung tissue is cultured with cigarette smoke extract for at least 6 h, for at least 12 h, for at least 18 h or for at least 24 h prior to incubation of the culture supernatant with the activated B cells. Preferably, the primary airway lung tissue is cultured with cigarette smoke extract for at least 12 h. However, more preferred, the primary airway lung tissue is cultured with cigarette smoke extract for at least 24 h prior to incubation with the activated B cells and even more preferred for 24 h prior to incubation of the culture supernatant with the activated B cells.

In another preferred embodiment of the method of the invention, the primary airway lung tissue is cultured with the compound to be tested for at least 15 minutes, at least 30 minutes, at least 45 minutes, at least 1 hour, at least 2 hours, at least 3 hours, at least 4 hours, at least 5 hours, at least 6 hours, at least 12 hours, at least 18 hours, or at least 24 hours prior to incubation of the culture supernatant with the activated B cells. However, preferably the primary airway lung tissue is cultured with the compound for at least 1 h, for at least 2 h or at least 3 hous prior to incubation with the activated B cells and even more preferred for 1 h prior to incubation of the culture supernatant with the activated B cells.

Thus, in a preferred embodiment the primary airway lung tissue is cultured with the cigarette smoke extract for 24 h prior to incubation of the culture supernatant with the activated B cells and with the compound to be tested for 1 h prior to incubation of the culture supernatant with the activated B cells. Thus, primary airway lung tissue is first cultured for 23 h only with cigarette smoke extract and subsequently with cigarette smoke extract and the compound to be tested for 1 hour.

In another preferred embodiment of the method of the invention, the primary airway lung tissue is cultured with cigarette smoke extract at a concentration of at least 1%, at least 2%, at least 5%, at least 10%, at least 15%, or at least 20%. Preferably, the primary airway lung tissue is cultured with cigarette smoke extract at a concentration of at least 5%. However, more preferably the primary airway lung tissue is cultured with cigarette smoke extract at a concentration of at least 10% and even more preferred of 10%.

In another preferred embodiment of the method of the invention, the compound is effective in inhibiting the formation of 7α,25-dihydroxycholesterol (25CH) and preferably in inhibiting Ch25h or CYP7B1 and even more preferably in inhibiting CYP7B1.

In another preferred embodiment of the method of the invention, the primary airway lung tissue and the B cells are obtained from a mammal, such as rat, rabbit, guinea pig, pig, horse, monkey, human and preferably from mouse.

Method for the Inhibition of the Gene Expression of at Least One of the Genes CH25h, Cyp7b1 and TNFα

The inventors surprisingly found that the compound described herein, in particular the compound according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them inhibits the gene expression of one or more of the CH25 gene, the Cyp7b1 gene and the TNFα gene. In one embodiment, the compound is the compound according to formula V, preferably clotrimazole. Preferably, the gene expression of two or of all three genes is inhibited by administration of a compound according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV.

The invention includes the compound according to formula I, II, III, IV, V, Va, VI, VII, IX, X, XI, XII, XIV, XV, XVa, XVI, XVIa, XVIb, XVIc, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them for use in a method for the inhibition of the gene expression in vivo of at least one of the CH25h gene, the Cyp7b1 gene and the TNFα gene. In one embodiment, the compound is the compound according to formula V, preferably clotrimazole. Preferably, the gene expression is inhibited by said compound by inhibition of the gene induction of one, two or all three of these genes.

Further, the invention includes an in vitro method for the inhibition of the gene expression of at least one of the genes CH25h, Cyp7b1 and TNFα, in a cell or in a system of functional parts of a cell by exposing the cell or the system of functional parts of a cell to the compound according to formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them. In one embodiment the compound is the compound according to formula V, preferably clotrimazole Preferably, the gene expression is inhibited by said compound by inhibition of the gene induction.

Moreover, the invention includes a method of inhibiting in a subject the gene expression of at least one of the genes selected from the group consisting of the CH25h gene, the Cyp7b1 gene and the TNFα gene, the method comprising administering to the subject a compound that inhibits the activity of CYP7B1 (CYP7B1 inhibitor). Wherein the compound is preferably the compound according to formula I, II, III, IV, V, Va, VI, VII, IX, X, XI, XII, XIV, XV, XVa, XVI, XVIa, XVIb, XVII, XVII, XVIII, XIX, XX, XXI, XXII, XXIII and XXIV all their stereoisomeric forms and mixtures of stereoisomeric forms in all ratios, and their physiologically acceptable salts, and the physiologically acceptable solvates of any of them. In one embodiment the compound is the compound according to formula V, preferably clotrimazole The gene CH25h encodes the enzyme Cholesterol 25 hydrolase (CH25h). The gene Cyp7b1 encodes the enzyme 25-hydroxycholesterol 7-alpha-hydroxylase (CYP7B1) and the gene TNFα encodes the tumor necrosis factor α (TNFα).

The term "gene expression" is used herein in its regular meaning and means using gene information in the biosynthesis of RNA and/or the biosynthesis of the gene products such as proteins. In case of the genes CH25h, Cyp7b1 and TNFα gene expression means using the information of these genes in the biosynthesis of the respective RNA and/or Cholesterol 25 hydrolase (CH25h), CYP7B1 and the tumor necrosis factor α (TNFα). The gene expression comprises the induction of the respective gene.

The term "Cholesterol 25 hydrolase (CH25h)" can, for example, comprise the gene coding for human Cholesterol 25 hydrolase (CH25h) (UniProt number 095992, Version 1 last modified May 1, 1999) and related polypeptides with a sequence identity of at least 70% or 80% or more.

The term "25-hydroxycholesterol 7-alpha-hydroxylase (CYP7B1)" can, for example, comprise the gene coding for human 25-hydroxycholesterol 7-alpha-hydroxylase (CYP7B1) (UniProt number 075881, Version 2 Feb. 11, 2002) and related polypeptides with a sequence identity of at least 70% or 80% or more.

The term "tumor necrosis factor α (TNFα)" can, for example, comprise the gene coding for human tumor necrosis factor α (UniProt number P01375, Version 1, last modified Jul. 21, 1986) and related polypeptides with a sequence identity of at least 70% or 80% or more.

DNA and RNA in the gene expression as defined above, is DNA and RNA encoding Cholesterol 25 hydrolase (CH25h), 25-hydroxycholesterol 7-alpha-hydroxylase (CYP7B1) and/or the tumor necrosis factor α (TNFα).

The system of functional parts of a cell is defined as any assembly of parts of a cell comprising at least those parts of a cell, for example cell organelles, a medium, signal factors, RNA, DNA or enzymes, which are required for the expression of the specified genes.

Further, the invention shall be explained in more detail by the following Examples.

EXAMPLES

Material and Methods
Transcriptomic Data Analysis.

Microarray data was obtained from data series held at the NCBI Gene Expression Omnibus (GEO) database (Barrett et al. NCBI GEO: archive for functional genomics data sets—update. Nucleic acids research 41, D991-995 (2013)). Mouse whole lung data of filtered air (FA) versus chronic CS-exposed animals was obtained from accession GSE52509 (John-Schuster et al., American journal of physiology. Lung cellular and molecular physiology 307, L692-706 (2014)), and human data comparing gene expression in the small airway epithelial cells of COPD patients with healthy non-smoking controls from accession GSE11784 (Tilley et al., PloS one 6, e22798 (2011)) and GSE20257 (Shaykhiev et al., Cellular and molecular life sciences: CMLS 68, 877-892 (2011)). Data was analyzed using the GEO web tool GEO2R with default settings, to generate the $\log_2$ transformed expression values for each gene relative to FA or healthy controls. Gene Ontology pathway analysis was undertaken on gene expression data with a P value less than 0.05 using the web-based gene set analysis toolkit WebGestalt (Wang et al., Nucleic acids research 41, W77-83 (2013)). A heatmap of selected genes from the Gene Ontology pathway analysis was generated by Genesis software (Sturn et al., Bioinformatics 18, 207-208 (2002)), (Release 1.7.7, Institute for Genomics and Bioinformatics, Graz University of Technology).

RNA-Seq Analysis.

Total RNA of human lungs derived from COPD explants or healthy donor controls was sequenced using the Illumina system (HiSeq 2000) by the company GATC Biotech. Genomatix Software was used to analyze the raw data. Expression values were calculated as RPKM (Reads per kilobase million per mapped reads) for all loci available from reads uniquely aligned to the human genome. In this study we only present the expression of Ch25h.

Mice.

B6.129S6-Ch25h$^{tm1Rus}$/J (Ch25h$^{-/-}$) mice were obtained from The Jackson Laboratory. Age-matched female C57BL/6J mice obtained from Charles River Laboratories were used as controls. Mice were housed under specific pathogen free conditions at a constant temperature and humidity with a 12-hour light cycle and allowed food and water ad libitum.

Mouse COPD Models and Treatment.

8-12 week old mice were used in all experiments. For the CS induced COPD model, mice were exposed to 100% mainstream CS (John et al., Clinical science 126, 207-221 (2014)) at a particle concentration of 500 mg/m$^3$, generated from 3R4F research cigarettes (Filter removed, Tobacco Research Institute, University of Kentucky), for 50 min twice/day, 5 days/week for 4 or 6 months. Mice exposed to filtered air were used as controls. For the elastase induced iBALT-independent COPD model, mice were instilled oropharyngeally with a single application of 80 U/Kg body weight Porcine Pancreatic Elastase (PPE) (Sigma Aldrich) in 80 µl PBS. Mice treated with 80 µl PBS were included as controls. For Cyp7b1 inhibition, clotrimazole (Sigma Aldrich) 10 mM in DMSO, was further diluted in Corn oil (Mazola, Unilever) and applied i.p. at a dose of 80 mg/Kg body weight 3 times/week for two months. Mice were treated after two or four months of CS exposure and smoked for a further two months in parallel with the clotrimazole treatment.

Lung function analysis.

Mice were anaesthetized with ketamine-xylazine, tracheostomized, cannulated and the diffusing capacity for carbon monoxide (DFCO) calculated (Fallica et al., Journal of applied physiology 110, 1455-1459 (2011)). Briefly, 0.8 ml mixed gas (0.5% Ne, 21% $O_2$, 0.5% CO and 78% $N_2$) was instilled into the mice lungs and withdrawn 2 s later for analysis on a 3000 Micro GC Gas Analyzer (Infinicon). DFCO was calculated as $1-(CO_1/CO_0)/(Ne_1/Ne_0)$ where 0 and 1 refers to the gas concentration before and after instillation respectively. Respiratory function was analyzed using a forced pulmonary maneuver system (Vanoirbeek et al., American journal of respiratory cell and molecular biology 42, 96-104 (2010)) (Buxco Research Company, Data Sciences International) running FinePointe Software (version 6, Data Sciences International) and the quasistatic PV maneuver protocol.

Bronchoalveolar lavage (BAL).

After lung function analysis lungs were lavaged with 3×500 ul aliquots of sterile PBS (Gibco, Life Technologies) supplemented with Complete Protease Inhibitor Cocktail tablets (Roche Diagnostics). Cells were pelleted at 400 g for 20 min and resuspended in 500 µl RPMI-1640 medium (Gibco, Life Technologies) for the total cell count using a Neubauer Chamber. Cytospins of the cell suspension were then prepared and stained using May-Grünwald-Giemsa for differential cell counting (200 cells/sample) using morphological criteria. BAL fluid was retained for mass spectrometry analysis.

Mouse Lung Processing.

The two right lower lung lobes were snap frozen in liquid nitrogen, homogenized and total RNA isolated (peqGOLD Total RNA Kit, Peqlab). The right upper two lobes were dissociated into single cell suspensions in PBS supplemented with 0.1% FCS and 2 mM EDTA using the lung dissociation kit and gentleMACS Dissociator from Miltenyi Biotec for flow cytometry analysis. The left lung was inflation fixed with 6% paraformaldehyde under a constant pressure of 20 cm and then embedded into paraffin.

Quantitative Real Time RT-PCR 1 ug RNA was reverse transcribed using Random Hexamers and MuLV Reverse Transcriptase (Applied Biosystems). Gene expression was analyzed using SensiFAST SYBR Hi-ROX Kit (Bioline) on a StepOnePlus 96 well Real-Time PCR System (Applied Biosystems). Primer sequences can be found in Table 1. Expression of each gene was calculated relative to the housekeeping gene HPRT1 or Hprt1 as $2^{-\Delta Ct}$.

TABLE 1

Primer sequences used for the quantitative real time RT-PCR.

| Gene | Forward primer | Reverse Primer |
|---|---|---|
| Ch25h | CTC TAC CAG CAT GTG ATG TTT GT | CAT GTC GAA GAG TAG CAG GCA |
| CXCL8 | GGC TCT CTT GGC AGC CTT C | GGT TTG GAG TAT GTC TTT ATG CAC |

TABLE 1-continued

Primer sequences used for the quantitative real time RT-PCR.

| Gene | Forward primer | Reverse Primer |
|---|---|---|
| CXCL13 | CAA GTC AAT TGT GTG TGT GGA | GGG AAT CTT TCT CTT AAA CAC TGG |
| HPRT1 | AGG AAA GCA AAG TCT GCA TTG TT | GGT GGA GAT GAT CTC TCA ACT TTA A |
| Arg1 | GGA ACC CAG AGA GAG CAT GA | TTT TTC CAG CAG ACC AGC TT |
| Ccl19 | TGG GAA CAT CGT GAA AGC CT | GTG GTG AAC ACA ACA GCA GG |
| Ccl21 | CGG CTG TCC ATC TCA CCT AC | AGG GAA TTT TCT TCT GGC TGT |
| Ch25h | GAC CTT CTT CGA CGT GCT GA | CCA CCG ACA GCC AGA TGT TA |
| Cxcl1 | CCG AAG TCA TAG CCA CAC | GTG CCA TCA GAG CAG TCT |
| Cxcl13 | TCT CTC CAG GCC ACG GTA TTC T | ACC ATT TGG CAC GAG GAT TCA C |
| Cxcl9 | CGA GGC ACG ATC CAC TAC AA | AGG CAG GTT TGA TCT CCG TT |
| Cxcr5 | TGG ATG ACC TGT ACA AGG AAC TG | CGG TGC CTC TCC AGG ATT AC |
| Cyp27a1 | GGA GGG CAA GTA AAT AA | CCC TTC AGC AGC CTC TGT TTC AA |
| Cyp7b1 | GGA GCC ACG ACC CTA GAT G | GCC ATG CCA AGA TAA GGA AGC |
| Ebi2 | ATG GCT AAC AAT TTC ACT ACC CC | ACC AGC CCA ATG ATG AAG ACC |
| Fizz1 | TGC CAA TCC AGC TAA CTA TCC C | ACG AGT AAG CAC AGG CAG TT |
| Gmcsf | ATG CCT GTC ACG TTG AAT GA | CCG TAG ACC CTG CTC GAA TA |
| Hprt1 | AGC TAC TGT AAT GAT CAG TCA ACG | AGA GGT CCT TTT CAC CAG CA |
| Hsd3b7 | AGT GGT GGG GCC TAA CAT CA | CTG CTC AGC AAG GGC TTT AC |
| Il12p35 | ACT AGA GAG ACT TCT TCC ACA ACA AGA G | GCA CAG GGT CAT CAT CAA AGA C |
| Il1a | AGC GCT CAA GGA GAA GAC | CTG TCA TAG AGG GCA GTC C |
| Il1b | CAA CCA ACA AGT GAT ATT CTC CAT G | GAT CCA CAC TCT CCA GCT GCA |
| Il6 | GTT CTC TGG GAA ATC GTG GA | TGT ACT CCA GGT AGC TAT GG |
| Irf4 | AAA GGC AAG TTC CGA GAA GGG | CTC GAC CAA TTC CTC AAA GTC A |
| Lta | TCC ACT CCC TCA GAA GCA CT | AGA GAA GCC ATG TCG GAG AA |
| Ltb | TAC ACC AGA TCC AGG GGT TC | ACT CAT CCA AGC GCC TAT GA |
| Ltbr | AAG CCG AGG TCA CAG ATG AAA | CGA GGG GAG GAA GTG TTC TG |

TABLE 1-continued

Primer sequences used for the quantitative real time RT-PCR.

| Gene | Forward primer | Reverse Primer |
|---|---|---|
| Mcp1 | CTT CTG GGC CTG CTG TTC A | CCA GCC TAC TCA TTG GGA TCA |
| Mmp12 | TGT ACC CCA CCT ACA GAT ACC TTA | CCA TAG AGG GAC TGA ATG TTA CGT |
| Nos2 | CGG CAA ACA TGA CTT CAG GC | GCA CAT CAA AGC GGC CAT AG |
| Timp1 | CAC TGA TAG CTT CCA GTA AGG CC | CTT ATG ACC AGG TCC GAG TTG C |
| Tnfa | CAC CAC GCT CTT CTG TCT | GGC TAC AGG CTT GTC ACT C |

Immunofluorescence Staining.

3 µm sections from mouse left lung or human core samples were stained as described (John-Schuster et al., Oncotarget Epub ahead of print, DOI: 10.18632/oncotarget.14027 (2015)). Briefly, sections were deparaffinized, rehydrated and heat-induced epitope retrieval undertaken using HIER Citrate Buffer (pH 6.0, Zytomed Systems). Sections were blocked using rodent blocking buffer (Biocare Medical), and then incubated overnight at 4° C. with the primary antibody, followed by 30 min with the secondary antibody and counterstained with DAPI (1:4000, Sigma-Aldrich), mounted in fluorescent mounting medium (Dako) and imaged with a fluorescent Olympus BX51 microscope running cellSens software (Olympus). Primary antibodies: rat IgG2a anti-mouse CD45r (1:50, clone: RA3-6B2, BD Biosciences), mouse IgG1 anti-mouse CD3 (1:300, clone: PC3/188A, Santa Cruz Biotech), Ch25h human and mouse (1:500, Clone AAH17843, Abcam). Secondary antibodies: Alexa Fluor 488 conjugated goat anti-mouse IgG antibody (1:300, Cat. No. A11008, ThermoFisher Scientific), Alexa Fluor 568 conjugated goat anti-rat IgG antibody (1:300, Cat. No. A11077, ThermoFisher Scientific).

Quantitative Morphometry.

H&E stained tissue sections were analyzed by design-based stereology using an Olympus BX51 light microscope equipped with the new Computer Assisted Stereological Toolbox (newCAST, Visiopharm) as described (John-Schuster et al., American journal of physiology. Lung cellular and molecular physiology 307, L692-706 (2014)), by readers blinded to the study groups. Briefly, for mean chord length (MCL) measurements, 20 frames were selected randomly across multiple sections by the software, using the ×20 objective, and superimposed by a line grid and points. The intercepts of lines on alveolar wall ($L_{septa}$) and points localized on air space ($P_{air}$) were counted and calculated as $MCL=\Sigma P_{air} \times L(p)/\Sigma L_{septa} \times 0.5$, where L(p) is the line length per point. The volume of inflammation (V) was quantified in 50 frames, using the ×40 objective, by counting points hitting inflammatory cell zones ($P_{inflam}$). For calculation, the $P_{inflam}$ were referenced to intercepts of lines with both airways and vessels ($I_{airway/vessel}$): $V=\Sigma P_{inflam} \times L(p)/\Sigma I_{airway/vessel}$. Further, airway, vessel or septum associated inflammation quantification was classified by the location of the inflammation, and was calculated referring to intercept of lines with airway, vessel, or both, respectively.

Flow Cytometry.

$10^6$ cells from filtered single cell lung suspensions were blocked with purified anti-mouse CD16/CD32 (Clone: 93, eBioscience) before incubating for 30 min on ice with antibody cocktails. After washing and re-suspending in MACS buffer, cells were analyzed on a BD FACSCanto II flow cytometer (BD Biosciences) and BD FACSDiva software. B cell and T cell staining was performed with: APC-conjugated anti-CD19 (clone: 6D5, Miltenyi Biotec), APC-Vio770-conjugated anti-CD3e (clone: 17A2, Miltenyi Biotec), PE-Vio770-conjugated anti-CD22 (clone: Cy34.1, Miltenyi Biotec), PE-conjugated anti-CD80 (clone: 16-10A1, Miltenyi Biotec), PerCP-Vio700-conjugated anti-MHCII (clone: M5/114.15.2, Miltenyi Biotec), VioGreen-conjugated anti-CD69 (clone: H1.2F3, Miltenyi Biotec), FITC-conjugated anti-IgG (Biolegend), VioBlue-conjugated anti-GI7 (Biolegend). For the macrophage profile: VioGreen-conjugated anti-CD45 (clone: 30F11, Miltenyi Biotec), APC-Vio770-conjugated anti-Ly6C (clone: 1G7.G10, Miltenyi Biotec), VioBlue-conjugated anti-Ly6G (clone: 1A8, Miltenyi Biotec), FITC-conjugated anti-MHCII (clone: M5/114.15.2, Miltenyi Biotec), PerCP-Vio700-conjugated anti-F4/80 (clone: REA126, Miltenyi Biotec), PE-conjugated anti-CD11b (clone: M1/70.15.11.5, Miltenyi Biotec), APC-conjugated anti-CD11c (clone: N418, Miltenyi Biotec), PE-Vio770-conjugated anti-CD64 (clone: REA286, Miltenyi Biotec).

Microdissection of Airways.

Middle and distal airways from C57BL/6J and Ch25h$^{-/-}$ mice were isolated and incubated ex vivo as described by Yildirim et al. (Eur Respir J 32, 694-704 (2008)). Briefly, after sacrifice by a ketamine-xylazine over dose, the trachea was cannulated, the lungs removed from the thorax and infused with 1% low-melting agarose dissolved in 1:1 Ham's F12 nutrient medium (Sigma-Aldrich) and distilled water (Gibco, Life Technologies). Airways were dissected under a microscope (Zeiss) from the left lung after the agarose had solidified on ice for 30 min. The isolated airways were washed and cultured in airway epithelial cell medium (PromoCell) at 37° C., 5% $CO_2$.

B Cell Isolation and Migration Assay.

B cells were purified from the spleens of C57BL/6J mice by negative selection (B cell Isolation Kit, mouse, Miltenyi Biotec). For the migration assay, primary mouse airways were isolated 1 day prior, treated with 10% cigarette smoke extract (CSE) in airway epithelial cell culture medium or culture medium alone for 24 h and at the same time to inhibit Cyp7b1, clotrimazole was also diluted with culture medium to a final concentration of 1 µM for 1 h prior to the migration assay. Further tested another Cyp7b1 inhibitors included Clotrimazole with 10% cigarette smoke extract (CSE, 10%)+lipopolysaccharide (LPS, 10 µg/mL), supplemented or not with the 18 CYP7B1 inhibitors at concentration of 1 µM. The supernatants were transferred as conditioned medium to the lower well of 24-well transwell plates (Permeable Polycarbonate Membrane Inserts, Corning, Fisher Scientific), for inducing B cell migration, while the airway samples were snap frozen in liquid nitrogen for RNA isolation. Freshly isolated B cells at $2.5 \times 10^6$/ml in 100 µl were activated by unconjugated AffiniPure F(ab')$_2$ Fragment Goat anti-mouse IgM, µchain specific antibody (1.3 µg/ml, 115-006-020, Jackson Immunoresearch Laboratories) for 1 hr at 37° C. in 5.0 µm pore sized transwell inserts (Permeable Polycarbonate Membrane Inserts, Corning, Fisher Scientific). Transwell inserts were then placed into the wells of conditioned medium and incubated for 3 hr at 37° C. Migrated B cells were collected and counted by Neubauer Chamber and reported as percentage of input.

Isolation and Stimulation of Professional APCs.

Primary alveolar macrophages were isolated from the lungs of C57BL/6J and Ch25h$^{-/-}$ mice by BAL with ten washes of 1 ml PBS (Gibco, Life Technologies). Cells were pelleted at 400 g for 20 min and resuspended in complete RPM1-1640 medium supplemented with 10% fetal bovine serum, 50 µM β-mercaptoethanol and 100 U/ml penicillin and streptomycin (all from Gibco, Life Technologies). $5\times10^4$ cells in 1 ml were seeded in 24-well plates and allowed to adhere for 1 h. Non-adherent cells were removed by washing twice with PBS. To generate bone marrow derived macrophages (BMDM) and DCs (BMDC), bone marrow was flushed from femurs and tibias of C57BL/6J and Ch25h$^{-/-}$ mice with RPMI-1640 medium. Cells were disaggregated by passing through a 40 µm mesh, and cultured in complete RPMI-1640 medium supplemented with 5% fetal bovine serum, 50 µM β-mercaptoethanol and 100 U/ml penicillin and streptomycin at a concentration of $1\times10^6$ cells/ml in 24-well plates. For BMDMs, the medium was supplemented with 20 ng/ml murine recombinant M-CSF (ImmunoTools), and for BMDCs, the medium was supplemented with 20 ng/ml murine recombinant GM-CSF (ImmunoTools) and cultured at 37° C., 5% $CO_2$. Cells were maintained by replacing the medium with fresh medium on alternate days ensuring removal of non-adherent cells. On day 6 adherent BMDMs were collected. For BMDCs, on day 7 to 8 adherent cells were harvested and resuspended at $1\times10^6$ cells/ml in 10 ml complete RPMI-1640 medium in 100 mm petri dishes and cultured for a further 24-48 h. The non-adherent, non-proliferating, maturing DCs were collected as they were released. Primary alveolar macrophages and BMDMs were polarized towards M1 by culturing with complete RPMI-1640 medium containing 1 µg/ml LPS (from *E. coli* 011134, Sigma-Aldrich) and 20 ng/ml recombinant murine IFNγ (ImmunoTools) for 24 h or an M2 phenotype with 20 ng/ml recombinant murine IL-4 (ImmunoTools) for 24 h. BMDCs were stimulated with 1 µg/ml LPS for 24 h.

Mass Spectrometry to Determine 25-Hydroxycholesterol Levels.

Determination of 25-HC in cell culture supernatant and Bronchoalveolar lavage fluid (BALF) was undertaken using esterification and ultra-high pressure liquid chromatography (UHPLC) coupled with high resolution time of flight mass spectrometry (LC-HRTOF-MS) as described previously (Honda et al., Journal of lipid research 50, 350-357 (2009); Huang et al., Biomedical chromatography: BMC 28, 794-801 (2014)). UHPLC separation was performed on a 1290 Infinity Binary LC-System using an Eclipse C-18, 1.8 µm, 50×2.1 mm I.D. analytical column (both from Agilent Technologies). Mass spectrometric detection was accomplished on a Citius® High Resolution Time of Flight mass spectrometer (Leco).

Metabolomics Analysis.

The targeted metabolomics approach was based on LC-ESI-MS/MS and FIA-ESI-MS/MS measurements by Absolute/DQ™ p180 kit (BIOCRATES Life Sciences AG) (Zukunft et al., Chromatographia 76, 1295-1305 (2013)). Frozen lung tissue was homogenized and extracted as described previously (Romisch-Margl et al., Metabolomics 8, 133-142 (2012)). Mass spectrometric analyses were done on an API 4000 triple quadrupole system (Sciex Deutschland GmbH) equipped with a 1200 Series HPLC (Agilent Technologies) and a HTC PAL auto sampler (CTC Analytics) controlled by the software Analyst 1.5.1. Data evaluation for quantification of metabolite concentrations and quality assessment was performed with the MetIDQ™ software package, which is an integral part of the AbsoluteIDQ™ kit.

Statistical Analysis.

No statistical methods were used to predetermine sample size. GraphPad Prism (Version 6, GraphPad Software) was used for all statistical analysis. Data are presented as mean±s.d. with sample size and number of repeats indicated in the figure legends. For comparison between two groups statistical significance was analyzed with Student's t test. For multiple comparisons one-way ANOVA followed by Bonferroni's post hoc test was used. P values less than 0.05 were considered significant.

Figure 1:
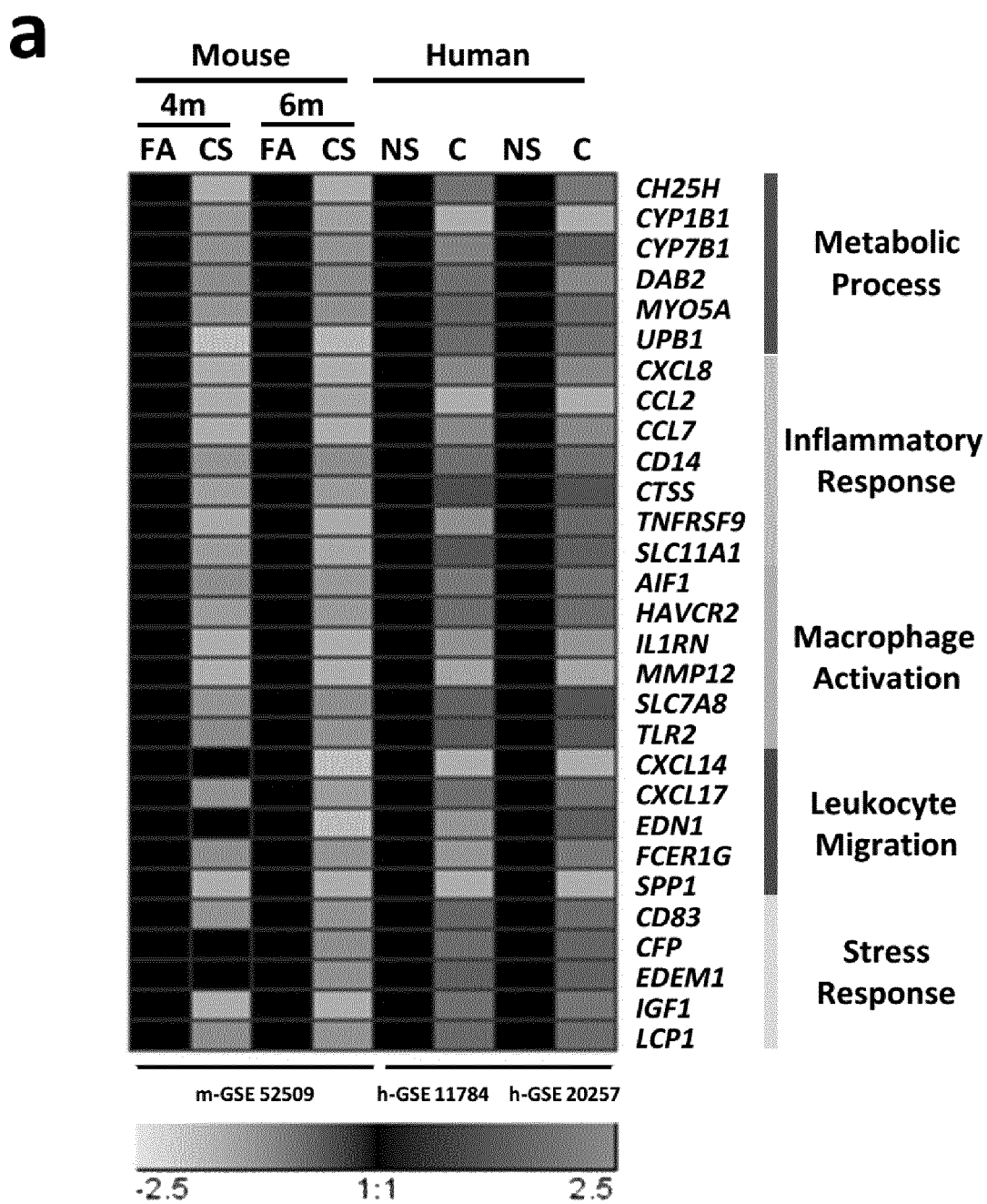
FIG. 1: Increased expression of the oxysterol metabolizing enzyme Ch25h in airway epithelial cells of COPD patients. (a) Heat map of microarray data obtained from the NCBI GEO data series indicated, with genes grouped according to GO pathway membership. FA, filtered air; CS, cigarette smoke; NS, non-smoker; C, COPD. (b) RNA-Seq data of Ch25h expression in an independent COPD cohort. n=3 patients per group. Data are mean±s.d. *P<0.05 two-tailed unpaired t-test. (c) Representative immunofluorescence analysis of airway from lungs of Human (Hu) non-smokers (NS) or COPD patients and from mice (Mo) exposed to filtered air (FA) or cigarette smoke (CS) for 6 months, stained to detect Ch25h (Red) and DAPI (Blue). Scale bar 50 µm. (d) Ch25h mRNA abundance in isolated airways from C57BL/6 mice exposed to cigarette smoke (CS) for the duration indicated, shown relative to filtered air (FA). n=5 mice per group. Data are mean±s.d. *P<0.05, *P<0.001 and **P<0.0001 one-way ANOVA and Bonferroni's post hoc test. (e) Levels of 25-hydroxycholesterol in the bronchoalveolar lavage fluid of C57BL/6 mice exposed to FA or CS for 6 months as determined by mass spectrometry. n=4 mice per group. Data are mean±s.d. *P<0.05 two-tailed unpaired t-test.
Figure 1:
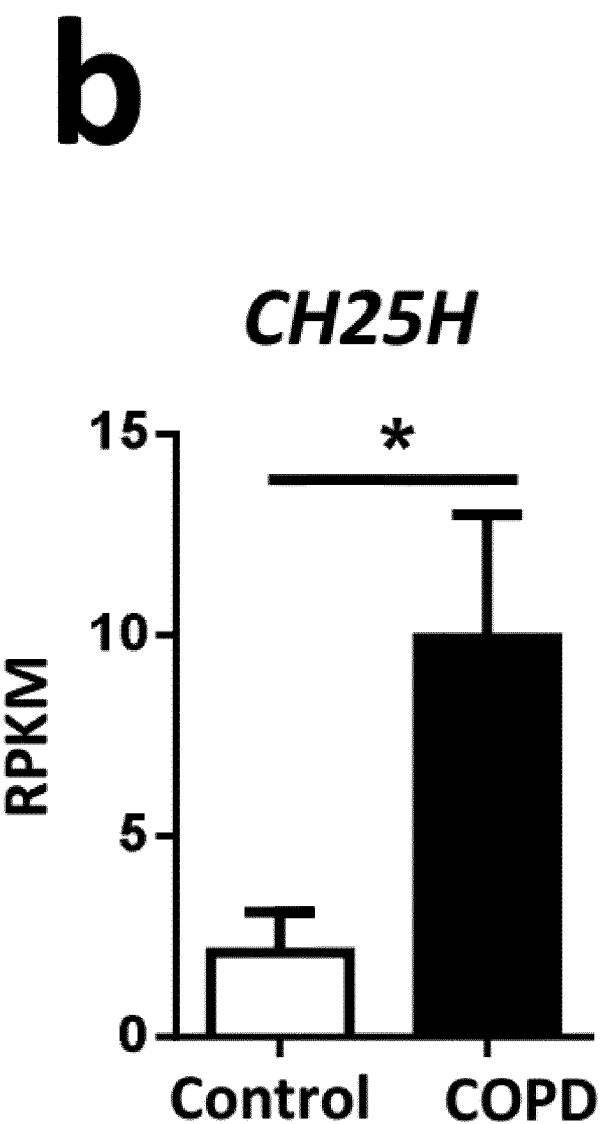
Figure 1:
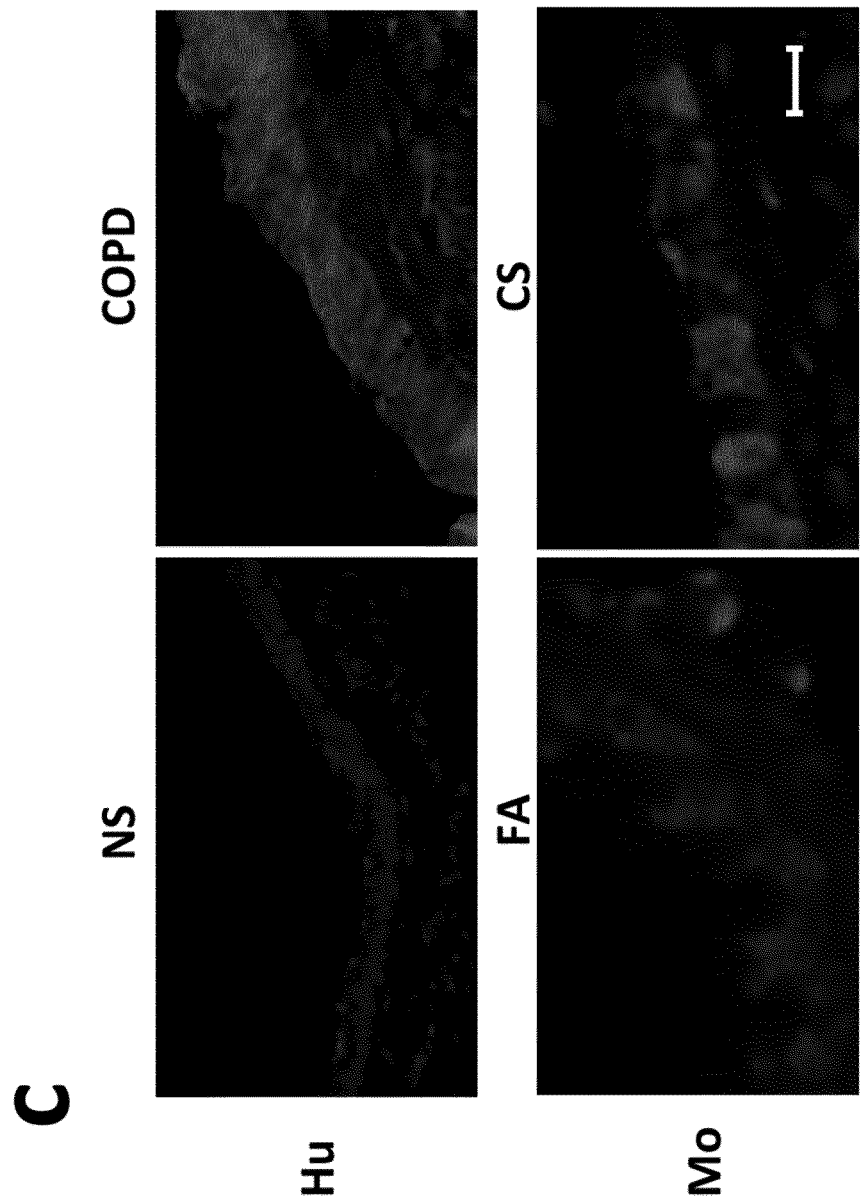
Figure 1:
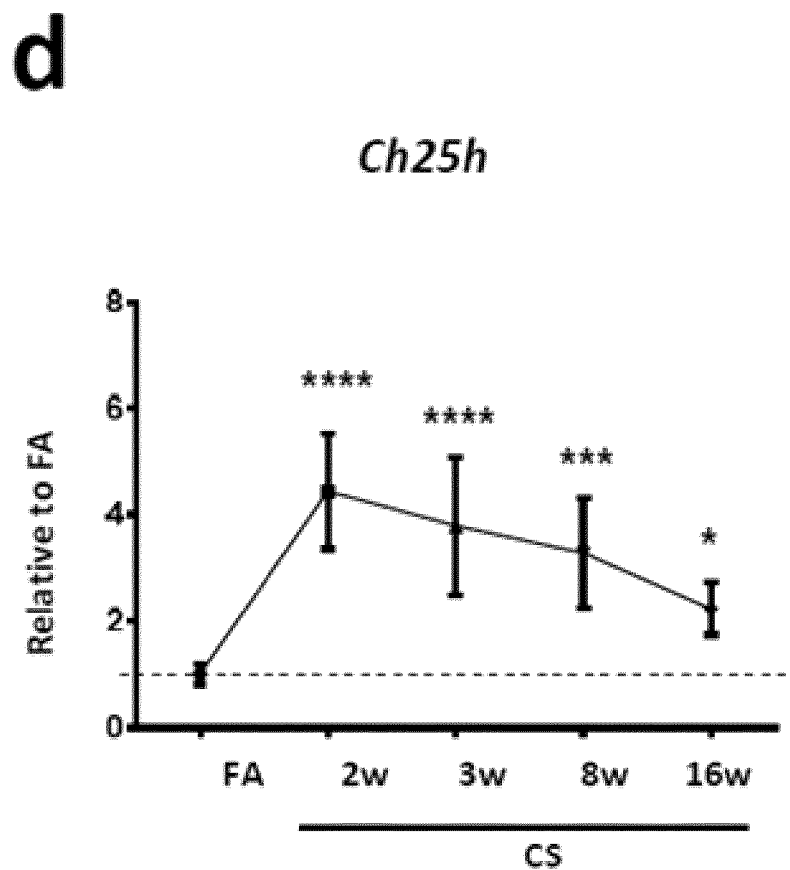
Figure 1:
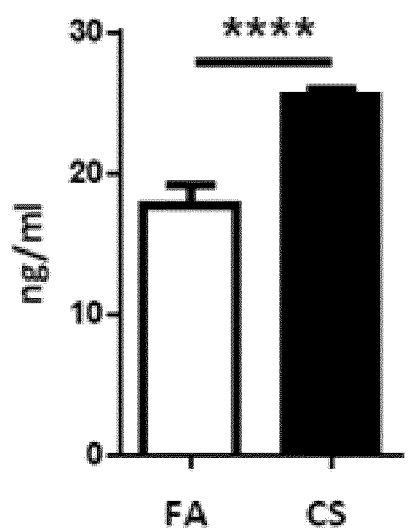

Results and Discussion iBALT composed of B and T cells (Randall et al., Advances in immunology 107, 187-241 (2010)) are positioned within the lung predominantly alongside the bronchial epithelium (Gregson et al., British journal of experimental pathology 60, 471-482 (1979)). However, the functional presence of iBALT for pulmonary diseases remains poorly understood. Airway epithelial cells secrete a plethora of immune mediators (Benam et al., Nature methods 13, 151-157 (2016)), yet pulmonary factors that orchestrate iBALT positioning remains to be defined. The present inventors compared transcriptomics data from two publically available datasets of small airway epithelial cells from COPD patients (Tilley et al., PloS one 6, e22798 (2011); Shaykhiev et al., Cellular and molecular life sciences: CMLS 68, 877-892 (2011)) combined with data derived from chronically CS-exposed mice lungs (John-Schuster et al., American journal of physiology. Lung cellular and molecular physiology 307, L692-706 (2014)), revealing a conserved interspecies signature for the expression of key genes related to the Gene Ontology pathways (Wang et al., WEB-based GEne SeT Analysis Toolkit (WebGestalt): update 2013. Nucleic acids research 41, W77-83 (2013)) of "Inflammatory Response", "Macrophage Activation" and "Leukocyte Migration" (FIG. 1*a*). Gene similarities were also evident in the Gene Ontology pathway "Metabolic Process", in particular Ch25h and CYP7B1, were upregulated following both CS-exposure in mice and in COPD patients (FIG. 1*a*). Similarly, RNAseq analysis of lung homogenates from an independent COPD patient cohort confirmed higher Ch25h expression in the lungs of COPD patients compared to non-smoking control individuals (FIG. 1*b*), supporting a previous observation (Sugiura et al., Respirology 17, 533-540 (2012)). Staining of airway sections revealed that Ch25h was localized to the airway epithelial cells in both human and mice (FIG. 1*c*), suggesting that the initiating lesion in both patients and mice following chronic CS exposure emanates from the airways. Ch25h mRNA expression was elevated in isolated airway epithelial cells from COPD patients (FIG. 1*d*) as well as occurred in isolated mouse airways after CS-exposure and remained elevated for at least 16 weeks (FIG. 1*f*) as well as isolated airway epithelial cells from COPD patients (FIG. 1*e*). Bronchoalveolar lavage fluid obtained from mice exposed to chronic CS revealed a higher concentration of 25-hydroxycholesterol as assessed by mass spectrometry (FIG. 1*f*). These translational results indicate that CS-activated Ch25h signaling in the airway epithelium confers iBALT formation.

Figure 2:
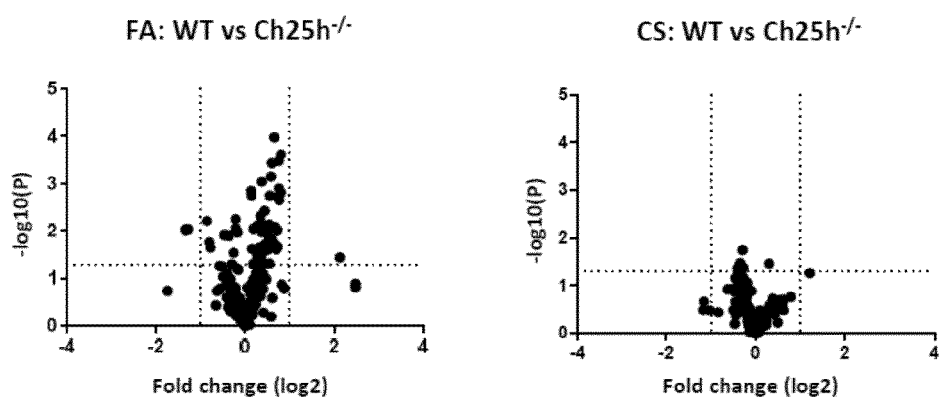
FIG. 2: Ch25h-deficient mice display similar metabolic profiles and inflammatory responses following chronic cigarette smoke exposure as wild-type animals. (a) Volcano plots of the mean $\log_2$(relative fold change) versus $-\log_{10}$(P value) for each individual metabolite in whole lung tissue as determined by the Absolute/DQ™ p180 Kit from wild-type (WT) versus Ch25h$^{-/-}$ mice. Left: following four month FA exposure (n=4 mice per group). Right: following four month CS exposure (n=6 mice per group) (b) Heat map of mRNA abundance of the genes shown relative to Hprt1 and FA controls as determined by RT-qPCR from the lungs of WT and Ch25h$^{-/-}$ mice exposed to filtered air (FA) or cigarette smoke (CS) for 4 and 6 months. Experiment repeated twice. n=4 mice per FA groups and n=6 mice per CS groups. (c) Bronchoalveolar lavage fluid (BALF) total and differential cell counts from mice described in b. Data are mean±s.d.
Figure 2:
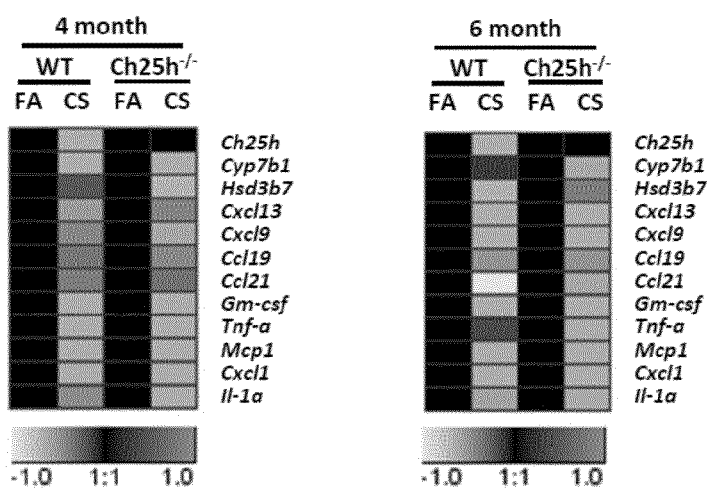
Figure 2:
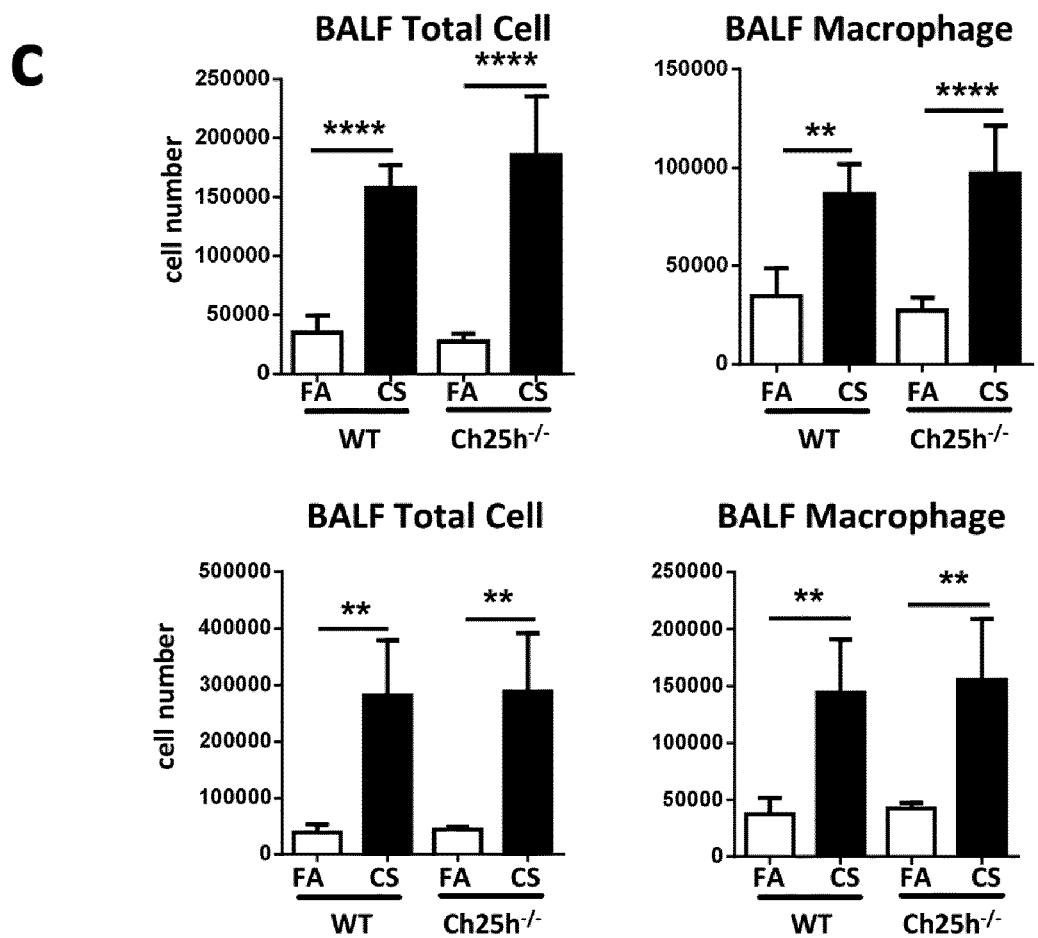
Figure 2:
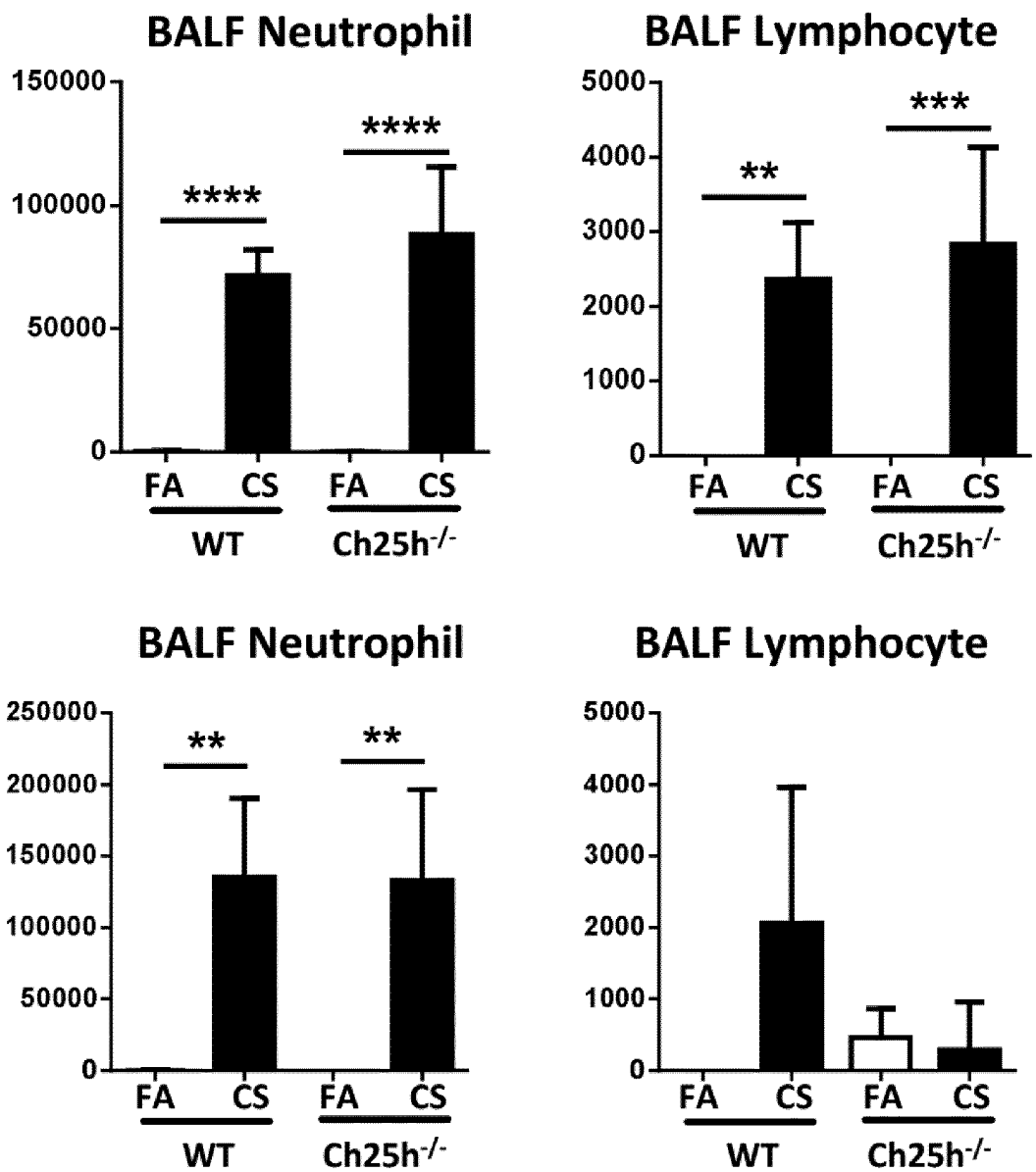
Figure 3:
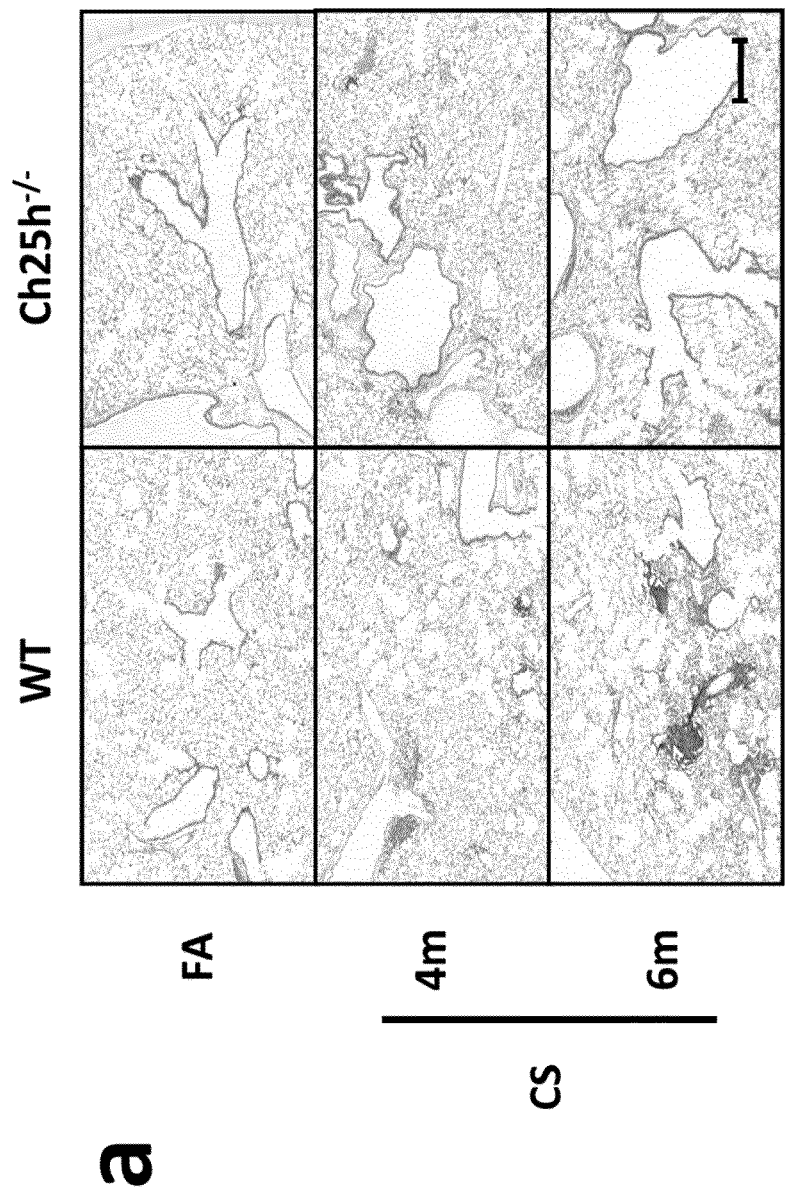
FIG. 3: Impaired iBALT formation and attenuated cigarette smoke-induced COPD in Ch25h-deficient mice. (a) Representative H&E stained lung from wild-type (WT) and Ch25h-deficient (Ch25h$^{-/-}$) mice exposed to filtered air (FA) or cigarette smoke (CS) for 4 and 6 months. Experiment repeated twice. n=4 mice per FA groups and n=6 mice per CS groups. (b) Mean chord length (MCL) quantification of lung sections and lung volume measurements from the mice described in a. Data are mean±s.d. P<0.01, *P<0.001 and ****P<0.0001 one-way ANOVA and Bonferroni's post hoc test. ## P<0.01 two-tailed unpaired t-test. (c) Left: Quantification of total iBALT and that localized on the airway, vessels and septal area from the mice described in a. Data are mean±s.d. *P<0.05, **P<0.01 one-way ANOVA and Bonferroni's post hoc test. Right: Representative immunofluorescence images of the three regions quantified, stained to detect CD45R (B cells, Red), CD3 (T cells, Green) and DAPI (Blue). A, airway; V, vessel. Scale bar 500 µm. (d,e) Flow cytometric analysis of whole lung single cell suspensions from mice described in a, to detect CD69 positive CD19 cells (d) and CD3 cells (e). Left: example dot plots of FA and CS exposed mice. Right: frequency of CD69 positive cells. n=4 mice per FA groups and n=6 mice per CS groups.
Figure 3:
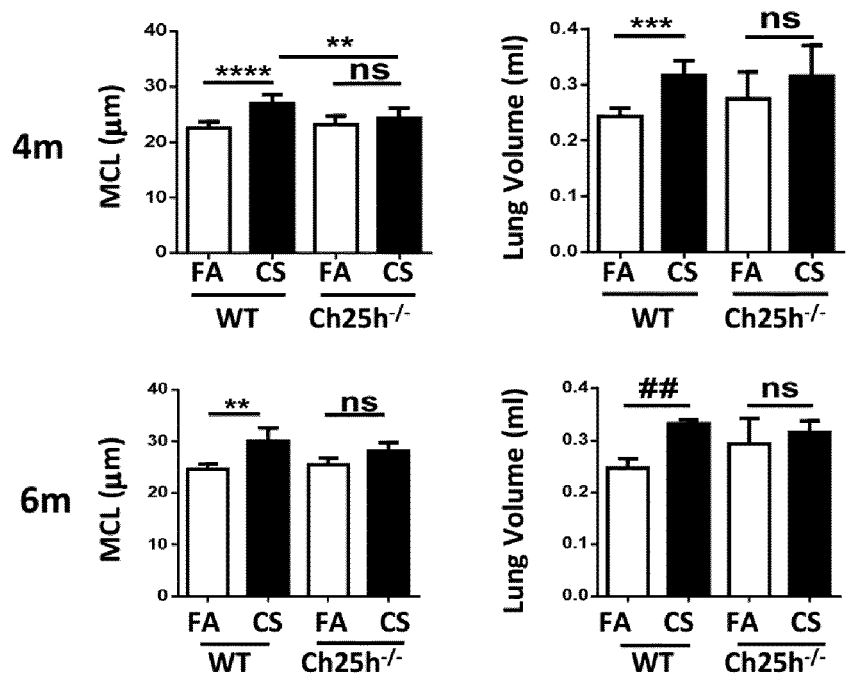
Figure 3:
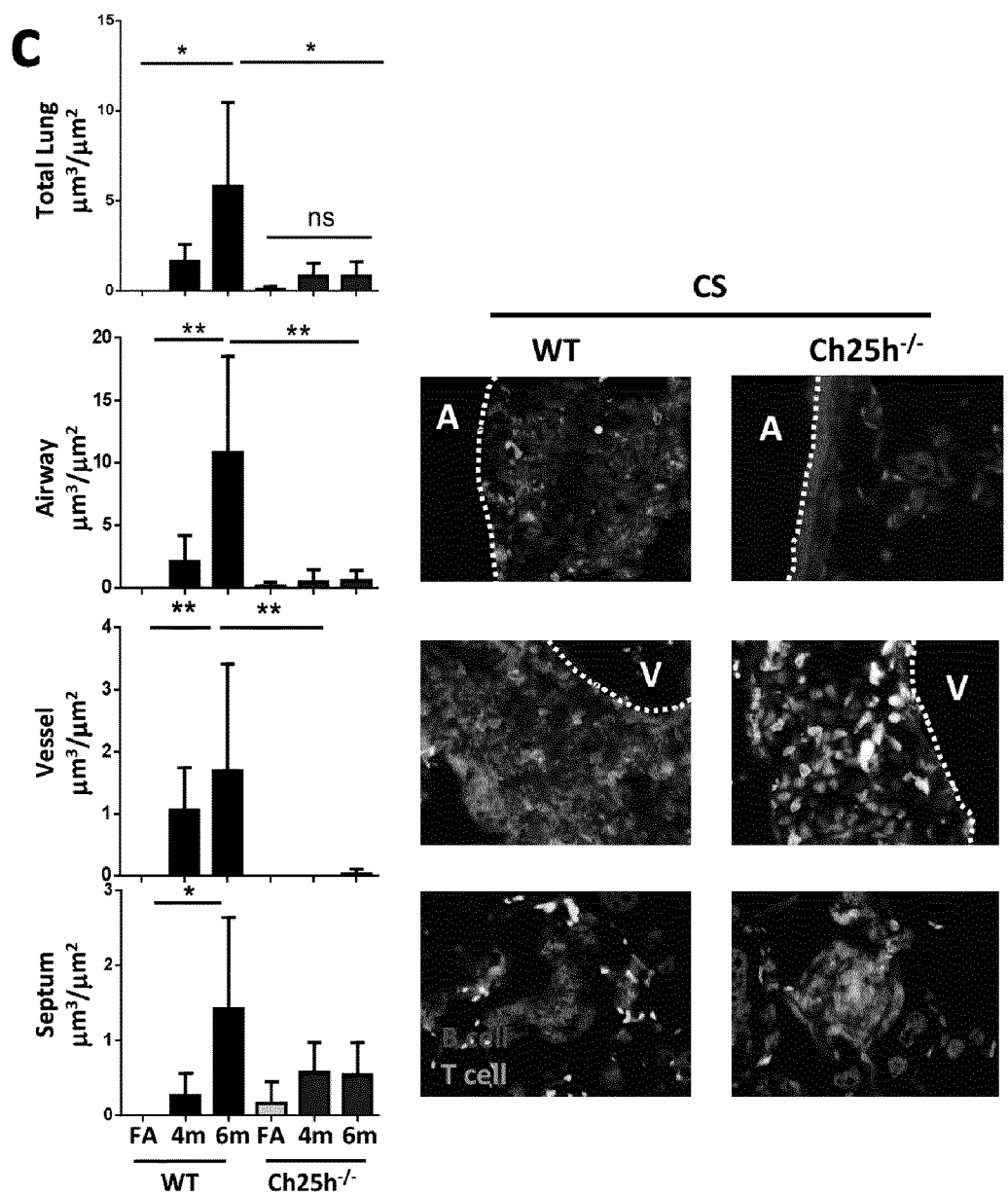
Figure 3:
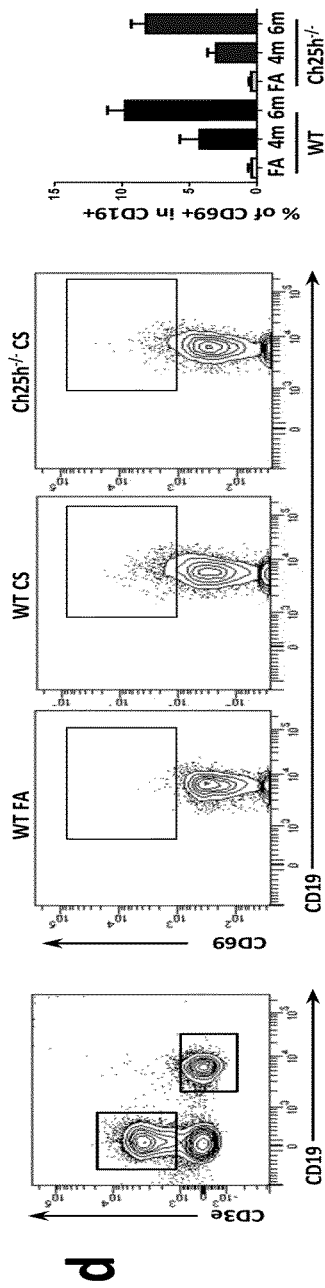
Figure 3:
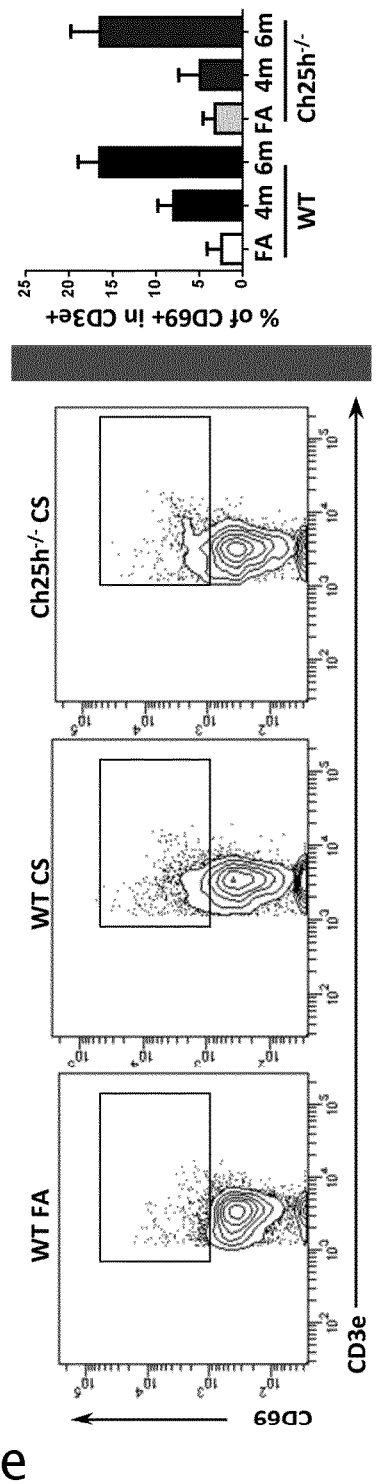

To determine the role of Ch25h in iBALT formation in vivo, Ch25h deficient mice were exposed to CS for 4 and 6 months to induce emphysema development (John-Schuster et al., American journal of physiology. Lung cellular and molecular physiology 307, L692-706 (2014); Yoshida et al., Nature medicine 16, 767-773 (2010); Cloonan et al., Nature medicine 22, 163-174 (2016)). Importantly, the lungs of these mice showed no general metabolic differences, even after CS exposure, compared to the wild-type animals (FIG. 2a), confirming the importance of Ch25h in the synthesis of 7α,25-OHC. Wild-type mice developed clear evidence of emphysema accompanied by iBALT formation from 4 months onwards (FIG. 3a, b), that specifically associated with the airways vessels and septal tissue (FIG. 3c), whereas in Ch25h−/− mice formation of iBALT and the hallmarks of emphysema failed to develop (FIG. 3a-c). Flow cytometric analysis of whole lung cells showed that both T and B cells were activated after CS exposure similarly in both Ch25h−/− and wild-type mice (FIG. 3d-e). Suggesting that Ch25h is important for cellular positioning within the iBALT and not recruitment and activation of T and B cells to the lung. In support, cellular recruitment as well as mRNA expression of Cxcl13, Cxcl9, Ccl19, Ccl21, Cxcl1 and Mcp1 was equivalently increased in both wild-type and Ch25h−/− mice following CS-exposure (FIGS. 2b and c).

Figure 4:
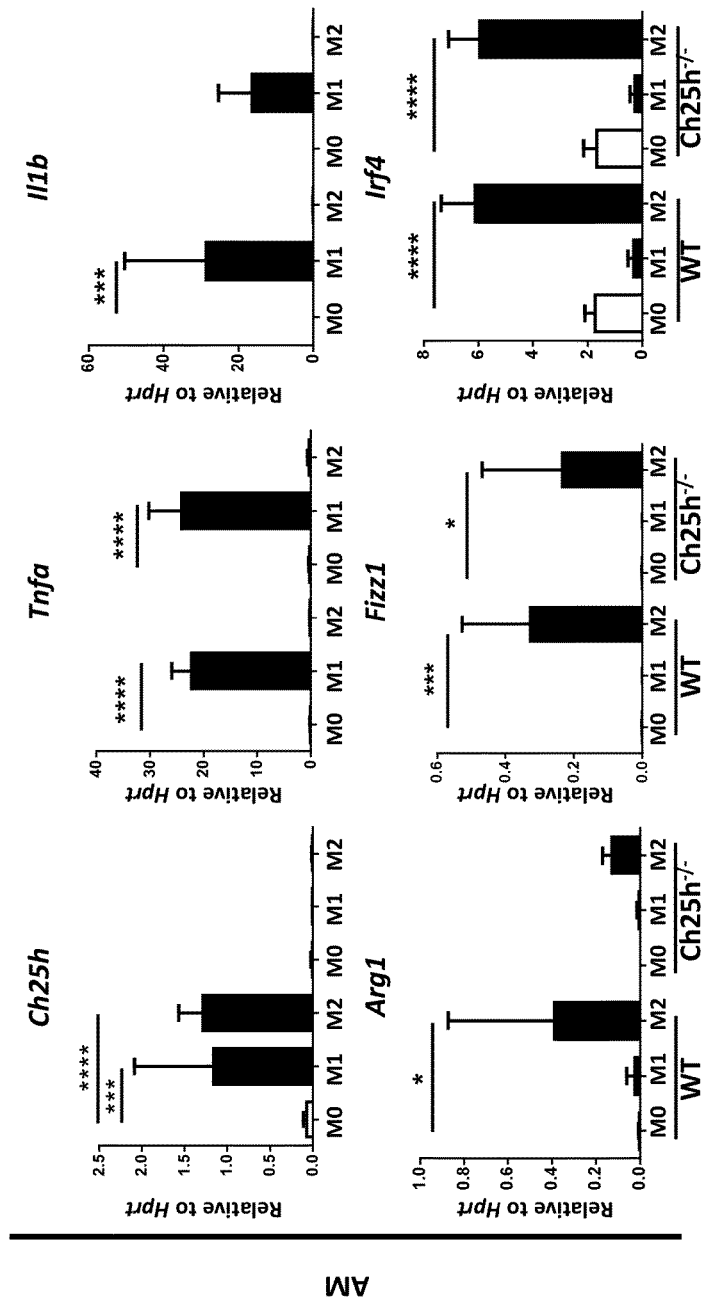
FIG. 4: Professional APCs isolated from wild-type and Ch25h$^{-/-}$ mice respond similarly to stimulation with LPS, IFNγ and IL4. (a, b) Ch25h, Tnfa, Il1b, Arg1, Fizz1 and Irf4 mRNA abundance in alveolar macrophages (a) and bone marrow derived macrophages (b) isolated from wild-type (WT) and Ch25h$^{-/-}$ mice polarized under M0, M1 or M2 conditions. Experiment repeated three times (a) or twice (b), pooled data shown. n=7 (a) or 5 (b) per group. Data are mean±s.d. *P<0.05, P<0.01, *P<0.001 and **P<0.0001 one-way ANOVA and Bonferroni's post hoc test. (c) Ch25h, Il12p35, Tnfa and Nos2 mRNA abundance in bone marrow derived DCs isolated from WT or Ch25h$^{-/-}$ mice treated with LPS. n=4 per group. Data are mean±s.d. P<0.01 and ****P<0.0001 one-way ANOVA and Bonferroni's post hoc test.
Figure 4:
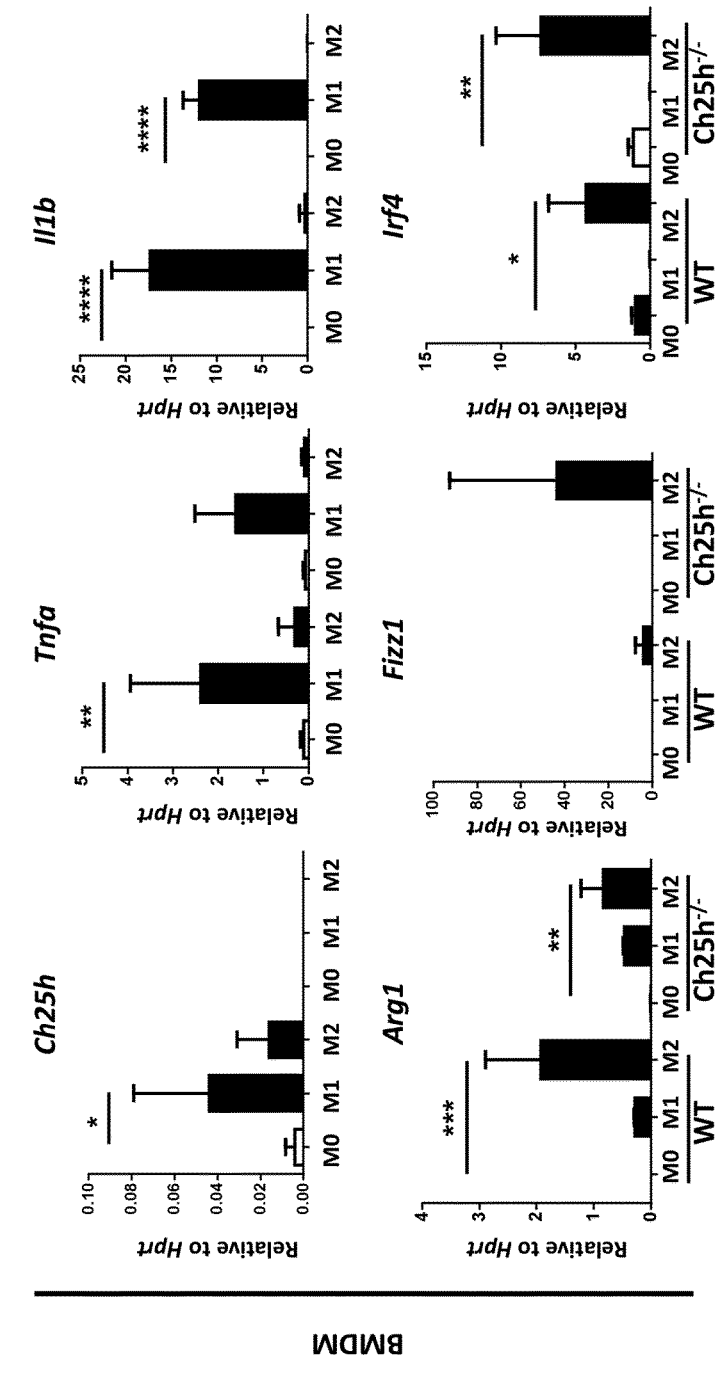
Figure 4:
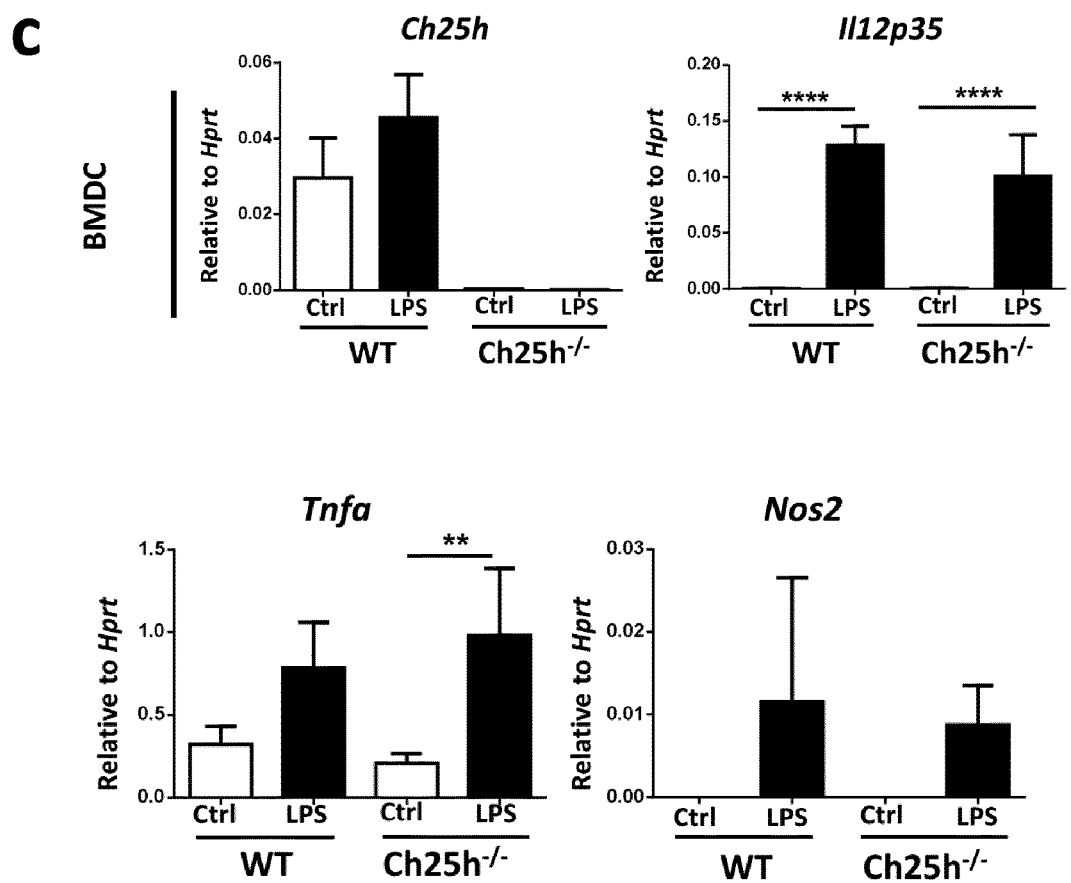
Figure 5:
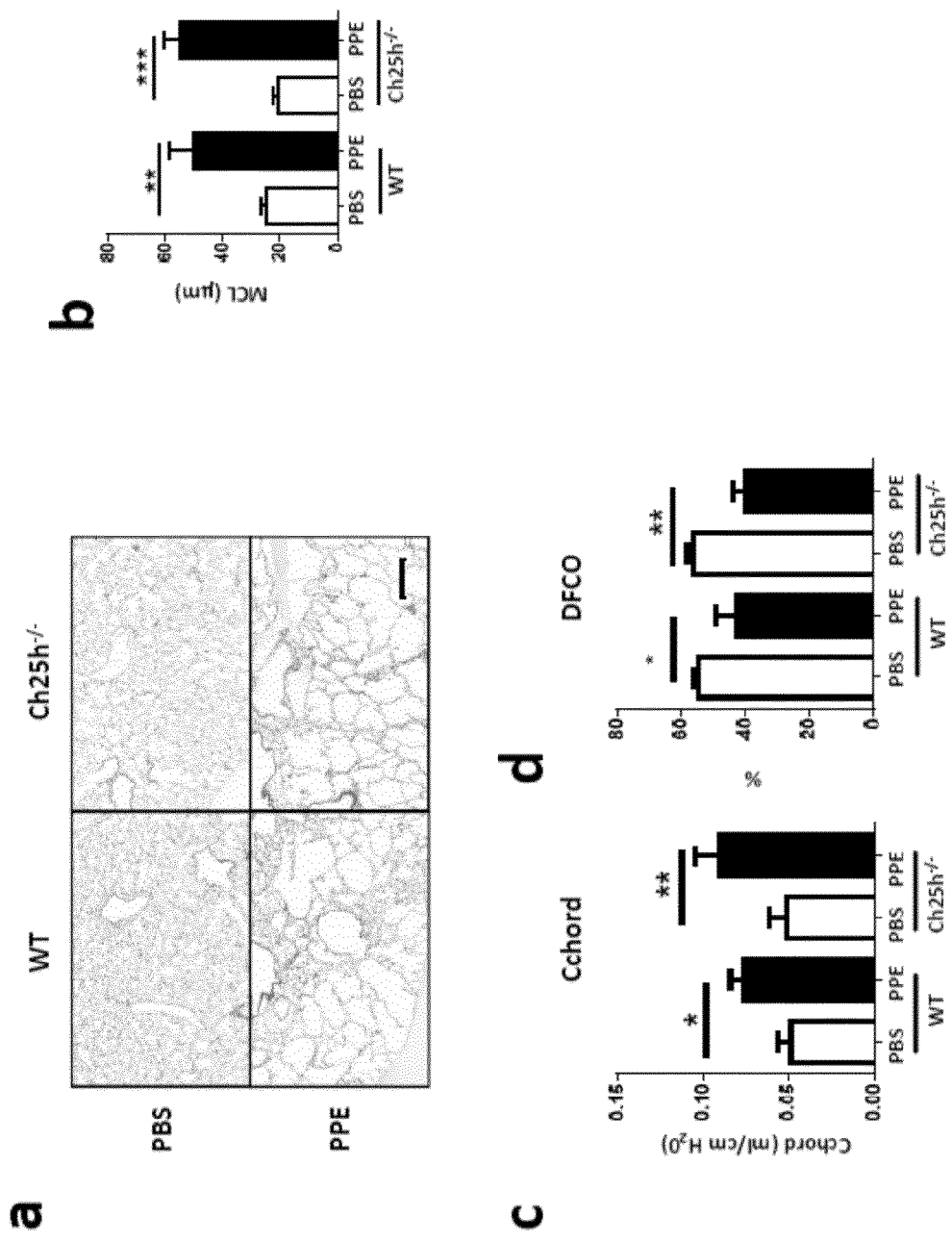
FIG. 5: Ch25h deficiency does not protect against iBALT independent emphysema. (a) Representative H&E stained lung from wild-type (WT) and Ch25h$^{-/-}$ mice treated with a single oropharyngeal application of PBS or porcine pancreatic elastase (PPE) 80 U/Kg and analyzed on day 28. Experiment repeated twice. n=4 mice per PBS groups and n=5 mice per PPE groups. (b) Mean chord length (MCL) quantification of lung sections from the mice described in a. (c) Chord compliance pulmonary function data and lung volumes from the mice described in a. (d) Diffusing capacity for carbon monoxide values from the mice described in a. (b-d) Data are mean±s.d. *P<0.05, P<0.01 and *P<0.001 one-way ANOVA and Bonferroni's post hoc test. (e) Bronchoalveolar lavage fluid (BALF) total and differential cell counts from mice described in a. Data are mean±s.d.
Figure 5:
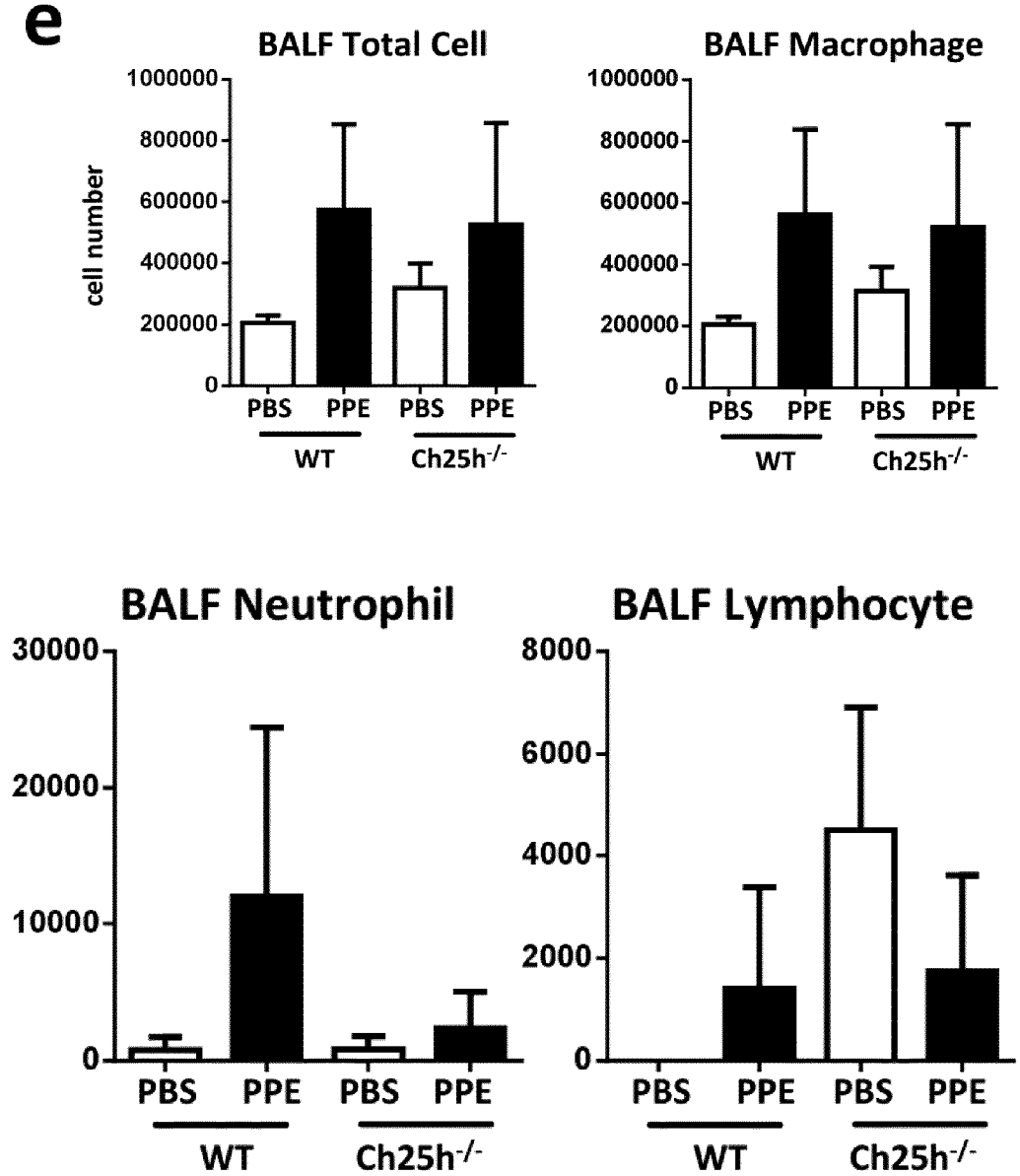

Next, the present inventors assessed whether differential cytokine secretion by resident alveolar or bone-marrow (BMDM) recruited macrophages deficient in Ch25h was involved in emphysema development. Isolated alveolar macrophages significantly increased expression of Ch25h under both polarizing conditions (FIG. 4a), while BMDM from wild-type mice significantly increased expression of Ch25h only under M1-polarizing conditions (FIG. 4b) compared to Ch25h−/− mice isolated cells. Importantly, both alveolar and bone-marrow macrophages from wild-type and Ch25h−/− mice induced strong expression of Tnfa and Il1b under M1-polarizing conditions as well as Irf4 and Fizz1 as key transcription factors regulating M2 polarization (Satoh et al., Nature immunology 11, 936-944 (2010)) after culturing with IL-4 (FIG. 4a-b). To extend these findings, bone marrow-derived DCs isolated from wild-type and Ch25h−/− mice were cultured with LPS and found similarly increased expression of Il12a, Tnfa and Nos2 from both mice (FIG. 4c). In combination, this suggests that impaired cytokine secretion by professional APCs is not a contributing factor in Ch25h-deficient mice. Furthermore, recent evidence revealed that depletion of alveolar macrophages ameliorated elastase-induced emphysema (Ueno et al., Nature communications 6, 6332 (2015)), an iBALT-independent emphysema mouse model. Therefore, we utilized this model to demonstrate that loss of Ch25h in macrophages did not impact upon emphysema development. Both wild-type and Ch25h$^{-/-}$ mice developed a severe emphysema following elastase treatment, with no evidence of iBALT formation in either mice (FIG. 5a-e). These data further demonstrate that Ch25h deficient macrophages are not protective against elastase-induced emphysema, implying the role of Ch25h in iBALT-mediated COPD pathogenesis.

Figure 6:
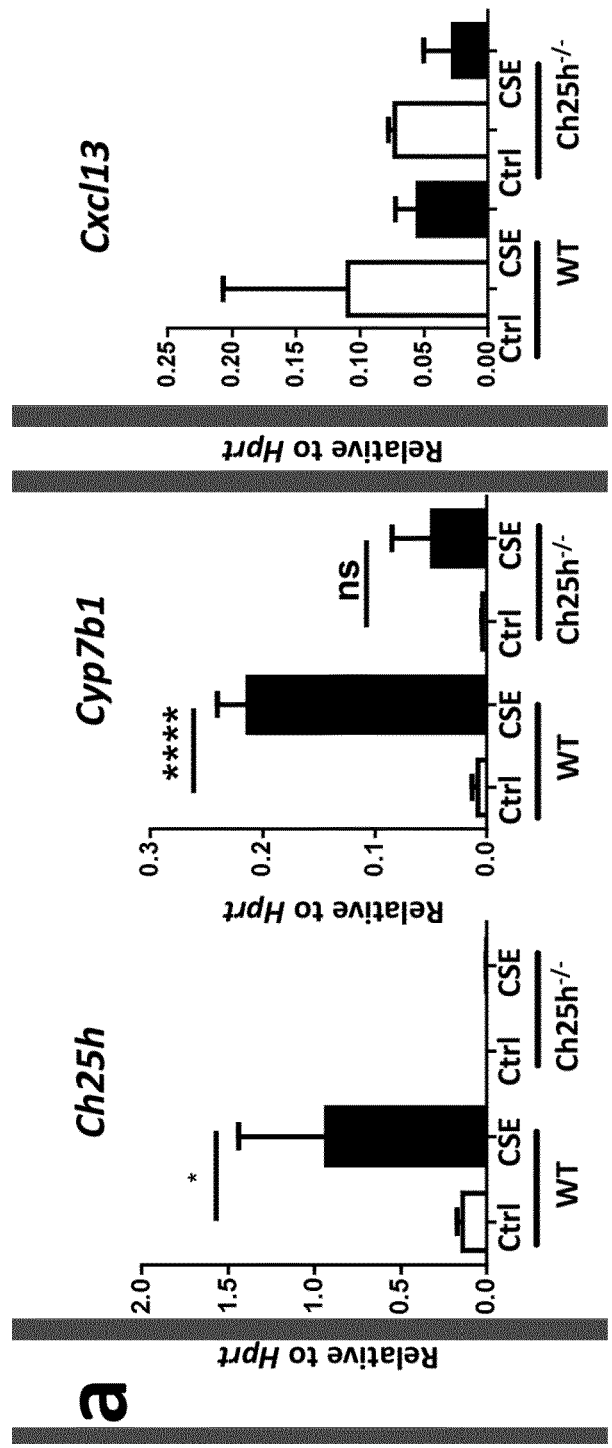
FIG. 6: Ch25h deficiency or attenuation of Cyp7b1 activity with clotrimazole impairs B cell migration towards CSE treated airways ex vivo.
Figure 6:
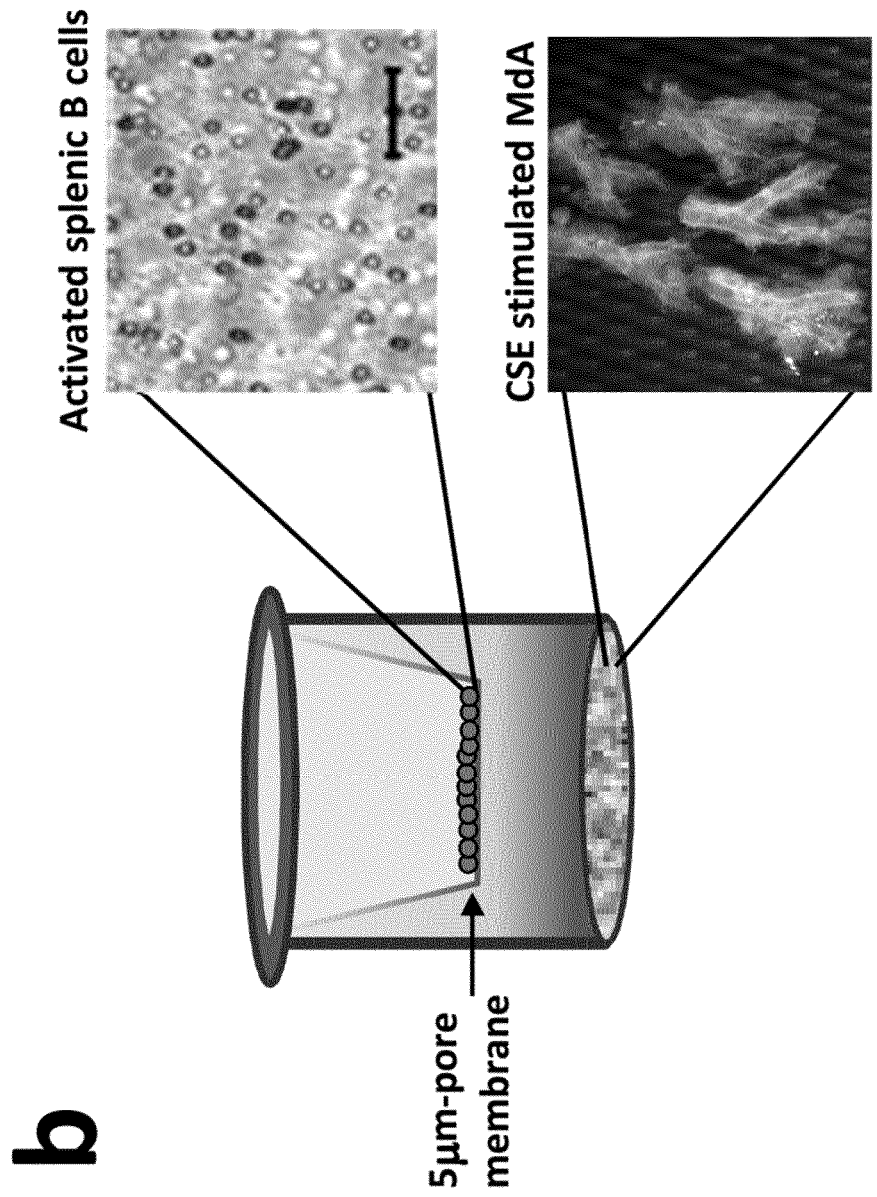
Figure 6:
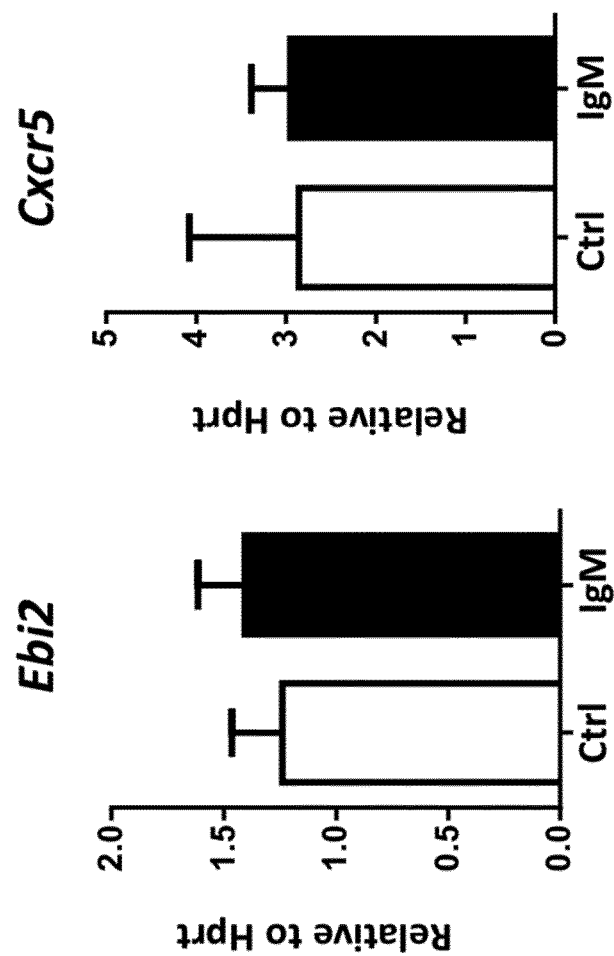
Figure 6:
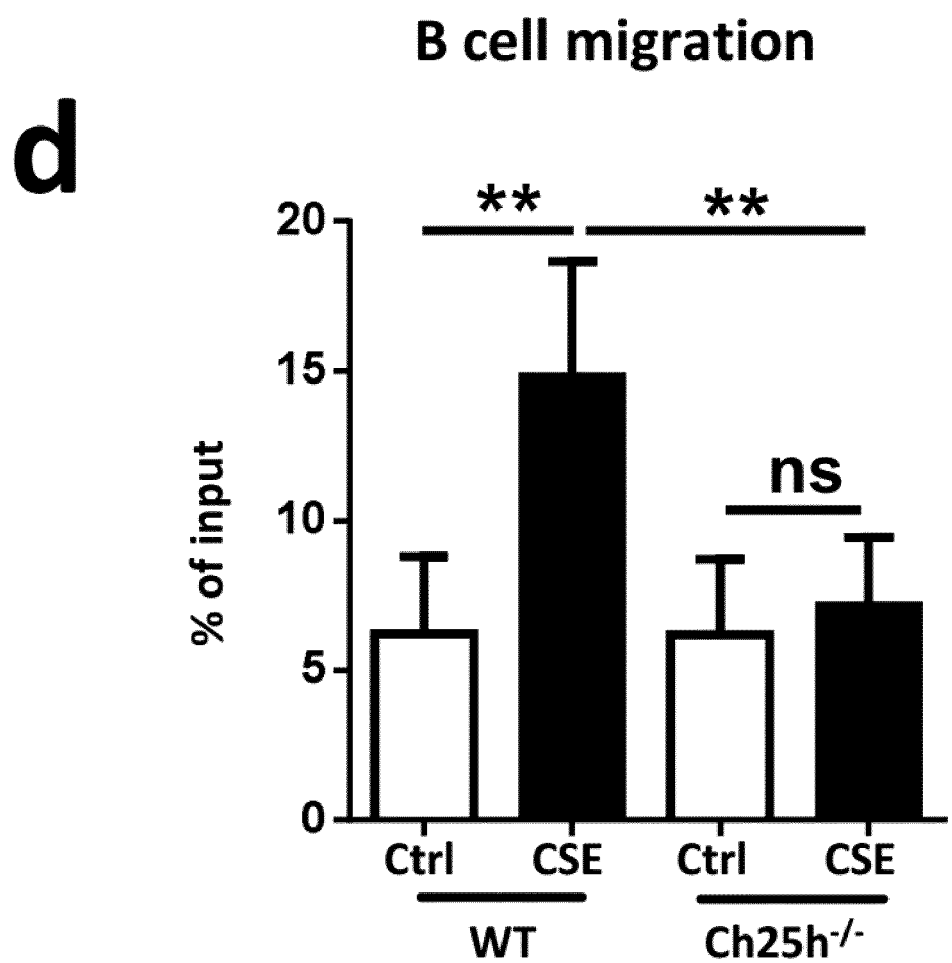
Figure 6:
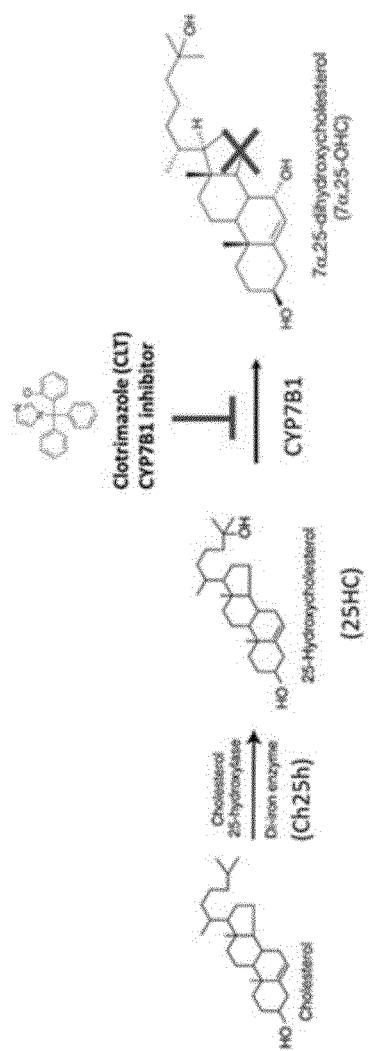
Figure 6:
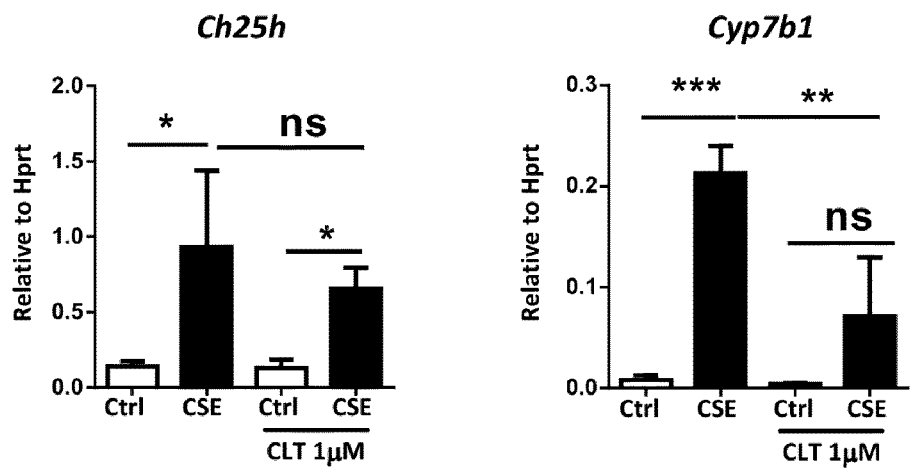
Figure 6:
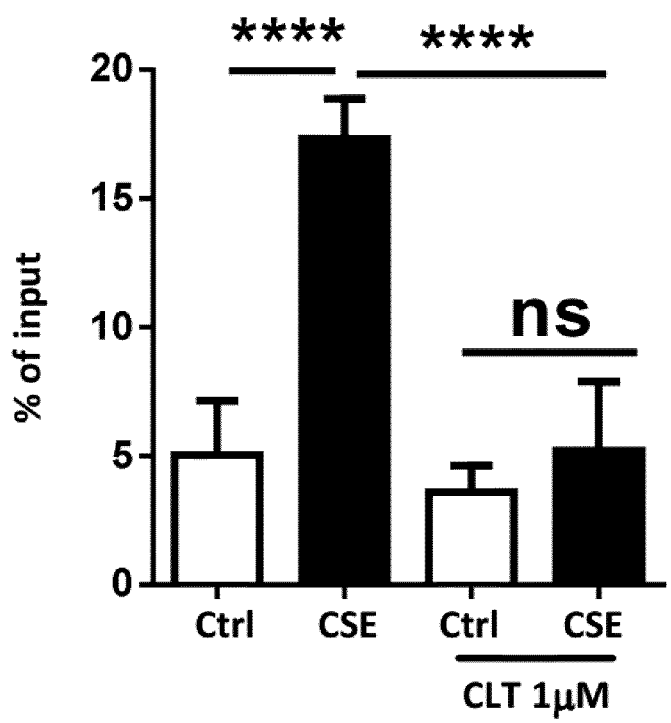

To address the role of airway specific Ch25h in guiding B cells, dissected airway trees stimulated with cigarette smoke extract (CSE) were used ex vivo, which demonstrated increased expression of Ch25h and Cyp7b1 in airways from wild-type mice, whereas Ch25h−/− mice did not express Ch25h and failed to increase the expression of Cyp7b1. Isolated airways from both mice showed no differences in Cxcl13 expression (FIG. 6a). To further corroborate these findings, a novel ex vivo assay was utilized in which IgM cross-linked activated splenic B cells were tested for their ability to migrate towards the culture supernatant from CSE-stimulated airway trees (FIG. 6b). mRNA analysis of IgM cross-linked B cells revealed no change in the expression levels of the 7α,25-OHC receptor Ebi2 (Hannedouche et al., Nature 475, 524-527 (2011); Liu et al., Nature 475, 519-523 (2011)) and the Cxcl13 receptor Cxcr5 (Gunn et al., Nature 391, 799-803 (1998); Legler et al., The Journal of experimental medicine 187, 655-660 (1998)) (FIG. 6c). Consistent with increased Ch25h and Cyp7b1, we observed a strong increase in the number of activated B cells migrating towards culture supernatant from wild-type CSE-activated airways (FIG. 6d).

To demonstrate that increased expression of Ch25h and Cyp7b1 mediated oxysterol 7α,25-OHC guided B cell migration, dissected wild-type airways were cultured in the presence of clotrimazole, a Cyp7b1 inhibitor (Liu et al., Nature 475, 519-523 (2011)) (FIG. 6e). This treatment did not affect Ch25h levels, but was sufficient to reduce Cyp7b1 mRNA expression (FIG. 6f) and significantly impaired the ability of activated B cells to migrate towards culture supernatant from CSE-treated airways (FIG. 6g). Furthermore, the present inventors tested other well-known Cyp7b1 inhibitors e.g. Ritonavir (0.1 and 1 µM), Miconazole (1 µM) and Metyrapone (1 µM). These inhibitors also impaired B cell migration (FIG. 6h). These results show that the CS-induced airway epithelial oxysterols are capable of driving B cell migration, which contribute to iBALT generation on the airways in experimental COPD.

Figure 7:
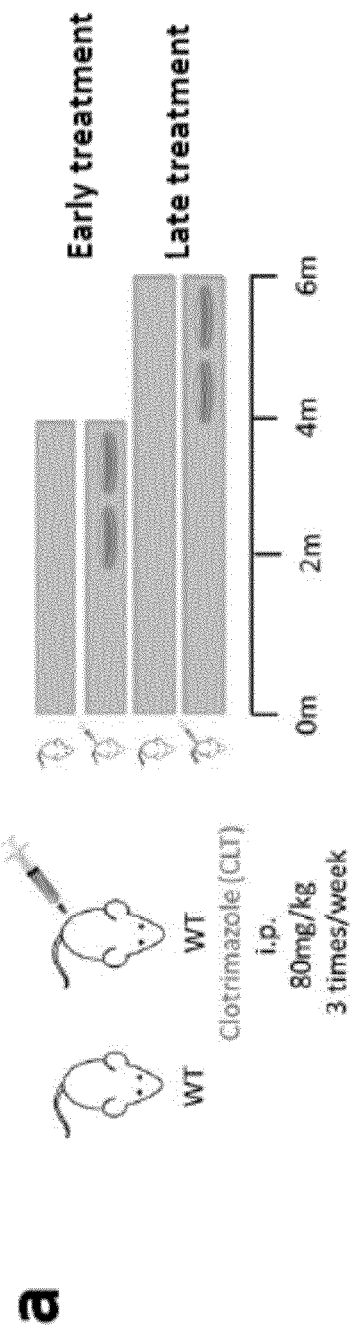
FIG. 7: Clotrimazole therapeutic dosing strategy showing that clotrimazole does not attenuate lung inflammatory responses following exposure to chronic cigarette smoke. Experimental design: In the early treatment group C57BL/6 mice were exposed to filtered air (FA) or cigarette smoke (CS) for 4 months and treated with clotrimazole (i.p. 80 mg/Kg 3 times per week) from months 2 to 4 or oil controls. In the late treatment group C57BL/6 mice were exposed to FA or CS for 6 months and treated with clotrimazole from months 4 to 6 or oil controls.
Figure 8:
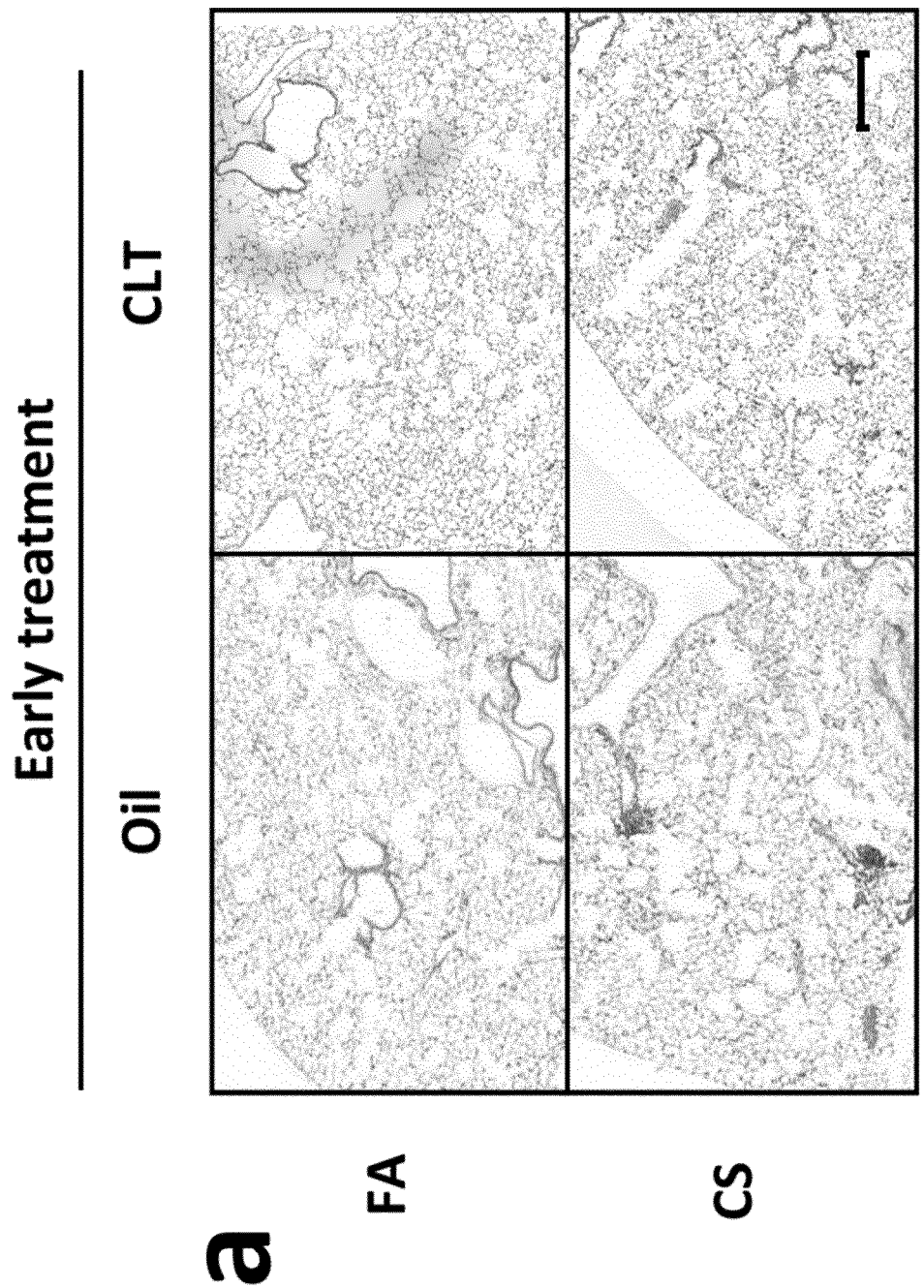
FIG. 8: Clotrimazole protects against and reverses cigarette smoke-induced COPD. (a) Representative H&E stained lung from C57BL/6 mice exposed to filtered air (FA) or cigarette smoke (CS) for 4 months and treated with clotrimazole (i.p. 80 mg/Kg 3 times per week) from months 2 to 4 or oil controls (Early treatment group). Experiment repeated twice. n=4 mice per FA groups and n=6 mice per CS groups. (b) Quantification of total iBALT and that localized on the airway, vessels and septal area from mice described in a. (c) Mean chord length (MCL) quantification of lung sections from mice described in a. (d) Lung volumes from mice described in a. (e) Bronchoalveolar lavage fluid (BALF) total and differential cell counts from mice in a. (b-e) Data are mean±s.d. *P<0.05, P<0.01, *P<0.001 and ****P<0.0001 one-way ANOVA and Bonferroni's post hoc test. (f) Representative H&E stained lung from C57BL/6 mice exposed to filtered air (FA) or cigarette smoke (CS) for 6 months and treated with clotrimazole (i.p. 80 mg/Kg 3 times per week) from months 4 to 6 or oil controls (Late treatment group). Experiment repeated twice. n=4 mice per FA groups and n=5 mice per CS groups. (g) Quantification of total iBALT and that localized on the airway, vessels and septal area from mice described in f. (h) Mean chord length (MCL) quantification of lung sections from mice described in f. (i) Lung volumes from mice described in f. (j) Bronchoalveolar lavage fluid (BALF) total and differential cell counts from mice in f. (g j) Data are mean±s.d. *P<0.05 **P<0.01 one-way ANOVA and Bonferroni's post hoc test.
Figure 8:
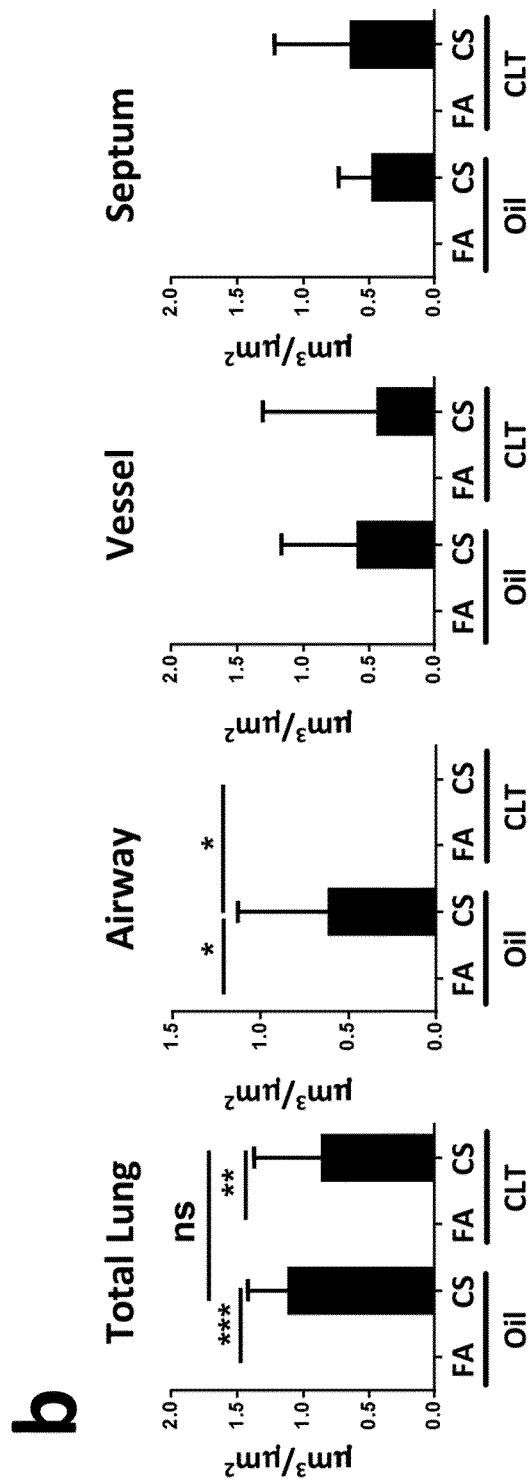
Figure 8:
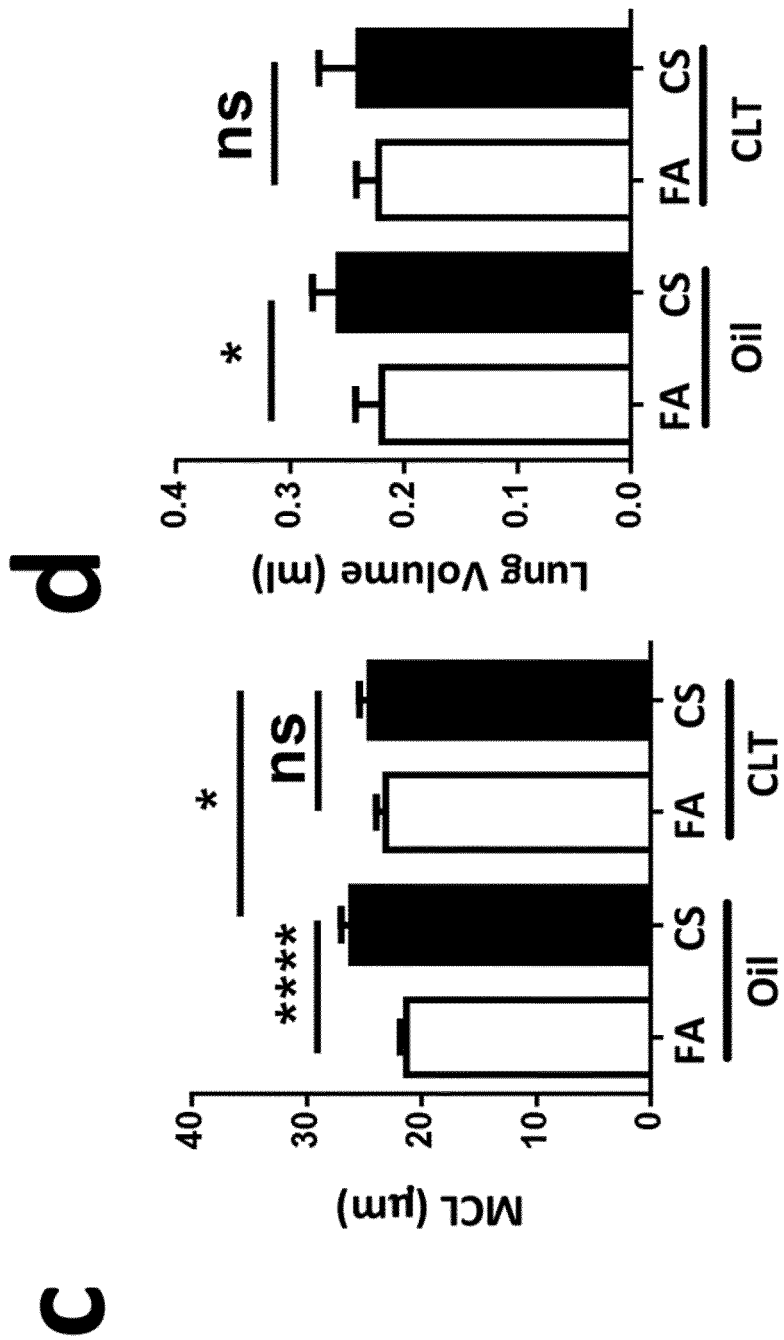
Figure 8:
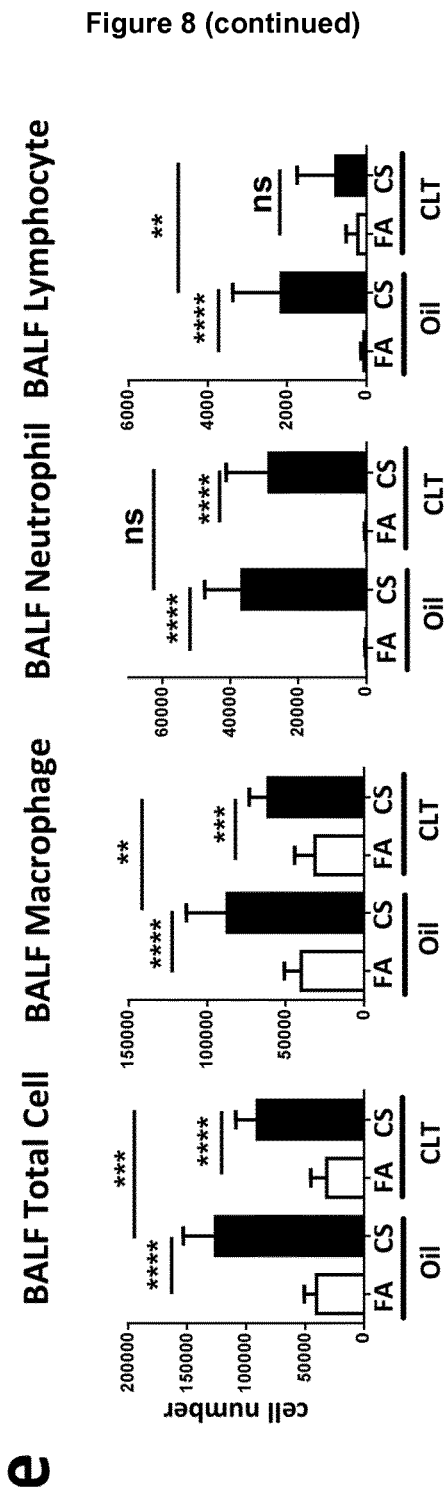
Figure 8:
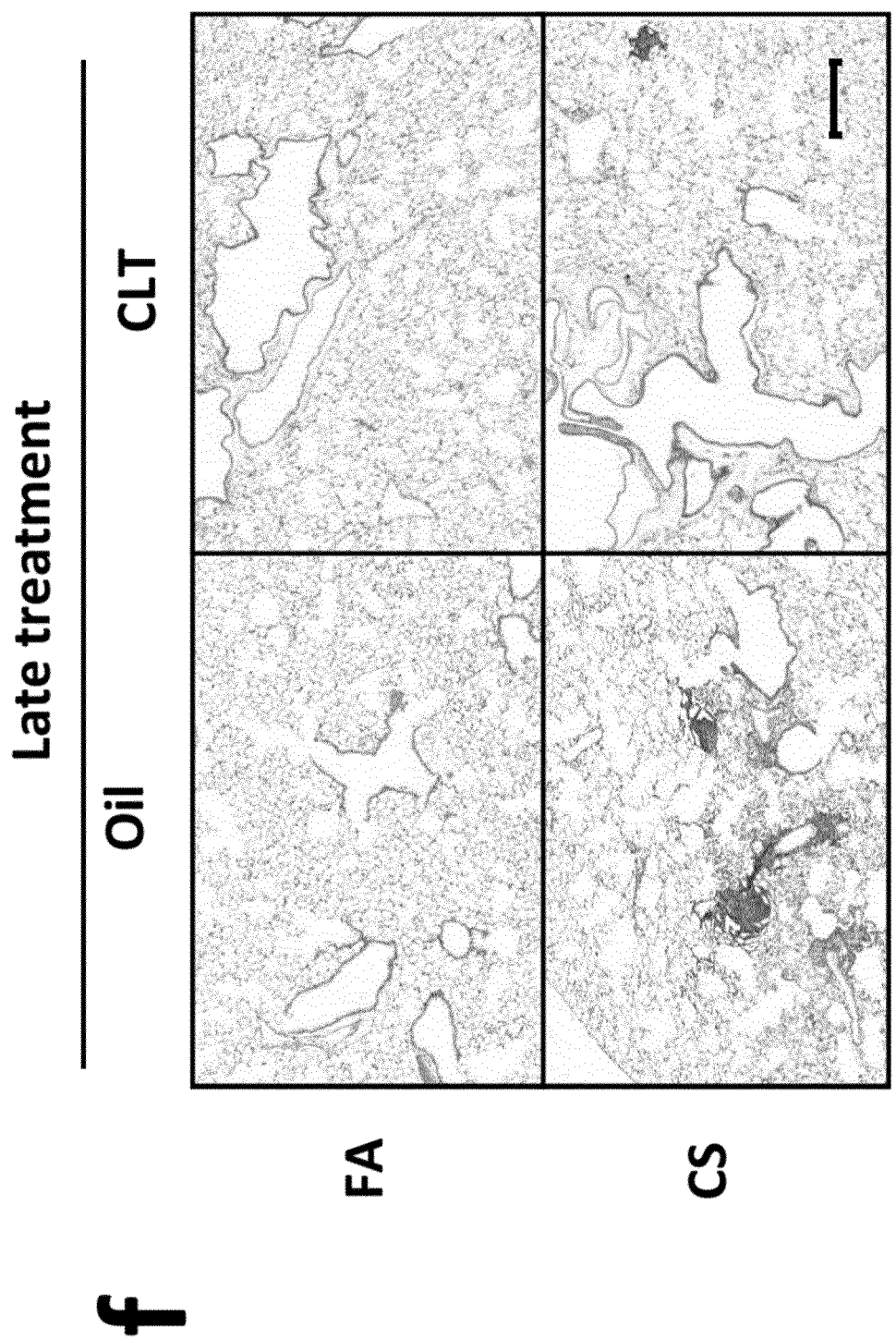
Figure 8:
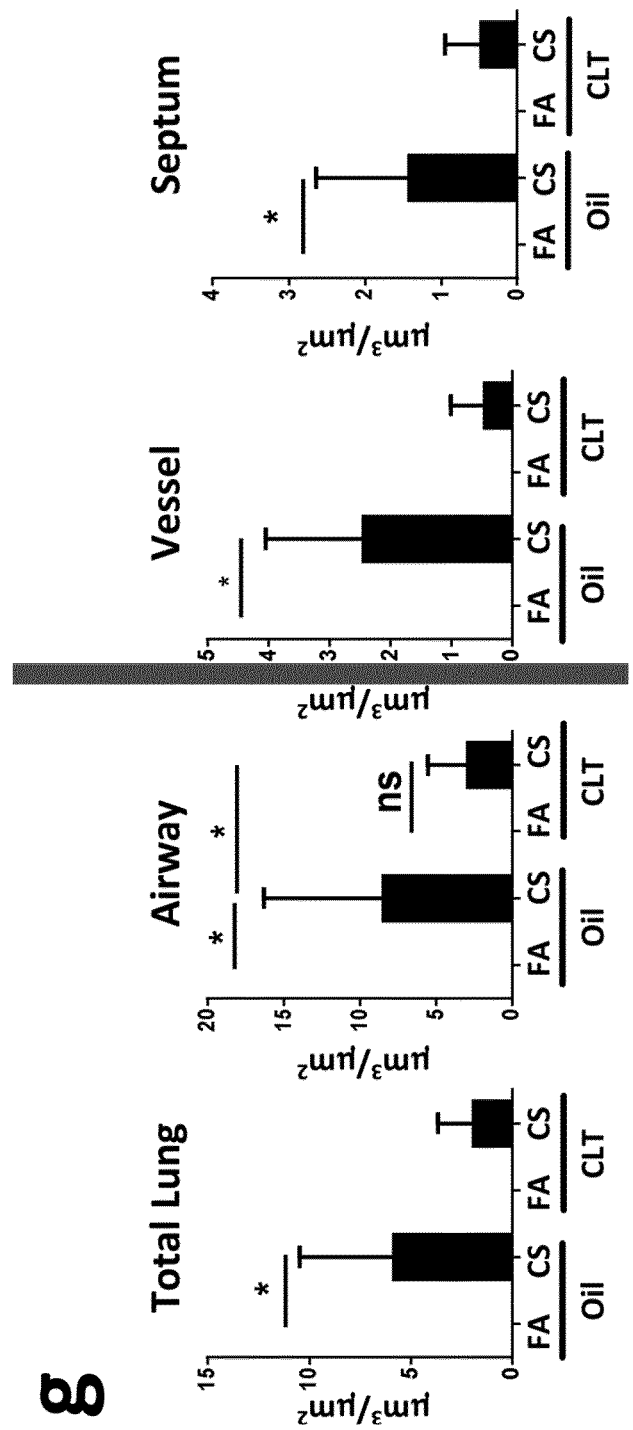
Figure 8:
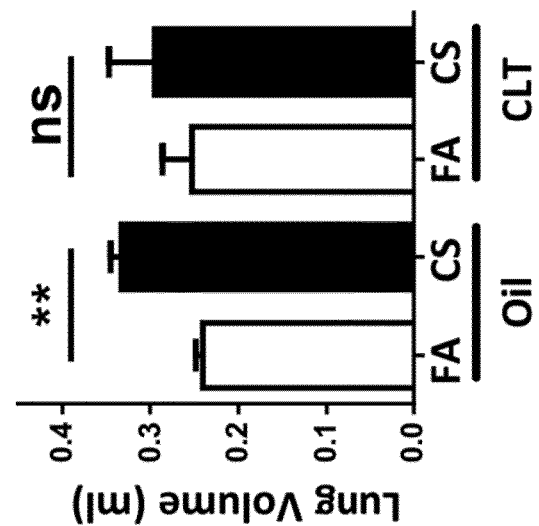
Figure 8:
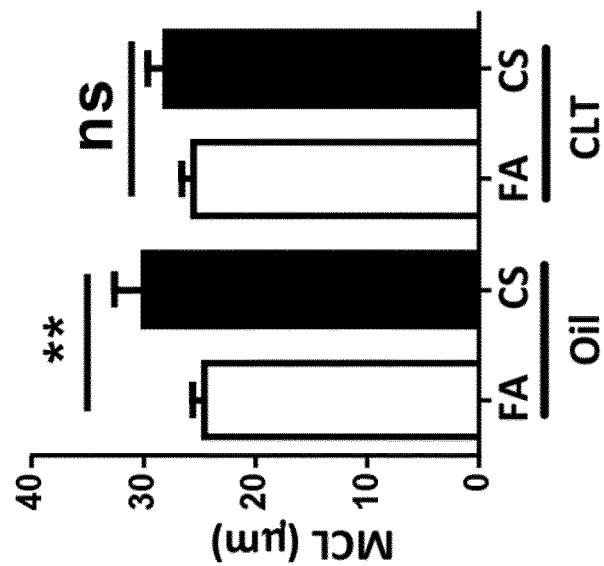
Figure 8:
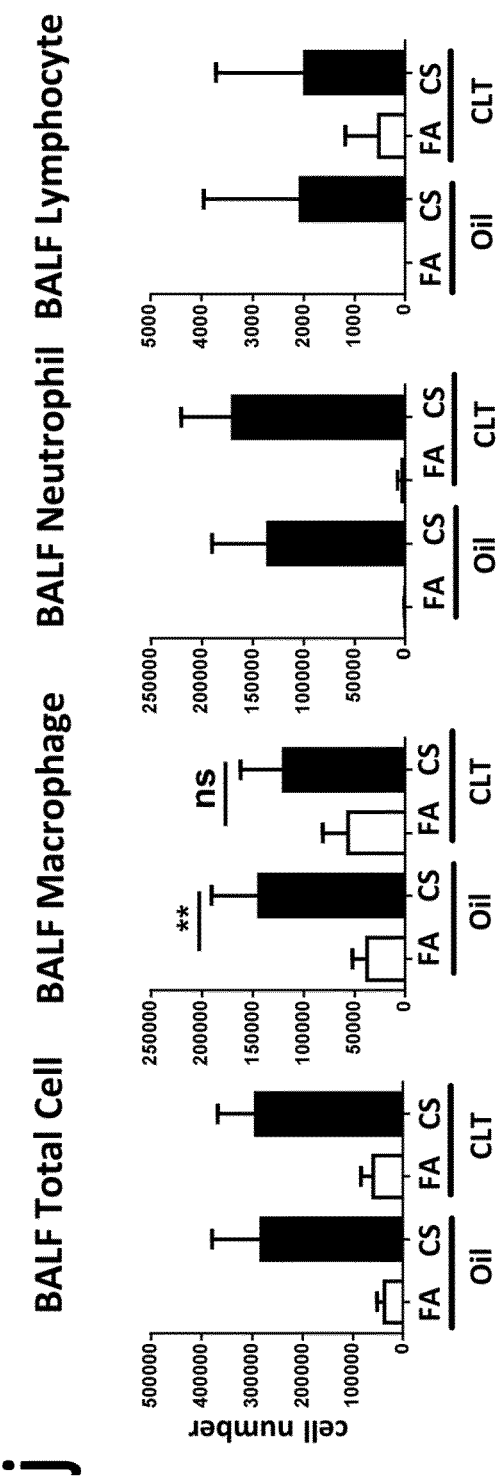

Finally, we evaluated whether inhibiting generation of 7α,25-OHC could alleviate established experimental COPD when clotrimazole was administrated as a therapeutic dosing strategy. Wild-type mice with pulmonary inflammation following two months chronic CS exposure (comparable with human COPD GOLD stages 0 to 1), were treated with clotrimazole during months two to four (FIG. 7a), leading to significantly reduced iBALT formation (FIG. 8a, b), lack of emphysema development (FIG. 8c) and no deterioration in lung volume (FIG. 8d). At the cellular level, we observed reduced macrophage and lymphocyte cell numbers in BAL fluid of these clotrimazole treated CS-exposed mice (FIG. 8e). Importantly, wild-type mice exposed to CS for four months (comparable with human COPD GOLD stages 1 to 2), presenting clear signs of iBALT formation and COPD (FIG. 3a-c and FIG. 8a-c), then treated with clotrimazole, showed attenuated iBALT, emphysema and reduced lung volume (FIG. 8f-i). There was also reduced macrophage cell numbers in the BAL fluid of late cotrimazole treated CS-exposed mice (FIG. 8j).

This work establishes a role for oxysterol metabolism in guiding iBALT generation to the airways during COPD pathogenesis. The present inventors consider that T cell migration may also be disrupted, especially since EB12 is expressed by CD4 T cells and activated-T cell positioning in the outer T zone of lymphoid follicles is directed by 7α,25-OHC (Li et al., Nature 533, 110-114 (2016)). However, the present inventors recently demonstrated that B cell deficient mice were protected from CS-induced COPD despite normal function of CD4 T cells (John-Schuster et al., American journal of physiology. Lung cellular and molecular physiology 307, L692-706 (2014)). In addition, 25-hydroxycholesterol promotes fibroblast-mediated tissue remodeling through NFkB signaling (Ichikawa et al., Experimental cell research 319, 1176-1186 (2013)), proposing that impairing oxysterol metabolism may have additional direct effects on lung tissue regeneration, an issue requiring further investigations in experimental models of COPD. Thus, disruption of iBALT generation through targeting oxysterols, rather than complete B cell depletion, particularly as a recent rituximab trial in COPD patients failed because of increased risk of infectious complications (Brusselle et al., The European respiratory journal 34, 219-230 (2009)), opens new therapeutic strategies on a broader perspective for diseases associated with ectopic lymphoid tissue beyond COPD, such as pulmonary hypertension, cancer, transplant rejection and autoimmunity (Pitzalis et al., Nature reviews. Immunology 14, 447-462 (2014)).

Target Associated Diseases

This work establishes a role for oxysterol metabolism in guiding iBALT generation to the airways during COPD pathogenesis. The present inventors recently demonstrated that B cell deficient mice were protected from CS-induced COPD despite normal function of CD4 T cells (John-Schuster et al., American journal of physiology. Lung cellular and molecular physiology 307, L692-706 (2014)). In addition, 25-hydroxycholesterol promotes fibroblast-mediated tissue remodeling through NFkB signaling (Ichikawa et al., Experimental cell research 319, 1176-1186 (2013)), proposing that impairing oxysterol metabolism may have additional direct effects on lung tissue regeneration, an issue requiring further investigations in experimental models of COPD. Thus, disruption of iBALT generation through targeting oxysterols, rather than complete B cell depletion, particularly as a recent rituximab trial in COPD patients failed because of increased risk of infectious complications (Brusselle et al., The European respiratory journal 34, 219-230 (2009)), opens new therapeutic strategies on a broader perspective for diseases associated with ectopic lymphoid tissue beyond COPD, such as pulmonary hypertension, lung cancer, transplant rejection and pulmonary fibrosis, cystic fibrosis and autoimmunity (Pitzalis et al., Nature reviews. Immunology 14, 447-462 (2014)).

Inhibition of the Gene Expression of the Genes CH25h, Cyp7b1 and TNFα and Reduction of B Cell Migration B Cell Isolation and Migration.

The cells were incubated for 24h at 37° C., 5% $CO_2$, in a 24 well-plate with or without 10% cigarette smoke extract (CSE, 10%)+lipopolysaccharide (LPS, 10 µg/mL), supplemented or not with the 18 CYP7B1 inhibitors (0.3 and 1 µM). B cells were purified from the spleens of C57BL/6J mice by negative selection (B cell Isolation Kit, mouse, Miltenyi Biotec). Freshly isolated B cells at $2.0\times10^6$/mL in 100 µL were activated by unconjugated AffiniPure F(ab')$_2$ Fragment Goat anti-mouse IgM, µchain specific antibody (10 µg/mL, 115-006-020, Jackson Immunoresearch Laboratories) for 1 hr at 37° C. in 5.0 µm pore sized transwell inserts (Permeable Polycarbonate Membrane Inserts, Corning, Fisher Scientific). Migrated B cells were collected, and counted by fluorescence-activated cell sorting (FACS) (Trucount tubes, BD Biosciences).

Quantitative Real Time RT-PCR.

10 ng RNA was reverse transcribed using Random Hexamers and MuLV Reverse Transcriptase (Applied Biosystems). Gene expression was analyzed using SensiFAST SYBR Hi-ROX Kit (Bioline) on a StepOnePlus 96 well Real-Time PCR System (Applied Biosystems). Primer sequences were as follows: Ch25h: Forward: GAC CTT CTT CGA CGT GCT GA, Reverse: CCA CCG ACA GCC AGA TGT TA; Cyp7b1: Forward: GGA GCC ACG ACC CTA GAT G, Reverse: GCC ATG CCA AGA TAA GGA AGC; TNFα: Forward: CAC CAC GCT CTT CTG TCT, Reverse: GGC TAC AGG CTT GTC ACT C. Expression of each gene was calculated relative to the housekeeping gene 18S as $2^{-\Delta Ct}$.

Figure 10:
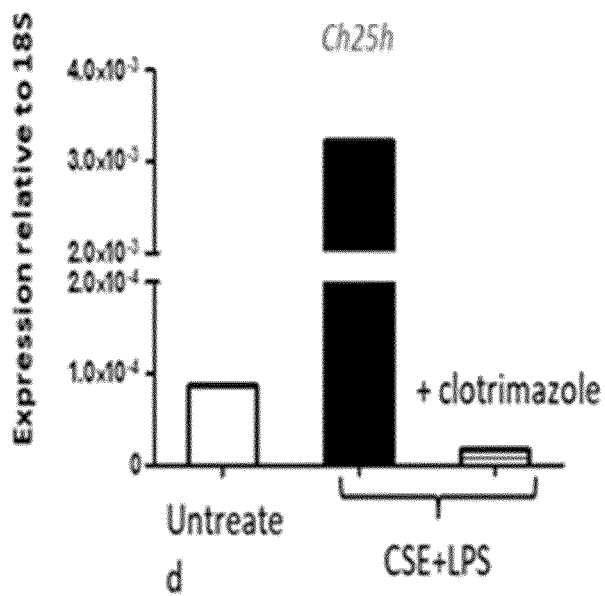
FIG. 10: Clotrimazole inhibits the gene expression of CH25h, Cyp7b1 and TNFα.
Figure 10:
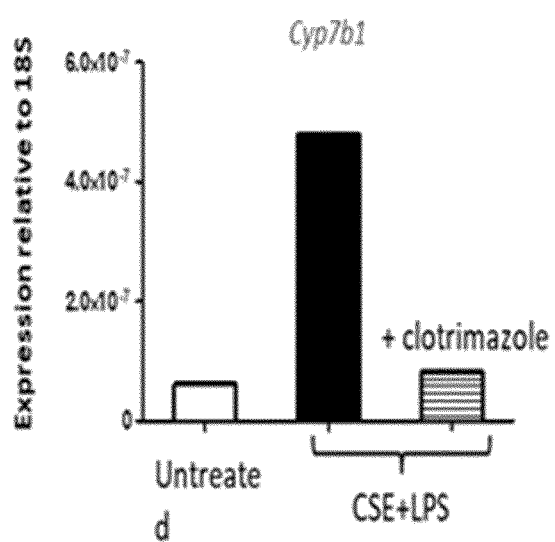
Figure 10:
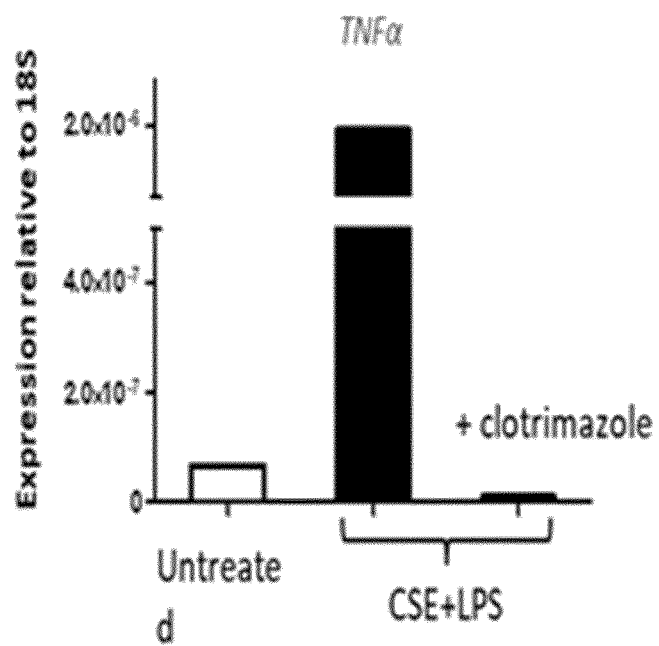

Results 10% CSE+ 10 µg/mL LPS stimulation to induce the expression of CH25H and CYP7B1, the 2 key enzymes that lead to the production of 7α-25,OHC (FIG. 10). The combination of CSE and LPS efficiently induced Ch25h and Cyp7b1 expression, and the pro-inflammatory effect of this treatment was confirmed by the increase in Tnf expression (FIG. 10). The induction of all three genes was inhibited by clotrimazole.

Moreover, the B cell migration assay has been used to screen the effect of 18 compounds described as Cyp7b1 inhibitors on B cell migration. As displayed in FIG. 11, all 18 compounds showed a lower level of migration than compared to the positive control (CSE+LPS) already at 1 µM dose.

It will be clear that the invention may be practiced otherwise than as particularly described in the foregoing description and examples. Numerous modifications and variations of the present invention are possible in light of the above teachings and, therefore, are within the scope of the appended claims.

The invention claimed is:

1. A method of treating a disease associated with cytochrome P450 family 7 subfamily B member 1 (CYP7B1), the method comprising administering a CYP7B1 inhibitor to a subject suffering from the disease associated with CYP7B1 or being at risk of developing the disease associated with CYP7B1, wherein the disease associated with CYP7B1 is a pulmonary disease, transplant rejection or an autoimmune disease; and wherein the CYP7B1 inhibitor is (a) a compound having the structure of formula (IV):

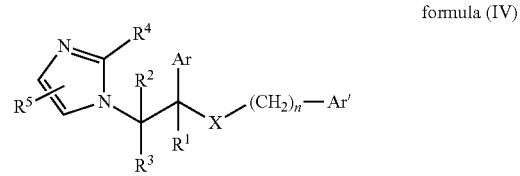

formula (IV)

or a pharmaceutically acceptable salt, solvate or hydrate thereof, wherein $R^1$, $R^2$, and $R^3$ are each, independently, a member selected from the group consisting of hydrogen and ($C_1$-$C_6$)alkyl;

X is a member selected from the group consisting of oxygen and NH;

n is an integer of 0,1 or 2;

Ar is a member selected from the group consisting of phenyl, substituted phenyl, thienyl and halothienyl, said substituted phenyl containing at least one substituent selected from the group consisting of halogen, ($C_1$-$C_6$)alkyl and ($C_1$-$C_6$)alkoxy;

Ar' is a member selected from the group consisting of phenyl, substituted phenyl and α-tetralyl, said substituted phenyl containing at least one substituent selected from the group consisting of halogen, ($C_1$-$C_6$)alkyl, ($C_1$-$C_6$)alkoxy, cyano, $NO_2$ and amino;

$R^4$ is a member selected from the group consisting of hydrogen, methyl and ethyl; and $R^5$ is a member selected from the group consisting of hydrogen and methyl;

provided that:

(i) when said X is NH, then said R is hydrogen;

(ii) when said Ar' is a substituted phenyl containing at least one substituent selected from the group consisting of $NO_2$ and amino, then said X is oxygen and said n is 0;

(iii) when said Ar' is a α-tetralyl, then said X is NH and said n is 0; and (iv) when said X is oxygen and said Ar' is a member selected from the group consisting of phenyl and substituted phenyl containing at least one substituent selected from the group consisting of halogen, $(C_1-C_6)$alkyl, $(C_1-C_6)$alkoxy and cyano, then said n is other than 0;

(b) a compound having the structure of formula (V):

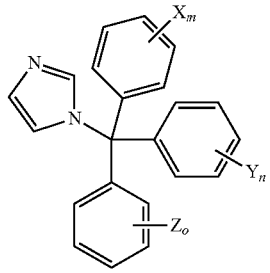

formula (V)

or a pharmaceutically acceptable salt, solvate or hydrate thereof, wherein X, Y and Z are each, independently, selected from the group consisting of $(C_1-C_4)$alkyl and an electronegative substituent, wherein preferably the electronegative substituent is selected from the group consisting of F, Cl, Br, I, $NO_2$, $CF_3$, CN, $SCH_3$ and $OCH_3$; and m, n and o are each independently 0, 1 or 2;

(c) a compound having the structure of formula (XV):

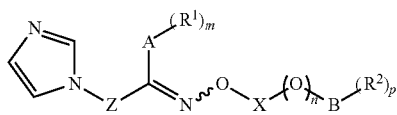

formula (XV)

or a pharmaceutically acceptable salt, solvate or hydrate thereof, wherein Z is selected from the group consisting of straight and branched chain $(C_1-C_4)$alkylene group;

A is selected from the group consisting of phenyl and naphthyl;

$R^1$ is selected from the group consisting of halogen, $NO_2$, $(C_1-C_6)$alkyl and $(C_1-C_6)$alkoxy;

X is a $(C_1-C_8)$alkylene group;

B is selected from the group consisting of hydrogen, phenyl and naphthyl;

$R^2$ is selected from the group consisting of halogen, $NO_2$, $(C_1-C_6)$alkyl and $(C_1-C_6)$alkoxy;

m is 0 or an integer of from 1 to 3;

n is 0 or 1; and p is 0 or an integer of from 1 to 3 with the proviso that when B is hydrogen both n and p are 0;

(d) a compound having the structure of formula (XVII):

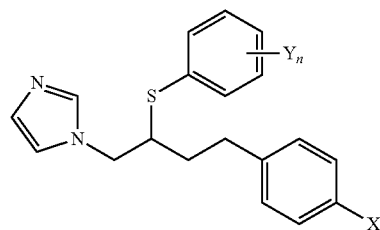

formula (XVII)

or a pharmaceutically acceptable salt, solvate or hydrate thereof, wherein X is Cl or F;

Y is Br or Cl or F, at least one Y being in the 2'-position; and n is an integer of from 1 to 5 when Y is Cl; or n is 1 or 2 when Y is other than Cl;

(e) a compound having the structure of formula (XIX):

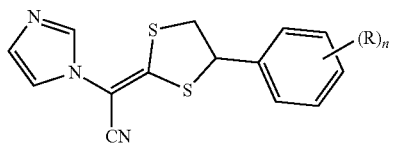

formula (XIX)

or a pharmaceutically acceptable salt, solvate or hydrate thereof, wherein R is each, independently, halogen selected from the group consisting of F, Cl and Br; and n is an integer of 0, 1, 2 or 3; or (f) a compound having the structure of formula (XX):

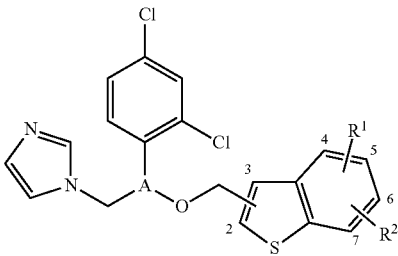

formula (XX)

or a pharmaceutically acceptable salt, solvate or hydrate thereof, wherein A is an imino-

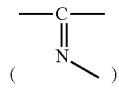

or methine

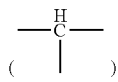

group; and

R¹ and R², which may be the same or different, are hydrogen or halogen, said halogen being attached to the benzo[b]-thiophene group in the 2, 4, 5, 6 or 7 position and the methylene group being bonded to the benzo[b]-thiophene group in 2 or 3 position.

2. The method of claim 1, wherein the CPYP7B1 inhibitor reduces or prevents the formation of inducible bronchus-associated lymphoid tissue (iBALT) by inhibiting the activity of CPY7B1.

3. The method of claim 1, wherein the pulmonary disease is selected from the group consisting of lung cancer, emphysema, cystic fibrosis, pulmonary hypertension, chronic obstructive pulmonary disease, and pulmonary fibrosis.

4. The method of claim 1, wherein
(a) the CPYP7B1 inhibitor is selected from the group consisting of bifonazole, miconazole, clotrimazole, voriconazole, econazole, tioconazole, fluconazole, isoconazole, itraconazole, oxiconazole, posaconazole, butoconazole, luliconazole, and sertaconazole; or
(b) the CPYP7B1 inhibitor reduces or prevents the formation of inducible bronchus-associated lymphoid tissue (iBALT) by inhibiting the activity of CPY7B1.

5. A method of treating a disease associated with cytochrome P450 family 7 subfamily B member 1 (CYP7B1), the method comprising administering a CYP7B1 inhibitor to a subject suffering from the disease associated with CYP7B1 or being at risk of developing the disease associated with CYP7B1, wherein the disease associated with CYP7B1 is a pulmonary disease, transplant rejection or an autoimmune disease; and wherein the CPYP7B1 inhibitor is selected from the group consisting of bifonazole, miconazole, clotrimazole, voriconazole, econazole, tioconazole, fluconazole, metyrapone, isoconazole, itraconazole, oxiconazole, posaconazole, butoconazole, efinaconazole, luliconazole, and sertaconazole.

* * * * *